(12) United States Patent
Ahn et al.

(10) Patent No.: US 8,394,792 B2
(45) Date of Patent: Mar. 12, 2013

(54) HETEROCYCLIC DERIVATIVES

(75) Inventors: Sung Oh Ahn, Hwaseong (KR); Chan Hee Park, Hwaseong (KR); Jun Hwan Im, Hwaseong (KR); Soon Ok Lee, Hwaseong (KR); Kyoung June Lee, Hwaseong (KR); Seong Wook Cho, Hwaseong (KR); Kwang Seok Ko, Hwaseong (KR); Sun Young Han, Hwaseong (KR); Won Il Lee, Hwaseong (KR)

(73) Assignee: C&C Research Laboratories, Hwaseong (KR)

( * ) Notice: Subject to any disclaimer, the term of this patent is extended or adjusted under 35 U.S.C. 154(b) by 223 days.

(21) Appl. No.: 12/935,478

(22) PCT Filed: Mar. 31, 2009

(86) PCT No.: PCT/KR2009/001659
§ 371 (c)(1),
(2), (4) Date: Sep. 29, 2010

(87) PCT Pub. No.: WO2009/145456
PCT Pub. Date: Dec. 3, 2009

(65) Prior Publication Data
US 2011/0028467 A1 Feb. 3, 2011

(30) Foreign Application Priority Data
Mar. 31, 2008 (KR) .................. 10-2008-0030067

(51) Int. Cl.
*C07D 498/04* (2006.01)
*A61K 31/538* (2006.01)
(52) U.S. Cl. .................... 514/230.5; 544/105
(58) Field of Classification Search .............. 544/105; 514/230.5
See application file for complete search history.

(56) References Cited

U.S. PATENT DOCUMENTS

| | | |
|---|---|---|
| 2007/0010670 A1 | 1/2007 | Hirata et al. |
| 2007/0197512 A1 | 8/2007 | Inoue et al. |
| 2008/0064871 A1 | 3/2008 | Hirata et al. |

FOREIGN PATENT DOCUMENTS

| | | |
|---|---|---|
| EP | 1 820 515 A1 | 8/2007 |
| JP | 2002220389 A * | 8/2002 |
| JP | 3988832 B2 | 10/2007 |
| WO | WO 2006/057460 A1 | 6/2006 |
| WO | WO 2007/089034 A1 | 8/2007 |
| WO | WO 2007/093507 A1 | 8/2007 |
| WO | WO 2009/120660 A2 | 10/2009 |

OTHER PUBLICATIONS

Ames et al., "Uric acid provides an antioxidant defense in humans against oxidant- and radical-caused aging and cancer: A hypothesis," Proc. Natl. Acad. Sci. USA, vol. 78, No. 11, pp. 6858-6862, Nov. 1981.

Anzai et al., "Organic Anion Transporter Family: Current Knowledge," Journal of Pharmacological Sciences, vol. 100, pp. 411-426, 2006.
Arai et al., "Fulminant Hepatic Failure Associated With Benzbromarone Treatment: A Case Report," Journal of Gastroenterology and Hepatology, vol. 17, pp. 625-626, 2002.
Becker, "Towards the Physiological Function of Uric Acid," Free Radical Biology & Medicine, vol. 14, pp. 615-631, 1993.
Borges et al., "Progess Towards the Discovery of Xanthine Oxidase Inhibitors," Current Medicinal Chemistry, vol. 9, pp. 195-217, 2002.
Campion et al., "Asymptomatic Hyperuricemia Risks and Consequences in the Normative Aging Study," The American Journal of Medicine, vol. 82, pp. 421-426, Mar. 1987.
Choi et al., "Pathogenesis of Gout," Annals of Internal Medicine, vol. 143, pp. 499-516, 2005.
Chu-Moyer et al., "Preparation of the Four Regioisomeric 2-(Methylthio)oxazolopyridines: Useful Synthons for Elaboration to 2-(Amino substituted)oxazolopyridines," J. Org. Chem., vol. 60, pp. 5721-5725, 1995.
Enomoto et al., "Molecular identification of a renal urate-anion exchanger that regulates blood urate levels," Nature, vol. 417, pp. 447-452, May 23, 2002.
Fields et al., "Allopurinol, An Inhibitor Of Xanthine Oxidase, Reduces Uric Acid Levels And Modifies The Signs Associated With Copper Deficiency In Rats Fed Fructose," Free Radical Biology & Medicine, vol. 20, No. 4, pp. 595-600, 1996.
Fujimori, "Hyperuricemia—Definition and classification," Nippon Rinsho, vol. 61, Suppl. 1, pp. 161-165, 2003.
Halliwell, "Uric Acid: An Example of Antioxidant Evaluation," Handbook of Antioxidants, edited by Cadenas et al., Chapter 9, pp. 243-256, 1996.
Hautekeete et al., "Severe hepatotoxicity related to benzarone: a report of three cases with two fatalities," Liver, vol. 15, pp. 25-29, 1995.
Kaufmann et al., "Mechanisms of Benzarone and Benzbromarone-Induced Hepatic Toxicity," Hepatology, vol. 41, No. 4, pp. 925-935, Apr. 2005.

(Continued)

*Primary Examiner* — Kahsay T Habte
(74) *Attorney, Agent, or Firm* — Birch, Stewart, Kolasch & Birch, LLP

(57) ABSTRACT

Disclosed are heterocyclic derivatives, and more particularly heterocyclic derivatives having the following Formula I which are useful for the preparation of medicaments for treating diseases related to uric acid:

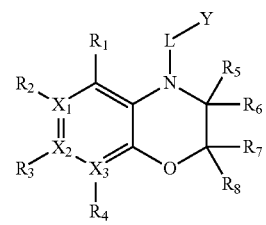

Formula I wherein $R_1$, $R_2$, $R_3$, $R_4$, $R_5$, $R_6$, $R_7$, $R_8$, $X_1$, $X_2$, $X_3$, L and Y are the same as defined in the detailed description.

28 Claims, No Drawings

OTHER PUBLICATIONS

Keller et al., "Mitochondrial Manganese Superoxide Dismutase Prevents Neural Apoptosis and Reduces Ischemic Brain Injury: Suppression of Peroxynitrite Production, Lipid Peroxidation, and Mitochondrial Dysfunction," The Journal of Neuroscience, vol. 18, No. 2, pp. 687-697, Jan. 15, 1998.

McGinnity et al., "Prediction of CYP2C9-Mediated Drug-Drug Interactions: A Comparison Using Data From Recombinant Enzymes And Human Hepatocytes," Drug Metabolism and Disposition, vol. 33, No. 11, pp. 1700-1707, 2005.

Oikawa et al., "Metabolism Study of Benzbromarone: In Vitro Metabolism and Pharmacokinetics in Healthy Volunteers," J. New Rem. & Clin., vol. 53, No. 6, pp. 30-39, 2004.

Tsutani et al., "Typing of hyperuricemia (uric acid clearance)," Nippon Rinsho, vol. 61, Suppl. 1, pp. 166-171, 2003.

Urinorm Tab 25/50mg, Medical Product Interview Form, Jul. 2005.

Vervaeck et al., "Sudden hypotonic paraparesis caused by tophaceous gout of the lumbar spine," Clin. Neurol. Neurosurg., vol. 93, No. 3, pp. 233-236, 1991.

Yutaka Miura et al., Synthesis of 2,3-fused quinolines from 3-substituted quinoline 1-oxides, Heterocycles (1992), 34(5), pp. 1055-1063.

* cited by examiner

HETEROCYCLIC DERIVATIVES

TECHNICAL FIELD

The present invention relates to novel heterocycle derivative compounds useful in preparing drugs for treatment of diseases associated with uric acid. More specifically, these novel heterocycle derivatives are useful in preparing drugs for the treatment of diseases which are included in area of diseases treated by using uricosuric agent to target human urate anion transporter 1 (hURAT1). These drugs are useful in treatment of cardiovascular diseases and metabolic syndrome associated with uric acid such as, in particular, hyperuricemia, acute gouty arthritis, chronic gouty arthritis, tophus, gout nephrosis, nephritis, chronic renal failure, nephrolithiasis, uremia, urolithiasis, hyperlipidemia, ischemic heart disease, myocardial infarction, cerebral infarction, cerebrovascular disease, diabetes or hypertension.

BACKGROUND ART

Uric acid is the final oxidation product of purine metabolism and is mainly excreted in urine. It has been reported to have an antioxidative activity and also a function of protecting neuronal cell [Ames, B. N. et al. Proc. Natl. Acad. Sci. USA, 78, 6858-6862 (1981); Becker, B. F., et al., Free Racical Biol. Med. 14, p 615-631 (1993); Keller, J. N. et al., J. Neurosci. p 687-697 (1998)].

Purine sources, generated from nucleotides existing in cells constituting a living body, and excessively purine-free diet converge at the common intermediate xanthine by in vivo biosynthesis procedure, and uric acid is finally produced by enzymatic reaction with xanthine oxidase, the key enzyme in taking the purines all of the way to uric acid, in liver [F. Borges et al. Current Medi. Chem., 9, p 195-217 (2002)]. The level of daily uric acid produced in body is approximately 700 mg. Of this total, 60~70% (~500 mg/day) is excreted through kidney and the residual amount (~200 mg/day) is excreted through intestine [Japan Clinic History, Japan Clinic Hyperuricemia Hypouricemia, p 161, 166 (2003)].

Hyperuricemia is the abnormally high level of uric acid in blood. In human, it is defined the condition that serum uric acid concentration is higher than normal (7-8 mg/dl for male, 6 mg/dl for female). It is associated with underexcretion of uric acid in the kidney or overproduction of uric acid in the liver. Gouty patient has a remarkably higher level uric acid in blood than normal (7~8 mg/dl for male, 6 mg/dl for female). Gout is often associated with hyperuricemia. Gout is a type of inflammatory arthritis that is triggered by the crystallization of uric acid within the joint—mostly peripheral ones like the toes and fingers. Acute gout is typically intermittent, constituting one of the most painful experienced by human. Chronic gout usually develops after years of acute intermittent gout. Needle-like monosodium urate (MSU) crystals can be deposited on connective soft tissues such as the articular cartilage in the joint, tendon and ligament. These crystals prick muscles or chondrocyte around the joint and then lead to inflammatory arthritis, which causes swelling, redness, heat, pain, and stiffness in the joints. Urate crystals are directly able to initiate, to amplify, and to sustain an intense inflammatory attack because of their ability to stimulate the release of inflammatory mediators. The urate crystals are deposited mainly in metatarsophalangeal joint of big toe, and rarely in lumbar spine [Vervaeck M., et al., Clinical Neurology and Neurosurgery, 93, p 233-236 (1991)].

Gout is a very dangerous factor because it may cause a complication of various metabolic diseases such as diabetes, hypertension, heart disease, obesity, nephrolithiasis, urolithiasis or the like. Peak incidence of gout is observed predominantly male in age of 40 to 50's and female patients increase in postmenopausal period. Also, the onset frequency is high in obese persons and those exercising extremely.

Incidence of gouty attack is closely associated with patients who have had hyperuricemia for years. It has been reported that incidence of gouty attack is 4.9% when uric acid level in body is 9 mg/dl or higher, 0.5% when uric acid level in body is 7.0~8.9 mg/dl and 0.1% when uric acid level in body is 7.0 mg/dl or lower, and accumulated incidence of gouty attack for 5 years is about 22% in patients having uric acid level in body of 9 mg/dl or higher [Campion E. W. et al., Am. J. Med., 82, p 421-426 (1987)].

As mentioned above, the amount of urate in the body depends on the balance between dietary intake, synthesis, and the excretion rate. For patients having an high level of uric acid in blood, pathogenesis of hyperuricemia and gout result from urate underexcretion (90%), overproduction (10%) or often a combination of the two [Choi et al., Ann. Intern. Med. p 499-516 (2005)]. Considering such causes of hyperuricemia and gout, development of uricosuric agent is more effective in hyperuricemia/gout management than those suppressing uric acid production. Urate level in human plasma is higher than those of most other mammals. Human are the only mammals in whom gout is known to develop spontaneously. This is because during evolutionary process, human and primate have lost the gene for uricase in liver which is known as enzyme for degradation of uric acid (Uricase enzyme; catalyzing the conversion of uric acid to more soluble compound allantoin) [Fields, M. et al., Free Radical Biol. Med., 20, p 595 (1996); Haliwell, B. Uric acid: an example of antioxidant evaluation, E. Cadenas and L. Packer Editors, Handbook of Antioxidants, Marcel Dekker New York (1996)] and have had a reuptake system of uric acid in kidney by which most of filtered urate from glomerulus is reabsorbed through renal tubule.

A recent literature has reported a gene (SLC22A12) encoding human urate anion transporter 1 (hURAT1), an anion exchange membrane transporter specifically responsible for the function of reabsorption of filtered urate in kidney. The transporter (hURAT1) belongs to organic anion transporter family (OATs) and it has been reported that human urate anion transporters exist in proximal renal tubule through immunochemical experiments and is an important role in urate reuptake through urate absorption experiments by using brush border membrane vesicle (BBMV) of human kidney. Therefore, the human urate anion transporter 1 (hURAT1) has been proved as a useful target molecule for developing treatment agents of diseases associated with uric acid such as hyperuricemia and gout [Enomoto A. et al., Nature, 417, p 447-452 (2002)].

In physicochemical properties, uric acid has the acidity (pKa) of 5.75 and exists in acid form (uric acid) or anionic form (urate) depending on pH. Thus, the protein structure of human urate anion transporter 1 (hURAT1) having a functional similarity is expected to have similar structural characteristics with proteins belonging to organic anion transporter family (OATs). Actually, it has been reported that the amino acid sequence of OAT4 (SLC22A12) among organic anion transporter family (OATs) transporting anion present in apical membrane of proximal tubule has a homology of 42% with that of human urate anion transporter 1 (hURAT1) protein [Enomoto A. et al., Nature, 417, p 447-452 (2002)].

Up to the present, six (6) of transporters in living body have been identified (OAT1 to 4 and URAT1, and OATS of rodents) which are involved in absorption and excretion of anionic substances in kidney that are made from various endogenous substances, xenobiotics and drugs. Their main target substrates are various and different from each other. Meanwhile, as a main substrate for human urate anion transporter 1 (hURAT1), only the uric acid is known [Nahohiko Anzai, et al., J phamacol. Sci., 100, p 411-426 (2006)].

As treatment or prophylaxis agents for hyperuricemia and gout, benzbromarone that is an uricosuric agent having the inhibitory activity of hURAT1-mediated urate reabsorption, as well as probenecid and sulfinpyrazone is currently used. However, these drugs do not have sufficient activities to URAT1. In particular, benzbromarone has some demerits in view of adverse effects. Benzbromarone shows a strong inhibitory function to 2C9 protein among cytochrome P450 (CYP450) proteins and thus has a possibility of drug-drug interaction. Formation of reactive metabolite also has been reported from glutathione (GSH) conjugate formation experiments [Dermot F. McGinnity et al., Drug Metabolism and Disposition, 33, p 1700-1707 (2005)]. Furthermore, because benzbromarone has a benzofuran backbone similar with drug structures of benziodarone, benzarone and amiodarone which are drugs reported to show hepatotoxicity, it has a problem of death due to hepatotoxicity induction as well as adverse effect of liver injury. Therefore, a liver function of patients who intend to take this drug must be examined before the administration, and even during the administration, it is recommended in therapy to check out for a certain period (six months) on whether the hepatotoxicity is induced or not. For these reason, there still remains an unmet medical need for the treatment of diseases associated with uric acid such as hyperuricemia and gout [Hautekeete M. L., et al., Liver, 15, p 25-29 (1995); Makoto Arai, et al., Journal of Gastroenterology and Hepatology 17, p 625-626 (2002); Saitama medical college magazine, 30, 187-194 (2003); Priska Kaufmann, et al., HEPATOLOGY, 41, p 925-935 (2005)].

Pharmacokinetic data of benzbromarone are as follows: As for the concentration in blood, when 2 tablets (50 mg/tablet) are administered one time to a healthy and fasting adult, time of maximum drug concentration in blood ($T_{max}$) of unmodified benzbromarone is 2.7±1.0 hr, half-life of drug is 5.4±1.9 hr, area under the curve (AUC) is 15.9±3.3 µg·h/ml, and maximum concentration of drug ($C_{max}$) is 2.3±0.8 µg/ml. In case of 6-hydroxy benzbromarone which is a metabolite of benzbromarone, time of maximum drug concentration in blood ($T_{max}$) is 4.8±1.3 hr, half-life of drug is 18.0±2.9 hr, area under the curve (AUC) is 39.9±4.4 h/ml, and maximum concentration of drug ($C_{max}$) is 1.7±0.4 µg/ml. As for the part and amount of drug excretion, the excretion rate of 6-hydroxy benzbromarone in urine was 1.2% of the administered amount until 72 hours after administration. However, the benzbromarone was not detected in urine at all [Urinome international interview (2005); Oikawa Tosihiro et al., New drug and Clinic, 53, p 682 (2004)].

Recently, one patent was disclosed and registered in Japan for compounds which inhibit human urate anion transporter 1 (hURAT1) as an uricosuric agent and have a weak inhibitory effect on cytochrome P450 2C9 (CYP2C9) [Japan Tobacco, WO2006/057460 and JP3988832 B2].

DISCLOSURE OF INVENTION

Technical Purpose

The present invention is to solve the problems of prior arts as set forth in the foregoing. Thus, the purpose of the present invention is to provide novel heterocycle derivative compounds having a therapeutic activity to hyperuricemia which show a strong inhibition activity on human urate anion transporter 1 (hURAT1), no drug-drug interaction on cytochrome P450 (CYP450), especially CYP2C9 and a selectivity between organic anion transporters, and can be administered with lower dose and long-term treatment since they have higher solubility and metabolic stability so as to show advantageous pharmacokinetics, as compared with conventional inhibitor of hURAT1 activity; and a pharmaceutical composition comprising the same. Because the novel heterocycle derivative compounds according to the present invention and pharmaceutical composition comprising the same show a strong inhibition activity to human urate anion transporter 1 (hURAT1), they control the uric acid reuptake and thus are useful in treatment or prophylaxis of hyperuricemia, acute gouty arthritis, chronic gouty arthritis, tophus, gout nephrosis, nephritis, chronic renal failure, nephrolithiasis, uremia, urolithiasis and complications reported to be accompanied with uric acid increase in blood such as hyperlipidemia, ischemic heart disease, myocardial infarction, arteriosclerosis, cerebral infarction, cerebrovascular disease, diabetes and hypertension.

Technical Solution

According to the present invention, a heterocycle derivative compound having a structure of the following Formula I, or racemate, isomer or pharmaceutically acceptable salt thereof is provided:

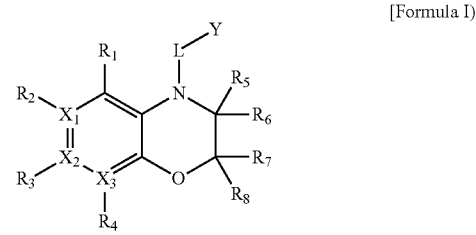

[Formula I]

wherein, in Formula I,
each of $X_1$, $X_2$ and $X_3$ is independently carbon or nitrogen, provided that at least one of $X_1$, $X_2$ and $X_3$ is nitrogen,
each of $R_1$, $R_2$, $R_3$ and $R_4$ may be same or different and is independently selected from the group consisting of hydrogen; hydroxy; unsubstituted or substituted $C_1$-$C_6$ alkyl; unsubstituted or substituted $C_2$-$C_7$ alkenyl; unsubstituted or substituted $C_2$-$C_7$ alkynyl; $C_1$-$C_6$ hydroxyalkyl; unsubstituted or substituted $C_1$-$C_6$ haloalkyl; unsubstituted or substituted $C_1$-$C_6$ alkoxy; unsubstituted or substituted $C_1$-$C_6$ haloalkoxy; halogen; unsubstituted or substituted phenyl; cyano; nitro; amino; carboxylic acid group; phosphoric acid group; N-oxide; amide; $C_1$-$C_6$ alkylamide; aldehyde; hydroxamic acid; unsubstituted or substituted $C_1$-$C_6$ alkylsulfide; unsubstituted or substituted $C_1$-$C_6$ alkylthionyl; unsubstituted or substituted $C_1$-$C_6$ alkylsulfonyl; unsubstituted or substituted $C_1$-$C_6$ oximealkyl; unsubstituted or substituted $C_1$-$C_6$ aminoalkyl; unsubstituted or substituted $C_3$-$C_8$ alkylcarbonylalkyl; unsubstituted or substituted $C_2$-$C_7$ alkanoyl; unsubstituted or substituted $C_2$-$C_7$ alkoxycarbonyl; unsubstituted or substituted $C_2$-$C_7$ alkanoyloxy; unsubstituted or substituted $C_3$-$C_{12}$ mono or bicycloalkyl; unsubstituted or substituted $C_4$-$C_{12}$ cycloalkylalkyl; unsubstituted or substituted $C_6$-$C_{12}$ aryl; unsubstituted or substituted, saturated or unsaturated $C_3$-$C_{12}$ mono or polycarbocyclyl; and unsubstituted or substituted, saturated or unsaturated 3- to 12-membered mono or polyheterocyclyl containing 1 to 3 heteroatoms (preferably, the heteroatom is selected from N, O and S), provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a saturated or unsaturated 5- to 11-membered carbocycle or heterocycle (preferably, the heterocycle contains 1 to 3 heteroatoms selected from N, O and S), each of $R_5$, $R_6$, $R_7$ and $R_8$ may be same or different and is independently selected from the group consisting of hydrogen; hydroxy; unsubstituted or substituted $C_1$-$C_6$ alkyl; unsubstituted or substituted $C_2$-$C_7$ alkenyl; unsubstituted or substituted $C_2$-$C_7$ alkynyl; $C_1$-$C_6$ hydroxyalkyl; unsubstituted or substituted $C_1$-$C_6$ haloalkyl; unsubstituted or substituted $C_1$-$C_6$ alkoxy; unsubstituted or substituted $C_1$-$C_6$ haloalkoxy; unsubstituted or substituted $C_2$-$C_7$ alkanoyl; phosphoric acid group; N-oxide; amide; aldehyde; hydroxamic acid; unsubstituted or substituted $C_1$-$C_6$ alkylsulfide; unsubstituted or substituted $C_1$-$C_6$ alkylthionyl; unsubstituted or substituted $C_1$-$C_6$ alkylsulfonyl; unsubstituted or substituted $C_1$-$C_6$ oximealkyl; unsubstituted or substituted $C_1$-$C_6$ aminoalkyl; unsubstituted or substituted $C_3$-$C_8$ alkylcarbonylalkyl; halogen; unsubstituted or substituted phenyl; cyano; nitro; amino; and carboxylic acid group, or $R_5$ and $R_6$ together with a carbon atom to which they are attached may form a carbonyl group (C=O) or thionyl group (C=S), or $R_7$ and $R_8$ together with a carbon atom to which they are attached may form a carbonyl group (C=O) or thionyl group (C=S), L may form a carbonyl group (—C(=O)—), sulfonyl group (—S(=O)$_2$—), $C_1$-$C_6$ alkyl carbonyl (for example, —CH$_2$C(=O)—), carbonyl $C_1$-$C_6$ alkyl (for example, —C(=O)CH$_2$—) or thionyl group (—C(=S)—), and Y is selected from the group consisting of saturated or unsaturated $C_3$-$C_{12}$ mono or polycarbocyclyl substituted with $R_9$, $R_{10}$ and $R_{11}$; and saturated or unsaturated 3- to 12-membered mono or polyheterocyclyl containing 1 to 3 heteroatoms (preferably, the heterocycle contains 1 to 3 heteroatoms selected from N, O and S) and being substituted with $R_9$, $R_{10}$ and $R_{11}$, wherein each of $R_9$, $R_{10}$ and $R_{11}$ is independently selected from the group consisting of hydrogen; hydroxy; unsubstituted or substituted $C_1$-$C_6$ alkyl; unsubstituted or substituted $C_2$-$C_7$ alkenyl; unsubstituted or substituted $C_2$-$C_7$ alkynyl; $C_1$-$C_6$ hydroxyalkyl; unsubstituted or substituted $C_1$-$C_6$ haloalkyl; unsubstituted or substituted $C_1$-$C_6$ alkoxy; unsubstituted or substituted $C_1$-$C_6$ haloalkoxy; halogen; unsubstituted or substituted $C_1$-$C_6$ alkylsulfide; unsubstituted or substituted $C_1$-$C_6$ alkylthionyl; hydroxamic acid; unsubstituted or substituted phenyl; cyano; nitro; amino; carboxylic acid group; amide; $C_1$-$C_6$ alkylamide; unsubstituted or substituted $C_2$-$C_7$ alkanoyl; aldehyde; unsubstituted or substituted $C_3$-$C_8$ ester; unsubstituted or substituted $C_3$-$C_8$ esteroxy; unsubstituted or substituted $C_1$-$C_6$ alkylsulfonyl; unsubstituted or substituted $C_1$-$C_6$ oximealkyl; unsubstituted or substituted $C_1$-$C_6$ aminoalkyl; unsubstituted or substituted $C_3$-$C_8$ alkylcarbonylalkyl; phosphoric acid group; and N-oxide, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen.

Preferably, in the above Formula I, L may form a carbonyl group (—C(=O)—), sulfonyl group (—S(=O)$_2$—) or thionyl group (—C(=S)—).

Preferably, in the above Formula I, each of $R_5$, $R_6$, $R_7$ and $R_8$ may be same or different and is independently selected from the group consisting of hydrogen; hydroxy; unsubstituted or substituted $C_1$-$C_4$ alkyl; unsubstituted or substituted $C_1$-$C_4$ haloalkyl; unsubstituted or substituted $C_1$-$C_4$ alkoxy; unsubstituted or substituted $C_1$-$C_4$ haloalkoxy; unsubstituted or substituted $C_2$-$C_5$ alkanoyl; halogen; unsubstituted or substituted phenyl; cyano; nitro; amino; and carboxylic acid group; or $R_5$ and $R_6$ together with a carbon atom to which they are attached may form a carbonyl group (C=O) or thionyl group (C=S), or $R_7$ and $R_8$ together with a carbon atom to which they are attached may form a carbonyl group (C=O) or thionyl group (C=S).

Preferably, in the above Formula I, Y is selected from the group consisting of saturated or unsaturated $C_5$-$C_6$ carbocyclyl substituted with $R_9$, $R_{10}$ and $R_{11}$; and saturated or unsaturated 5- to 6-membered heterocyclyl containing 1 to 3 heteroatoms (preferably, the heterocycle contains 1 to 3 heteroatoms selected from N, O and S) and being substituted with $R_9$, $R_{10}$ and $R_{11}$, wherein $R_9$, $R_{10}$ and $R_{11}$ are the same as defined in the above Formula I.

Preferably, in the above Formula I, each of $R_9$, $R_{10}$ and $R_{11}$ is independently selected from the group consisting of hydrogen; hydroxy; unsubstituted or substituted $C_1$-$C_4$ alkyl; unsubstituted or substituted $C_1$-$C_4$ haloalkyl; unsubstituted or substituted $C_1$-$C_4$ alkoxy; unsubstituted or substituted $C_1$-$C_4$ haloalkoxy; halogen; unsubstituted or substituted phenyl; cyano; nitro; amino; carboxylic acid group; amide; $C_1$-$C_6$ alkylamide; unsubstituted or substituted $C_2$-$C_5$ alkanoyl; aldehyde; unsubstituted or substituted $C_3$-$C_7$ ester; unsubstituted or substituted $C_3$-$C_7$ esteroxy; unsubstituted or substituted $C_1$-$C_4$ alkylsulfonyl; unsubstituted or substituted $C_1$-$C_4$ oximealkyl; unsubstituted or substituted $C_1$-$C_4$ aminoalkyl; unsubstituted or substituted $C_3$-$C_7$ alkylcarbonylalkyl; phosphoric acid group; and oxide, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen.

Preferably, in the above Formula I, each of $R_1$-$R_2$, $R_2$-$R_3$ and $R_3$-$R_4$ pairs may be independently fused to form a saturated or unsaturated 5- to 6-membered carbocycle or heterocycle, wherein the heterocycle preferably contains 1 to 3 heteroatoms selected from N, O and S.

Preferably, in the above Formula I, each of $R_1$, $R_2$, $R_3$ and $R_4$ may be same or different and is independently selected from the group consisting of hydrogen; hydroxy; unsubstituted or substituted $C_1$-$C_4$ alkyl; unsubstituted or substituted $C_1$-$C_4$ haloalkyl; unsubstituted or substituted $C_1$-$C_4$ alkoxy; unsubstituted or substituted $C_1$-$C_4$ haloalkoxy; halogen; unsubstituted or substituted phenyl; cyano; nitro; amino; carboxylic acid group; unsubstituted or substituted $C_2$-$C_5$ alkanoyl; unsubstituted or substituted $C_2$-$C_5$ alkoxycarbonyl; unsubstituted or substituted $C_2$-$C_5$ alkanoyloxy; unsubstituted or substituted $C_3$-$C_{10}$ mono or bicycloalkyl; unsubstituted or substituted $C_4$-$C_{11}$ cycloalkylalkyl; unsubstituted or substituted $C_6$-$C_{10}$ aryl; unsubstituted or substituted, saturated or unsaturated $C_3$-$C_{10}$ mono or polycarbocyclyl; and unsubstituted or substituted, saturated or unsaturated 3- to 10-membered mono or polyheterocyclyl containing 1 to 3 heteroatoms (preferably, the heteroatom is selected from N, O and S), provided that when $X_1$ is nitrogen, $R_2$ does not exist; when $X_2$ is nitrogen, $R_3$ does not exist; and when $X_3$ is nitrogen, $R_4$ does not exist.

In the above Formula I, a preferable example of "$C_3$-$C_{12}$ mono or bicycloalkyl" can be a monocycloalkyl such as cyclopropyl, cyclobutyl, cyclopentyl, cyclohexyl, cycloheptyl, cyclooctyl and cyclononyl, or a bicycloalkyl obtained by the fusion of the same or different two of said monocycloalkyls, but not limited thereto.

In the above Formula I, a preferable example of "$C_3$-$C_{12}$ mono or polycarbocyclyl" can be a monocycloalkyl such as cyclopropyl, cyclobutyl, cyclopentyl, cyclohexyl, cycloheptyl, cyclooctyl and cyclononyl, or a polycycloalkyl obtained by the fusion of the same or different two or more of said monocycloalkyls, or carboaryl (for example, phenyl or naphthyl), but not limited thereto.

In the above Formula I, a preferable example of "saturated or unsaturated 3- to 12-membered mono or polyheterocyclyl containing 1 to 3 heteroatoms" can be thienyl, thiazolyl, imidazolyl, benzimidazolyl, triazolyl, tetrahydropyranyl, pyridinyl, furanyl, pyranyl, pyrrolyl, pyrazolyl, pyrazinyl, pyrimidinyl, isothiazolyl, isoxazolyl, pyridazinyl, isobenzopyranyl, chromenyl, indolyl, indazolyl, quinolinyl, purinyl, pyrrolinyl, chromanyl, pyrazolidinyl, piperidinyl, piperazinyl or the like, but not limited thereto.

In the above Formula I, a preferable example of "$C_4$-$C_{12}$ cycloalkylalkyl" can be cyclopropylmethyl, cyclobutylmethyl, cyclopentylmethyl, cyclohexylmethyl, cyclopentylethyl, cyclohexylethyl, cycloheptylmethyl, cycloheptylethyl, cyclooctylmethyl or the like, but not limited thereto.

Preferably, in the above Formula I, $X_2$ is carbon, and each of $X_1$ and $X_3$ is independently carbon or nitrogen, provided that at least one of $X_1$ and $X_3$ is nitrogen.

Preferably, in the above Formula I, each of $R_1$, $R_2$, $R_3$ and $R_4$ may be same or different and is independently selected from the group consisting of hydrogen; unsubstituted or substituted $C_1$-$C_4$ alkyl; unsubstituted or substituted $C_1$-$C_4$ haloalkyl; halogen; unsubstituted or substituted phenyl; cyano; and unsubstituted or substituted, saturated or unsaturated 3- to 10-membered mono or polyheterocyclyl containing 1 to 3 heteroatoms (preferably, the heteroatom is selected from N, O and S); or each of $R_1$-$R_2$, $R_2$-$R_3$ and $R_3$-$R_4$ pairs may be independently fused to form a saturated or unsaturated 5- to 6-membered carbocycle; provided that when $X_1$ is nitrogen, $R_2$ does not exist; when $X_2$ is nitrogen, $R_3$ does not exist; and when $X_3$ is nitrogen, $R_4$ does not exist.

Preferably, in the above Formula I, Y is an aromatic 5- to 6-membered carbocycle or heterocycle (preferably, the heterocycle contains 1 to 3 heteroatoms selected from N, O and S) substituted with $R_9$, $R_{10}$ and $R_{11}$, wherein $R_9$, $R_{10}$ and $R_{11}$ are the same as defined in the above Formula I.

Preferably, in the above Formula I, each of $R_9$, $R_{10}$, and $R_{11}$ is independently selected from the group consisting of hydrogen; hydroxy; unsubstituted or substituted $C_1$-$C_4$ alkyl; unsubstituted or substituted $C_1$-$C_4$ haloalkyl; unsubstituted or substituted $C_1$-$C_4$ alkoxy; unsubstituted or substituted $C_1$-$C_4$ haloalkoxy; halogen; nitro; carboxylic acid group; and unsubstituted or substituted esteroxy, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen.

According to a preferred embodiment of the present invention, in the above Formula I, each of $X_1$, $X_2$ and $X_3$ is independently carbon or nitrogen, provided that at least one of $X_1$, $X_2$ and $X_3$ is nitrogen, each of $R_1$, $R_2$, $R_3$ and $R_4$ may be same or different and is independently selected from the group consisting of hydrogen; hydroxy; unsubstituted or substituted $C_1$-$C_4$ alkyl; unsubstituted or substituted $C_1$-$C_4$ haloalkyl; unsubstituted or substituted $C_1$-$C_4$ alkoxy; unsubstituted or substituted $C_1$-$C_4$ haloalkoxy; halogen; cyano; nitro; amino; carboxylic acid group; unsubstituted or substituted $C_2$-$C_5$ alkanoyl; unsubstituted or substituted $C_2$-$C_5$ alkoxycarbonyl; unsubstituted or substituted $C_2$-$C_5$ alkanoyloxy; $C_6$-$C_{12}$ aryl; and unsubstituted or substituted, saturated or unsaturated $C_3$-$C_{12}$ mono or polycarbocyclyl or heterocyclyl, provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a saturated or unsaturated 5- to 6-membered carbocycle or heterocycle, each of $R_5$, $R_6$, $R_7$ and $R_8$ may be same or different and is independently selected from the group consisting of hydrogen; hydroxy; unsubstituted or substituted $C_1$-$C_4$ alkyl; unsubstituted or substituted $C_1$-$C_4$ haloalkyl; unsubstituted or substituted $C_1$-$C_4$ alkoxy; unsubstituted or substituted $C_1$-$C_4$ haloalkoxy; unsubstituted or substituted $C_2$-$C_5$ alkanoyl; halogen; cyano; nitro; amino; and carboxylic acid group, or $R_5$ and $R_6$ together with a carbon atom to which they are attached may form a carbonyl group (C=O), or $R_7$ and $R_8$ together with a carbon atom to which they are attached may form a carbonyl group (C=O), L may form a carbonyl group (—C(=O)—), sulfonyl group (—S(=O)$_2$—) or thionyl group (—C(=S)—), and Y is selected from the group consisting of saturated or unsaturated $C_3$-$C_{12}$ mono or polycarbocyclyl substituted with $R_9$, $R_{10}$ and $R_{11}$; and saturated or unsaturated 3- to 12-membered mono or polyheterocyclyl containing 1 to 3 heteroatoms and being substituted with $R_9$, $R_{10}$ and $R_{11}$, wherein the heterocycle preferably contains 1 to 3 heteroatoms selected from N, O and S, wherein each of $R_9$, $R_{10}$ and $R_{11}$ is independently selected from the group consisting of hydrogen; hydroxy; unsubstituted or substituted $C_1$-$C_4$ alkyl; unsubstituted or substituted $C_1$-$C_4$ haloalkyl; unsubstituted or substituted $C_1$-$C_4$ alkoxy; unsubstituted or substituted $C_1$-$C_4$ haloalkoxy; halogen; cyano; nitro; amino; carboxylic acid group; and unsubstituted or substituted $C_3$-$C_7$ esteroxy, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen.

According to another preferred embodiment of the present invention, in the above Formula I, each of $X_1$, $X_2$ and $X_3$ is independently carbon or nitrogen, provided that at least one of $X_1$, $X_2$ and $X_3$ is nitrogen, each of $R_1$, $R_2$, $R_3$ and $R_4$ may be same or different and is independently selected from the group consisting of hydrogen; unsubstituted or substituted $C_1$-$C_4$ alkyl; unsubstituted or substituted $C_1$-$C_4$ haloalkyl; unsubstituted or substituted $C_1$-$C_4$ alkoxy; halogen; cyano; nitro; amino; and unsubstituted or substituted, saturated or unsaturated $C_5$-$C_6$ carbocyclyl or heterocyclyl, provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a phenyl or a 6-membered heterocycle containing 1 to 2 atoms of nitrogen or oxygen, each of $R_5$, $R_6$, $R_7$ and $R_8$ may be same or different and is independently selected from the group consisting of hydrogen; unsubstituted or substituted $C_1$-$C_4$ alkyl; unsubstituted or substituted $C_1$-$C_4$ alkoxy; halogen; cyano; nitro; and amino, L is a carbonyl group (—C(=O)—) or thionyl group (—C(=S)—), and Y is a phenyl which has a hydroxy group in para-position to the attachment position of L and is further substituted with 1 to 3 substituents independently selected from halogen and nitro.

As representative examples of the compound of Formula I according to the present invention, the following compounds may be mentioned:

(3,5-dibromo-4-hydroxy-phenyl)-(2,3-dihydro-pyrido[2,3-b][1,4]oxazin-1-yl)-methanone (compound 1);
(3,5-dibromo-4-methoxy-phenyl)-(2,3-dihydro-pyrido[4,3-b][1,4]oxazin-4-yl)-methanone (compound 2);
(3,5-dibromo-4-hydroxy-phenyl)-(2,3-dihydro-pyrido[4,3-b][1,4]oxazin-4-yl)-methanone bromic acid salt (compound 3);
(3,5-dibromo-4-hydroxy-phenyl)-(2,3-dihydro-pyrido[4,3-b][1,4]oxazin-4-yl)-methanone (compound 4);
(3,5-dibromo-4-methoxy-phenyl)-(2,3-dihydro-pyrido[3,4-b][1,4]oxazin-1-yl)-methanone (compound 5);
(3,5-dibromo-4-hydroxy-phenyl)-(2,3-dihydro-pyrido[3,4-b][1,4]oxazin-1-yl)-methanone (compound 6);
(3,5-dibromo-4-hydroxy-phenyl)-(6-methyl-2,3-dihydro-pyrido[2,3-b][1,4]oxazin-1-yl)-methanone (compound 7);
(3,5-dibromo-4-hydroxy-phenyl)-(2,2-dimethyl-2,3-dihydro-pyrido[4,3-b][1,4]oxazin-4-yl)-methanone (compound 8);
(3,5-dibromo-4-hydroxy-phenyl)-(7-cyclopropyl-2,3-dihydro-pyrido[2,3-b][1,4]oxazin-1-yl)-methanone (compound 9);
(3-chloro-4-hydroxy-phenyl)-(2,3-dihydro-pyrido[4,3-b][1,4]oxazin-4-yl)-methanone bromic acid salt (compound 10);
(3-bromo-4-hydroxy-phenyl)-(2,3-dihydro-pyrido[4,3-b][1,4]oxazin-4-yl)-methanone bromic acid salt (compound 11);
(2,3-dihydro-pyrido[4,3-b][1,4]oxazin-4-yl)-(4-hydroxy-3-trifluoromethyl-phenyl)-methanone (compound 12);
(3,5-dichloro-4-hydroxy-phenyl)-(2,3-dihydro-pyrido[4,3-b][1,4]oxazin-4-yl)-methanone bromic acid salt (compound 13);
(3-chloro-4-hydroxy-5-nitro-phenyl)-(2,3-dihydro-pyrido[4,3-b][1,4]oxazin-4-yl)-methanone (compound 14);
(3,5-dichloro-4-hydroxy-phenyl)-(2,3-dihydro-pyrido[3,4-b][1,4]oxazin-1-yl)-methanone bromic acid salt (compound 15);
(3-bromo-4-hydroxy-phenyl)-(2,3-dihydro-pyrido[3,4-b][1,4]oxazin-1-yl)-methanone bromic acid salt (compound 16);
(3-chloro-4-hydroxy-5-nitro-phenyl)-(2,3-dihydro-pyrido[3,4-b][1,4]oxazin-1-yl)-methanone bromic acid salt (compound 17);
(3-chloro-4-hydroxy-phenyl)-(2,3-dihydro-pyrido[3,4-b][1,4]oxazin-1-yl)-methanone bromic acid salt (compound 18);
(2,3-dihydro-pyrido[3,4-b][1,4]oxazin-1-yl)-(4-hydroxy-3-trifluoromethyl-phenyl)-methanone (compound 19);
(3,5-dibromo-4-hydroxy-phenyl)-(7-phenyl-2,3-dihydro-pyrido[2,3-b][1,4]oxazin-1-yl)-methanone (compound 20);
2,6-dichloro-4-(2,3-dihydro-pyrido[4,3-b][1,4]oxazin-4-sulfonyl)-phenol (compound 21);
(3,5-dibromo-4-methoxy-phenyl)-(7-trifluoromethyl-2,3-dihydro-pyrido[2,3-b][1,4]oxazin-1-yl)-methanone (compound 22-1);
(3,5-dibromo-4-hydroxy-phenyl)-(7-trifluoromethyl-2,3-dihydro-pyrido[2,3-b][1,4]oxazin-1-yl)-methanone (compound 22-2);
2,5-dibromo-4-(2,3-dihydro-pyrido[4,3-b][1,4]oxazin-4-carbonyl)-benzoic acid (compound 23);
(2,6-dibromo-4-(2,3-dihydro-pyrido[4,3-b][1,4]oxazin-4-carbonyl)-phenoxy]-acetic acid methyl ester (compound 24);
(7-bromo-2,3-dihydro-pyrido[2,3-b][1,4]oxazin-1-yl)-(3,5-dibromo-4-hydroxy-phenyl)-methanone (compound 25);
(2,3-dihydro-pyrido[4,3-b][1,4]oxazin-4-yl)-(3-fluoro-4-hydroxy-phenyl)-methanone (compound 26);
(3,5-dibromo-4-methoxy-phenyl)-(7-methyl-2,3-dihydro-pyrido[2,3-b][1,4]oxazin-1-yl)-methanone (compound 27-1);
(3,5-dibromo-4-hydroxy-phenyl)-(7-methyl-2,3-dihydro-pyrido[2,3-b][1,4]oxazin-1-yl)-methanone (compound 27-2);
(3,5-difluoro-4-methoxy-phenyl)-(2,3-dihydro-pyrido[4,3-b][1,4]oxazin-4-yl)-methanone (compound 28);
(3,5-difluoro-4-hydroxy-phenyl)-(2,3-dihydro-pyrido[4,3-b][1,4]oxazin-4-yl)-methanone (compound 29);
(5-chloro-2,3-dihydro-pyrido[4,3-b][1,4]oxazin-4-yl)-(3,5-dibromo-4-hydroxy-phenyl)-methanone (compound 30);
(2,6-dichloro-pyridin-4-yl)-(2,3-dihydro-pyrido[4,3-b][1,4]oxazin-4-yl)-methanone (compound 31);
(2,3-dihydro-pyrido[4,3-b][1,4]oxazin-4-yl)-(6-hydroxy-pyridin-3-yl)-methanone (compound 32);
(3,5-dibromo-4-hydroxy-phenyl)-(2,3-dihydro-pyrido[4,3-b][1,4]oxazin-4-yl)-methanone hydrochloric acid salt (compound 33);
(3-chloro-4-hydroxy-phenyl)-(2,3-dihydro-pyrido[3,4-b][1,4]oxazin-1-yl)-methanone (compound 34);
4-(2,3-dihydro-pyrido[4,3-b][1,4]oxazin-4-sulfonyl)-phenol (compound 35-1);
2,6-dibromo-4-(2,3-dihydro-pyrido[4,3-b][1,4]oxazin-4-sulfonyl)-phenol (compound 35-2);
(3-chloro-4-hydroxy-5-nitro-phenyl)-(2,3-dihydro-pyrido[3,4-b][1,4]oxazin-1-yl)-methanone (compound 36);
(3-chloro-4-hydroxy-phenyl)-(2,3-dihydro-pyrido[4,3-b][1,4]oxazin-4-yl)-methanone (compound 37);
(3-bromo-4-hydroxy-phenyl)-(2,3-dihydro-pyrido[4,3-b][1,4]oxazin-4-yl)-methanone (compound 38);
(3,5-dichloro-4-hydroxy-phenyl)-(2,3-dihydro-pyrido[4,3-b][1,4]oxazin-4-yl)-methanone (compound 39);
(3-bromo-4-hydroxy-phenyl)-(2,3-dihydro-pyrido[3,4-b][1,4]oxazin-1-yl)-methanone (compound 40);
(3,5-dichloro-4-hydroxy-phenyl)-(2,3-dihydro-pyrido[3,4-b][1,4]oxazin-1-yl)-methanone (compound 41);
2-(3,5-dibromo-4-hydroxy-phenyl)-1-(2,3-dihydro-pyrido[4,3-b][1,4]oxazin-4-yl)-ethanone (compound 42);
(2,3-dihydro-pyrido[4,3-b][1,4]oxazin-4-yl)-(3-methoxy-isoxazol-5-yl)-methanone (compound 43);
(2,3-dihydro-pyrido[4,3-b][1,4]oxazin-4-yl)-(3-hydroxy-isoxazol-5-yl)-methanone (compound 44);
(3,5-dibromo-4-hydroxy-phenyl)-[7-(4-trifluoromethyl-phenyl)-2,3-dihydro-pyrido[2,3-b][1,4]oxazin-1-yl]-methanone (compound 45);

(3,5-dibromo-4-hydroxy-phenyl)-[7-(2-trifluoromethyl-phenyl)-2,3-dihydro-pyrido[2,3-b][1,4]oxazin-1-yl]-methanone (compound 46);

1-(3,5-dibromo-4-methoxy-benzoyl)-2,3-dihydro-1H-pyrido[2,3-b][1,4]oxazin-7-carbonitrile (compound 47-1);

1-(3,5-dibromo-4-hydroxy-benzoyl)-2,3-dihydro-1H-pyrido[2,3-b][1,4]oxazin-7-carbonitrile (compound 47-2);

(3,5-dibromo-4-methoxy-phenyl)-[7-(3-nitro-phenyl)-2,3-dihydro-pyrido[2,3-b][1,4]oxazin-1-yl]-methanone (compound 48);

(3,5-dibromo-4-methoxy-phenyl)-[7-(3-nitro-phenyl)-2,3-dihydro-pyrido[2,3-b][1,4]oxazin-1-yl]-methanone (compound 49);

(3,5-dibromo-4-hydroxy-phenyl)-[7-(3-dimethylamino-phenyl)-2,3-dihydro-pyrido[2,3-b][1,4]oxazin-1-yl]-methanone (compound 50);

(3,5-dibromo-4-hydroxy-phenyl)-(2,3-dihydro-pyrido[4,3-b][1,4]oxazin-4-yl)-methanethione (compound 51);

(3,5-dibromo-4-hydroxy-phenyl)-(7-pyridin-3-yl-2,3-dihydro-pyrido[2,3-b][1,4]oxazin-1-yl)-methanone (compound 52);

(3,5-dibromo-4-hydroxy-phenyl)-(7-furan-3-yl-2,3-dihydro-pyrido[2,3-b][1,4]oxazin-1-yl)-methanone (compound 53);

1-(3,5-dibromo-4-hydroxy-phenyl)-2-(2,3-dihydro-pyrido[4,3-b][1,4]oxazin-4-yl)-ethanone (compound 54);

(3,5-dibromo-4-hydroxy-phenyl)-(2,3-dihydro-4-oxa-1,9-diaza-phenanthren-1-yl)-methanone (compound 55);

4-[2-(3,5-dibromo-4-hydroxy-phenyl)-2-oxo-ethyl)]-4H-pyrido[4,3-b][1,4]oxazin-3-one (compound 56);

4-(3,5-dibromo-4-methoxy-benzoyl)-4H-pyrido[4,3-b][1,4]oxazin-3-one (compound 57);

(3,5-dibromo-4-methoxy-phenyl)-(6-methyl-2,3-dihydro-pyrido[2,3-b][1,4]oxazin-1-yl)-methanone (compound 58);

(2,3-dihydro-pyrido[4,3-b][1,4]oxazin-4-yl)-(2,4-dihydroxy-pyrimidin-5-yl)-methanone (compound 59);

(2,3-dihydro-pyrido[4,3-b][1,4]oxazin-4-yl)-(2,6-dihydroxy-pyrimidin-4-yl)-methanone (compound 60);

(3,5-dibromo-4-hydroxy-phenyl)-(7-isoquinolin-4-yl-2,3-dihydro-pyrido[2,3-b][1,4]oxazin-1-yl)-methanone (compound 61);

(3,5-dibromo-4-hydroxy-phenyl)-(6,7-dihydro-pyrimido[4,5-b][1,4]oxazin-5-yl)-methanone (compound 62);

(3,5-dibromo-4-hydroxy-phenyl)-[7-(3-trifluoromethyl-phenyl)-2,3-dihydro-pyrido[2,3-b][1,4]oxazin-1-yl]-methanone (compound 63); (3,5-dibromo-4-hydroxy-phenyl)-[7-(3-fluoromethyl-phenyl)-2,3-dihydro-pyrido[2,3-b][1,4]oxazin-1-yl]-methanone (compound 64);

4-[1-(3,5-dibromo-4-hydroxy-benzoyl)-2,3-dihydro-1H-pyrido[2,3-b][1,4]oxazin-7-yl]-benzonitrile (compound 65);

(3,5-dibromo-4-hydroxy-phenyl)-[7-(4-trifluoromethoxy-phenyl)-2,3-dihydro-pyrido[2,3-b][1,4]oxazin-1-yl]-methanone (compound 66);

1-{4-[1-(3,5-dibromo-4-hydroxy-benzoyl)-2,3-dihydro-1H-pyrido[2,3-b][1,4]oxazin-7-yl]-phenyl}-ethanone (compound 67);

(3,5-dibromo-4-hydroxy-phenyl)-[7-(5-methoxy-pyridin-3-yl)-2,3-dihydro-pyrido[2,3-b][1,4]oxazin-1-yl]-methanone (compound 68);

(4-hydroxy-3-trifluoromethyl-phenyl)-(7-methyl-2,3-dihydro-pyrido[2,3-b][1,4]oxazin-1-yl)-methanone (compound 69);

(3,5-dibromo-4-hydroxy-phenyl)-[7-(1H-indol-4-yl)-2,3-dihydro-pyrido[2,3-b][1,4]oxazin-1-yl]-methanone (compound 70);

(3,5-dibromo-4-hydroxy-phenyl)-(2,3-dihydro-pyrido[4,3-b][1,4]oxazin-4-yl)-methanone sulfuric acid salt (compound 71);

(2,6-dibromo-4-(2,3-dihydro-pyrido[4,3-b][1,4]oxazin-4-carbonyl)-phenolate sodium salt (compound 72);

(2,6-dibromo-4-(2,3-dihydro-pyrido[4,3-b][1,4]oxazin-4-carbonyl)-phenolate potassium salt (compound 73);

(3,5-dibromo-4-hydroxy-phenyl)-(2,3-dihydro-pyrido[4,3-b][1,4]oxazin-4-yl)-methanethione trifluoroacetic acid salt (compound 74); and 1-[1-(3,5-dibromo-4-hydroxy-benzoyl)-2,3-dihydro-1H-pyrido[2,3-b][1,4]oxazin-7-nyl]-pyrrolidin-2-one (compound 75).

The names of the compounds described in the above are in accordance with the nomenclature method (AutoNom version 2.1) using the structures provided by CS ChemDraw Ultra software of CambridgeSoft.

As used herein, the term "unsubstituted or substituted" refers to unsubstituted condition, or substituted condition with one or more of proper substituents, for example, such as hydroxy; oxo (=O); $C_1$-$C_6$ alkyl or haloalkyl; $C_1$-$C_6$ alkoxy or haloalkoxy; $C_1$-$C_6$ alkanoyl or haloalkanoyl; halogen; cyano; nitro; amino; mono- or di-($C_1$-$C_6$)alkylamino; or carboxylic acid group $C_2$-$C_7$ alkenyl; $C_2$-$C_7$ alkynyl; $C_1$-$C_6$ hydroxyalkyl; phenyl; phosphoric acid group; N-oxide; amide; $C_1$-$C_6$ alkylamide; aldehyde; hydroxamic acid; $C_1$-$C_6$ alkylsulfide; $C_1$-$C_6$ alkylthionyl; $C_1$-$C_6$ alkylsulfonyl; $C_1$-$C_6$ oximealkyl; $C_1$-$C_6$ aminoalkyl; $C_3$-$C_8$ alkylcarbonylalkyl; $C_2$-$C_7$ alkoxycarbonyl; $C_2$-$C_7$ alkanoyloxy or the like.

Unless mentioned otherwise, alkyl substituent as referred herein and alkyl residue in other substituents (for example, alkoxy) as referred herein may be linear or branched. Also, halogen includes fluorine (F), chlorine (Cl), bromine (Br) and iodine (I).

The compound of Formula I according to the present invention may be a racemate. The racemate can be separated into each isomer by conventional separation methods, for example, a method using a general column chromatography filled with normal phase silica gel (Merk, 0.040~0.063 mm and 0.0630.200 mm), a general column chromatography filled with amine silica gel (chromatorex, 100-200 mesh) or a column chromatography for pressurized fractionation filled in reverse phase (Young-rin, SDV 30 plus) with corresponding solvent, preferably mixed solvent of hexane, ethyl acetate, dichloromethane and methanol for normal phase and mixture of water and acetonitrile for reverse phase.

The compound of Formula I according to the present invention may also form pharmaceutically acceptable salts. The pharmaceutically acceptable salts includes acid addition salts prepared by acids forming non-toxic acid addition salts containing pharmaceutically acceptable anion, for example, inorganic acids such as hydrochloric acid, sulfuric acid, nitric acid, phosphoric acid, hydrobromic acid, hydroiodic acid, etc.; organic carbon acids such as tartaric acid, formic acid, citric acid, acetic acid, trichloroacetic acid or trifluoroacetic acid, gluconic acid, benzoic acid, lactic acid, fumaric acid, maleic acid, etc.; and sulfonic acids such as methanesulfonic acid, benzenesulfonic acid, p-toluenesulfonic acid or naphthalsulfonic acid. Salts with alkali metal such as sodium, potassium or the like are also included. In addition, salts with other acids or bases which are conventionally used in a field of art relating to aromatic amidine derivative or lactam derivative, may be included. They are prepared according to conventionally known processes.

The compound of the present invention is useful as an inhibitor, specifically a selective inhibitor, of uric acid reuptake through human urate anion transporter 1 (hURAT1).

The compounds of the present invention having the above Formula I structure can be prepared according to the methods described below. Therefore, it is another object of the present invention to provide the methods for preparing the Formula I compound.

More concretely, the compound of Formula I can be obtained by each of the Preparation Methods 1 to 5 explained below, but not limited thereto.

Preparation Method 1

The following Formula II compound which is a compound of Formula I wherein L is —C(=O)—, can be prepared by a method comprising the steps of: reducing Formula VII compound to obtain Formula VI compound; cyclizing the obtained Formula VI compound with Formula V compound to obtain Formula IV compound; and peptide-bonding the obtained Formula IV compound with Formula III compound.

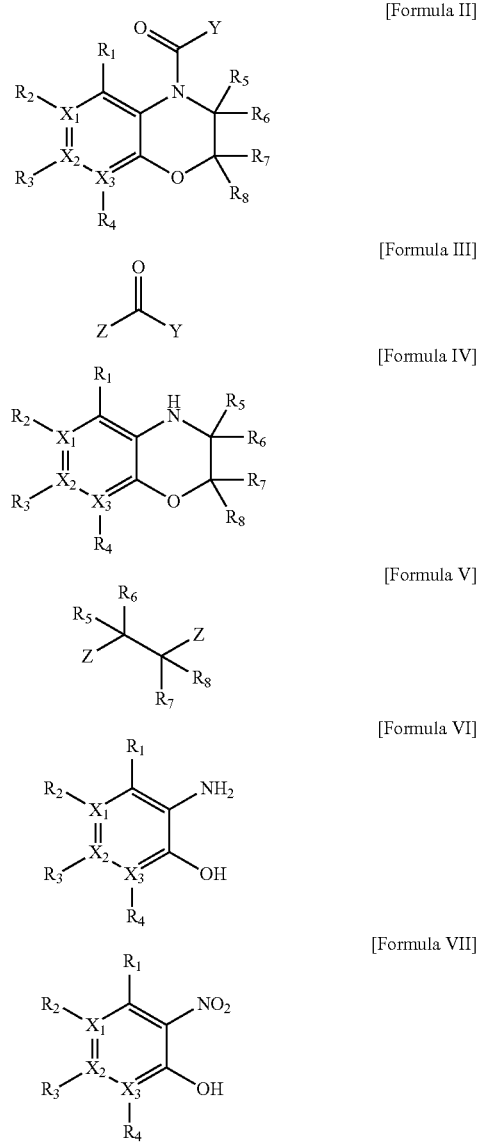

[Formula II]

[Formula III]

[Formula IV]

[Formula V]

[Formula VI]

[Formula VII]

In Formulae II to VII above, $X_1$, $X_2$, $X_3$, $R_1$, $R_2$, $R_3$, $R_4$, $R_8$, $R_6$, $R_7$, $R_8$ and Y are the same as mentioned Formula I above, and Z represents a reactive leaving group, preferably hydroxy or halogen.

Preparation Method 1 is explained in detail below.

Compounds of Formulae VI and VII used as starting materials can be prepared according to the method described in JOC. 60, 1995, 5721-5725, or are commercially available from chemical reagent companies such as Sigma Aldrich, Merck, etc.

The reduction of Formula VII compound to obtain Formula VI compound is carried out according to known synthetic methods in the presence of suitable solvent, reduction catalyst and hydrogen gas. The solvent is not particularly limited but examples thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, N,N-dimethyl formamide, N,N-dimethyl acetamide, dimethyl sulfoxide, acetonitrile, etc. A mixture solvent of two or more of solvents as described above also can be used. Methanol, ethyl acetate and tetrahydrofuran are particularly preferable as the solvent for this reaction. The reducing agents used in this reaction include general reduction catalysts such as palladium on active carbon (5 w/w %), palladium on active carbon (10 w/w %), palladium hydroxide on active carbon (10 w/w %), and Raney-nickel, etc. Palladium on active carbon (10 w/w %) is preferable for this reaction. The reaction can be carried out for the time between 1 hour and 24 hours, preferably for about 18 hours, at the temperature between 0° C. and room temperature, preferably at room temperature, under hydrogen pressure between atmospheric pressure and 3 atm, preferably under atmospheric hydrogen pressure, but not limited thereto.

In the next step, the cyclization reaction of the Formula VI compound obtained according to the above method is carried out by known synthetic methods in the presence of suitable solvent, Formula V compound and base. The solvent is not particularly limited but examples thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, N,N-dimethyl formamide, N,N-dimethyl acetamide, dimethyl sulfoxide, acetonitrile, etc. A mixture solvent of two or more of solvents as described above also can be used. Acetonitrile and N,N-dimethyl formamide are particularly preferable as the solvent for this reaction. Examples of the base used in the reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, cesium carbonate, etc.; and alkali metal hydrogen carbonates such as sodium hydrogen carbonate, potassium hydrogen carbonate, etc. Potassium carbonate is preferable for this reaction. The cyclization reaction is carried out for the time between 1 hour and 24 hours, preferably for about 18 hours, at room temperature or reflux condition depending on the used solvent, preferably between room temperature and 150□. More preferably 100□ condition in N,N-dimethyl formamide solvent.

Also Formula IV compounds can be prepared from another intermediate depending on the structure of Formula V compound. For example, in the case of ketone structure wherein $R_7$ and $R_8$ form carbonyl(—C(=O)—), Formula IV compounds can be prepared by a reduction reaction using proper solvent and reducing agent. The solvent is not particularly limited but examples thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, N,N-dimethyl formamide, N,N-dimethyl acetamide, dimethyl sulfoxide, acetonitrile, etc. A mixture solvent of two or more of solvents as described above also can be used. Tetrahydrofuran, dichloromethane, dimethyl ether and toluene are particularly preferable as the solvent for this reaction. Examples of the reducing agent include lithium aluminum hydride, sodium borohydride, diborane, diisobutyl aluminum hydride, borane-tetrahydrofuran complex, sodium bis(2-methoxyethoxy)aluminum hydride (Red-Al), tetra-n-butyl ammonium borohydride, etc. Preferably, lithium aluminum hydride or tetra-n-butyl ammonium borohydride is used. The reaction starts at 0□, and is further carried out at the temperature between 0□ and 150□, preferably between room temperature and 50□, for the time between 10 minutes and 10 hours, preferably for about 2 hours to obtain a compound of Formula IV wherein $R_7$ and $R_8$ are reduced.

Also, Formula IV compounds, which are substituted by $R_1$, $R_2$, $R_3$ and $R_4$, can be prepared from the coupling reaction of commercially available arylboronic acid or vinylboronic acid from chemical reagent companies such as Sigma Aldrich, Merck, etc. in the presence of metal catalyst. The solvent is not particularly limited but examples thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, N,N-dimethyl formamide, N,N-dimethyl acetamide, dimethyl sulfoxide, acetonitrile, etc. A mixture solvent of two or more of solvents as described above also can be used. A mixture of acetonitrile and water is particularly preferable as the solvent for this reaction. Examples of the metal catalyst used in this reaction include palladium acetate, tetrakis(triphenylphosphine) palladium, tris(dibenzylidene acetone) dipalladium, palladium dichloride, (1,1-bis(diphenylphosphino)ferrocene) palladium dichloride, bis(triphenylphosphine) palladium chloride, etc. Palladium acetate is particularly preferable for this reaction. Examples of the base for used in this reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, cesium carbonate, etc.; alkali metal hydrogen carbonates such as sodium hydrogen carbonate, potassium hydrogen carbonate, etc.; and potassium phosphate. Potassium carbonate and potassium phosphate are preferable for this reaction. The reaction can be further carried out at the temperature between room temperature and 180□, preferably between room temperature and 100□, for the time between 1 hour and 24 hours, preferably for about 18 hours to obtain another compound within Formula IV wherein the substituent as mentioned above is introduced in $R_1$, $R_2$, $R_3$, $R_4$.

In the next step, Formula II compound is obtained by the condensation reaction of the Formula IV compound with the intermediate formed from Formula III compound using general halogenating agent, preferably oxalyl chloride or thionyl chloride thereto or by the peptide bond formation of the Formula IV compound with Formula III compound using peptide coupling reagents such as HATU, HBTU, BOP, PyBOP, EDC hydrochloric acid salt, TBTU, HOBt, DEPBT, CDI, etc. in a solvent such as N,N-dimethyl acetamide, dichloromethane, tetrahydrofuran. In the reaction with the reaction product formed from Formula III compound by adding general halogenating agent thereto, organic base can be selected according to Formula III compound and in this case, the reaction is carried out under basic condition by using triethylamine preferably. The solvent is not particularly limited but examples thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, N,N-dimethyl formamide, N,N-dimethyl acetamide, dimethyl sulfoxide, acetonitrile, etc. A mixture solvent of two or more of solvents as described above also can be used. Dichloromethane and N,N-dimethyl acetamide are particularly preferable as the solvent for this reaction. Examples of the base used in this reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, etc.; and alkali metal hydrogen carbonates such as sodium hydrogen carbonate, potassium hydrogen carbonate, etc. Triethylamine is preferable for this reaction. The reaction under basic condition is carried out for the time between 10 minutes and 10 hours, preferably for about 2 hours, at the temperature between 0□ and 60□, preferably at room temperature. The reaction without basic condition is carried out for the time between 1 hour and 24 hours, preferably for about 18 hours. The reaction starts at 0□ and is further carried out at the temperature between room temperature and 60□, preferably at room temperature.

The preparation method of Formula II compound as mentioned above will be explained in detail in the Examples.

Preparation Method 2

The Formula II compound also can be prepared by a method comprising the steps of: halogenating Formula VII compound to obtain Formula X compound and then reacting the obtained Formula X compound with Formula IX compound to obtain Formula VIII compound, or caning out a Mitsunobu reaction of Formula VII compound and Formula IX compound to obtain Formula VIII compound; cyclizing the obtained Formula VIII compound to obtain Formula IV compound; and caning out peptide coupling reaction of the obtained Formula IV compound with Formula III compound.

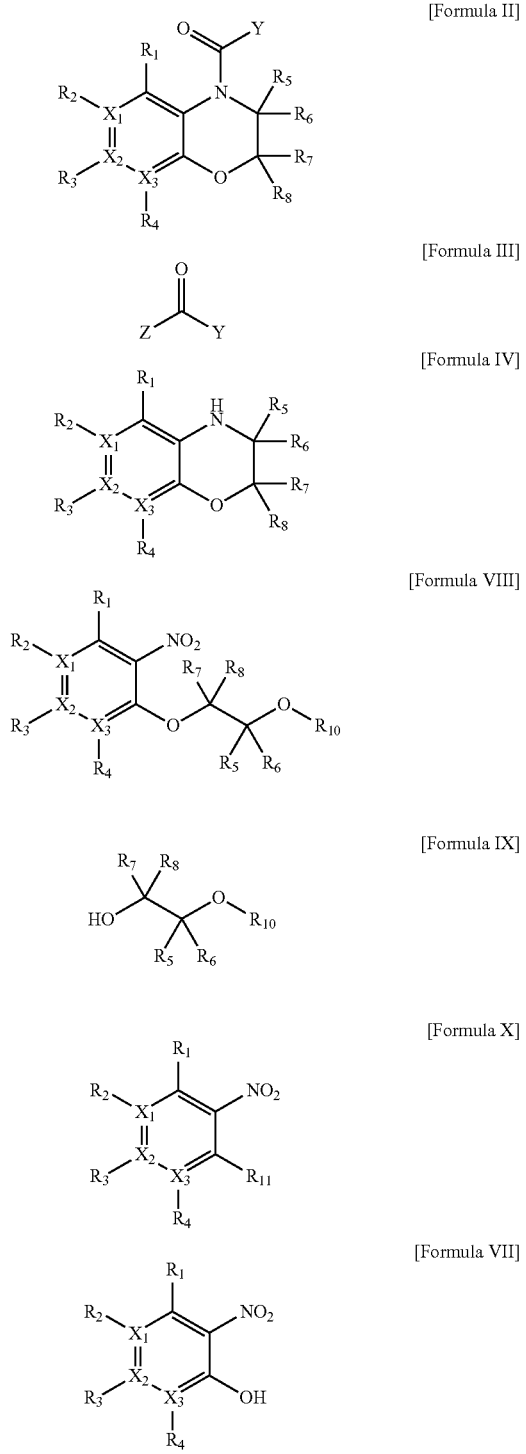

In Formulae II to X above, $X_1$, $X_2$, $X_3$, $R_1$, $R_2$, $R_3$, $R_4$, $R_5$, $R_6$, $R_7$, $R_8$ and Y are the same as defined as mentioned Formula I above; $R_{10}$ is a non-hydrogen substituent, preferably $C_1$-$C_4$ alkyl, more preferably methyl or ethyl; and $R_{11}$ represents a leaving group, preferably halogen.

Preparation Method 2 is explained in detail below.

Compounds of Formulae VII and IX used as starting materials are commercially available from chemical reagent companies such as Sigma Aldrich, Merck, etc.

The reaction of halogenating Formula VII compound to obtain Formula X compound is carried out according to known synthetic methods in the presence of suitable solvent, and halogenating agent. The solvent is not particularly limited but examples thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, N,N-dimethyl formamide, N,N-dimethyl acetamide, dimethyl sulfoxide, acetonitrile, etc. A mixture solvent of two or more of solvents as described above also can be used. Acetonitrile is particularly preferable as the solvent for this reaction. Examples of the halogenating agent used in this reaction include general halogenating agents such as phosphorus oxychloride, phosphorus oxybromide, phosphorus pentachloride or phosphorus pentabromide, etc. Phosphorus oxychloride is preferable for this reaction. The reaction can be carried out for the time between about 2 hours and about 6 hours under heating condition at the temperature between 80□ and 100□, but not limited thereto.

In the next step, the Formula X compound is carried out a substitution reaction with Formula IX compound according to known synthetic methods in the presence of suitable solvent and base. The solvent is not particularly limited but examples thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, acetonitrile, N,N-dimethyl formamide, N,N-dimethyl acetamide, dimethyl sulfoxide, etc. A mixture solvent of two or more of solvents as described above also can be used. Tetrahydrofuran and diethyl ether are particularly preferable as the solvent for this reaction. Examples of the base used in this reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, cesium carbonate, etc.; and alkali metal hydrogen carbonates such as sodium hydrogen carbonate, potassium hydrogen carbonate, etc. Sodium hydride is preferable for this reaction. The substitution reaction is carried out for the time between about 1 hour and about 6 hours at room temperature, preferably for about 1 hour at room temperature, to obtain Formula VIII compound substituted with Formula IX compound.

In a different manner, the Formula VIII compound can be prepared by caning out a generally -known Mitsunobu condensation reaction between Formula VII compound and Formula IX compound, not undergoing Formula X compound. As the condensation reagent, triphenylphosphine and diethyl azodicarboxylate (DEAD) can be used conventionally, but not limited thereto. Reagents modified from them also can be used. The solvent is not particularly limited but example thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, acetonitrile, N,N-dimethyl formamide, N,N-dimethyl acetamide, dimethyl sulfoxide, etc. A mixture solvent of two or more of solvents as described above also can be used. Tetrahydrofuran and diethyl ether are particularly preferable as the solvent for this reaction. The condensation reaction is carried out for the time between about 6 hours and about 18 hours at 0□ or room temperature, preferably for about 6 hours at room temperature.

In the next step, for the Formula VIII compound obtained according to the above method, a cyclization reaction is carried out according to known synthetic methods in the presence of suitable solvent, nitro group reducing agent and acid. The solvent is not particularly limited but example thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, acetonitrile, N,N-dimethyl formamide, N,N-dimethyl acetamide, dimethyl sulfoxide, etc. A mixture solvent of two or more of solvents as described above also can be used. Acidic solution of concentrated hydrochloric acid, acetic acid or other acids, aqueous ammonium solution, methanol and toluene are particularly preferable as the solvent for this reaction. Examples of the reducing agent include general reduction catalysts such as tin tetrachloride, iron, zinc, palladium on active carbon (5 w/w %), palladium on active carbon (10 w/w %), palladium hydroxide on active carbon (10 w/w %), Raney-nickel, etc. Tin tetrachloride is particularly preferable for this reaction. The cyclization reaction is carried out for the time between about 1 hour and about 6 hours under heating condition of the temperature between 80□ and 100□, preferably for about 1 hour under heating condition of 800, to obtain the cyclized Formula IV compound.

From the obtained Formula IV compound, another compound within Formula IV can be prepared by earring our a proper reaction, for example, a reduction reaction using proper solvent and reducing agent in case of ketone structure wherein $R_7$ and $R_8$, together with a carbon atom to which they are attached, form carbonyl(—C(=O)—). The solvent is not particularly limited but example thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, acetonitrile, N,N-dimethyl formamide, N,N-dimethyl acetamide, dimethyl sulfoxide, etc. A mixture solvent of two or more of solvents as described above also can be used. Tetrahydrofuran, dichloromethane, dimethyl ether and toluene are particularly preferable as the solvent for this reaction. Examples of the reducing agent include lithium aluminum hydride, sodium borohydride, diborane, diisobutyl aluminum hydride, borane-tetrahydrofuran complex, sodium bis(2-methoxyethoxy)aluminum hydride (Red-Al), tetra-n-butyl ammonium borohydride, etc. Preferably, lithium aluminum hydride or tetra-n-butyl ammonium borohydride is used. The reaction starts at 0□, and is further carried out at the temperature between 0□ and 150□, preferably between room temperature and 50□, for the time between 10 minutes and 10 hours, preferably for about 2 hours to obtain a compound of formula IV wherein $R_7$ and $R_8$ are reduced.

If needed, Formula IV compounds, which are substituted by $R_1$, $R_2$, $R_3$ and $R_4$, can be prepared from the coupling reaction of commercially available arylboronic acid or vinylboronic acid from chemical reagent companies such as Sigma Aldrich, Merck, etc. in the presence of metal catalyst. The solvent is not particularly limited but example thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, acetonitrile, N,N-dimethyl formamide, N,N-dimethyl acetamide, dimethyl sulfoxide, etc. A mixture solvent of two or more of solvents as described above also can be used. A mixture of acetonitrile and water is particularly preferable as the solvent for this reaction. Examples of the metal catalyst used in this reaction include palladium acetate, tetrakis(triphenylphosphine) palladium, tris(dibenzylidene acetone) dipalladium, palladium dichloride, (1,1-bis(diphenylphosphino)ferrocene) palladium dichloride, bis(triphenylphosphine) palladium chloride, etc. Palladium acetate is particularly preferable for this reaction. Examples of the base used in this reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, cesium carbonate, etc.; alkali metal hydrogen carbonates such as sodium hydrogen carbonate, potassium hydrogen carbonate, etc.; and potassium phosphate. Potassium carbonate and potassium phosphate are preferable for this reaction. The reaction can be further carried out at the temperature between room temperature and 180□, preferably between room temperature and 100□, for the time between 1 hour and 24 hours, preferably for about 18 hours to obtain another compound within Formula IV wherein the substituent as mentioned above is introduced in $R_1$, $R_2$, $R_3$, $R_4$.

In the next step, Formula II compound is obtained by the condensation reaction of the Formula IV compound with the intermediate formed from Formula III compound using general halogenating agent, preferably oxalyl chloride or thionyl chloride thereto or by the peptide bond formation of the Formula IV compound with Formula III compound using peptide coupling reagents such as HATU, HBTU, BOP, PyBOP, EDC hydrochloric acid salt, TBTU, HOBt, DEPBT, CDI, etc. in a solvent such as N,N-dimethyl acetamide, dichloromethane, tetrahydrofuran. In the reaction with the reaction product formed from Formula III compound by adding general halogenating agent thereto, organic base can be selected according to Formula III compound and in this case, the reaction is carried out under basic condition by using triethylamine preferably. The solvent is not particularly limited but example thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, acetonitrile, N,N-dimethyl formamide, N,N-dimethyl acetamide, dimethyl sulfoxide, etc. A mixture solvent of two or more of solvents as described above also can be used. Dichloromethane and N,N-dimethyl acetamide are particularly preferable as the solvent for this reaction. Examples of the base used in this reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, cesium carbonate, etc.; and alkali metal hydrogen carbonates such as sodium hydrogen carbonate, potassium hydrogen carbonate, etc. Triethylamine is preferable for this reaction. The reaction under basic condition is carried out for the time between 10 minutes and 10 hours, preferably for about 2 hours, at the temperature between 0□ and 60□, preferably at room temperature. The reaction without basic condition is carried out for the time between 1 hour and 24 hours, preferably for about 18 hours. The reaction starts at 0□ and is further conducted at the temperature between room temperature and 60□, preferably at room temperature.

The preparation method of Formula II compound as mentioned above will be explained in detail in the Examples below.

Preparation Method 3

The following Formula XI compound which is a compound of Formula I wherein L is —C(=S)—, can be prepared from Formula II compound by reacting with Lawesson's reagent.

Preparation Method 3 is explained in detail below.

Compound of Formula II used as starting material can be prepared by the same method as described above, and the obtained Formula II compound can be reacted in a solvent with commercially available Lawesson's reagent from Sigma Aldrich, Merck, etc. to prepare Formula XI compound.

The solvent is not particularly limited but example thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, acetonitrile, N,N-dimethyl formamide, N,N-dimethyl acetamide, dimethyl sulfoxide, etc. A mixture solvent of two or more of solvents as described above also can be used. Tetrahydrofuran and toluene are particularly preferable as the solvent for this reaction. The reaction is carried out, for example, for the time between 1 hour and 24 hours at the temperature between 0□ and 150□, preferably for about 18 hours at about 120□, to obtain Formula XI compound.

The preparation method of Formula XI compound as mentioned above will be explained in detail in the Examples.

Preparation Method 4

The following Formula XII compound which is a compound of Formula I wherein L is —S(=O)$_2$—, can be prepared from sulfonamide formation reaction of Formula IV compound with Formula XIII compound in the presence of base.

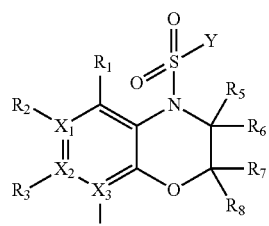

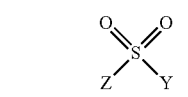

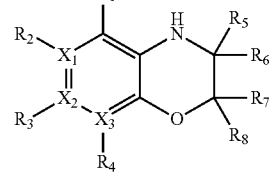

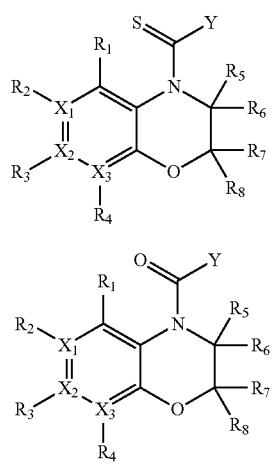

In Formulae II and X$_1$ above, X$_1$, X$_2$, X$_3$, R$_1$, R$_2$, R$_3$, R$_4$, R$_5$, R$_6$, R$_7$, R$_8$ and Y are the same as defined as mentioned Formula I above.

In Formulae IV, XII and XIII above, X$_1$, X$_2$, X$_3$, R$_1$, R$_2$, R$_3$, R$_4$, R$_5$, R$_6$, R$_7$, R$_8$ and Y are the same as mentioned Formula I above; and Z represents a leaving group, preferably halogen.

Preparation Method 4 is explained in detail below.

Compound of Formula IV used as starting material can be prepared by the same method as described above, and the obtained Formula IV compound can be used in sulfonamide formation reaction with commercially available Formula XIII compound from Sigma Aldrich, Merck, etc. in a solvent in the presence of base, to prepare Formula XII compound.

The solvent is not particularly limited but example thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, acetonitrile, N,N-dimethyl formamide, N,N-dimethyl acetamide, dimethyl sulfoxide, etc. A mixture solvent of two or more of solvents as described above also can be used. Dichloromethane and tetrahydrofuran are particularly preferable as the solvent for this reaction. Examples of the base used in this reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, cesium carbonate, etc.; and alkali metal hydrogen carbonates such as sodium hydrogen carbonate, potassium hydrogen carbonate, etc. Triethylamine is preferable for this reaction. The sulfonamide formation reaction is carried out for the time between about 10 minutes and about 8 hours at the temperature between 0☐ and 60☐, preferably for about 2 hours at room temperature, to obtain Formula XII compound.

The preparation method of Formula XII compound as mentioned above will be explained in detail in the Examples.

Preparation Method 5

The following Formula XIV compound which is a compound of Formula I wherein L is alkylcarbonyl or carbonylalkyl, can be prepared from Formula IV compound by alkylating Formula with Formula XV compound in the presence of base.

In Formulae IV to XV above, $X_1$, $X_2$, $X_3$, $R_1$, $R_2$, $R_3$, $R_4$, $R_5$, $R_6$, $R_7$, $R_8$ and Y are the same as mentioned Formula I above; Z represents a leaving group, preferably halogen; and each of $R_5$, $R_6$, $R_7$ and $R_8$ may be same or different and is independently selected from the group consisting of hydrogen; hydroxy; unsubstituted or substituted $C_1$-$C_6$ alkyl; unsubstituted or substituted $C_1$-$C_6$ haloalkyl; unsubstituted or substituted $C_1$-$C_6$ alkoxy; unsubstituted or substituted $C_1$-$C_6$ haloalkoxy; unsubstituted or substituted $C_2$-$C_7$ alkanoyl; halogen; unsubstituted or substituted phenyl; cyano; nitro; amino; and carboxylic acid group; or $R_5$ and $R_6$ together with a carbon atom to which they are attached may form a carbonyl group (C=O) or thionyl group (C=S), or $R_7$ and $R_8$ together with a carbon atom to which they are attached may form a carbonyl group (C=O) or thionyl group (C=S).

Preparation Method 5 is explained in detail below.

Compound of Formula IV used as starting material can be prepared by the same method as described above, and the obtained Formula IV compound can be subjected to an alkylation reaction in a solvent in the presence of base with Formula XV compound which is prepared by known synthetic methods or purchased from Sigma Aldrich, Merck, etc. to prepare Formula XIV compound.

The solvent is not particularly limited but example thereof preferably includes ether solvents such as diethyl ether, tetrahydrofuran, dioxane, 1,2-dimethoxyethane, diglyme, etc.; hydrocarbon solvents such as benzene, toluene, hexane, xylene, etc.; halogenated hydrocarbon solvents such as dichloromethane, chloroform, carbon tetrachloride, 1,2-dichloroethane, etc.; alcohol solvents such as methanol, ethanol, isopropyl alcohol, tert-butyl alcohol, etc.; ester solvents such as ethyl acetate, methyl acetate, butyl acetate, etc.; and polar solvents such as acetone, acetonitrile, N,N-dimethyl formamide, N,N-dimethyl acetamide, dimethyl sulfoxide, etc. A mixture solvent of two or more of solvents as described above also can be used. Dichloromethane and tetrahydrofuran are particularly preferable as the solvent for this reaction. Examples of the base used in this reaction include organic bases such as triethylamine, pyridine, 4-methylaminopyridine, 4-methylmorpholine, piperazine, N-methylpiperazine, etc.; alkali metal hydroxides such as lithium hydroxide, sodium hydroxide, potassium hydroxide, calcium hydroxide, etc.; alkali metal hydrides such as sodium hydride, potassium hydride, etc.; alkali metal carbonates such as sodium carbonate, potassium carbonate, cesium carbonate, etc.; and alkali metal hydrogen carbonates such as sodium hydrogen carbonate, potassium hydrogen carbonate, etc. Triethylamine is preferable for this reaction. The alkylation reaction is carried out for the time between about 10 minutes and about 8 hours at the temperature between 0☐ and 600, preferably for about 2 hours at room temperature, to obtain Formula XIV compound.

The preparation method of Formula XIV compound as mentioned above will be explained in detail in the Examples.

Formula I compound of the invention as explained above has a strong inhibitory activity on human urate anion transporter 1 (hURAT1). The pharmaceutical composition containing the Formula I compound or racemate, stereochemical isomer or pharmaceutically acceptable salt thereof as an active ingredient may be prepared using a suspension in combination with pharmaceutically acceptable carrier, excipient, receptor, binder, stabilizer, and other additives generally used in formulation.

Also, when the pharmaceutical composition of the invention is prepared in an injection form, a pharmaceutically acceptable buffer, dissolution aid, and/or isotoner can be

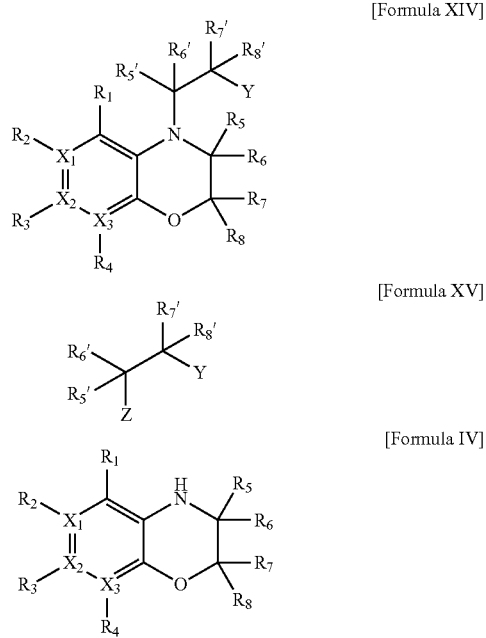

[Formula XIV]

[Formula XV]

[Formula IV]

mixed with the Formula I compound of the invention or racemate, stereochemical isomer or pharmaceutically acceptable salt thereof.

The pharmaceutical composition of the invention has a strong activity on inhibiting human urate anion transporter 1 (hURAT1) and thus is useful for the treatment or prophylaxis of hyperuricemia; gout disease such as acute gouty arthritis, chronic gouty arthritis, tophus or gout nephrosis; nephritis; chronic renal failure; nephrolithiasis; uremia; urolithiasis; disease associated with uric acid such as hyperlipidemia, ischemic heart disease, myocardial infarction, cerebral infarction, cerebrovascular disease, diabetes or hypertension; and the like.

The pharmaceutical composition of the invention can be prepared in forms of pharmaceutical formulation suitable for oral or parenteral administration. The pharmaceutical formulation can be administered orally in form of powder, granule, tablet, pill, capsule, sylup or suspension, or parenteral administration by means of injection such as intravaneous or intramuscular injection by using solution, emulsion or suspension thereof.

Administration time and dosage may be suitably determined, depending on individual cases in consideration of the symptom, age, sex, body weight, and dosage form. For adults, the pharmaceutical composition of the present invention may be administered in amount of 0.1~2,000 mg, preferably 1~200 mg per day, in a single dose or multiple doses, but not limited thereto.

ADVANTAGEOUS EFFECT

The novel heterocycle derivative compounds of the invention has a strong inhibition activity to human urate anion transporter 1 (hURAT1), no drug-drug interaction to cytochrome P450 (CYP450) and a selectivity between organic anion transporters, and can be administered with lower dosage and fewer administration time since they have higher solubility and metabolic stability so as to show advantageous pharmacokinetics, as compared with conventional inhibitor of hURAT1 activity. As a result of pharmacokinetic analysis and comparison with a conventional drug of benzbromarone and a compound disclosed in WO2006/057460 by using animal model such as mouse, rat and monkey, the heterocycle derivative compounds of the invention showed superior effects. In addition, in experiments of urinary drug excretion, the heterocycle derivative compounds of the invention showed superior results, by which it was confirmed that the drug delivery to kidney is easy.

Therefore, the novel heterocycle derivative compound of the invention and a pharmaceutical composition containing the Formula I can show superior effects to conventional drugs in the treatment or prophylaxis of hyperuricemia, acute gouty arthritis, chronic gouty arthritis, tophus, gout nephrosis, nephritis, chronic renal failure, nephrolithiasis, uremia, urolithiasis and complications reported to be accompanied with uric acid increase in blood such as hyperlipidemia, ischemic heart disease, myocardial infarction, arteriosclerosis, cerebral infarction, cerebrovascular disease, diabetes, hypertension or the like.

EMBODIMENTS FOR CARRYING OUT THE INVENTION

The following will explain the preparation methods of Formula I of the invention in further detail with reference to following examples and experiments. However, the invention is not limited to the invention of the compounds described in following examples. Also, preparation methods of intermediates are shown as Intermediate Synthesis Examples.

The names of the compounds described in the following examples are in accordance with the nomenclature method (AutoNom version 2.1) using the structures provided by CS ChemDraw Ultra software of CambridgeSoft.

EXAMPLE 1

Synthesis of (3,5-dibromo-4-hydroxy-phenyl)-(2,3-dihydro-pyrido[2,3-b][1,4]oxazin-1-yl)-methanone (compound 1)

a) Synthesis of 3-amino-pyridin-2-ol

In a 500 ml flask, 3-nitro-pyridin-2-ol (1 g, 71.4 mmol) was dissolved in methanol (200 ml), and then added 10% palladium on active carbon (100 mg, 10 w/w %). The reaction mixture was stirred for 3 hours under hydrogen atmosphere at room temperature. The resulting reaction solution was filtered on celite and then evaporated under reduced pressure to obtain white solid (800 mg, quantitative yield).

$^1$H-NMRCD$_3$OD, 300 MHz); δ=6.78-6.73 (m, 2H), 6.23 (t, J=6.5 Hz, 1H).

MS (ESI); 111.1 (M$^+$+1).

b) Synthesis of 1H-pyrido[2,3-b][1,4]oxazin-2-one

In a 20 ml flask equipped with a reflux apparatus, 3-amino-pyridin-2-ol (300 mg, 2.72 mmol) was dissolved in acetonitrile (27 ml). To the reaction solution was added chloroacetyl chloride (0.24 ml, 3.0 mmol) dropwise at room temperature, followed by Potassium carbonate (940 mg, 6.80 mmol). The mixture was heated at 1000 for 15 hours. After completion of the reaction, acetonitrile was evaporated under the reduced pressure. To the residue was added water and then the mixture was extracted with ethyl acetate. The combined organic layer was dried over anhydrous sodium sulfate (Na$_2$SO$_4$), filtered and evaporated under reduced pressure to obtain white solid (113 mg, 28%).

$^1$H-NMR(CD$_3$OD, 300 MHz); δ=7.79 (dd, J=5.0 Hz, 1.5 Hz, 1H), 7.29 (dd, J=7.6 Hz, 1.9 Hz, 1H), 7.03 (dd, J=7.6 Hz, 5.0 Hz, 1H), 4.82 (s, 2H).

MS(ESI); 151.1 (M$^+$+1).

c) Synthesis of 2,3-dihydro-1H-pyrido[2,3-b][1,4]oxazine 1H-pyrido[2,3-b][1,4]oxazin-2-one (113 mg, 0.75 mmol) was dissolved in tetrahydrofuran (3.5 ml) and then cooled to 0□. 1.0M Lithium aluminum hydride dissolved in tetrahydrofuran (1.5 ml, 1.5 mmol) was added thereto dropwise. After stirring for 2 hours at room temperature, 0.1 ml of water, 0.2 ml of 10% aqueous solution of sodium hydroxide, and 0.3 ml of water were added in this order under stirring. After filtering precipitates, the filtrate was extracted with ethyl acetate. The combined organic layer was dried over anhydrous sodium sulfate (Na$_2$SO$_4$), filtered and evaporated under reduced pressure to obtain colorless liquid (90 mg, 88%).

$^1$H-NMR(DMSO-d, 300 MHz); δ=7.35 (dd, J=5.0 Hz, 1.9 Hz, 1H), 6.86 (dd, J=7.6 Hz, 1.5 Hz, 1H), 6.72 (dd, J=7.6 Hz, 4.6 Hz, 1H), 6.00 (s, 1H), 4.23 (m, 2H), 3.25 (m, 2H).

MS(ESI); 136.9 (M$^+$+1).

d) Synthesis of (3,5-dibromo-4-hydroxy-phenyl)-(2,3-dihydro-pyrido[2,3-b][1,4]oxazin-1-yl)-methanone 3,5-dibromo-4-hydroxy-benzoic acid (65 mg, 0.22 mmol) was dissolved in N,N-dimethyl acetamide (1.5 ml) and then cooled to −5□. Thionyl chloride (0.024 ml, 0.33 mmol) was added thereto and stirred at −5□ for 30 minutes. 2,3-dihydro-1H-pyrido[2,3-b][1,4]oxazine dissolved in N,N-dimethyl acetamide (0.7 ml) was added thereto and then stirred at −5□ for 20 minutes, and subsequently stirred at room temperature for 15 hours. Water was added and the mixture was extracted with dichloromethane, and then the (extracted) combined organic layer was dried over anhydrous sodium sulfate ($Na_2SO_4$), filtered and evaporated under reduced pressure. The residue was purified by column chromatography on silica eluting with a solvent of n-hexane:ethyl acetate=1:1. The fractions containing the product were collected and evaporated to obtain pale-yellow solid (28 mg, 31%).

$^1$H-NMR($CDCl_3$, 300 MHz); δ=10.58 (s, 1H), 7.93 (dd, J=4.6 Hz, 1.5 Hz, 1H), 7.81-7.55 (m, 3H), 6.92 (dd, J=8.0 Hz, 4.6 Hz, 1H), 4.41 (m, 2H), 3.87 (m, 2H).

MS(ESI); 412.9 ($M^+$+1).

EXAMPLE 2

Synthesis of (3,5-dibromo-4-methoxy-phenyl)-(2,3-dihydro-pyrido[4,3-b][1,4]oxazin-4-yl)-methanone (compound 2)

a) Synthesis of 3-amino-pyridin-4-ol

In a 1000 ml flask, 3-nitro-pyridin-4-ol (11.6 g, 82.8 mmol) was dissolved in methanol (800 ml), and then added 10% palladium on active carbon (1.2 g, 10 w/w %). The reaction mixture was stirred for 3 hours under hydrogen atmosphere at room temperature. The resulting reaction solution was filtered on celite and then evaporated under reduced pressure to obtain white solid (9.4 g, quantitative yield).

$^1$H-NMR(DMSO-d, 300 MHz); δ=7.34 (dd, J=6.5 Hz, 1.5 Hz, 1H), 7.13 (d, J=1.5 Hz, 1H), 5.99 (d, J=6.5 Hz, 1H), 4.53 (s, 2H), 3.90-2.90 (br s, 1H).

MS(ESI); 111.1 ($M^+$+1).

b) Synthesis of 4H-pyrido[4,3-b][1,4]oxazin-3-one

In a 500 ml flask equipped with a reflux apparatus, 3-amino-pyridin-4-ol (7.8 g, 71 mmol) was dissolved in N,N-dimethyl formamide (350 ml). To the reaction solution was added chloroacetyl chloride (6.2 ml, 78 mmol) dropwise at room temperature and then stirred at room temperature for 30 minutes. Potassium carbonate (24 g, 177 mmol) was added thereto and the mixture was heated at 100□ for 40 hours. After completion of the reaction, water was added thereto. The mixture was extracted with ethyl acetate. The combined organic layer was dried over anhydrous sodium sulfate ($Na_2SO_4$), filtered and evaporated under reduced pressure. The residue was purified by recrystallizing from solvents of ethyl acetate and n-hexane to obtain white solid (5.6 g, 53%).

$^1$H-NMR(DMSO-$d_6$, 300 MHz); δ=10.90 (s, 1H), 8.06-8.04 (m, 2H), 6.96 (d, J=5.3 Hz, 1H), 4.71 (s, 2H).

MS(ESI); 150.8 ($M^+$+1).

c) Synthesis of 3,4-dihydro-2H-pyrido[4,3-b][1,4]oxazine 4H-pyrido[4,3-b][1,4]oxazin-3-one (4.3 g, 28 mmol) was dissolved in tetrahydrofuran (140 ml) and then cooled to 0□. 1.0M Lithium aluminum hydride dissolved in tetrahydrofuran (57 ml, 57 mmol) was added thereto dropwise. After stirring for 2 hours at room temperature, 1.4 ml of water, 2.8 ml of 10% aqueous solution of sodium hydroxide, and 4.2 ml of water were added in this order under stirring. After filtering precipitates, the filtrate was extracted with ethyl acetate. The combined organic layer was dried over anhydrous sodium sulfate ($Na_2SO_4$), filtered and evaporated under reduced pressure. The residue was purified by column chromatography on amine silica eluting with a solvent of dichloromethane. The fractions containing the product were collected and evaporated to obtain colorless liquid (3.5 g, 91%).

$^1$H-NMR($CDCl_3$, 300 MHz); δ=7.89 (s, 1H), 7.83 (d, J=5.3 Hz, 1H), 6.67 (d, J=5.3 Hz, 1H), 4.30 (m, 2H), 4.25-3.80 (br s, 1H), 3.42 (m, 2H).

MS(ESI); 136.8 ($M^+$+1).

d) Synthesis of (3,5-dibromo-4-methoxy-phenyl)-(2,3-dihydro-pyrido[4,3-b][1,4]oxazin-4-yl)-methanone To a 10 ml flask, 3,4-dihydro-2H-pyrido[4,3-b][1,4]oxazine (100 mg, 0.73 mmol) and 3,5-dibromo-4-methoxy-benzoyl chloride (240 mg, 0.73 mmol) were dissolved in dichloromethane. Triethylamine (0.51 ml, 3.7 mmol) was added thereto and then stirred at room temperature for 5 hours. After neutralizing with 1N hydrochloric acid solution, the mixture was extracted with dichloromethane and the combined organic layer was dried over anhydrous sodium sulfate ($Na_2SO_4$), filtered and evaporated under reduced pressure. The residue was purified by column chromatography on silica eluting with a solvent of dichloromethane:methanol=20:1. The fractions containing the product were collected and evaporated to obtain the target compound 2 as white solid (190 mg, 61%).

$^1$H-NMR($CDCl_3$, 300 MHz); δ=8.30 (s, 1H), 8.16 (d, J=5.7 Hz, 1H), 7.66 (s, 2H), 6.87 (d, J=5.3 Hz, 1H), 4.44 (m, 2H), 4.01 (m, 2H), 3.93 (s, 3H).

MS(ESI); 426.8 ($M^+$+1).

EXAMPLE 3

Synthesis of (3,5-dibromo-4-hydroxy-phenyl)-(2,3-dihydro-pyrido[4,3-b][1,4]oxazin-4-yl)-methanone bromic acid salt (compound 3)

To a 20 ml flask, (3,5-dibromo-4-methoxy-phenyl)-(2,3-dihydro-pyrido[4,3-b][1,4]oxazin-4-yl)-methanone (310 mg, 0.72 mmol) obtained in the example 2 was dissolved in dichloromethane, and then cooled to 0□. 1.0M Boron tribromide dissolved in dichloromethane (4.3 ml, 4.3 mmol) was added thereto and then stirred at 0□ for 10 hours. The resulting solid by addition of n-hexane was filtered and collected, and purified by recrystallizing from methanol to obtain the target compound 3 as white solid (130 mg, 43%).

$^1$H-NMR(DMSO-$d_6$, 300 MHz); δ=9.02 (s, 1H), 8.45 (d, 1H, J=6.5 Hz), 7.82 (s, 2H), 7.53 (d, 1H, J=6.5 Hz), 4.57 (m, 2H), 3.99 (m, 2H).

MS(ESI); 412.8 ($M^+$+1).

Elementary Analysis: C14H10Br2N2O3.HBr C, 34.47; H, 2.26; N, 5.63

EXAMPLE 4

Synthesis of (3,5-dibromo-4-hydroxy-phenyl)-(2,3-dihydro-pyrido[4,3-b][1,4]oxazin-4-yl)-methanone (compound 4)

(3,5-dibromo-4-hydroxy-phenyl)-(2,3-dihydro-pyrido[4,3-b][1,4]oxazin-4-yl)-methanone bromic acid salt (45 mg, 0.091 mmol) obtained in the example 3 was added to water (5 ml) and neutralized (pH=7) by using saturated solution of sodium hydrogen carbonate, and then extracted with ethyl acetate. The combined organic layer was dried over anhydrous sodium sulfate ($Na_2SO_4$), filtered and evaporated under reduced pressure. The resulting solid was recrystallized from dichloromethane and n-hexane to obtain the target compound 4 as white solid (20 mg, 53%).

$^1$H-NMR(DMSO-$d_6$, 300 MHz); δ=10.63 (br s, 1H), 8.44 (br s, 1H), 8.74 (d, J=5.1 Hz, 1H), 7.74 (s, 2H), 6.95 (d, J=5.7 Hz, 1H), 4.37-4.40 (m, 2H), 3.90-3.92 (m, 2H).

MS(ESI): 412.8 ($M^+$+1).

Elementary Analysis: C14H10Br2N2O3 C, 40.83; H, 2.46; N, 6.52

EXAMPLE 5

Synthesis of (3,5-dibromo-4-methoxy-phenyl)-(2,3-dihydro-pyrido[3,4-b][1,4]oxazin-1-yl)-methanone (compound 5)

a) Synthesis of 2,2-dimethyl-N-pyridin-4-yl-propionamide 4-pyridylamine (2 g, 21.3 mmol) was dissolved in dichloromethane (20 ml), and pyvaloyl chloride (3.1 ml, 25.6 mmol) and triethylamine (8.9 mg, 63.9 mmol) were added thereto in this order at room temperature dropwise. The reaction solution was stirred at room temperature for 15 hours and the reaction was quenched by adding water. The organic layer was extracted with ethyl acetate, and then the combined organic layer was washed with saturated saline solution (50 ml), dried over anhydrous sodium sulfate ($Na_2SO_4$), filtered and evaporated under reduced pressure. The residue was purified by column chromatography on silica eluting with a solvent of dichloromethane: methanol=20:1. The fractions containing the product were collected and evaporated to obtain the target compound as white solid (3.6 g, 95%).

$^1$H-NMR(CDCl$_3$, 300 MHz); δ=8.47 (d, J=6.1 Hz, 2H), 7.79 (br s, 1H), 7.52 (d, J=6.0 Hz, 2H), 1.32 (s, 9H).

b) Synthesis of N-(3-hydroxy-4-pyridinyl)-2,2-dimethyl-propionamide 2,2-dimethyl-N-pyridin-4-yl-propionamide (1.6 g, 8.977 mol) was dissolved in anhydrous tetrahydrofuran (20 ml) under nitrogen atmosphere and then cooled to −780, and then 2.5M solution of n-butyl lithium (n-BuLi) in n-hexane (9 ml, 22.443 mmol) was added thereto dropwise and then stirred at 0□ for 2.5 hours until yellow crystals were formed. After cooling the reaction mixture to −78□, trimethylboron (2.5 ml, 22.443 mmol) was added thereto dropwise for 10 minutes, and the temperature was raised slowly up to □0. After stirring for 2 hours, acetic acid (1.9 ml) and 30% w/w aqueous solution of hydrogen peroxide were added dropwise to the reaction solution at 0□, and then after stirring for 30 minutes, water (1 ml) was added thereto dropwise and then stirred at room temperature for 18 hours. Water was added and the mixture was evaporated under reduced pressure, and the residue was extracted by using water and 10% isopropanol/chloroform. The combined organic layer was treated with active carbon and the filtrate was washed with saturated saline solution, dried over anhydrous sodium sulfate ($Na_2SO_4$), filtered and evaporated under reduced pressure. The residue was purified by column chromatography on silica eluting with a solvent of dichloromethane:methanol=20:1. The fractions containing the product were collected and evaporated to obtain white solid (1.16 g, 67%).

$^1$H-NMR(CDCl$_3$, 300 MHz); δ=8.83 (s, 1H), 8.39 (d, J=6.0 Hz, 1H), 7.83 (s, 1H), 7.80 (d, J=6.0 Hz, 1H), 5.30 (br s, 1H), 1.35 (s, 9H).

c) Synthesis of 4-amino-3-pyridinol

At room temperature, N-(3-hydroxy-4-pyridinyl)-2,2-dimethyl-propionamide (1.15 g, 5.921 mmol) was suspended by dropwise addition to 3N hydrochloric acid solution. The heterogenous solution was heated at 90□ for 18 hours. The reaction mixture was cooled to 0□ and neutralized by adding 6N sodium hydroxide solution dropwise, and evaporated under reduced pressure. The residue was dissolved in methanol and then filtered to remove the byproduct. The filtrate was evaporated under reduced pressure to obtain solid. Again, the resulting solid was dissolved in ethanol solution, filtered and evaporated under reduced pressure to obtain white solid (660 mg, quantitative yield).

$^1$H-NMR(CD$_3$OD, 300 MHz); δ=7.42 (d, J=6.1 Hz, 1H), 7.24 (s, 1H), 6.67 (d, J=6.1 Hz, 1H).

d) Synthesis of 1H-pyrido[3,4-b][1,4]-oxazin-2-one 4-amino-3-pyridinol (650 mg, 5.904 mmol) was dissolved in anhydrous N,N-dimethyl formamide (15 ml) under nitrogen atmosphere, and chloroacetyl chloride (0.52 ml, 6.494 mmol) solution was added thereto dropwise at room temperature and then stirred for 30 minutes. Then, potassium carbonate (2.0 g, 14.760 mmol) was added thereto dropwise at room temperature, and the reaction mixture was heated at 100□ for 18 hours. The reaction mixture was cooled to room temperature and water was added to quench the reaction. The organic layer was extracted with ethyl acetate and the combined organic layer was washed with water and saturated saline solution, dried over anhydrous sodium sulfate ($Na_2SO_4$), filtered and evaporated under reduced pressure to obtain white solid. The obtained white solid was recrystallized from ethyl acetate and n-hexane to obtain white solid (520 mg, 59%).

$^1$H-NMR(DMSO-$d_6$, 300 MHz); δ=11.05 (br s, 1H), 8.16 (s, 1H), 8.07 (d, J=5.8 Hz, 1H), 6.87 (d, J=5.8 Hz, 1H), 4.68 (s, 2H).

MS(ESI); 150.9 ($M^+$+1).

e) Synthesis of 2,3-dihydro-1H-pyrido[3,4-b][1,4]-oxazine 1H-pyrido[3,4-b][1,4]-oxazin-2-one (510 mg, 3.397 mmol) was dissolved in anhydrous tetrahydrofuran (20 ml) under nitrogen atmosphere and then cooled to 0□. 1.0M Lithium aluminum hydride dissolved in tetrahydrofuran (6.8 ml, 6.794 mmol) was added thereto dropwise. The mixture was stirred for 30 minutes, and the temperature was raised to room temperature, and then the mixture was stirred for 1 hour. After completion of the reaction, the mixture was cooled to 0□ again, and then water (0.25 ml), 10% aqueous solution of sodium hydroxide (0.5 ml) and water (0.8 ml) were added thereto dropwise in this order, and the resulting solution was vigorously stirred at room temperature for 1 hour. The produced solid was filtered and washed with excessive ethyl acetate, and then the filtrate was washed with water and saturated saline solution, dried over anhydrous sodium sulfate ($Na_2SO_4$), filtered and evaporated under reduced pressure to obtain white solid (300 mg, 65%).

$^1$H-NMR(DMSO-$d_6$, 300 MHz); δ=7.74 (s, 1H), 7.67 (d, J=5.8 Hz, 1H), 6.67 (br s, 1H), 6.46 (d, J=5.8 Hz, 1H), 4.10 (m, 2H), 3.34 (m, 2H).

MS(ESI); 136.7 ($M^+$+1)

f) Synthesis of (3,5-dibromo-4-methoxy-phenyl)-(2,3-dihydro-pyrido[3,4-b][1,4]oxazin-1-yl)-methanone By the same method as in the step d) of Example 2, 2,3-dihydro-1H-pyrido[3,4-b][1,4]-oxazine (180 mg, 0.587 mmol) and 3,5-dibromo-4-methoxy-benzoyl chloride (193 mg, 0.587 mmol) were reacted to obtain the target compound 5, (3,5-dibromo-4-methoxy-phenyl)-(2,3-dihydro-pyrido[3,4-b][1,4]oxazin-1-yl)-methanone, as white solid (85 mg, 34%).

$^1$H-NMR(DMSO-$d_6$, 300 MHz); δ=8.23 (s, 1H), 7.99 (d, J=5.7 Hz, 1H), 7.92 (s, 2H), 7.56 (m, 1H), 4.33 (m, 2H), 3.86 (m, 5H).

MS(ESI); 426.9 (M$^+$+1).

EXAMPLE 6

Synthesis of (3,5-dibromo-4-hydroxy-phenyl)-(2,3-dihydro-pyrido[3,4-b][1,4]oxazin-1-yl)-methanone (compound 6)

By the same method as in Example 3, (3,5-dibromo-4-methoxy-phenyl)-(2,3-dihydro-pyrido[3,4-b][1,4]oxazin-1-yl)-methanone (60 mg, 0.140 mmol) and 1M solution of boron tribromide (0.84 ml, 0.840 mmol) were reacted, and then the reaction mixture was neutralized (pH=7) by using saturated solution of sodium hydrogen carbonate and extracted with ethyl acetate. The combined organic layer was dried over anhydrous sodium sulfate (Na$_2$SO$_4$), filtered and evaporated under reduced pressure to obtain solid. The obtained solid was recrystallized from dichloromethane and n-hexane to obtain the target compound 6, (3,5-dibromo-4-hydroxy-phenyl)-(2,3-dihydro-pyrido[3,4-b][1,4]oxazin-1-yl)-methanone, as white solid (28 mg, 48%).

$^1$H-NMR(DMSO-$d_6$, 300 MHz); δ=10.74 (br s, 1H), 8.23 (s, 1H), 7.96 (d, J=5.7 Hz, 1H), 7.80 (s, 2H), 7.41 (d, J=5.7 Hz, 1H), 4.34 (m, 2H), 3.89 (m, 2H).

MS(ESI); 412.9 (M$^+$+1).

EXAMPLE 7

Synthesis of (3,5-dibromo-4-hydroxy-phenyl)-(6-methyl-2,3-dihydro-pyrido[2,3-b][1,4]oxazin-1-yl)-methanone (compound 7)

a) Synthesis of 3-amino-6-methyl-pyridin-2-ol 6-hydroxy-5-nitro-2-picoline (500 mg, 3.247 mmol) was dissolved in methanol:dichloromethane (5:1, 60 ml) and 10% palladium on active carbon was added thereto slowly, and then stirred for 2 hours with adding hydrogen gas at room temperature. The reaction mixture was filtered by using celite and evaporated under reduced pressure to quantitatively obtain white solid (400 mg).

$^1$H-NMR(CDCl$_3$, 300 MHz); δ=11.67 (br s, 1H), 6.57 (d, J=7.2 Hz, 1H), 5.88 (d, J=7.2 Hz, 1H), 3.20 (br s, 2H), 2.25 (s, 3H).

MS(ESI); 125.1 (M$^+$+1).

b) Synthesis of 6-methyl-1H-pyrido[2,3-b][1,4]oxazin-2-one

By the same method as in the step d) of Example 5,3-amino-6-methyl-pyridin-2-ol (400 mg, 3.222 mmol) was reacted with chloroacetyl chloride (0.26 ml, 3.222 mmol) to obtain the target compound, 6-methyl-1H-pyrido[2, 3-1)][1,4]oxazin-2-one (230 mg, 44%).

$^1$H-NMR(CDCl$_3$, 300 MHz); δ=8.37 (s, 1H), 7.10 (d, J=5.2 Hz, 1H), 6.81 (d, J=5.2 Hz, 1H), 4.80 (s, 2H), 2.44 (s, 3H).

MS(ESI); 165.1 (M$^+$+1).

c) Synthesis of 6-methyl-2,3-dihydro-1H-pyrido[2,3-b][1,4]oxazine

By the same method as in the step e) of Example 5,6-methyl-1H-pyrido[2,3-b][1,4]oxazin-2-one (230 mg, 1.401 mmol) was reacted with 1.0M Lithium aluminum hydride dissolved in tetrahydrofuran (3.0 ml, 3.082 mmol) to obtain the target compound, 6-methyl-2,3-dihydro-1H-pyrido[2,3-b][1,4]oxazine, as white solid (160 mg, 76%).

$^1$H-NMR(CDCl$_3$, 300 MHz); δ=6.79 (d, J=7.8 Hz, 1H), 6.59 (d, J=7.5 Hz, 1H), 4.39 (m, 2H), 3.65 (m, 2H), 2.35 (s, 3H).

MS(ESI); 151.1 (M$^+$+1).

d) Synthesis of (3,5-dibromo-4-hydroxy-phenyl)-(6-methyl-2,3-dihydro-pyrido[2,3-b][1,4]oxazin-1-yl)-methanone By the same method as in the step d) of Example 1,6-methyl-2,3-dihydro-1H-pyrido[2,3-b][1,4]oxazine (50 mg, 0.333 mmol), thionyl chloride (53 μl, 0.733 mmol) and 3,5-dibromo-4-hydroxy-benzoyl chloride (197 mg, 0.666 mmol) were reacted to obtain the target compound 8, (3,5-dibromo-4-hydroxy-phenyl)-(6-methyl-2,3-dihydro-1H-pyrido[2,3-1)][1,4]oxazin-1-yl)-methanone, as white solid (40 mg, 28%).

$^1$H-NMR(DMSO-$d_6$, 300 MHz); δ=10.42 (br s, 1H), 7.58 (s, 2H), 7.42 (m, 1H), 6.63 (br s, 1H), 4.21 (m, 2H), 3.68 (m, 2H), 2.15 (s, 3H)

MS(ESI); 426.9 (M$^+$+1).

EXAMPLE 8

Synthesis of (3,5-dibromo-4-hydroxy-phenyl)-(2,2-dimethyl-2,3-dihydro-pyrido[4,3-b][1,4]oxazin-4-yl)-methanone (compound 8)

a) Synthesis of 3-aminopyridin-4-ol

By the same method as in the step a) of Example 2,3-nitropyridin-4-ol (3.0 g, 21 mmol) was reduced with palladium on active carbon to obtain 3-aminopyridin-4-ol (2.4 g, quantitative yield).

$^1$H-NMR(DMSO-$d_6$, 300 MHz); δ=7.35 (dd, J=6.9 Hz, 1.5 Hz, 1H), 7.13 (d, J=1.5 Hz, 1H), 6.00 (d, J=6.9 Hz, 1H), 4.53 (br s, 3H).

MS(ESI); 111.1 (M$_+$+1).

b) Synthesis of 2,2-dimethyl-4H-pyrido[4,3-b][1,4]oxazin-3-one

By the same method as in the step b) of Example 2,3-aminopyridin-4-ol (300 mg, 2.7 mmol) was reacted with 2-bromo-2-methyl-propionyl bromide (0.37 ml, 3.0 mmol) to obtain 2,2-dimethyl-4H-pyrido[4,3-b][1,4]oxazin-3-one (122 mg, 25%).

$^1$H-NMR(DMSO-$d_6$, 300 MHz); δ=10.84 (s, 1H), 8.05 (m, 2H), 8.00 (br s, 1H), 6.96 (d, J=5.4 Hz, 1H), 1.44 (s, 6H).

MS(ESI); 179.0 (M$^+$+1).

c) Synthesis of 2,2-dimethyl-3,4-dihydro-2H-pyrido[4,3-b][1,4]oxazine

By the same method as in the step c) of Example 2, 2,2-dimethyl-4H-pyrido[4,3-b][1,4]oxazin-3-one (120 mg, 0.67 mmol) was reacted with 1.0M Lithium aluminum hydride dissolved in tetrahydrofuran (1.4 ml, 1.4 mmol) to obtain 2,2-dimethyl-3,4-dihydro-2H-pyrido[4,3-b][1,4]oxazine (110 mg, quantitative yield).

$^1$H-NMR(CDCl$_3$, 300 MHz); δ=7.95 (s, 1H), 7.86 (d, J=5.4 Hz, 1H), 6.67 (d, J=5.7 Hz, 1H), 3.88 (br s, 1H), 3.12 (s, 2H), 1.36 (s, 6H).

MS(ESI); 165.0 (M$^+$+1).

d) Synthesis of (3,5-dibromo-4-methoxy-phenyl)-(2,2-dimethyl-2,3-dihydro-pyrido[4,3-b][1,4]oxazin-4-yl)-methanone By the same method as in the step d) of Example 2, 2,2-dimethyl-3,4-dihydro-2H-pyrido[4,3-b][1,4]oxazine (60 mg, 0.36 mmol) was reacted with 3,5-dibromo-4-methoxy-benzoyl chloride (120 mg, 0.36 mmol) to obtain the target compound, (3,5-dibromo-4-methoxy-phenyl)-(2,2-dimethyl-2,3-dihydro-pyrido[4,3-b][1,4]oxazin-4-yl)-methanone (73 mg, 44%).

$^1$H-NMR(CDCl$_3$, 300 MHz); δ=8.36 (br s, 1H), 8.17 (d, J=5.4 Hz, 1H), 7.66 (s, 2H), 6.83 (d, J=5.4 Hz, 1H), 3.9 (s, 3H), 3.7 (br s, 2H), 1.4 (s, 6H).

MS(ESI); 454.9 (M$^+$+1).

e) Synthesis of (3,5-dibromo-4-hydroxy-phenyl)-(2,2-dimethyl-2,3-dihydro-pyrido[4,3-b][1,4]oxazin-4-yl)-methanone By the same method as in Example 6, (3,5-dibromo-4-methoxy-phenyl)-(2,2-dimethyl-2,3-dihydro-pyrido[4,3-b][1,4]oxazin-4-yl)-methanone (70 mg, 0.15 mmol) was reacted with 1M solution of boron tribromide (0.9 ml, excess amount) to obtain the target compound 9, (3,5-dibromo-4-hydroxy-phenyl)-(2,2-dimethyl-2,3-dihydro-pyrido[4,3-b][1,4]oxazin-4-yl)-methanone (33 mg, 49%).

$^1$H-NMR(DMSO-d, 300 MHz); δ=10.71 (br s, 1H), 8.54 (br s, 1H), 8.11 (d, J=5.7 Hz, 1H), 7.72 (s, 2H), 6.92 (d, J=5.7 Hz, 1H), 3.73 (br s, 2H) 1.26 (s, 6H).

MS(ESI); 440.9 (M$^+$+1).

EXAMPLE 9

Synthesis of (7-cyclopropyl-2,3-dihydro-pyrido[2,3-b][1,4]oxazin-1-yl)-(3,5-dibromo-4-hydroxy-phenyl)-methanone (compound 9)

a) Synthesis of 7-cyclopropyl-1H-pyrido[2,3-b][1,4]oxazin-2-one

To a 10 ml flask, 7-bromo-1H-pyrido[2,3-b][1,4]oxazin-2-one (400 mg, 1.746 mmol), cyclopropyl boronic acid (165 mg, 1.921 mmol), palladium acetate (39.1 mg, 0.174 mmol), triphenylphosphine (91.5 mg, 0.349 mmol) and potassium carbonate (482.6 mg, 3.492 mmol) were dissolved in a solvent of acetonitrile/water (6/1, 4.2 ml/0.9 ml). The reaction mixture was stirred for 60 minutes at 100□ using microwave (100 W) apparatus. After cooling to room temperature, the reaction mixture was extracted with ethyl acetate and the organic layer was washed with saturated saline solution. The combined organic layer was dried over anhydrous magnesium sulfate (MgSO$_4$), filtered and evaporated under reduced pressure. The residue was purified by column chromatography on silica eluting with a solvent of dichloromethane and ethyl acetate. The fractions containing the product were collected and evaporated to obtain a mixture (40 mg, 0.8%) containing triphenyl phosphoxide.

$^1$H-NMR(CDCl$_3$, 300 MHz); δ=8.95 (s, 1H), 7.72 (d, J=1.8 Hz, 1H), 6.82 (d, J=2.1 Hz, 1H), 4.77 (s, 2H), 1.80-1.87 (m, 1H), 0.64-0.99 (m, 2H), 0.57-0.63 (m, 2H).

b) Synthesis of 7-cyclopropyl-2,3-dihydro-1H-pyrido[2,3-b][1,4]oxazine 7-cyclopropyl-1H-pyrido[2,3-b][1,4]oxazin-2-one (40 mg, 0.052 mmol) was dissolved in 1 ml anhydrous tetrahydrofuran under nitrogen atmosphere and then cooled to 0□. 1.0M Lithium aluminum hydride dissolved in tetrahydrofuran (0.1 ml, 0.104 mmol) was added thereto dropwise and then stirred at room temperature for 5 hours. Water (0.3 ml) was added thereto dropwise. The resulting solution was evaporated under reduced pressure to obtain a mixture containing 7-cyclopropyl-2,3-dihydro-1H-pyrido[2,3-b][1,4]oxazine and triphenyl phosphoxide as white solid (10 mg).

c) Synthesis of (7-cyclopropyl-2,3-dihydro-pyrido[2,3-b][1,4]oxazin-1-yl)-(3,5-dibromo-4-methoxy-phenyl)-methanone To a 10 ml flask, 7-cyclopropyl-2,3-dihydro-1H-pyrido[2,3-b][1,4]oxazine (10 mg, 0.057 mmol) and 3,5-dibromo-4-methoxy-benzoyl chloride (28 mg, 0.085 mmol) were dissolved in dichloromethane (1.2 ml). After cooling to 0□, triethylamine (0.04 ml, 0.285 mmol) was added thereto and then stirred at room temperature for 3 hours. The reaction mixture was neutralized with 1N hydrochloric acid solution and extracted with dichloromethane, and then the combined organic layer was dried over anhydrous magnesium sulfate (MgSO$_4$), filtered and evaporated under reduced pressure. The residue was purified by column chromatography on silica eluting with a solvent of ethyl acetate and n-hexane (1:1). The fractions containing the product were collected and evaporated to obtain the target compound as white solid (9.0 mg, 33%).

$^1$H-NMR(CDCl$_3$, 300 MHz); δ=7.86 (d, J=2.4 Hz, 1H), 7.45 (s, 2H), 7.21 (s, 1H), 4.43-4.47 (m, 2H), 3.95-3.97 (m, 2H), 3.94 (s, 3H), 1.73-1.82 (m, 1H), 0.85-0.91 (m, 2H), 0.39-0.45 (m, 2H).

d) Synthesis of (7-cyclopropyl-2,3-dihydro-pyrido[2,3-b][1,4]oxazin-1-yl)-3,5-dibromo-4-hydroxy-phenyl)-methanone To a 10 ml flask, (7-cyclopropyl-2,3-dihydro-pyrido[2,3-b][1,4]oxazin-1-yl)-(3,5-dibromo-4-methoxy-phenyl)-methanone (9.0 mg, 0.019 mmol) was dissolved in dichloromethane, and then cooled to 0□. 1.0M Boron tribromide dissolved in dichloromethane (0.2 ml*2, 0.203 mmol) was added thereto and then stirred at room temperature for 16 hours. The pH was adjusted to 6 with 1N sodium hydroxide solution and the reaction mixture was extracted with dichloromethane, and the combined organic layer was dried over anhydrous sodium sulfate (Na$_2$SO$_4$), filtered and evaporated under reduced pressure to obtain solid. The resulting solid was recrystallized from dichloromethane to obtain white solid (6.7 mg, 84%).

$^1$H-NMR(DMSO-d$_6$, 300 MHz); δ=10.59 (s, 1H), 7.78 (d, J=2.1 Hz, 1H), 7.72 (s, 2H), 7.25 (s, 1H), 4.35-4.38 (m, 2H), 3.82-3.84 (m, 2H), 1.79-1.81 (m, 1H), 0.80-0.86 (m, 2H), 0.28-0.39 (m, 2H).

MS(ESI); 452.8 (M$^+$+1).

EXAMPLE 10

Synthesis of (3-chloro-4-hydroxy-phenyl)-(2,3-dihydro-pyrido[4,3-b][1,4]oxazin-4-yl)-methanone bromic acid salt (compound 10)

a) Synthesis of (3-chloro-4-methoxy-phenyl)-(2,3-dihydro-pyrido[4,3-b][1,4]oxazin-4-yl)-methanone To a 10 ml flask, 3,4-dihydro-2H-pyrido[4,3-b][1,4]oxazine (150 mg, 1.102 mmol) and 3-chloro-4-methoxy-benzoyl chloride (249 mg, 1.212 mmol) were dissolved in dichloromethane. Triethylamine (0.77 ml, 5.510 mmol) was added thereto and then stirred at room temperature for 2 hours. The reaction mixture was neutralized with 1N hydrochloric acid solution and extracted with dichloromethane. And the combined organic layer was dried over anhydrous magnesium sulfate ($MgSO_4$), filtered and evaporated under reduced pressure. The residue was purified by column chromatography on silica eluting with a solvent of ethyl acetate. The fractions containing the product were collected and evaporated to obtain ivory-colored solid (238 mg, 71%).

$^1$H-NMR(DMSO-d$_s$); δ=8.39 (br, 1H), 8.07 (d, J=5.7 Hz, 1H), 7.66 (d, J=2.3 Hz, 1H), 7.55 (dd, J=1.9 Hz, 8.4 Hz, 1H), 7.23 (d, J=8.4 Hz, 1H), 6.95 (d, J=5.7 Hz, 1H), 4.40 (m, 2H), 3.92 (s, 5H).

MS(ESI); 305 (M$^+$+1).

b) Synthesis of (3-chloro-4-hydroxy-phenyl)-(2,3-dihydro-pyrido[4,3-b][1,4]oxazin-4-yl)-methanone bromic acid salt To a 10 ml flask, (3-chloro-4-methoxy-phenyl)-(2,3-dihydro-pyrido[4,3-b][1,4]oxazin-4-yl)-methanone (100 mg, 0.328 mmol) was dissolved in dichloromethane, and then cooled to 0□. 1.0M Boron tribromide dissolved in dichloromethane (2.0 ml, 1.969 mmol) was added thereto and then stirred at room temperature for 16 hours. The solid formed by adding ethyl acetate solvent was filtered and collected, and purified by recrystallizing from dichloromethane to obtain white solid (45 mg, 47%).

$^1$H-NMR(DMSO-d$_6$, 300 MHz); δ=11.03 (br s, 1H), 9.04 (s, 1H), 8.48 (d, J=6.9 Hz, 1H), 7.65 (d, J=1.9 Hz, 1H), 7.58 (d, J=6.5 Hz, 1H), 7.46 (dd, J=1.5 Hz, 8.4 Hz, 1H), 7.09 (d, J=8.4 Hz, 1H), 4.58 (m, 2H), 4.01 (m, 2H).

MS(ESI); 291.2 (M$^+$+1).

EXAMPLE 11

Synthesis of (3-bromo-4-hydroxy-phenyl)-(2,3-dihydro-pyrido[4,3-b][1,4]oxazin-4-yl)-methanone bromic acid salt (compound 11)

a) Synthesis of (3-bromo-4-methoxy-phenyl)-(2,3-dihydro-pyrido[4,3-b][1,4]oxazin-4-yl)-methanone To a mixture of 3,4-dihydro-2H-pyrido[4,3-b][1,4]oxazine (50 mg, 0.37 mmol) and 3-bromo-4-methoxy-benzoic acid (102 mg, 0.44 mmol), phosphorus oxychloride (2 ml) was added and stirred at 100° C. for 12 hours. The reaction mixture was cooled to 0° C., neutralized with saturated solution of sodium hydrogen carbonate to pH of 8-9 and extracted with ethyl acetate.

And then the combined organic layer was washed with saturated saline solution, dried over anhydrous sodium sulfate ($Na_2SO_4$), filtered and evaporated under reduced pressure. The residue was purified by column chromatography on silica eluting with a solvent of n-hexane:dichloromethane=1:1. The fractions containing the product were collected and evaporated to obtain white solid (38 mg, 51%).

$^1$H-NMR(CDCl$_3$, 300 MHz); δ=8.19 (s, 1H), 8.12 (d, J=5.7 Hz, 1H), 7.77 (d, J=1.9 Hz, 1H), 7.44 (dd, J=8.6 Hz, 1.9 Hz, 1H), 6.91-6.81 (m, 2H), 4.44 (m, 2H), 4.03 (m, 2H), 3.93 (s, 3H).

b) Synthesis of (3-bromo-4-hydroxy-phenyl)-(2,3-dihydro-pyrido[4,3-b][1,4]oxazin-4-yl)-methanone bromic acid salt By the same method as in Example 3, (3-bromo-4-methoxy-phenyl)-(2,3-dihydro-pyrido[4,3-b][1,4]oxazin-4-yl)-methanone (30 mg, 0.086 mmol) and 1M solution of boron tribromide (0.86 ml, 0.86 mmol) were reacted to obtain the target compound, (3-bromo-4-hydroxy-phenyl)-(2,3-dihydro-pyrido[4,3-b][1,4]oxazin-4-yl)-methanone bromic acid salt (26 mg, 72%).

$^1$H-NMR(DMSO-d$_6$, 300 MHz); δ=11.1 (br s, 1H), 8.97 (s, 1H), 8.42 (d, J=6.5 Hz, 1H), 7.78 (d, J=1.9 Hz, 1H), 7.54-7.44 (m, 2H), 7.05 (d, J=8.4 Hz, 1H), 4.56 (m, 2H), 4.01 (m, 2H).

MS(ESI); 335.1 (M$^+$+1).

EXAMPLE 12

Synthesis of (2,3-dihydro-pyrido[4,3-b][1,4]oxazin-4-yl)-(4-hydroxy-3-trifluoromethyl-phenyl)-methanone (compound 12)

a) Synthesis of (2,3-dihydro-pyrido[4,3-b][1,4]oxazin-4-yl)-(4-methoxy-3-trifluoromethyl-phenyl)-methanone To a 50 ml flask, 3,4-dihydro-2H-pyrido[4,3-b][1,4]oxazine (1.0 g, 7.34 mmol) and 3-trifluoromethyl-4-methoxy-benzoyl chloride (2.1 g, 8.80 mmol) were dissolved in dichloromethane. Triethylamine (2.0 ml, 14.68 mmol) was added thereto and then stirred at room temperature for 4 hours. To the reaction mixture, water was added to quench the reaction and the mixture was extracted with dichloromethane, and the combined organic layer was washed with water and saturated saline solution, dried over anhydrous sodium sulfate ($Na_2SO_4$), filtered and evaporated under reduced pressure.

The residue was purified by column chromatography on silica eluting with a solvent of ethyl acetate:n-hexane=2:1. The fractions containing the product were collected and evaporated to obtain yellow solid (1.19 g, 80%).

$^1$H-NMR(CDCl$_3$, 300 MHz); δ=8.41 (s, 1H), 8.08 (d, J=5.7 Hz, 1H), 7.88 (dd, J=8.7 Hz, 2.1 Hz, 1H), 7.82 (s, 1H), 7.36 (d, J=8.7 Hz, 1H), 6.96 (d, J=5.7 Hz, 1H), 4.42 (m, 2H), 3.96 (s, 3H), 3.93 (m, 2H).

MS(ESI); 339.0 (M$^+$+1).

b) Synthesis of (2,3-dihydro-pyrido[4,3-b][1,4]oxazin-4-yl)-(4-hydroxy-3-trifluoromethyl-phenyl)-methanone To a 100 ml flask, 2,3-dihydro-pyrido[4,3-b][1,4]oxazin-4-yl)-(4-methoxy-3-trifluoromethyl-phenyl)-methanone (1.19 g, 3.52 mmol) was dissolved in dichloromethane. After cooling to 0□, 1.0M Boron tribromide dissolved in dichloromethane (35.2 ml, 35.2 mmol) was added thereto and then stirred at room temperature for 10 hours. The solid formed by adding a solvent of n-hexane and water was filtered. The crude was purified by recrystallizing from dichloromethane to obtain white solid. The obtained solid was further purified by preparative high pressure chromatography using Waters LC/MS apparatus eluting a solvent of acetonitrile and distilled water containing 0.1% trifluoroacetic acid (TFA) to obtain the compound as salt form of trifluoroacetic acid (TFA). The obtained compound was washed with 10% aqueous solution of sodium hydrogen carbonate (NaHCO$_3$) and extracted with dichloromethane. The combined organic layer was washed with water and saturated saline solution, dried over anhydrous sodium sulfate (Na$_2$SO$_4$), filtered and evaporated under reduced pressure to obtain the target compound 12 as white solid (13.52 mg, 1.2%).

$^1$H-NMR(CDCl$_3$, 300 MHz); δ=11.34 (s, 1H), 8.39 (s, 1H), 8.07 (d, J=5.7 Hz, 1H), 7.73 (s, 1H), 7.68 (dd, J=8.7 Hz, 1H), 7.06 (d, J=8.7 Hz, 1H), 6.95 (d, J=5.4 Hz, 1H), 4.40 (m, 2H), 3.93 (m, 2H).

MS(ESI); 325.0 (M$^+$+1).

EXAMPLE 13

Synthesis of (3,5-dichloro-4-hydroxy-phenyl)-(2,3-dihydro-pyrido[4,3-b][1,4]oxazin-4-yl)-methanone bromic acid salt (compound 13)

a) Synthesis of (3,5-dichloro-4-methoxy-phenyl)-(2,3-dihydro-pyrido[4,3-b][1,4]oxazin-4-yl)-methanone To a mixture of 3,4-dihydro-2H-pyrido[4,3-b][1,4]oxazine (80 mg, 0.58 mmol) and 3,5-dichloro-4-methoxy-benzoic acid (141 mg, 0.64 mmol), phosphorus oxychloride (4 ml) was added and then stirred at 100□ for 12 hours. The reaction mixture was cooled to 0□ and adjusted to pH of 8-9 by using saturated solution of sodium hydrogen carbonate and extracted with ethyl acetate. The combined organic layer was washed with saturated saline solution, dried over anhydrous sodium sulfate (Na$_2$SO$_4$), filtered and evaporated under reduced pressure. The residue was purified by column chromatography on silica eluting with a solvent of n-hexane:ethyl acetate=4:1. The fractions containing the product were collected and evaporated to obtain white solid (107 mg, 54%).

$^1$H-NMR(CDCl$_3$, 300 MHz); δ=7.67 (s, 2H), 7.12-6.96 (m, 1H), 6.87 (dd, J=5.3 Hz, 9.2 Hz, 1H), 6.78 (td, J=3.1 Hz, 8.8 Hz, 1H), 4.31 (m, 2H), 3.97-3.88 (m, 5H).

MS(ESI); 339.0 (M$^+$+1).

b) Synthesis of (3,5-dichloro-4-hydroxy-phenyl)-(2,3-dihydro-pyrido[4,3-b][1,4]oxazin-4-yl)-methanone bromic acid salt By the same method as in Example 3, (3,5-dichloro-4-methoxy-phenyl)-(2,3-dihydro-pyrido[4,3-b][1,4]oxazin-4-yl)-methanone (116 mg, 0.342 mmol) was reacted with 1M solution of boron tribromide (3.42 ml, 3.42 mmol) to obtain the target compound, (3,5-dichloro-4-hydroxy-phenyl)-(2,3-dihydro-pyrido[4,3-b][1,4]oxazin-4-yl)-methanone bromic acid salt (65 mg, 67%).

$^1$H-NMR(DMSO-d$_6$, 300 MHz); δ=11.0 (br s, 1H), 9.04 (s, 1H), 8.46 (d, J=6.5 Hz, 1H), 7.66 (s, 2H), 7.55 (d, J=6.5 Hz, 1H), 4.58 (m, 2H), 4.00 (m, 2H).

MS(ESI); 325.0 (M$^+$+1).

EXAMPLE 14

Synthesis of (3-chloro-4-hydroxy-5-nitro-phenyl)-(2,3-dihydro-pyrido[4,3-b][1,4]oxazin-4-yl)methasone (compound 14)

a) Synthesis of (3-chloro-4-methoxy-5-nitro-phenyl)-(2,3-dihydro-pyrido[4,3-b][1,4]oxazin-4-yl)-methanone To phosphorus oxychloride (3.00 ml), 3,4-dihydro-2H-pyrido[4,3-b][1,4]oxazine (177 mg, 1.30 mmol) and 3-chloro-4-methoxy-5-nitro benzoic acid (200 mg, 0.87 mmol) were added and then stirred at 95□ for 16 hours. After completion of the reaction, the reaction mixture was poured into ice water and neutralized with saturated solution of sodium hydroxide, and extracted with ethyl acetate. The combined organic layer was dried over anhydrous sodium sulfate (Na$_2$SO$_4$), filtered and evaporated under reduced pressure. The residue was purified by column chromatography on silica eluting with a solvent of dichloromethane:methanol=20:1. The fractions containing the product were collected and evaporated to obtain yellow solid (132 mg, 29%).

$^1$H-NMR(DMSO-d$_6$, 300 MHz); δ=8.70 (br s, 1H), 8.16 (d, J=1.9 Hz, 1H), 8.14-8.09 (m, 2H), 6.98 (d, J=5.3 Hz, 1H), 4.40 (m, 2H), 4.00 (s, 3H), 3.90 (m, 2H).

MS(ESI); 350.1 (M$^+$+1).

b) Synthesis of (3-chloro-4-hydroxy-5-nitro-phenyl)-(2,3-dihydro-pyrido[4,3-b][1,4]oxazin-4-yl)-methanone bromic acid salt To a 20 ml flask, (3-chloro-4-methoxy-5-nitro-phenyl)-(2,3-dihydro-pyrido[4,3-b][1,4]oxazin-4-yl)-methanone (132 mg, 0.38 mmol) was dissolved in dichloromethane and then cooled to 0□. 1.0M Boron tribromide dissolved in dichloromethane (3 ml, 3.00 mmol) was added thereto and then stirred at 0□ for 10 hours. After completion of the reaction, the concentrated liquid was purified by HPLC. The resulting solid was further purified by recrystallizing from ethanol to obtain the target compound 14, (3-chloro-4-hydroxy-5-nitro-phenyl)-(2,3-dihydro-pyrido[4,3-b][1,4]oxazin-1-yl)-methanone, as white solid (80 mg, 63%).

$^1$H-NMR(DMSO-d$_6$, 300 MHz); δ=8.45 (br s, 1H), 8.10 (br s, 1H), 7.98 (d, J=2.7 Hz, 1H), 6.58 (d, J=2.7 Hz, 1H), 6.98 (d, 1H), 4.38 (m, 2H), 3.96 (m, 2H).

MS(ESI); 336.1 (M$^+$+1).

EXAMPLE 15

Synthesis of (3,5-dichloro-4-hydroxy-phenyl)-(2,3-dihydro-pyrido[3,4-b][1,4]oxazin-1-yl)-methanone bromic acid salt (compound 15)

By the same method as in Example 3, (3,5-dichloro-4-methoxy-phenyl)-(2,3-dihydro-pyrido[3,4-b][1,4]oxazin-1-yl)-methanone (114 mg, 0.33 mmol) was reacted with 1M solution of boron tribromide (3.3 ml, 3.3 mmol) The target compound, (3,5-dichloro-4-hydroxy-phenyl)-(2,3-dihydro-pyrido[3,4-b][1,4]oxazin-1-yl)-methanone bromic acid salt, was purified by recrystallizing from ethanol to obtain brown solid (19.7 mg, 14%).

$^1$H-NMR(DMSO-d$_6$, 300 MHz); δ=8.63 (s, 1H), 8.25 (d, J=6.5 Hz, 1H), 7.89 (d, J=6.5 Hz, 1H), 7.74 (s, 2H), 4.44 (m, 2H), 3.98 (m, 2H).

MS(ESI); 325.1 (M$^+$+1).

EXAMPLE 16

Synthesis of (3-bromo-4-hydroxy-phenyl)-(2,3-dihydro-pyrido[3,4-b][1,4]oxazin-1-yl)-methanone bromic acid salt (compound 16)

By the same method as in Example 3, (3-bromo-4-methoxy-phenyl)-(2,3-dihydro-pyrido[3,4-b][1,4]oxazin-1-yl)-methanone (68 mg, 0.19 mmol) was reacted with 1M solution of boron tribromide (1.9 ml, 1.9 mmol). The target compound, (3-bromo-4-hydroxy-phenyl)-(2,3-dihydro-pyrido[3, 4-b][1,4]oxazin-1-yl)-methanone bromic acid salt, was purified by recrystallizing from ethanol to obtain brown solid (48.6 mg, 60%).

$^1$H-NMR(DMSO-$d_6$, 300 MHz); δ=11.2 (s, 1H), 8.63 (s, 1H), 8.30 (d, J=6.9 Hz, 1H), 7.88 (d, J=1.8 Hz, 1H), 7.83 (d, J=6.6 Hz, 1H), 7.58 (dd, J=8.3, 1.8 Hz, 1H), 7.05 (d, J=8.3 Hz, 1H), 4.44 (m, 2H), 3.98 (m, 2H).

MS(ESI); 335.1 (M$^+$+1).

EXAMPLE 17

Synthesis of (3-chloro-4-hydroxy-5-nitro-phenyl)-(2,3-dihydro-pyrido[3,4-b][1,4]oxazin-1-yl)-methanone bromic acid salt (compound 17)

a) Synthesis of (3-chloro-4-methoxy-5-nitro-phenyl)-(2,3-dihydro-pyrido[3,4-b][1,4]oxazin-1-yl)-methanone To a 10 ml flask, 2,3-dihydro-1H-pyrido[3,4-b][1,4]oxazine (57 mg, 0.42 mmol) and 3-chloro-4-methoxy-5-nitro-benzoyl chloride (117 mg, 0.47 mmol) were dissolved in dichloromethane. Triethylamine (0.29 ml, 2.1 mmol) was added thereto and then stirred at room temperature for 2 hours. After neutralizing with 1N hydrochloric acid solution, the reaction mixture was extracted with dichloromethane. The combined organic layer was dried over anhydrous sodium sulfate (Na$_2$SO$_4$) and filtered and the solvent was removed under reduced pressure. The residue was purified by column chromatography on silica with a solvent of ethyl acetate:n-hexane=1:2. The fractions containing the product were collected and evaporated to obtain yellow solid (118 mg, 81%).

$^1$H-NMR(DMSO-$d_6$, 300 MHz); δ=8.24 (s, 1H), 8.19 (d, J=2.1 Hz, 1H), 8.14 (d, J=1.8 Hz, 1H), 8.00 (d, J=6.0 Hz, 1H), 7.61 (d, J=5.1 Hz, 1H), 4.34 (m, 2H), 3.99 (s, 3H), 3.88 (m, 2H).

b) Synthesis of (3-chloro-4-hydroxy-5-nitro-phenyl)-(2,3-dihydro-pyrido[3,4-b][1,4]oxazin-1-yl)-methanone bromic acid salt To a 20 ml flask, (3-chloro-4-methoxy-5-nitro-phenyl)-(2,3-dihydro-pyrido[3,4-b][1,4]oxazin-1-yl)-methanone (109 mg, 0.31 mmol) was dissolved in dichloromethane and then cooled to 0□. 1.0M Boron tribromide dissolved in dichloromethane (3.1 ml, 3.1 mmol) was added thereto and then stirred at 0□ for 18 hours. The reaction was quenched by using a small amount of water and then evaporated under reduced pressure. The resulting residue was purified by recrystallizing from methanol to obtain yellow solid (67 mg, 52%).

$^1$H-NMR(DMSO-$d_6$, 300 MHz); δ=8.67 (s, 1H), 8.27 (d, J=6.9 Hz, 1H), 8.24 (d, J=2.1 Hz, 1H), 8.08 (d, J=1.8 Hz, 1H), 7.98 (d, J=6.6 Hz, 1H), 4.45 (m, 2H), 3.99 (m, 2H).

MS(ESI); 336.0 (M$^+$+1).

EXAMPLE 18

Synthesis of (3-chloro-4-hydroxy-phenyl)-(2,3-dihydro-pyrido[3,4-b][1,4]oxazin-1-yl)-methanone bromic acid salt (compound 18)

By the same method as in Example 3, (3-chloro-4-methoxy-phenyl)-(2,3-dihydro-pyrido[3,4-b][1,4]oxazin-1-yl)-methanone (100 mg, 0.328 mmol) was reacted with 1M solution of boron tribromide (3.28 ml, 3.28 mmol) to obtain the target compound, (3-chloro-4-hydroxy-phenyl)-(2,3-dihydro-pyrido[3,4-b][1,4]oxazin-1-yl)-methanone bromic acid salt, as white solid (45 mg, 37%).

$^1$H-NMR(DMSO-$d_6$, 300 MHz); δ=11.17 (s, 1H), 8.65 (s, 1H), 8.25 (d, J=6.4 Hz, 1H), 7.85 (d, J=6.4 Hz, 1H), 7.75 (d, J=2.1 Hz 1H), 7.55 (dd, J=8.4, 2.1 Hz, 1H), 7.06 (d, J=8.4 Hz, 1H), 4.44 (m, 2H), 3.99 (m, 2H).

MS(ESI); 291.1 (M$^+$+1).

EXAMPLE 19

Synthesis of (2,3-dihydro-pyrido[3,4-b][1,4]oxazin-1-yl)-(4-hydroxy-3-trifluoromethyl-phenyl)-methanone (compound 19)

By the same method as in the step b) of Example 12, (2,3-dihydro-pyrido[3,4-b][1,4]oxazin-1-yl)-(4-methoxy-3-trifluoromethyl-phenyl)-methanone (110 mg, 0.325 mmol) was reacted with 1M solution of boron tribromide (3.25 ml, 3.25 mmol) to obtain the target compound, (2,3-dihydro-pyrido[3,4-b][1,4]oxazin-1-yl)-(4-hydroxy-3-trifluoromethyl-phenyl)-methanone, as white solid (11 mg, 10%).

$^1$H-NMR(CD$_3$OD, 300 MHz); δ=8.16 (s, 1H), 7.85 (d, J=5.7 Hz, 1H), 7.81 (d, J=1.8 Hz, 1H), 7.66 (dd, J=8.4, 1.8 Hz, 1H), 7.32 (d, J=5.7 Hz, 1H), 7.00 (d, J=8.4 Hz, 1H), 4.37 (m, 2H), 3.98 (m, 2H).

MS(ESI); 325.1 (M$^+$+1).

EXAMPLE 20

Synthesis of (3,5-dibromo-4-hydroxy-phenyl)-(7-phenyl-2,3-dihydro-pyrido[2,3-b][1,4]oxazin-1-yl)-methanone (compound 20)

a) Synthesis of 7-phenyl-1H-pyrido[2,3-b][1,4]oxazin-2-one

To a 10 ml flask equipped with refluxing apparatus, 7-bromo-1H-pyrido[2,3-b][1,4]oxazin-2-one (48 mg, 0.21 mmol), phenyl boronic acid (PhB(OH)$_2$, 28 mg, 0.23 mmol), triphenylphosphine (PPh$_3$, 11 mg, 0.04 mmol), palladium acetate (Pd(OAc)$_2$, 5 mg, 0.02 mmol), potassium carbonate (44 mg, 0.31 mmol) were dissolved in acetonitrile (1.6 ml) and water (0.4 ml). The mixture was heated to 90□ and then refluxed for 15 hours. The mixture was evaporated and water was added, and then the mixture was extracted with ethyl acetate. The combined organic layer was dried over anhydrous sodium sulfate (Na$_2$SO$_4$), filtered and evaporated under reduced pressure. The resulting residue was purified by column chromatography on silica eluting with a solvent of dichloromethane:methanol=30:1. The fractions containing the product were collected and evaporated to obtain pale-brown solid (21 mg, 44%).

MS(ESI); 227.1 (M$^+$+1).

b) Synthesis of 7-phenyl-2,3-dihydro-1H-pyrido[2,3-b][1,4]oxazine 7-phenyl-1H-pyrido[2,3-b][1,4]oxazin-2-one (21 mg, 0.09 mmol) was dissolved in tetrahydrofuran (0.5 ml) and then cooled to 0□. 1.0M Lithium aluminum hydride dissolved in tetrahydrofuran (0.19 ml, 0.19 mmol) was added thereto dropwise. After stirring for 5 hours at room temperature, 0.1 ml of water, 0.2 ml of 10% aqueous solution of sodium hydroxide, and 0.3 ml of water were added in this order under stirring. After filtering precipitates, the filtrate was extracted with ethyl acetate. The combined organic layer was dried over anhydrous sodium sulfate (Na$_2$SO$_4$), filtered and evaporated under reduced pressure. The residue was purified by column chromatography on silica eluting with a solvent of dichloromethane:methanol=40:1. The fractions containing the product were collected and evaporated to obtain pale-grey solid (10 mg, 50%).

MS(ESI); 213.0 (M$^+$+1).

c) Synthesis of (3,5-dibromo-4-methoxy-phenyl)-(7-phenyl-2,3-dihydro-pyrido[2,3-b][1,4]oxazin-1-yl)-methanone To a 5 ml flask, 7-phenyl-2,3-dihydro-1H-pyrido[2,3-b][1,4]oxazine (10 mg, 0.05 mmol) and 3,5-dibromo-4-methoxy-benzoyl chloride (17 mg, 0.05 mmol) were dissolved in dichloromethane. Triethylamine (0.02 ml, 0.14 mmol) was added thereto and then stirred at room temperature for 1 hour. After neutralizing with 1N hydrochloric acid solution, the mixture was extracted with dichloromethane and the combined organic layer was dried over anhydrous sodium sulfate (Na$_2$SO$_4$), filtered and evaporated under reduced pressure. The residue was purified by column chromatography on silica eluting with a solvent of dichloromethane:methanol=40:1. The fractions containing the product were collected and evaporated to obtain white solid (14 mg, 59%).

MS(ESI); 503.0 (M$^+$+1).

d) Synthesis of (3,5-dibromo-4-hydroxy-phenyl)-(7-phenyl-2,3-dihydro-pyrido[2,3b][1,4]oxazin-1-yl)-methanone To a 5 ml flask, (3,5-dibromo-4-methoxy-phenyl)-(7-phenyl-2,3-dihydro-pyrido[2,3-b][1,4]oxazin-1-yl)-methanone (14 mg, 0.03 mmol) was dissolved in dichloromethane and then cooled to 0□. 1.0M Boron tribromide dissolved in dichloromethane (0.17 ml, 0.17 mmol) was added and then stirred at 0□ for 15 hours. After completion of the reaction, water was added thereto and the mixture was extracted with ethyl acetate and the combined organic layer was dried over anhydrous sodium sulfate (Na$_2$SO$_4$), filtered and evaporated under reduced pressure. The residue was purified by column chromatography on silica eluting with a solvent of dichloromethane:methanol=40:1. The fractions containing the product were collected and evaporated to obtain the target compound 20 as white solid (8.7 mg, 64%).

$^1$H-NMR(DMSO-d$_6$, 300 MHz); δ=10.53 (br s, 1H), 8.23 (d, 1H, J=2.28 Hz), 8.02 (s, 1H), 7.79 (s, 2H), 7.43-7.32 (m, 5H), 4.45 (m, 2H), 3.92 (m, 2H).

MS(ESI); 488.9 (M$^+$+1).

EXAMPLE 21

Synthesis of 2,6-dichloro-4-(2,3-dihydro-pyrido[4,3-b][1,4]oxazin-4-sulfonyl)-phenol (compound 21)

To a 5 ml flask, 3,4-dihydro-2H-pyrido[4,3-b][1,4]oxazine (30 mg, 0.220 mmol) was dissolved in tetrahydrofuran (3 ml). Diisopropylethylamine (0.153 ml, 0.878 mmol) was added and then stirred at 0□ for 10 minutes, and then 3,5-dichloro-4-hydroxy-benzenesulfonyl chloride (69 mg, 0.264 mmol) was added thereto and then stirred at 0□ for 1 hour. The reaction mixture was evaporated under reduced pressure. The residue was purified by column chromatography on silica eluting with a solvent of dichloromethane:ethyl acetate=1:2. The fractions containing the product were collected and evaporated to obtain the target compound 21 as pale-yellow solid (2.7 mg, 3.4%).

$^1$H-NMR(CD$_3$OD, 300 MHz); δ=8.80 (s, 1H), 8.12 (d, J=5.3 Hz, 1H), 7.38 (s, 2H), 6.90 (d, J=5.3 Hz, 1H), 3.86-3.84 (br s, 4H).

MS(ESI); 361.0 (M$^+$+1).

EXAMPLE 22

Synthesis of (3,5-dibromo-4-hydroxy-phenyl)-(7-trifluoromethyl-2,3-dihydro-pyrido[2,3-b][1,4]oxazin-1-yl)-methanone (compound 22-2)

a) Synthesis of 2-chloro-3-nitro-5-trifluoromethyl-pyridine

In a 25 ml flask, 3-nitro-5-trifluoromethyl-pyridin-2-ol (300 mg, 1.44 mmol) was dissolved in acetonitrile (4.5 ml), and then phosphorus oxychloride (0.4 ml, 4.33 mmol) and benzyltrimethyl ammonium chloride (164 mg, 0.721 mmol) were added thereto. The mixture was stirred for 3 hours at 800. After completion of the reaction, water was added thereto and the mixture was extracted with ethyl acetate. The combined organic layer was dried over anhydrous sodium sulfate (Na$_2$SO$_4$), filtered and evaporated under reduced pressure to obtain white solid (300 mg, 92%).

$^1$H-NMR(DMSO-d$_6$, 300 MHz); δ=9.21 (s, 1H), 9.08 (s, 1H).

b) Synthesis of (3-nitro-5-trifluoromethyl-pyridin-2-yloxy)-acetic acid methyl ester In a 10 ml flask, hydroxy-acetic acid methyl ester (0.4 ml, 0.53 mmol) was dissolved in tetrahydrofuran (1.5 ml), and then sodium hydride (23 mg, 0.57 mmol) was added thereto. After 40 minutes, 2-chloro-3-nitro-5-trifluoromethyl-pyridine (100 mg, 0.44 mmol) was added and then stirred for 2 hours at room temperature. After completion of the reaction, water was added thereto and the mixture was extracted with ethyl acetate. The combined organic layer was dried over anhydrous sodium sulfate (Na$_2$SO$_4$), filtered and evaporated under reduced pressure. The residue was purified by column chromatography on silica eluting with a solvent of n-hexane:ethyl acetate=9:1. The fractions containing the product were collected and evaporated to obtain white solid (84 mg, 68%).

$^1$H-NMR(DMSO-d$_6$, 300 MHz); δ=8.95 (s, 1H), 8.92 (s, 1H), 5.23 (s, 2H), 3.69 (s, 3H).

c) Synthesis of 7-trifluoromethyl-1H-pyrido[2,3-b][1,4]oxazin-2-one

In a 10 ml flask, (3-nitro-5-trifluoromethyl-pyridin-2-yloxy)-acetic acid methyl ester (84 mg, 0.30 mmol) was dissolved in concentrated hydrochloric acid (1.5 ml) and then tin tetrachloride (227 mg, 1.2 mmol) was added thereto. The mixture was stirred for 30 minutes at 80□. After completion of the reaction, water was added thereto at room temperature and the mixture was extracted with a solvent of methanol:dichloromethane=1:9. The combined organic layer was dried over anhydrous sodium sulfate (Na$_2$SO$_4$), filtered and evaporated under reduced pressure. The residue was purified by column chromatography on silica eluting with a solvent of methanol:dichloromethane=1:50. The fractions containing the product were collected and evaporated to obtain white solid (40 mg, 62%).

$^1$H-NMR(DMSO-d$_6$, 300 MHz); δ=11.1 (s, 1H), 8.19 (s, 1H), 7.40 (s, 1H), 4.91 (s, 2H).

MS(ESI); 219 (M$^+$+1).

d) Synthesis of 7-trifluoromethyl-2,3-dihydro-1H-pyrido[2,3-b][1,4]oxazine

In a 5 ml flask, 7-trifluoromethyl-1H-pyrido[2,3-b][1,4]oxazin-2-one (60 mg, 0.28 mmol) was dissolved in tetrahydrofuran (1.0 ml), and then 1.0M Lithium aluminum hydride dissolved in tetrahydrofuran (0.33 ml, 0.33 mmol) was added thereto dropwise and stirred for 1 hour at 0□. Water and saturated solution of sodium hydrogen carbonate were added and the mixture was extracted with ethyl acetate. The combined organic layer was dried over anhydrous sodium sulfate ($Na_2SO_4$), filtered and evaporated under reduced pressure. The residue was purified by column chromatography on silica eluting with a solvent of methanol:dichloromethane=1:50. The fractions containing the product were collected and evaporated to obtain white solid (29 mg, 52%).

$^1$H-NMR(DMSO-$d_6$, 300 MHz); δ=7.69 (br s, J=2.29 Hz, 1H), 7.10 (br s, J=2.29 Hz, 1H), 6.48-6.54 (m, 1H), 4.31-4.37 (m, 2H), 3.33-3.39 (m, 2H).

MS(ESI); 205 ($M^+$+1).

e) Synthesis of (3,5-dibromo-4-methoxy-phenyl)-(7-trifluoromethyl-2,3-dihydro-pyrido[2,3-b][1,4]oxazin-1-yl)-methanone (compound 22-1)

In a 5 ml flask, 7-trifluoromethyl-2,3-dihydro-1H-pyrido[2,3-b][1,4]oxazine (27 mg, 0.23 mmol) and 3,5-dibromo-4-methoxy-benzoyl chloride (65 mg, 0.20 mmol) were dissolved in dichloromethane (0.6 ml), and then triethylamine (0.55 ml, 0.33 mmol) was added thereto dropwise at 0□. After stirring for 4 hours at room temperature, water was added and the mixture was extracted with ethyl acetate. The combined organic layer was dried over anhydrous sodium sulfate ($Na_2SO_4$), filtered and evaporated under reduced pressure. The residue was purified by column chromatography on silica eluting with a solvent of methanol:dichloromethane=1:100. The fractions containing the product were collected and evaporated to obtain white solid (64 mg, 98%).

$^1$H-NMR(DMSO-$d_6$, 300 MHz); δ=8.37 (s, 2H), 7.91 (s, 2H), 4.46-4.53 (m, 2H), 3.86-3.92 (m, 2H), 3.84 (s, 3H).

MS(ESI); 494.8 ($M^+$+1).

f) Synthesis of (3,5-dibromo-4-hydroxy-phenyl)-(7-trifluoromethyl-2,3-dihydro-pyrido[2,3-b][1,4]oxazin-1-yl)-methanone (compound 22-2)

In a 5 ml flask, (3,5-dibromo-4-methoxy-phenyl)-(7-trifluoromethyl-2,3-dihydro-pyrido[2,3-b][1,4]oxazin-1-yl)-methanone (30 mg, 0.061 mmol) was dissolved in N,N-dimethyl formamide (0.3 ml), and then lithium bromide (10 mg, 0.12 mmol) and piperazine (7.8 mg, 0.091 mmol) were added thereto. After stirring for 1 hour, the solvent was removed by evaporation under reduced pressure. The residue was neutralized with water and 1N hydrochloric acid. The resulting solid was filtered to obtain the target compound 22-2 as white solid (25 mg, 86%).

$^1$H-NMR(DMSO-$d_6$, 300 MHz); δ=10.7 (s, 1H), 8.34 (s, 1H), 8.29 (s, 1H), 7.79 (s, 2H), 4.45-4.50 (m, 2H), 3.86-3.93 (m, 2H).

MS(ESI); 480.8 ($M^+$+1).

EXAMPLE 23

Synthesis of 2,5-dibromo-4-(2,3-dihydro-pyrido[4,3-b][1,4]oxazin-4-carbonyl)-benzoic acid (compound 23)

In a 20 ml flask, 2,5-dibromo-terephthalic acid (100 mg, 0.31 mmol) and N,N-dimethyl formamide (3 drops) were dissolved in thionyl chloride (2 ml). After stirring for 2 hours at 800, the reaction mixture was cooled to room temperature and concentrated. Crude 2,5-dibromo-terephthaloic dichloride (112 mg, 0.31 mmol) was dissolved in dichloromethane (6 ml) and was added to 3,4-dihydro-2H-pyrido[4,3-b][1,4]oxazine (20.9 mg, 0.15 mmol) dissolved in dichloromethane (1 ml). Triethylamine (3 drops) were slowly added thereto and stirred at room temperature for 16 hours. After completion of the reaction, the residue was purified by preparative LC/Mass to obtain the target compound 23, i.e., 2,5-dibromo-4-(2,3-dihydro-pyrido[4,3-b][1,4]oxazin-4-carbonyl)-benzoic acid, as white solid (23 mg, 5%).

$^1$H-NMR($CD_3OD$, 300 MHz); δ=9.70 (s, 1H), 8.47 (d, J=7.2 Hz, 1H), 7.83 (d, J=12.6 Hz, 2H), 7.58 (d, J=6.9 Hz, 1H), 4.72 (m, 2H), 4.12-3.88 (m, 2H).

MS(ESI); 440.9 ($M^+$+1).

EXAMPLE 24

Synthesis of (2,6-dibromo-4-(2,3-dihydro-pyrido[4,3-b][1,4]oxazin-4-carbonyl)-phenoxy]-acetic acid methyl ester (compound 24)

In a 25 ml flask, (3,5-dibromo-4-hydroxy-phenyl)-(2,3-dihydro-pyrido[4,3-b][1,4]oxazin-4-yl)-methanone (100 mg, 0.24 mmol) was dissolved in N,N-dimethyl formamide (2.4 ml), and potassium carbonate (37 mg, 0.266 mmol) was added thereto dropwise at room temperature. After stirring at room temperature for 10 minutes, bromo-methyl acetate was added dropwise and then stirred for 40 minutes at room temperature. The reaction mixture was filtered on celite and evaporated under reduced pressure. The residue was purified by column chromatography on silica eluting with a solvent of dichloromethane:methanol=20:1 to obtain the target compound 24 as white foam (48 mg, 41.0%).

$^1$H-NMR(DMSO-d, 300 MHz); δ=8.63 (br s, 1H), 8.11 (d, J=5.7 Hz, 1H), 7.90 (s, 2H), 6.97 (d, J=5.7 Hz, 1H), 4.70 (s, 2H), 4.42-4.37 (m, 2H), 3.90-3.85 (m, 2H), 3.75 (s, 3H).

MS(ESI); 484.9 ($M^+$+1).

EXAMPLE 25

Synthesis of (7-bromo-2,3-dihydro-pyrido[2,3-b][1,4]oxazin-1-yl)-(3,5-dibromo-4-hydroxy-phenyl)-methanone (compound 25)

a) Synthesis of 7-bromo-2,3-dihydro-1H-pyrido[2,3-b][1,4]oxazine

To a 1.0 ml flask, 7-bromo-2,3-dihydro-1H-pyrido[2,3-b][1,4]oxazin-2-one (100 mg, 0.436 mmol) was dissolved in tetrahydrofuran (1.0 ml). To the reaction mixture, 1.0M Lithium aluminum hydride dissolved in tetrahydrofuran (0.524 ml, 0.524 mmol) was added dropwise at 0□, and then stirred for 20 minutes. After completion of the reaction by adding water to the reaction mixture, the organic layer was extracted with ethyl acetate and the combined organic layer was washed with water and saturated saline solution, dried over anhydrous sodium sulfate ($Na_2SO_4$), filtered and evaporated under reduced pressure. The residue was recrystallized from dichloromethane and diisopropyl ether to obtain white solid (63 mg, 67%).

$^1$H-NMR(CDCl$_3$, 300 MHz); δ=7.38 (d, J=2.4 Hz, 1H), 7.01 (d, J=2.1 Hz, 1H), 6.37 (s, 1H), 4.22 (m, 2H), 3.25 (m, 2H).

MS(ESI); 215 (M$^+$+1).

b) Synthesis of (7-bromo-2,3-dihydro-pyrido[2,3-b][1,4]oxazin-1-yl)-(3,5-dibromo-4-methoxy phenyl)-methanone To a 10 ml flask, 7-bromo-2,3-dihydro-1H-pyrido[2,3-b][1,4]oxazine (37 mg, 0.172 mmol) and 3,5-dibromo-4-methoxy-benzoyl chloride (113 mg, 0.344 mmol) were dissolved in dichloromethane (0.5 ml). Triethylamine (0.120 ml, 0.860 mmol) was added thereto and then stirred at room temperature for 1 hour. After completion of the reaction by adding water to the reaction mixture, the organic layer was extracted with dichloromethane and the combined organic layer was washed with water and saturated saline solution, dried over anhydrous sodium sulfate (Na$_2$SO$_4$), filtered and evaporated under reduced pressure. The residue was purified by column chromatography on silica eluting with a solvent of dichloromethane:ethyl acetate:n-hexane=1:2:5. The fractions containing the product were collected and evaporated to obtain white solid (55 mg, 63%).

$^1$H-NMR(CDCl$_3$, 300 MHz); δ=8.14 (s, 1H), 8.08 (d, J=2.1 Hz, 1H), 7.82 (s, 2H), 4.41 (m, 2H), 3.95 (s, 3H), 3.90 (m, 2H).

MS(ESI); 504.8 (M$^+$+1).

c) Synthesis of (7-bromo-2,3-dihydro-pyrido[2,3-b][1,4]oxazin-1-yl)-(3,5-dibromo-4-hydroxy-phenyl)-methanone To a 100 ml flask, (7-bromo-2,3-dihydro-pyrido[2, 3-1)][1,4]oxazin-1-yl)-(3,5-dibromo-4-methoxy-phenyl)-methanone (55 mg, 0.108 mmol) was dissolved in dichloromethane and then cooled to 0□. 1.0M Boron tribromide dissolved in dichloromethane (1.63 ml, 1.63 mmol) was added thereto and stirred at room temperature for 10 hours. n-hexane and water were added and the resulting solid was filtered. And then the crude was purified by recrystallizing from dichloromethane to obtain white solid as TFA salt. The resulting solid was dissolved in dichloromethane and then washed with 10% aqueous solution of sodium hydrogen carbonate, water and saturated saline solution. The combined organic layer was dried over anhydrous sodium sulfate (Na$_2$SO$_4$), filtered and evaporated under reduced pressure to obtain the target compound 25 as white solid (16.6 mg, 31%).

$^1$H-NMR(CDCl$_3$, 300 MHz); δ=10.66 (s, 1H), 8.19 (s, 1H), 8.05 (d, J=2.4 Hz, 1H), 7.78 (s, 2H), 4.36 (m, 2H), 3.83 (m, 2H).

MS(ESI); 490.7 (M$^+$+1).

EXAMPLE 26

Synthesis of (2,3-dihydro-pyrido[4,3-b][1,4]oxazin-4-yl)-(3-fluoro-4-hydroxy-phenyl)-methanone (compound 26)

a) Synthesis of (2,3-dihydro-pyrido[4,3-b][1,4]oxazin-4-yl)-(3-fluoro-4-methoxy-phenyl)-methanone In a 10 ml flask, 3,4-dihydro-2H-pyrido[4,3-b][1,4]oxazine (50 mg, 0.441 mmol) and 3-fluoro-4-methoxy-benzoyl chloride (125 mg, 0.661 mmol) were dissolved in dichloromethane. Triethylamine (0.77 ml, 1.288 mmol) was added thereto and then stirred at room temperature for 2 hours. After neutralizing with 1N hydrochloric acid solution, the mixture was extracted with dichloromethane and the combined organic layer was dried over anhydrous sodium sulfate (Na$_2$SO$_4$), filtered and evaporated under reduced pressure. The residue was purified by column chromatography on silica eluting with a solvent of ethyl acetate. The fractions containing the product were collected and evaporated to obtain white solid (42.1 mg, 33%).

$^1$H-NMR(CDCl$_3$, 300 MHz); δ=8.15 (s, 1H), 8.11 (d, J=5.7 Hz, 1H), 7.31 (m, 1H), 7.27 (d, J=3.8 Hz, 1H), 6.92-6.98 (m, 1H), 6.85 (d, J=5.7 Hz, 1H), 4.43-4.46 (m, 2H), 4.02-4.05 (m, 2H), 3.92 (s, 3H).

MS(ESI); 289.1 (M$^+$+1).

b) Synthesis of (2,3-dihydro-pyrido[4,3-b][1,4]oxazin-4-yl)-(3-fluoro-4-hydroxy-phenyl)-methanone In a 10 ml flask, (2,3-dihydro-pyrido[4,3-b][1,4]oxazin-4-yl)-(3-fluoro-4-methoxy-phenyl)-methanone (30 mg, 0.104 mmol) was dissolved in dichloromethane and the mixture was cooled to 0□. 1.0M Boron tribromide dissolved in dichloromethane (1.25 ml, 1.25 mmol) was added thereto and stirred at room temperature for 10 hours. n-hexane and water were added and then filtered to obtain solid. The resulting solid was purified by preparative LC-Mass using 0.05% TFA in acetonitrile and 0.05% TFA in water solvent. The fractions containing the product were collected and adjusted to pH 6 to 7 with saturated solution of sodium hydrogen carbonate. The organic layer was extracted with ethyl acetate. The combined organic layer was evaporated under reduced pressure to obtain the target compound 26 as white solid (9 mg, 28%).

$^1$H-NMR(DMSO-d$_6$, 300 MHz); δ=8.37 (s, 1H), 8.05 (d, J=5.3 Hz, 1H), 7.39 (d, J=11.8 Hz, 1H), 7.25 (d, J=8.3 Hz, 1H), 6.97 (m, 2H), 4.36-4.39 (m, 2H), 3.93-3.90 (m, 2H).

MS(ESI); 275.2 (M$^+$+1).

EXAMPLE 27

Synthesis of (3,5-dibromo-4-hydroxy-phenyl)-(7-methyl-2,3-dihydro-pyrido[2,3-b][1,4]oxazin-1-yl)-methanone (compound 27-2)

a) Synthesis of (3,5-dibromo-4-methoxy-phenyl)-(7-methyl-2,3-dihydro-pyrido[2,3-b][1,4]oxazin-1-yl)-methanone (compound 27-1)

In a 10 ml flask, 7-methyl-2,3-dihydro-1H-pyrido[2,3-b][1,4]oxazine (79 mg, 0.52 mmol) and 3,5-dibromo-4-methoxy-benzoyl chloride (259 mg, 0.79 mmol) were dissolved in dichloromethane (2 ml). Triethylamine (0.22 ml, 1.58 mmol) was added thereto and then stirred at room temperature for 2 hours. After neutralizing with 1N hydrochloric acid solution, the mixture was extracted with dichloromethane and the combined organic layer was dried over anhydrous sodium sulfate (Na$_2$SO$_4$), filtered and evaporated under reduced pressure. The residue was purified by column chromatography on silica eluting with a solvent of methanol:dichloromethane=1:30. The fractions containing the product were collected and evaporated to obtain white solid (210 mg, 90%).

$^1$H-NMR(CDCl$_3$, 300 MHz); δ=8.25 (s, 1H), 7.87 (d, J=1.5 Hz, 1H), 7.68 (s, 1H), 4.45-4.42 (m, 2H), 3.95-3.91 (m, 2H), 3.94 (s, 3H), 2.21 (s, 3H).

MS(ESI); 439.9 (M$^+$+1).

b) Synthesis of (3,5-dibromo-4-hydroxy-phenyl)-(7-methyl-2,3-dihydro-pyrido[2,3-b][1,4]oxazin-1-yl)-methanone (compound 27-2)

In a 5 ml flask, (3,5-dibromo-4-methoxy-phenyl)-(7-methyl-2,3-dihydro-pyrido[2,3-b][1,4]oxazin-1-yl)-methanone (100 mg, 0.23 mmol), lithium bromide (39 mg, 0.45 mmol), piperazine (30 mg, 0.35 mmol) and N,N-dimethyl formamide (1 ml) were added and then stirred at 100□ for 30 minutes. Lithium bromide (39 mg, 0.45 mmol) was further added thereto and then stirred at 1000 for 1 hour. Lithium bromide (39 mg, 0.45 mmol) was further added thereto and then stirred for 1 hour. After neutralizing with saturated solution of sodium hydrogen carbonate to pH 8 to 9, the mixture was adjusted to pH 6 again by using 1N hydrochloric acid. The formed solid was filtered. The resulting solid was purified by column chromatography on silica eluting with a solvent of methanol:dichloromethane=1:30. The fractions containing the product were collected and evaporated to obtain the target compound 27-2 as white solid (74 mg, 76%).

$^1$H-NMR(DMSO-$d_6$, 300 MHz); δ=10.61 (br s, 1H), 7.77-7.75 (m, 4H), 4.35-4.32 (m, 2H), 3.85-3.82 (m, 2H), 2.15 (s, 3H).

MS(ESI); 426.8 (M$^+$+1).

EXAMPLE 28

Synthesis of (3,5-difluoro-4-methoxy-phenyl)-(2,3-dihydro-pyrido[4,3-b][1,4]oxazin-4-yl)-methanone (compound 28)

In a 10 ml flask, 3,4-dihydro-2H-pyrido[4,3-b][1,4]oxazine (60 mg, 0.44 mmol) and 3,5-difluoro-4-methoxy-benzoyl chloride (120 mg, 0.572 mmol) were dissolved in dichloromethane (1 ml). Triethylamine (0.080 ml, 0.57 mmol) was added thereto and stirred at room temperature for 1 hour. After completion of the reaction by adding water to the reaction mixture, the organic layer was extracted with dichloromethane, and the combined organic layer was washed with water and saturated saline solution, dried over anhydrous sodium sulfate (Na$_2$SO$_4$), filtered and evaporated under reduced pressure. The residue was purified by column chromatography on silica eluting with a solvent of dichloromethane:ethyl acetate:n-hexane=1:2:5. The fractions containing the product were collected and evaporated to obtain the target compound 28 as white solid (102 mg, 76%).

$^1$H-NMR(CDCl$_3$, 300 MHz); δ=8.17 (br s, 1H), 8.14 (d, J=5.7 Hz, 1H), 7.08 (d, J=7.2 Hz, 2H), 6.85 (d, J=5.7 Hz, 1H), 4.43 (m, 2H), 4.05 (s, 3H), 4.01 (m, 2H).

MS(ESI); 307.2 (M$^+$+1).

EXAMPLE 29

Synthesis of (3,5-difluoro-4-hydroxy-phenyl)-(2,3-dihydro-pyrido[4,3-b][1,4]oxazin-4-yl)-methanone (compound 29)

In a 10 ml flask, (3,5-difluoro-4-methoxy-phenyl)-(2,3-dihydro -pyrido[4,3-b][1,4]oxazin-4-yl)-methanone (50 g, 0.163 mmol), lithium bromide (57 mg, 0.65 mmol) and piperazine (21 mg, 0.24 mmol) were dissolved with N,N-dimethyl formamide, and stirred at 1000 for 3 hours. After completion of the reaction by adding water dropwise, the mixture was adjusted to weak acidic condition (pH=6) by using 1N hydrochloric acid, and the formed solid was filtered and washed with distilled water and ethyl acetate. The resulting solid was recrystallized from methanol to obtain the target compound 29, i.e., 3,5-difluoro-4-hydroxy -phenyl)-(2,3-dihydro-pyrido[4,3-b][1,4]oxazin-4-yl)-methanone (31 mg, 65%).

$^1$H-NMR(DMSO-d, 300 MHz); δ=10.9 (br s, 1H), 8.45 (br s, 1H), 8.01 (m, 1H), 7.81 (d, J=7.2 Hz, 2H), 6.95 (d, J=5.34 Hz, 1H), 4.38 (m, 2H), 3.91 (m, 2H).

MS(ESI); 293.1 (M$^+$+1).

EXAMPLE 30

Synthesis of (5-chloro-2,3-dihydro-pyrido[4,3-b][1,4]oxazin -4-yl)-(3,5-dibromo-4-hydroxy-phenyl)-methanone (compound 30)

a) Synthesis of (5-chloro-2,3-dihydro-pyrido[4,3-b][1,4]oxazin-4-yl)-(3,5-dibromo-4-methoxy-phenyl)-methanone In a 50 ml flask equipped with a reflux apparatus, 5-chloro-3,4-dihydro-2H-pyrido[4,3-b][1,4]oxazine (890 mg, 5.22 mmol) was dissolved in butyl ether (20 ml), and 60% sodium hydride in mineral oil (250 mg, 6.26 mmol) was added and stirred at 1250 for 3.5 hours. The mixture was cooled to room temperature and 3,5-dibromo-4-methoxy-benzoyl chloride (2.06 g, 6.26 mmol) was added thereto and then stirred at 1250 for 24 hours. The mixture was cooled to room temperature and filtered and evaporated under reduced pressure. The residue was washed with methanol and dried under reduced pressure to obtain white solid (1.2 g, 50%).

$^1$H-NMR(CDCl$_3$, 300 MHz); δ=8.09 (d, J=5.7 Hz, 1H), 7.78 (s, 2H), 6.86 (d, J=5.7 Hz, 1H), 4.47-4.31 (m, 2H), 4.02-3.82 (m, 2H), 3.93 (s, 3H).

MS(ESI); 461 (M$^+$+1).

b) Synthesis of (5-chloro-2,3-dihydro-pyrido[4,3-b][1,4]oxazin-4-3,5-dibromo-4-hydroxy-phenyl)-methanone In a 5 ml flask equipped with a reflux apparatus, (5-chloro-2,3-dihydro -pyrido[4,3-b][1,4]oxazin-4-yl)-(3,5-dibromo-4-methoxy-phenyl)-methanone (48 mg, 0.1 mmol) was dissolved in dichloroethane (0.5 ml) and chloroform (0.5 ml). 1.0M Boron tribromide dissolved in dichloromethane (1 ml, 1 mmol) was added thereto dropwise at room temperature. The reaction mixture was stirred at 450 for 18 hours. After cooling to room temperature, methanol (1 ml) was added and then stirred at room temperature for 10 minutes. After evaporating under reduced pressure, dichloromethane was added and then stirred. The reaction mixture was filtered to obtain the target compound 30 as white solid (24 mg, 54%).

$^1$H-NMR(DMSO-$d_6$, 300 MHz); δ=10.80 (br s, 1H), 8.06 (d, J=5.7 Hz, 1H), 7.78 (s, 2H), 7.04 (d, J=5.7 Hz, 1H), 4.55-4.16 (m, 2H), 4.04-3.91 (m, 2H).

MS(ESI); 447.0 (M$^+$+1).

EXAMPLE 31

Synthesis of (2,6-dichloro-pyridin-4-yl)-(2,3-dihydro-pyrido[4,3-b][1,4]oxazin-4-yl)-methanone (compound 31)

In a 25 ml flask, 2,6-dichloro-isonicotinic acid (100 mg, 0.52 mmol) was dissolved in thionylchloride (0.76 ml), and a catalytic amount of N,N-dimethyl formamide was added thereto and then stirred for 4 hours under reflux. Thionyl chloride was removed under reduced pressure, and 3,4-dihydro-2H-pyrido[4,3-b][1,4]oxazine (78 mg, 0.57 mmol) and pyridine (0.13 ml) were added to the reaction flask and dissolved in N,N-dimethyl acetamide (2.6 ml) and then stirred at room temperature for 18 hours. The reaction mixture was extracted with dichloromethane, and the combined organic layer was dried over anhydrous magnesium sulfate ($MgSO_4$) and evaporated under reduced pressure. The residue was purified by column chromatography on silica eluting with a solvent of n-hexane:ethyl acetate=2:1. The fractions containing the product were collected and evaporated to obtain the target compound 31 as yellow solid (116 mg, 72%).

$^1$H-NMR(DMSO-$d_6$, 300 MHz); δ=9.18 (br s, 1H), 8.15 (d, J=5.7 Hz, 1H), 7.81 (s, 2H), 6.99 (d, J=5.7 Hz, 1H), 4.55-4.25 (m, 2H), 3.94-3.86 (m, 2H).

MS(ESI); 310.1 ($M^+$+1).

EXAMPLE 32

Synthesis of (2,3-dihydro-pyrido[4,3-b][1,4]oxazin-4-yl)-(6-hydroxy-pyridin-3-yl)-methanone (compound 32)

In a 25 ml flask, 6-hydroxy-nicotinic acid (102 mg, 0.73 mmol) was dissolved in N,N-dimethyl acetamide (2.7 ml) and then cooled to −15□. Thionyl chloride (0.06 ml) was added thereto and the temperature was slowly raised up to −5□ and then stirred at −5□ for 30 minutes. The mixture was cooled again to −15□ and then 3,4-dihydro-2H-pyrido[4,3-b][1,4]oxazine (100 mg, 0.73 mmol) and potassium carbonate (127 mg, 0.82 mmol) were added thereto and stirred for 10 minutes. The temperature was raised up to room temperature and then stirred for 14 hours. Ethyl acetate was added to the reaction mixture, and the mixture was neutralized with saturated solution of sodium hydrogen carbonate and evaporated under reduced pressure. The residue was purified by column chromatography on amine silica eluting with a solvent of dichloromethane:methanol=50:1. The fractions containing the product were collected and evaporated to obtain the target compound 32 as white solid (86 mg, 45%).

$^1$H-NMR(DMSO-$d_6$, 300 MHz); δ=12.0 (br s, 1H), 8.43 (s, 1H), 8.06 (d, J=5.7 Hz, 1H), 7.77 (d, J=2.1 Hz, 1H), 7.56 (dd, J=2.7 Hz, 9.3 Hz, 1H), 6.94 (d, J=5.7 Hz, 1H), 6.34 (d, J=9.3 Hz, 1H), 4.45-4.25 (m, 2H), 4.00-3.92 (m, 2H).

MS(ESI); 258.1 ($M^+$+1).

EXAMPLE 33

Synthesis of (3,5-dibromo-4-hydroxy-phenyl)-(2,3-dihydro-pyrido[4,3-b][1,4]oxazin-4-yl)-methanone hydrochloric acid salt (compound 33)

In a 25 ml flask, (3,5-dibromo-4-hydroxy-phenyl)-(2,3-dihydro-pyrido[4,3-b][1,4]oxazin-4-yl)-methanone (510 mg, 1.23 mmol) and tetrahydrofuran (40 ml) were added and stirred at 750 for 20 minutes. 4.0M Hydrochloric acid dissolved in 1,4-dioxane (0.34 ml, 1.36 mmol) was added thereto dropwise and then stirred at 75□ for 10 minutes. The reaction mixture was filtered in hot state without cooling and washed with ether, and the resulting solid was dried under vacuum at 600 for 12 hours to obtain the target compound 33 as white solid (520 mg, 93.7%).

$^1$H-NMR(DMSO-$d_6$, 300 MHz); δ=8.88 (s, 1H), 8.36 (d, J=6.4 Hz, 1H), 7.80 (s, 2H), 7.39 (d, J=6.3 Hz, 1H), 4.54-4.51 (m, 2H), 3.98-3.95 (m, 2H).

MS(ESI); 413.1 ($M^+$+1).

EXAMPLE 34

Synthesis of (3-chloro-4-hydroxy-phenyl)-(2,3-dihydro-pyrido[3,4-b][1,4]oxazin-1-yl)-methanone (compound 34)

a) Synthesis of (3-chloro-4-methoxy-phenyl)-(2,3-dihydro-pyrido[3,4-b][1,4]oxazin-1-yl)-methanone In a 10 ml flask, 2,3-dihydro-1H-pyrido[3,4-b][1,4]oxazine (60 mg, 0.441 mmol) and 3-chloro-4-methoxy-benzoyl chloride (108 mg, 0.529 mmol) were dissolved in dichloromethane (3 ml). Triethylamine (0.12 ml, 0.881 mmol) was added thereto and then stirred at room temperature for 2 hours. After neutralizing with 1N hydrochloric acid solution, the mixture was extracted with dichloromethane, and the combined organic layer was dried over anhydrous sodium sulfate ($Na_2SO_4$), filtered and evaporated under reduced pressure. The residue was purified by column chromatography on silica eluting with a solvent of ethyl acetate:n-hexane=1:1. The fractions containing the product were collected and evaporated to obtain white solid (134 mg, 99.8%).

$^1$H-NMR(DMSO-$d_6$, 300 MHz); δ=8.28 (s, 1H), 7.94 (d, J=5.7 Hz, 1H), 7.64 (d, J=2.3 Hz, 1H), 7.45 (dd, J=2.3 Hz, 8.8 Hz, 1H), 6.98 (d, J=5.3 Hz, 1H), 6.94 (d, J=8.8 Hz, 1H), 4.41-4.38 (m, 2H), 4.01-3.98 (m, 2H), 3.96 (s, 3H).

MS(ESI); 305.1 ($M^+$+1).

b) Synthesis of (3-chloro-4-hydroxy-phenyl)-(2,3-dihydro-pyrido[3,4-b][1,4]oxazin-1-yl)-methanone In a 10 ml flask, (3-chloro-4-methoxy-phenyl)-(2,3-dihydro-pyrido[3,4-b][1,4]oxazin-1-yl)-methanone (134 mg, 0.441 mmol) was dissolved in dichloromethane (5 ml), and the mixture was cooled to 0□. 1.0M Boron tribromide dissolved in dichloromethane (2.2 ml, 2.2 mmol) was added thereto and stirred at room temperature for 16 hours. After neutralizing with saturated solution of sodium hydrogen carbonate to pH 8 to 9, the mixture was adjusted to pH 6 again by using 1N hydrochloric acid and extracted with dichloromethane. The combined organic layer was washed with saturated saline solution and dried over anhydrous sodium sulfate ($Na_2SO_4$), filtered and evaporated under reduced pressure. The residue was purified by column chromatography on silica eluting with a solvent of methanol:dichloromethane=1:20. The fractions containing the product were collected and evaporated to obtain the target compound 34 as white solid (65 mg, 50.9%).

$^1$H-NMR($CD_3OD$, 300 MHz); δ=8.17 (s, 1H), 7.88 (d, J=5.7 Hz, 1H), 7.64 (d, J=1.9 Hz, 1H), 7.42 (dd, J=1.9 Hz, 8.8 Hz, 1H), 7.33 (d, J=5.7 Hz, 1H), 6.98 (d, J=8.4 Hz, 1H), 4.39 (m, 2H), 4.00 (m, 2H).

MS(ESI); 291.1 ($M^+$+1).

EXAMPLE 35

Synthesis of 2,6-dibromo-4-(2,3-dihydro-pyrido[4,3-b][1,4]oxazin-4-sulfonyl)-phenol (compound 35-2)

a) Synthesis of 4-(4-methoxy-benzenesulfonyl)-3,4-dihydro-2H-pyrido[4,3-b][1,4]oxazine In a 25 ml flask, 3,4-dihydro-2H-pyrido[4,3-b][1,4]oxazine (370 mg, 2.72 mmol) and 4-methoxy-benzenesulfonyl chloride (618 mg, 2.99 mmol) were dissolved in dichloromethane (10 ml). Triethylamine (0.45 ml, 3.23 mmol) was added thereto and then stirred at room temperature for 2 hours. After neutralizing with 1N hydrochloric acid solution, the mixture was extracted with dichloromethane, and the combined organic layer was dried over anhydrous sodium sulfate (Na$_2$SO$_4$), filtered and evaporated under reduced pressure. The residue was purified by column chromatography on silica eluting with a solvent of dichloromethane. The fractions containing the product were collected and evaporated to obtain pale-green solid (700 mg, 84.1%).

$^1$H-NMR(DMSO-d$_6$, 300 MHz); δ=8.98 (s, 1H), 8.21 (d, J=5.3 Hz, 1H), 7.62-7.57 (m, 2H), 6.96-6.91 (m, 2H), 6.75 (d, J=5.7 Hz, 1H), 3.88-3.79 (m, 7H).

MS(ESI); 307 (M$^+$+1).

b) Synthesis of 4-(2,3-dihydro-pyrido[4,3-b][1,4]oxazin-4-sulfonyl)-phenol (compound 35-1)

In a 100 ml flask, 4-(4-methoxy-benzenesulfonyl)-3,4-dihydro-2H-pyrido[4,3-b][1,4]oxazine (699 mg, 2.282 mmol) was dissolved in dichloromethane (30 ml) and the mixture was cooled to 0□. 1.0M Boron tribromide dissolved in dichloromethane (11.4 ml, 11.4 mmol) was added thereto and stirred at room temperature for 16 hours. After neutralizing with saturated solution of sodium hydrogen carbonate to pH 8 to 9, the mixture was adjusted to pH 6 again by using 1N hydrochloric acid and extracted with dichloromethane. The combined organic layer was washed with saturated saline solution and dried over anhydrous sodium sulfate (Na$_2$SO$_4$), filtered and evaporated under reduced pressure. The residue was purified by column chromatography on silica eluting with a solvent of methanol:dichloromethane=1:20. The fractions containing the product were collected and evaporated to obtain white solid (375 mg, 56.2%).

$^1$H-NMR(DMSO-d$_6$, 300 MHz); δ=10.80 (br s, 1H), 8.73 (s, 1H), 8.15 (d, J=5.7 Hz, 1H), 7.50-7.45 (m, 2H), 6.91-6.87 (m, 3H), 3.85-3.82 (m, 2H), 3.75-3.72 (m, 2H).

MS(ESI); 293.1 (M$^+$+1).

c) Synthesis of 2,6-dibromo-4-(2,3-dihydro-pyrido[4,3-b][1,4]oxazin-4-sulfonyl)-phenol In a 25 ml flask, 4-(2,3-dihydro-pyrido[4,3-b][1,4]oxazin-4-sulfonyl)-phenol (364 mg, 1.25 mmol) and methanol (7 ml) were added and the temperature was set to −25□. 1,3-dibromo-5,5'-dimethylhydantoin (20.4 mg, 0.07 mmol) dissolved in methanol (1 ml) was added thereto dropwise at −25□. After stirring at −25□ for 30 minutes, 1,3-dibromo-5, 5'-dimethylhydantoin (20.4 mg, 0.07 mmol) dissolved in methanol (1 ml) was further added thereto dropwise at −25□. After completion of the reaction, water (10 ml) was added thereto and the mixture was extracted with ethyl acetate, and the combined organic layer was washed with saturated saline solution and dried over anhydrous sodium sulfate (Na$_2$SO$_4$), filtered and evaporated under reduced pressure. The residue was purified by column chromatography on silica eluting with a solvent of methanol:dichloromethane=1:20. The fractions containing the product were collected and evaporated to obtain pale-green solid. The resulting solid was recrystallized from diethyl ether to obtain the target compound 35-2 as white solid (392 mg, 69.9%).

$^1$H-NMR(DMSO-d$_6$, 300 MHz); δ=8.78 (s, 1H), 8.25 (d, J=5.3 Hz, 1H), 7.80 (s, 2H), 7.03 (d, J=5.7 Hz, 1H), 3.93 (s, 4H).

MS(ESI); 448.7 (M$^+$+1).

EXAMPLE 36

Synthesis of (3-chloro-4-hydroxy-5-nitro-phenyl)-(2, 3-dihydro-pyrido[3,4-b][1,4]oxazin-1-yl)-methanone (compound 36)

a) Synthesis of (3-chloro-4-methoxy-5-nitro-phenyl)-(2,3-dihydro-pyrido[3,4-b][1,4]oxazin-1-yl)-methanone In a 10 ml flask, 2,3-dihydro-1H-pyrido[3,4-b][1,4]oxazine (96.2 mg, 0.706 mmol) and 3-chloro-4-methoxy-5-nitro-benzoyl chloride (194 mg, 0.777 mmol) were dissolved in dichloromethane (3 ml). Triethylamine (0.15 ml, 1.059 mmol) was added thereto and then stirred at room temperature for 2 hours. After neutralizing with 1N hydrochloric acid solution, the mixture was extracted with dichloromethane, and the combined organic layer was dried over anhydrous sodium sulfate (Na$_2$SO$_4$), filtered and evaporated under reduced pressure. The residue was purified by column chromatography on silica eluting with a solvent of ethyl acetate: n-hexane=1:1. The fractions containing the product were collected and evaporated to obtain yellow solid (206 mg, 83.4%).

$^1$H-NMR(CDCl$_3$, 300 MHz); δ=8.33 (s, 1H), 8.03 (d, J=5.7 Hz, 1H), 7.90 (d, J=2.3 Hz, 1H), 7.83 (d, J=2.3 Hz, 1H), 7.11 (d, J=5.7 Hz, 1H), 4.44-4.40 (m, 2H), 4.10 (s, 3H), 4.01-3.98 (m, 2H).

b) Synthesis of (3-chloro-4-hydroxy-5-nitro-phenyl)-(2,3-dihydro-pyrido[3,4-b][1,4]oxazin-1-yl)-methanone In a 25 ml flask, (3-chloro-4-methoxy-5-nitro-phenyl)-(2, 3-dihydro-pyrido[3,4-b][1,4]oxazin-1-yl)-methanone (176 mg, 0.441 mmol), lithium chloride (42.7 mg, 1.006 mmol), piperazine (65 mg, 0.755 mmol) and N,N-dimethyl formamide (5 ml) were added and stirred at 1000 for 30 minutes. Lithium chloride (42.7 mg, 1.006 mmol) was further added thereto and then stirred at 1000 for 2 hours. After neutralizing with saturated solution of sodium hydrogen carbonate to pH 8 to 9, the mixture was adjusted to pH 6 again by using 1N hydrochloric acid to form solid. The resulting solid was filtered and recrystallized from methanol and tetrahydrofuran to obtain the target compound 36 as yellow solid (153 mg, 91%).

$^1$H-NMR(DMSO-d$_6$, 300 MHz); δ=8.38 (s, 1H), 8.13 (d, J=2.3 Hz, 1H), 8.06 (d, J=5.7 Hz, 1H), 7.85 (d, J=2.3 Hz, 1H), 7.56 (d, J=5.7 Hz, 1H), 4.40-4.36 (m, 2H), 3.96-3.93 (m, 2H).

MS(ESI); 336.0 (M$^+$+1).

EXAMPLE 37

Synthesis of (3-chloro-4-hydroxy-phenyl)-(2,3-dihydro-pyrido[4,3-b][1,4]oxazin-4-yl)-methanone (compound 37)

In a 25 ml flask, (3-chloro-4-methoxy-phenyl)-(2,3-dihydro-pyrido[4,3-b][1,4]oxazin-4-yl)-methanone (223 mg, 0.73 mmol) was dissolved in dichloromethane, and the mixture was cooled to 0□. 1.0M Boron tribromide dissolved in dichloromethane (3.65 ml, 3.65 mmol) was added thereto and stirred at room temperature for 16 hours. n-hexane solvent was added thereto and the formed solid was filtered. The resulting solid was dissolved in methanol and concentrated. After adding and dissolving in water, the mixture was adjusted to pH 6 with saturated solution of sodium hydrogen carbonate and then extracted with dichloromethane. The combined organic layer was dried over anhydrous sodium sulfate ($Na_2SO_4$), filtered and evaporated under reduced pressure. The residue was recrystallized from dichloromethane and n-hexane to obtain the target compound 37 as white solid (80 mg, 38%).

$^1$H-NMR(DMSO-$d_6$, 300 MHz); δ=10.92 (br s, 1H), 8.37 (br s, 1H), 8.05 (d, J=5.3 Hz, 1H), 7.58 (d, J=2.3 Hz, 1H), 7.38 (dd, J=8.4 Hz, 2.3 Hz, 1H), 7.01 (d, J=8.4 Hz, 1H), 6.94 (d, J=5.3 Hz, 1H), 4.38 (m, 2H), 3.91 (m, 2H).

MS(ESI); 291.2 ($M^+$+1).

EXAMPLE 38

Synthesis of (3-bromo-4-hydroxy-phenyl)-(2,3-dihydro-pyrido[4,3-b][1,4]oxazin-4-yl)-methanone (compound 38)

By the same method as in Example 3, (3-bromo-4-methoxy-phenyl)-(2,3-dihydro-pyrido[4,3-b][1,4]oxazin-4-yl)-methanone (296 mg, 0.85 mmol) and 1M solution of boron tribromide (4.25 ml, 4.25 mmol) were reacted to obtain the target compound 38, i.e., (3-bromo-4-hydroxy-phenyl)-(2,3-dihydro-pyrido[4,3-b][1,4]oxazin-4-yl)-methanone (256 mg, 89%).

$^1$H-NMR(DMSO-$d_6$, 300 MHz); δ=8.37 (br s, 1H), 8.05 (d, J=5.7 Hz, 1H), 7.71 (d, J=1.9 Hz, 1H), 7.41 (dd, J=8.0 Hz, 1.9 Hz, 1H), 6.98 (d, J=8.8 Hz, 1H), 6.94 (d, J=5.7 Hz, 1H), 4.56 (m, 2H), 4.01 (m, 2H).

MS(ESI); 335.1 ($M^+$+1).

EXAMPLE 39

Synthesis of (3,5-dichloro-4-hydroxy-phenyl)-(2,3-dihydro-pyrido[4,3-b][1,4]oxazin-4-yl)-methanone (compound 39)

In a 25 ml flask, (3,5-chloro-4-methoxy-phenyl)-(2,3-dihydro-pyrido[4,3-b][1,4]oxazin-4-yl)-methanone (344 mg, 1.0 mmol), lithium chloride (219 mg, 6 mmol) and piperazine (105 mg, 1.2 mmol) were dissolved in N,N-dimethyl formamide. After stirring at 100□ for 2 hours, water was added to quench the reaction. The mixture was adjusted to pH 6 by using 1N hydrochloric acid, and the formed solid was filtered and washed with distilled water and ether. The resulting solid was recrystallized from dichloromethane and n-hexane to obtain the target compound 39, i.e., (3,5-dibromo-4-hydroxy-phenyl)-(2,3-dihydro-pyrido[4,3-b][1,4]oxazin-4-yl)-methanone (48 mg, 16%).

$^1$H-NMR(DMSO-$d_6$, 300 MHz); δ=8.43 (br s, 1H), 8.08 (br s, 1H), 7.58 (s, 2H), 6.95 (d, J=5.3 Hz, 1H), 4.39 (m, 2H), 3.90 (m, 2H).

MS(ESI); 325.0 ($M^+$+1).

EXAMPLE 40

Synthesis of (3-bromo-4-hydroxy-phenyl)-(2,3-dihydro-pyrido[3,4-b][1,4]oxazin-1-yl)-methanone (compound 40)

By the same method as in Example 3, (3-bromo-4-methoxy-phenyl)-(2,3-dihydro-pyrido[3,4-b][1,4]oxazin-1-yl)-methanone (200 mg, 0.58 mmol) and 1M solution of boron tribromide (2.9 ml, 2.9 mmol)) were reacted to obtain the target compound 40, i.e., (3-bromo-4-hydroxy-phenyl)-(2,3-dihydro-pyrido[3,4-b][1,4]oxazin-1-yl)-methanone, as beige solid (95 mg, 49%).

$^1$H-NMR(DMSO-$d_6$, 300 MHz); δ=11.1 (br s, 1H), 8.21 (s, 1H), 7.94 (d, J=5.3 Hz, 1H), 7.77 (d, J=1.9 Hz, 1H), 7.47 (dd, J=8.4 Hz, 1.9 Hz, 1H), 7.32 (d, J=5.3 Hz, 1H), 7.01 (d, J=8.4 Hz, 1H), 4.33 (m, 2H), 3.90 (m, 2H).

MS(ESI); 335.1 ($M^+$+1).

EXAMPLE 41

Synthesis of (3,5-dichloro-4-hydroxy-phenyl)-(2,3-dihydro-pyrido[3,4-b][1,4]oxazin-1-yl)-methanone (compound 41)

By the same method as in Example 39, (3,5-dichloro-4-methoxy-phenyl)-(2,3-dihydro-pyrido[3,4-b][1,4]oxazin-1-yl)-methanone (100 mg, 0.29 mmol), lithium chloride (124 mg, 2.9 mmol) and piperazine (38 mg, 0.44 mmol) were reacted. The resulting solid was purified by recrystallizing from methanol to obtain the target compound 41 as pale-brown solid (40 mg, 47%).

$^1$H-NMR(DMSO-$d_6$, 300 MHz); δ=10.9 (br s, 1H), 8.21 (s, 1H), 7.95 (d, J=5.3 Hz, 1H), 7.64 (s, 2H), 7.40 (d, J=5.3 Hz, 1H), 4.33 (m, 2H), 3.89 (m, 2H).

MS(ESI); 325.1 ($M^+$+1).

EXAMPLE 42

Synthesis of 2-(3,5-dibromo-4-hydroxy-phenyl)-1-(2,3-dihydro-pyrido[4,3-b][1,4]oxazin-4-yl)-ethanone (compound 42)

a) Synthesis of 1-(2,3-dihydro-pyrido[4,3-b][1,4]oxazin-4-yl)-2-(4-methoxy-phenyl)-ethanone In a 10 ml flask, 3,4-dihydro-2H-pyrido[4,3-b][1,4]oxazine (100 mg, 0.73 mmol) and (4-methoxy-phenyl)-acetyl chloride (163 mg, 0.88 mmol) were dissolved in dichloromethane. Triethylamine (0.21 ml, 1.46 mmol) was added thereto and then stirred at room temperature for 2 hours. After completion of the reaction by adding water, the reaction mixture was extracted with dichloromethane. The combined organic layer was dried over anhydrous sodium sulfate ($Na_2SO_4$), filtered and evaporated under reduced pressure. The residue was purified by column chromatography on silica eluting with a solvent of dichloromethane:methanol=9:1. The fractions containing the product were collected and evaporated to obtain the target compound, i.e., 1-(2,3-dihydro-pyrido[4,3-b][1,4]oxazin-4-yl)-2-(4-methoxy-phenyl)-ethanone, as yellow liquid (198 mg, 95%).

$^1$H-NMR(CDCl$_3$, 300 MHz); δ=8.51 (br s, 1H), 8.22 (d, J=5.3 Hz, 1H), 7.23 (d, 2H, J=8.4 Hz), 6.85 (d, J=8.4 Hz, 2H), 6.81 (d, J=5.3 Hz, 1H), 4.21 (br s, 2H), 3.94 (br s, 2H), 3.91 (s, 2H), 3.79 (s, 3H).

MS(ESI); 285.1 ($M^+$+1).

b) Synthesis of 1-(2,3-dihydro-pyrido[4,3-b][1,4]oxazin-4-yl)-2-(4-hydroxy-phenyl)-ethanone By the same method as in Example 3,1-(2,3-dihydro-pyrido[4,3-b][1,4]oxazin-4-yl)-2-(4-methoxy-phenyl)-ethanone (130 mg, 0.46 mmol) and 1M solution of boron tribromide (2.3 ml, 2.3 mmol) were reacted to obtain the target compound, i.e., 1-(2,3-dihydro -pyrido[4,3-b][1,4]oxazin-4-yl)-2-(4-hydroxy-phenyl)-ethanone, as yellow liquid (100 mg, 81%).

$^1$H-NMR(CDCl$_3$, 300 MHz); δ=9.29 (br s, 1H), 8.97 (br s, 1H), 8.10 (d, J=5.7 Hz, 1H), 7.02 (d, 2H, J=8.4 Hz), 6.90 (d, J=5.7 Hz, 2H), 6.69 (d, J=8.4 Hz, 1H), 4.22 (m, 2H), 3.90 (br s, 2H), 3.85 (s, 2H).

MS(ESI); 271.1 ($M^+$+1).

c) Synthesis of 2-(3,5-dibromo-4-hydroxy-phenyl)-1-(2,3-dihydro-pyrido[4,3-b][1,4]oxazin-4-yl)-ethanone In a 10 ml flask, 1-(2,3-dihydro-pyrido[4,3-b][1,4]oxazin-4-yl)-2-(4-hydroxy-phenyl)-ethanone (88 mg, 0.33 mmol) and hydantoin (93 mg, 0.33 mmol) were dissolved in a solvent of methanol:dichloromethane=2:1. The mixture was stirred at −300 for 0.5 hour. After completion of the reaction by adding water, the reaction mixture was extracted with dichloromethane, and the combined organic layer was dried over anhydrous sodium sulfate ($Na_2SO_4$), filtered and evaporated under reduced pressure. The residue was purified by recrystallizing from dichloromethane to obtain the target compound 42, i.e., 2-(3,5-dibromo-4-hydroxy-phenyl)-1-(2,3-dihydro -pyrido[4,3-b][1,4]oxazin-4-yl)-ethanone, as beige solid (13.8 mg, 10%).

$^1$H-NMR($CDCl_3$, 300 MHz); δ=9.81 (br s, 1H), 8.94 (br s, 1H), 8.11 (d, J=5.3 Hz, 1H), 7.41 (s, 2H), 6.93 (d, J=5.3 Hz, 1H), 4.37 (m, 2H), 3.94 (m, 2H), 3.92 (s, 2H).

MS(ESI); 426.9 ($M^+$+1).

EXAMPLE 43

Synthesis of (2,3-dihydro-pyrido[4,3-b][1,4]oxazin-4-yl)-(3-methoxy-isoxazol-5-yl)-methanone (compound 43)

In a 10 ml flask, 3,4-dihydro-2H-pyrido[4,3-b][1,4]oxazine (100 mg, 0.73 mmol) and 3-methoxy-isoxazol-5-carbonyl chloride (131 mg, 0.80 mmol) were dissolved in dichloromethane. Triethylamine (0.51 ml, 3.65 mmol) was added thereto and then stirred at room temperature for 2 hours. After completion of the reaction by adding water dropwise, the reaction mixture was extracted with dichloromethane, and the combined organic layer was dried over anhydrous sodium sulfate ($Na_2SO_4$), filtered and evaporated under reduced pressure. The residue was purified by column chromatography on amine silica eluting with a solvent of dichloromethane:methanol=30:1. The fractions containing the product were collected and evaporated to obtain the target compound 43, i.e., (2,3-dihydro-pyrido[4,3-b][1,4]oxazin-4-yl)-(3-methoxy-isoxazol-5-yl)-methanone, as pale-brown solid (149 mg, 78%).

$^1$H-NMR($CDCl_3$, 300 MHz); δ=8.77 (br s, 1H), 8.16 (d, 1H, J=5.3 Hz), 6.98 (d, J=5.3 Hz, 1H), 6.88 (s, 1H), 4.42 (m, 2H), 4.04 (m, 2H), 3.96 (s, 3H).

MS(ESI); 262.1 ($M^+$+1).

EXAMPLE 44

Synthesis of (2,3-dihydro-pyrido[4,3-b][1,4]oxazin-4-yl)-(3-hydroxy-isoxazol-5-yl)-methanone (compound 44)

a) Synthesis of (3-benzyloxy-isoxazol-5-yl)-(2,3-dihydro-pyrido[4,3-b][1,4]oxazin-4-yl)-methanone To 10 ml of anhydrous tetrahydrofuran, 3-benzyloxy-isoxazol-5-carboxylic acid (50 mg, 0.23 mmol) and a catalytic amount of N,N-dimethyl formamide were added and dissolved, and then oxalyl chloride (35 mg, 0.28 mmol) was slowly added thereto and then stirred at room temperature for 4 hours.

The reaction mixture was concentrated under reduced pressure. The residue was dissolved in dichloromethane, triethylamine (115 mg, 1.15 mmol) and 3,4-dihydro-2H-pyrido[4,3-b][1,4]oxazine (31 mg, 0.23 mmol) were added thereto and then stirred at room temperature for 2 hours. After completion of the reaction by adding water dropwise, the reaction mixture was extracted with dichloromethane, and the combined organic layer was dried over anhydrous sodium sulfate ($Na_2SO_4$), filtered and evaporated under reduced pressure. The residue was purified by column chromatography on amine silica eluting with a solvent of dichloromethane:methanol=30:1. The fractions containing the product were collected and evaporated to obtain (3-benzyloxy-isoxazol-5-yl)-(2,3-dihydro-pyrido[4,3-b][1,4]oxazin-4-yl)-methanone as pale-brown liquid (55 mg, 54% in two steps).

$^1$H-NMR($CDCl_3$, 300 MHz); δ=8.23 (d, 1H, J=5.3 Hz), 7.32-7.48 (m, 6H), 6.87 (d, 1H, J=5.3 Hz), 6.52 (br s, 1H), 5.30 (s, 2H), 4.44 (m, 2H), 4.13 (m, 2H).

MS(ESI); 338.1 ($M^+$+1).

b) Synthesis of (2,3-dihydro-pyrido[4,3-b][1,4]oxazin-4-yl) -(3-hydroxy-isoxazol-5-yl)-methanone In 3 ml of 33% hydrobromic acid in acetic acid solution, (3-benzyloxy -isoxazol-5-yl)-(2,3-dihydro-pyrido[4,3-b][1,4]oxazin-4-yl)-methanone (45 mg, 0.13 mmol) was dissolved and then stirred at room temperature for 24 hours. After completion of the reaction by adding water dropwise, the mixture was adjusted to weak acidic condition (pH=6) by using saturated solution of sodium hydrogen carbonate and extracted with ethyl acetate. The aqueous layer was evaporated under reduced pressure and the residue was purified by using preparative TLC plate to obtain the target compound 44, i.e., (2,3-dihydro-pyrido[4,3-b][1,4]oxazin-4-yl)-(3-hydroxy-isoxazol-5-yl)-methanone, as white solid (8 mg, 24%).

$^1$H-NMR(DMSO-$d_6$, 300 MHz); δ=8.70 (br s, 1H), 8.13 (d, J=5.3 Hz, 1H), 6.97 (d, J=5.3 Hz, 1H), 6.25 (br s, 1H), 4.40 (m, 2H), 4.04 (m, 2H).

MS(ESI); 248.1 ($M^+$+1).

EXAMPLE 45

Synthesis of (3,5-dibromo-4-hydroxy-phenyl)-[7-(4-trifluoromethyl -phenyl)-2,3-dihydro-pyrido[2,3-b][1,4]oxazin-1-yl]-methanone (compound 45)

a) Synthesis of 7-bromo-2,3-dihydro-1H-pyrido[2,3-b][1,4]oxazine 7-bromo-1H-pyrido[2,3-b][1,4]oxazin-2-one (1.3 g, 5.68 mmol) was dissolved in 30 ml of anhydrous tetrahydrofuran under nitrogen atmosphere and the mixture was cooled to 0□. 1.0M Lithium aluminum hydride dissolved in tetrahydrofuran (6.90 ml, 6.82 mmol) was added thereto dropwise and then stirred for 30 minutes. To the reaction mixture, water (0.3 ml), 10% sodium hydroxide (0.6 ml) and water (0.9 ml) were added dropwise in this order and then stirred vigorously at room temperature for 1 hour. The resulting solid was filtered and washed with excess ethyl acetate. The filtrate was washed with water and saturated saline solution, dried over anhydrous sodium sulfate ($Na_2SO_4$), filtered and evaporated under reduced pressure to obtain 7-bromo-2,3-dihydro-1H-pyrido[2,3-b][1,4]oxazine as white solid (629 mg, 52%).

$^1$H-NMR($CDCl_3$, 300 MHz); δ=7.63 (d, J=2.3 Hz, 1H), 6.96 (d, J=2.3 Hz, 1H), 4.39 (m, 2H), 3.93 (br s, 1H), 3.42 (m, 2H).

MS(ESI); 215.0 ($M^+$+1).

b) Synthesis of 7-(4-trifluoromethyl-phenyl)-2,3-dihydro-1H-pyrido[2,3-b][1,4]oxazine To 3 ml of tetrahydrofuran and 0.5 ml of distilled water, 7-bromo-2,3-dihydro-1H-pyrido[2,3-b][1,4]oxazine (80.0 mg, 0.37 mmol), 4-fluoromethyl-phenyl boronic acid (78 mg, 0.41 mmol), potassium carbonate (103 mg, 0.74 mmol) and tetrakis triphenylphosphine palladium (21 mg, 0.02 mmol) were added and then stirred at 800 for 2 hours. After completion of the reaction, the mixture was extracted with ethyl acetate, and the combined organic layer was dried over anhydrous sodium sulfate ($Na_2SO_4$), filtered and evaporated under reduced pressure. The residue was purified by column chromatography on amine silica eluting with a solvent of dichloromethane:methanol=50:1. The fractions containing the product were collected and evaporated to obtain 7-(4-trifluoromethyl-phenyl)-2,3-dihydro-1H-pyrido[2,3-b][1,4]oxazine as white solid (77 mg, 74%).

$^1$H-NMR($CDCl_3$+$CD_3OD$, 300 MHz); δ=7.77 (d, J=2.3 Hz, 1H), 7.67 (d, J=8.4 Hz, 2H), 7.60 (d, J=8.4 Hz, 2H), 7.11 (d, J=2.3 Hz, 1H), 4.46 (m, 2H), 3.46 (m, 2H).

MS(ESI); 281.1 ($M^+$+1).

c) Synthesis of (3,5-dibromo-4-methoxy-phenyl)-[7-(4-trifluoromethyl-phenyl)-2,3-dihydro-pyrido[2,3-b][1,4]oxazin-1-yl]-methanone In a 10 ml flask, 7-(4-trifluoromethyl-phenyl)-2,3-dihydro-1H-pyrido[2,3-b][1,4]oxazine (67 mg, 0.24 mmol) and 3,5-dibromo-4-methoxy-benzoyl chloride (118 mg, 0.36 mmol) were dissolved in dichloromethane. Triethylamine (0.17 ml, 1.20 mmol) was added thereto and then stirred at room temperature for 2 hours. After completion of the reaction by adding water dropwise, the mixture was extracted with dichloromethane, and the combined organic layer was dried over anhydrous sodium sulfate ($Na_2SO_4$), filtered and evaporated under reduced pressure. The residue was purified by column chromatography on silica eluting with a solvent of dichloromethane:methanol=19:1. The fractions containing the product were collected and evaporated to obtain (3,5-dibromo-4-methoxy-phenyl)-[7-(4-trifluoromethyl-phenyl)-2,3-dihydro-pyrido[2,3-b][1,4]oxazin-1-yl]-methanone as white solid (122 mg, 89%).

$^1$H-NMR($CDCl_3$, 300 MHz); δ=8.29 (d, J=2.3 Hz, 1H), 8.24 (s, 1H), 7.73 (s, 2H), 7.67 (d, J=8.4 Hz, 2H), 7.50 (d, J=8.4 Hz, 2H), 4.53 (m, 2H), 4.02 (m, 2H), 3.95 (s, 3H).

MS(ESI); 570.9 ($M^+$+1).

d) Synthesis of (3,5-dibromo-4-hydroxy-phenyl)-[7-(4-trifluoromethyl-phenyl)-2,3-dihydro-pyrido[2,3-b][1,4]oxazin-1-yl]-methanone In a 10 ml flask, (3,5-dibromo-4-methoxy-phenyl)-[7-(4-trifluoromethyl-phenyl)-2,3-dihydro-pyrido[2,3-b][1,4]oxazin-1-yl]-methanone (122 mg, 0.21 mmol), lithium bromide (148 mg, 1.71 mmol) and piperazine (28 mg, 0.32 mmol) were dissolved in 3 ml of N,N-dimethyl formamide and then stirred at 1000 for 2 hours. After completion of the reaction by adding water dropwise, the mixture was adjusted to weak acidic condition (pH=6) by using 1N hydrochloric acid. The formed solid was filtered and washed with distilled water. The resulting solid was recrystallized from tetrahydrofuran and methanol to obtain the target compound 45, i.e., (3,5-dibromo-4-hydroxy-phenyl)-[7-(4-trifluoromethyl-phenyl)-2,3-dihydro-pyrido[2,3-b][1,4]oxazin-1-yl]-methanone (59 mg, 50%).

$^1$H-NMR($CDCl_3$, 300 MHz); δ=8.28 (d, J=1.9 Hz, 1H), 8.03 (br s, 1H), 7.73 (s, 2H), 7.67 (d, J=8.0 Hz, 2H), 7.51 (d, J=8.0 Hz, 2H), 6.28 (br s, 1H), 4.52 (m, 2H), 4.03 (m, 2H).

MS(ESI); 556.9 ($M^+$+1).

EXAMPLE 46

Synthesis of (3,5-dibromo-4-hydroxy-phenyl)-[7-(2-trifluoromethyl-phenyl)-2,3-dihydro-pyrido[2,3-b][1,4]oxazin-1-yl]-methasone (compound 46)

a) Synthesis of 7-(2-trifluoromethyl-phenyl)-2,3-dihydro-1H-pyrido[2,3-b][1,4]oxazine To 3 ml of tetrahydrofuran/0.5 ml of distilled water, 7-bromo-2,3-dihydro-1H-pyrido[2,3-b][1,4]oxazine (80.0 mg, 0.37 mmol), 2-trifluoromethyl-phenyl boronic acid (78 mg, 0.41 mmol), potassium carbonate (103 mg, 0.74 mmol) and tetrakis triphenylphosphine palladium (21 mg, 0.02 mmol) were added and then stirred at 800 for 2 hours. After completion of the reaction, the mixture was extracted with ethyl acetate, and the combined organic layer was dried over anhydrous sodium sulfate ($Na_2SO_4$), filtered and evaporated under reduced pressure. The residue was purified by column chromatography on amine silica eluting with a solvent of dichloromethane:methanol=50:1. The fractions containing the product were collected and evaporated to obtain 7-(2-trifluoromethyl-phenyl)-2,3-dihydro-1H-pyrido[2,3-b][1,4]oxazine as white solid (67 mg, 64%).

$^1$H-NMR($CDCl_3$, 300 MHz); δ=7.74 (d, J=7.2 Hz, 1H), 7.60-7.44 (m, 3H), 7.31 (d, J=7.6 Hz, 1H), 6.85 (d, J=1.9 Hz, 1H), 4.47 (m, 2H), 3.88 (br s, 1H), 3.48 (m, 2H).

MS(ESI); 281.1 ($M^+$+1).

b) Synthesis of (3,5-dibromo-4-methoxy-phenyl)-[7-(2-trifluoromethyl-phenyl)-2,3-dihydro-pyrido[2,3-b][1,4]oxazin-1-yl]-methanone In a 10 ml flask, 7-(2-trifluoromethyl-phenyl)-2,3-dihydro-1H-pyrido[2,3-b][1,4]oxazine (67 mg, 0.24 mmol) and 3,5-dibromo-4-methoxy-benzoyl chloride (118 mg, 0.36 mmol) were dissolved in dichloromethane. Triethylamine (0.17 ml, 1.20 mmol) was added thereto and then stirred at room temperature for 2 hours. After completion of the reaction by adding water dropwise, the mixture was extracted with dichloromethane, and the combined organic layer was dried over anhydrous sodium sulfate ($Na_2SO_4$), filtered and evaporated under reduced pressure. The residue was purified by column chromatography on silica eluting with a solvent of dichloromethane. The fractions containing the product were collected and evaporated to obtain (3,5-dibromo-4-methoxy-phenyl)-[7-(2-trifluoromethyl-phenyl)-2,3-dihydro-pyrido[2,3-b][1,4]oxazin-1-yl]-methanone as white solid (46 mg, 34%).

$^1$H-NMR($CDCl_3$, 300 MHz); δ=7.99 (d, J=2.3 Hz, 1H), 7.72 (d, J=7.2 Hz, 1H), 7.68 (s, 2H), 7.58-7.48 (m, 3H), 7.20 (d, J=7.6 Hz, 1H), 4.57 (m, 2H), 4.04 (m, 2H), 3.92 (s, 3H).

MS(ESI); 570.9 ($M^+$+1).

c) Synthesis of (3,5-dibromo-4-hydroxy-phenyl)-[7-(2-trifluoromethyl-phenyl)-2,3-dihydro-pyrido[2,3-b][1,4]oxazin-1-yl]-methanone In a 10 ml flask, (3,5-dibromo-4-methoxy-phenyl)-[7-(2-trifluoromethyl-phenyl)-2,3-dihydro-pyrido[2,3-b][1,4]oxazin-1-yl]-methanone (46 mg, 0.08 mmol), lithium bromide (56 mg, 0.64 mmol) and piperazine (10 mg, 0.04 mmol) were dissolved in 3 ml of N,N-dimethyl formamide, and then stirred at 100□ for 2 hours. After completion of the reaction by adding water dropwise, the mixture was adjusted to weak acidic condition (pH=6) by using 1N hydrochloric acid. The formed solid was filtered and washed with distilled water. The resulting solid was recrystallized from methanol to obtain the target compound 46, i.e., (3,5-dibromo-4-hydroxy-phenyl)-[7-(2-trifluoromethyl-phenyl)-2,3-dihydro-pyrido[2,3-b][1,4]oxazin-1-yl]-methanone (31 mg, 69%).

$^1$H-NMR(CDCl$_3$, 300 MHz); δ=7.99 (d, 1H, J=1.9 Hz), 7.72 (d, 1H, J=7.6 Hz), 7.68 (s, 2H), 7.60-7.46 (m, 3H), 7.21 (d, 1H, J=6.9 Hz), 6.22 (s, 1H), 4.56 (m, 2H), 4.05 (m, 2H).
MS(ESI); 556.9 (M$^+$+1).

EXAMPLE 47

Synthesis of 1-(3,5-dibromo-4-hydroxy-benzoyl)-2,3-dihydro-1H-pyridolo[2,3-b][1,4]oxazin-7-carbonitrile (compound 47-2)

a) Synthesis of 2,3-dihydro-1H-pyrido[2,3-b][1,4]oxazin-7-carbonitrile

In a 5 ml flask, 7-bromo-2,3-dihydro-1H-pyrido[2,3-b][1,4]oxazine (24 mg, 0.111 mmol) was dissolved in N-methylpyrrolidone (NMP) (20.3 ml), and cuprous cyanide (CuCN) (16 mg, 0.178 mmol) was added thereto and then stirred in microwave at 180□ for 10 minutes using microwave (100 W) apparatus. The reaction mixture was cooled to room temperature and water (10 ml) was added thereto, and extracted with ethyl acetate (10 ml*2). The combined organic layer was dried over anhydrous magnesium sulfate (MgSO$_4$), filtered and evaporated under reduced pressure. The residue was purified by column chromatography on silica eluting with a solvent of dichloromethane:methanol=20:1. The fractions containing the product were collected and evaporated to obtain pale-yellow solid (17 mg, quantitative yield).

$^1$H-NMR (CD$_3$OD, 300 MHz); δ=7.97-7.88 (m, 1H), 7.02 (s, 1H), 4.49 (t, J=4.3 Hz, 2H), 4.19 (br s, 1H), 3.47 (t, J=4.3 Hz, 2H).
MS(ESI); 162 (M$^+$+1).

b) Synthesis of 1-(3,5-dibromo-4-methoxy-benzoyl)-2,3-dihydro-1H-pyrido[2,3-b][1,4]oxazin-7-carbonitrile (compound 47-1)

By the same method as in the step d) of Example 2, 2,3-dihydro-1H-pyrido[2,3-b][1,4]oxazin-7-carbonitrile (7 mg, 0.043 mmol) was reacted with 3,5-dibromo-4-methoxy-benzoyl chloride (21 mg, 0.065 mmol) to obtain 1-(3,5-dibromo-4-methoxy-benzoyl)-2,3-dihydro-1H-pyrido[2,3-b][1,4]oxazin-7-carbonitrile as white solid (14.4 mg, 74%).

$^1$H-NMR (CD$_3$OD, 300 MHz); δ=8.39 (br s, 1H), 8.35 (d, J=1.9 Hz, 1H), 7.69 (s, 2H), 4.50 (t, J=4.5 Hz, 2H), 3.95 (m, 4H).
MS(ESI); 451.9 (M$^+$+1).

c) Synthesis of 1-(3,5-dibromo-4-hydroxy-benzoyl)-2,3-dihydro-1H-pyrido[2,3-b][1,4]oxazin-7-carbonitrile (compound 47-2)

By the same method as in the step f) of Example 22, 1-(3,5-dibromo-4-methoxy-benzoyl)-2,3-dihydro-1H-pyrido[2,3-b][1,4]oxazin-7-carbonitrile (12 mg, 0.026 mmol) was reacted with lithium bromide (LiBr) (4.62 mg, 0.053 mmol) and piperazine (3.4 mg, 0.0399 mmol) to obtain the target compound 47-2, i.e., 1-(3,5-dibromo-4-hydroxy-benzoyl)-2,3-dihydro-1H-pyrido[2,3-b][1,4]oxazin-7-carbonitrile as white solid (9 mg, 78%).

$^1$H-NMR (CD$_3$OD, 300 MHz); δ=8.37 (d, J=1.9 Hz, 1H), 8.32 (d, J=1.9 Hz, 1H), 7.70 (s, 2H), 4.53 (m, 2H), 4.023 (m, 2H).
MS(ESI); 437.8 (M$^+$+1).

EXAMPLE 48

Synthesis of (3,5-dibromo-4-methoxy-phenyl)-[7-(3-dimethylamino-phenyl)-2,3-dihydro-pyrido[2,3-b][1,4]oxazin-1-yl]-methasone (compound 48)

a) Synthesis of [3-(2,3-dihydro-1H-pyrido[2,3-b][1,4]oxazin-7-yl)-phenyl]-dimethyl-amine By the same method as in the step b) of Example 45, 7-bromo-2,3-dihydro-1H-pyrido[2,3-b][1,4]oxazine (98 mg, 0.45 mmol), 3-dimethyl phenyl boronic acid (112 mg, 0.68 mmol), tetrakis triphenylphosphine palladium (26 mg, 0.023 mol) and potassium carbonate (125 mg, 0.91 mmol) were dissolved in tetrahydrofuran/water (2.4 ml/0.4 ml) and reacted at 800 for 6 hours to obtain [3-(2,3-dihydro-1H-pyrido[2,3-b][1,4]oxazin-7-yl)-phenyl]-dimethyl-amine as white solid (102 mg, 89%).
MS(ESI); 256.1 (M$^+$+1).

b) Synthesis of (3,5-dibromo-4-methoxy-phenyl)-[7-(3-nitro-phenyl)-2,3-dihydro-pyrido[2,3-b][1,4]oxazin-1-yl]-methanone By the same method as in the step d) of Example 2, [3-(2,3-dihydro-1H-pyrido[2,3-b][1,4]oxazin-7-yl)-phenyl]-dimethyl-amine (102 mg, 0.39 mmol), 3,5-dibromo-4-methoxy-benzoyl chloride (197 mg, 0.59 mmol) and triethylamine (286 μl, 1.99 mmol) were dissolved in dichloromethane (5 ml) and then stirred at room temperature for 3 hours to obtain the target compound 48, i.e., (3,5-dibromo-4-methoxy-phenyl)-[7-(3-dimethylamino-phenyl)-2,3-dihydro-pyrido[2,3-b][1,4]oxazin-1-yl]-methanone, as white solid (135 mg, 62%).

$^1$H-NMR(CDCl$_3$, 300 MHz); δ=8.25 (d, J=2.3 Hz, 1H), 7.72 (s, 2H), 7.27-7.20 (m, 2H), 6.70 (dd, J=8.4, 2.7 Hz, 1H), 6.65 (d, J=7.6 Hz, 1H), 6.51 (br s, 1H), 4.57-4.51 (m, 2H), 4.07-4.00 (m, 2H), 3.92 (s, 3H), 2.94 (s, 6H).
MS(ESI); 545.9 (M$^+$+1).

EXAMPLE 49

Synthesis of (3,5-dibromo-4-methoxy-phenyl)-[7-(3-nitro-phenyl)-2,3-dihydro-pyrido[2,3-b][1,4]oxazin-1-yl]-methanone (compound 49)

a) Synthesis of 7-(3-nitro-phenyl)-2,3-dihydro-1H-pyrido[2,3-b][1,4]oxazine

By the same method as in the step b) of Example 45, 7-bromo-2,3-dihydro-1H-pyrido[2,3-b][1,4]oxazine (99 mg, 0.46 mmol), 3-nitrophenyl boronic acid (115 mg, 0.69 mmol), palladium triphenylphosphine (26 mg, 0.023 mol) and potassium carbonate (127 mg, 0.92 mmol) were dissolved in tetrahydrofuran/water (2.4 ml/0.4 ml) and then stirred at 80□ for 6 hours to obtain 7-(3-nitro-phenyl)-2,3-dihydro-1H-pyrido[2,3-b][1,4]oxazine as white solid (90.4 mg, 76%).
MS(ESI); 258.0 (M$^+$+1).

b) Synthesis of (3,5-dibromo-4-methoxy-phenyl)-[7-(3-nitro-phenyl)-2,3-dihydro-pyrido[2,3-b][1,4]oxazin-1-yl]-methanone By the same method as in the step d) of Example 2,7-(3-nitro-phenyl)-2,3-dihydro-1H-pyrido[2,3-b][1,4]oxazine (90 mg, 0.35 mmol), 3,5-dibromo-4-methoxy-benzoyl chloride (173 mg, 0.53 mmol), and triethylamine (252 µl, 1.76 mmol) were dissolved in dichloromethane (5 ml), and reacted at room temperature for 3 hours to obtain the target compound 49, i.e., (3,5-dibromo-4-methoxy-phenyl)-[7-(3-nitro-phenyl)-2,3-dihydro-pyrido[2,3-b][1,4]oxazin-1-yl]-methanone, as white solid (134 mg, 70%).

$^1$H-NMR(CDCl$_3$, 300 MHz); δ=8.31 (d, J=2.3 Hz, 1H), 8.27-8.19 (m, 2H), 8.15 (br s, 1H), 7.78-7.71 (m, 3H), 7.61 (t, J=6.8 Hz, 1H), 4.56-4.50 (m, 2H), 4.05-3.99 (m, 2H), 3.96 (s, 3H).

MS(ESI); 547.9 (M$^+$+1).

EXAMPLE 50

Synthesis of (3,5-dibromo-4-hydroxy-phenyl)-[7-(3-nitro-phenyl)-2,3-dihydro-pyrido[2,3-b][1,4]oxazin-1-yl]-methanone (compound 50)

By the same method as in the step f) of Example 22, (3,5-dibromo-4-methoxy-phenyl)-[7-(3-nitro-phenyl)-2,3-dihydro-pyrido[2,3-b][1,4]oxazin-1-yl]-methanone (101 mg, 0.18 mmol), lithium bromide (32 mg, 0.36 mmol), and piperazine (24 mg, 0.28 mmol) were dissolved in N,N-dimethyl formamide (3 ml), and reacted at 100□ to obtain the target compound 50, i.e., (3,5-dibromo-4-hydroxy-phenyl)-[7-(3-nitro-phenyl)-2,3-dihydro-pyrido[2,3-b][1,4]oxazin-1-yl]-methanone, as pale-brown solid (24 mg, 25%).

$^1$H-NMR(DMSO-d$_6$, 300 MHz); δ=8.32 (s, 1H), 8.28 (s, 1H), 8.19 (d, J=9.2 Hz, 2H), 7.99 (d, J=6.9 Hz, 1H), 7.80-7.62 (m, 3H), 4.50-4.32 (m, 2H), 4.10-3.80 (m, 2H).

MS(ESI); 533.9 (M$^+$+1).

EXAMPLE 51

Synthesis of (3,5-dibromo-4-hydroxy-phenyl)-(2,3-dihydro-pyrido[4,3-b][1,4]oxazin-4-yl)-methanethione (compound 51)

a) Synthesis of (3,5-dibromo-4-methoxy-phenyl)-(2,3-dihydro-pyrido[4,3-b][1,4]oxazin-4-yl)-methanethione In a 25 ml flask, (3,5-dibromo-4-methoxy-phenyl)-(2,3-dihydro-pyrido[4,3-b][1,4]oxazin-4-yl)-methanone (100 mg, 0.23 mmol) was suspended in toluene, and Lawesson's reagent (113 mg, 1.2 equivalents) was added thereto and then stirred at 120□ for 2 hours. Toluene was evaporated under reduced pressure and the residue was purified on amine silica by using a solvent of dichloromethane:methanol=50:1 to obtain (3,5-dibromo-4-methoxy-phenyl)-(2,3-dihydro-pyrido[4,3-b][1,4]oxazin-4-yl)-methanethione (100 mg, 98%).

$^1$H-NMR(CDCl$_3$, 300 MHz); δ=8.15 (d, J=5.4 Hz, 1H), 7.83 (br s, 1H), 7.55 (s, 2H), 6.88 (d, J=5.4 Hz, 1H), 4.60 (m, 4H), 3.89 (s, 3H).

MS(ESI); 442.8 (M$^+$+1).

b) Synthesis of (3,5-dibromo-4-hydroxy-phenyl)-(2,3-dihydro-pyrido[4,3-b][1,4]oxazin-4-yl)-methanethione In a 25 ml flask, (3,5-dibromo-4-methoxy-phenyl)-(2,3-dihydro-pyrido[4,3-b][1,4]oxazin-4-yl)-methanethione (100 mg, 0.22 mmol) was dissolved in N,N-dimethyl formamide, and piperazine (28.4 mg, 1.5 equivalents) and lithium bromide (76.4 mg, 4 equivalents) were added thereto and then stirred at 1000 for 15 hours. N,N-dimethyl formamide was removed under reduced pressure and water was added the residue. The mixture in suspension was adjusted to pH 6 to 7 by using 1N hydrochloric acid and stirred for 30 minutes. The mixture was filtered and the resulting solid was stirred in methanol solvent and then filtered to give the target compound 51 as yellow solid (100 mg, quantitative yield).

$^1$H-NMR(DMSO-d$_6$, 300 MHz); δ=8.06 (d, J=5.4 Hz, 1H), 7.83 (br s, 1H), 7.68 (s, 2H), 7.00 (d, J=5.4 Hz, 2H), 4.64 (m, 4H), 4.53 (m, 2H).

MS(ESI); 428.8 (M$^+$+1).

EXAMPLE 52

Synthesis of (3,5-dibromo-4-hydroxy-phenyl)-(7-pyridin-3-yl-2,3-dihydro-pyrido[2,3-b][1,4]oxazin-1-yl]-methanone (compound 52)

a) Synthesis of 7-pyridin-3-yl-1H-pyrido[2,3-b][1,4]oxazin-2-one

To 1.6 ml of acetonitrile/0.4 ml of distilled water, 7-bromo-1H-pyrido[2,3-b][1,4]oxazin-2-one (100 mg, 0.436 mmol), 3-pyridine boronic acid (29.5 mg, 0.240 mmol), palladium acetate (4.9 mg, 0.0218 mmol), triphenylphosphine (11.4 mg, 0.0436 mmol) and potassium carbonate (45.2 mg, 0.327 mmol) were added and then stirred at 1000 for 10 hours. After completion of the reaction, the mixture was extracted with ethyl acetate, and the combined organic layer was dried over anhydrous sodium sulfate (Na$_2$SO$_4$), filtered and evaporated under reduced pressure. The residue was purified by column chromatography on silica eluting with a solvent of dichloromethane:methanol=50:1. The fractions containing the product were collected and evaporated to obtain 7-pyridin-3-yl-1H-pyrido[2,3-b][1,4]oxazin-2-one as brown oil (60 mg, 60%).

$^1$H-NMR(DMSO-d$_s$): δ=10.99 (br s, 1H), 8.83 (d, J=2.4 Hz, 1H), 8.58 (dd, 1H, J=5.0 Hz, 1.6 Hz), 8.15 (d, J=2.4 Hz, 1H), 8.01 (m, 1H), 7.51-7.46 (m, 2H), 4.84 (s, 2H).

MS(ESI); 228.0 (M$^+$+1).

b) Synthesis of 7-pyridin-3-yl-2,3-dihydro-1H-pyrido[2,3-b][1,4]oxazine 7-pyridin-3-yl-1H-pyrido[2,3-b][1,4]oxazin-2-one (60 mg, 0.264 mmol) was dissolved in 4 ml of anhydrous tetrahydrofuran under nitrogen atmosphere, and the mixture was cooled to 0□, and 1.0M Lithium aluminum hydride dissolved in tetrahydrofuran (0.7 ml, 0.704 mmol) was added thereto dropwise at room temperature for 5 hours. To the reaction mixture, water (0.3 ml), 10% sodium hydroxide (0.6 ml) and water (0.9 ml) were added dropwise in this order, and then stirred vigorously at room temperature for 1 hour. The formed solid was filtered and washed with excess ethyl acetate. The filtrate was washed with water and saturated saline solution, dried over anhydrous Na$_2$SO$_4$, filtered and evaporated under reduced pressure to obtain 7-pyridin-3-yl-2,3-dihydro-1H-pyrido[2,3-b][1,4]oxazine as white solid (30 mg, 53%).

MS(ESI); 214.0 (M$^+$+1).

c) Synthesis of (3,5-dibromo-4-methoxy-phenyl)-(7-pyridin-3-yl-2,3-dihydro-pyrido[2,3-b][1,4]oxazin-1-yl]-methanone In a 10 ml flask, 7-pyridin-3-yl-2,3-dihydro-1H-pyrido[2,3-b][1,4]oxazine (30 mg, 0.140 mmol) and 3,5-dibromo-4-methoxy-benzoyl chloride (50.5 mg, 0.154 mmol) were dissolved in dichloromethane (2 ml). Triethylamine (0.058 ml, 0.42 mmol) was added thereto and then stirred at room temperature for 1 hour. After completion of the reaction by adding water dropwise, the mixture was extracted with dichloromethane, and the combined organic layer was dried over anhydrous sodium sulfate ($Na_2SO_4$), filtered and evaporated under reduced pressure. The residue was purified by preparative TLC eluting a solvent of ethyl acetate:methanol=20:1. Silica gels containing the product were eluted with dichloromethane and the solvent was evaporated to obtain (3,5-dibromo-4-methoxy-phenyl)-(7-pyridin-3-yl-2,3-dihydro-pyrido[2,3-b][1,4]oxazin-1-yl)-methanone as white solid (35 mg, 49%).

$^1$H-NMR(DMSO-$d_6$, 300 MHz); δ=8.54 (dd, J=4.7 Hz, 1.6 Hz, 2H), 8.32 (d, J=2.3 Hz, 1H), 7.92 (s, 2H), 7.86 (m, 1H), 7.45 (dd, J=4.7 Hz, 5.1 Hz, 1H), 4.50 (m, 2H), 3.92 (m, 2H), 3.85 (s, 3H).

MS(ESI); 503.9 ($M^+$+1).

d) Synthesis of (3,5-dibromo-4-hydroxy-phenyl)-(7-pyridin-3-yl-2,3-dihydro-pyrido[2,3-b][1,4]oxazin-1-yl]-methanone In a 5 ml flask, (3,5-dibromo-4-methoxy-phenyl)-(7-pyridin-3-yl-2,3-dihydro-pyrido[2,3-b][1,4]oxazin-1-yl)-methanone (35 mg, 0.069 mmol) was dissolved in dichloromethane (1 ml), and the mixture was cooled to 0□. 1.0M Boron tribromide dissolved in dichloromethane (0.4 ml, 0.415 mmol) was added thereto and then stirred at room temperature for 15 hours. n-hexane solvent was added thereto and the formed solid was filtered. The resulting solid was dissolved in methanol and concentrated. After dissolving by adding water, the mixture was adjusted to pH 6 with saturated solution of sodium hydrogen carbonate, and extracted with dichloromethane. The combined organic layer was dried over anhydrous sodium sulfate ($Na_2SO_4$), filtered and evaporated under reduced pressure. The residue was recrystallized from dichloromethane and n-hexane to obtain the target compound 52 as white solid (18 mg, 53%).

$^1$H-NMR(DMSO-$d_6$, 300 MHz); δ=10.67 (br s, 1H), 8.64 (s, 1H), 8.54 (dd, J=5.1 Hz, 1.5 Hz, 1H), 8.31 (d, J=1.5 Hz, 1H) 8.10 (br s, 1H), 7.89 (m, 1H), 7.79 (s, 2H), 7.46 (dd, J=4.9 Hz, 1.5 Hz, 1H), 4.48-4.45 (m, 2H), 3.94-3.91 (m, 2H).

MS(ESI); 489.9 ($M^+$+1).

EXAMPLE 53

Synthesis of (3,5-dibromo-4-hydroxy-phenyl)-(7-furan-3-yl-2,3-dihydro-pyrido[2,3-b][1,4]oxazin-1-yl]-methanone (compound 53)

a) Synthesis of 7-furan-3-yl-2,3-dihydro-1H-pyrido[2,3-b][1,4]oxazine

To 2.0 ml of acetonitrile/0.5 ml of distilled water, 7-bromo-2,3-dihydro-1H-pyrido[2,3-b][1,4]oxazine (80 mg, 0.372 mmol), 3-furan boronic acid (45.7 mg, 0.409 mmol), palladium acetate (8.3 mg, 0.0372 mmol), triphenylphosphine (19.5 mg, 0.0744 mmol) and potassium carbonate (102.8 mg, 0.744 mmol) were added and reacted at 100□ for 10 min using microwave (50 W) apparatus. After completion of the reaction, the mixture was extracted with ethyl acetate, and the combined organic layer was dried over anhydrous sodium sulfate ($Na_2SO_4$), filtered and evaporated under reduced pressure. The residue was purified by preparative TLC eluting a solvent of dichloromethane:methanol=20:1. Silica gels containing the product were eluted with dichloromethane and the solvent was evaporated to obtain 7-furan-3-yl-2,3-dihydro-1H-pyrido[2,3-b][1,4]oxazine in oil form (18 mg, 24%).

MS(ESI); 203.0 ($M^+$+1).

b) Synthesis of (3,5-dibromo-4-methoxy-phenyl)-(7-furan-3-yl-2,3-dihydro-pyrido[2,3-b][1,4]oxazin-1-yl)-methanone In a 5 ml flask, 7-furan-3-yl-2,3-dihydro-1H-pyrido[2,3-b][1,4]oxazine (18 mg, 0.089 mmol) and 3,5-dibromo-4-methoxy-benzoyl chloride (32.1 mg, 0.098 mmol) were dissolved in dichloromethane (1 ml). Triethylamine (0.037 ml, 0.267 mmol) was added thereto and then stirred at 0° C. for 3 hours. After completion of the reaction by adding water dropwise, the mixture was extracted with dichloromethane, and the combined organic layer was dried over anhydrous sodium sulfate ($Na_2SO_4$), filtered and evaporated under reduced pressure. The residue was purified by preparative TLC eluting a solvent of dichloromethane:methanol=20:1. Silica gels containing the product were eluted with dichloromethane and the solvent was evaporated to obtain (3,5-dibromo-4-methoxy-phenyl)-(7-furan-3-yl-2,3-dihydro-pyrido[2,3-b][1,4]oxazin-1-yl)-methanone as white solid (40 mg, 91%).

$^1$H-NMR(CDCl$_3$, 300 MHz); δ=8.17 (d, 1H, J=2.2 Hz), 7.70 (s, 2H), 7.57 (br s, 1H), 7.46 (dd, 1H, J=1.7 Hz, 1.8 Hz), 7.26 (s, 1H), 6.51 (m, 1H), 4.49-4.46 (m, 2H), 3.99-3.96 (m, 2H).

MS(ESI); 492.9 ($M^+$+1).

c) Synthesis of (3,5-dibromo-4-hydroxy-phenyl)-(7-furan-3-yl-2,3-dihydro-pyrido[b][1,4]oxazin-1-yl)-methanone In a 5 ml flask, (3,5-dibromo-4-methoxy-phenyl)-(7-furan-3-yl-2,3-dihydro-pyrido[2, 3-1)][1,4]oxazin-1-yl)-methanone (40 mg, 0.081 mmol) was dissolved in dichloromethane (1 ml) and then cooled to 0□. 1.0M Boron tribromide dissolved in dichloromethane (0.8 ml, 0.81 mmol) was added thereto and then stirred at room temperature for 15 hours. After completion of the reaction by adding water dropwise, the mixture was extracted with dichloromethane, and the combined organic layer was dried over anhydrous sodium sulfate ($Na_2SO_4$), filtered and evaporated under reduced pressure. The residue was purified by preparative TLC eluting a solvent of dichloromethane:methanol=20:1. Silica gels containing the product were eluted with dichloromethane and the solvent was evaporated to obtain the target compound 53, i.e., (3,5-dibromo-4-hydroxy-phenyl)-(7-furan-3-yl-2,3-dihydro-pyrido[2,3-b][1,4]oxazin-1-yl)-methanone as white solid (30 mg, 77%).

$^1$H-NMR (CD$_3$OD, 300 MHz); δ=8.11 (d, 1H, J=2.0 Hz), 7.99 (br s, 1H), 7.76 (s, 3H), 7.55 (d, 1H, J=1.8 Hz, 1.5 Hz), 6.63 (m, 1H), 4.48-4.45 (m, 2H), 4.02-3.99 (m, 2H).

MS(ESI); 478.9 ($M^+$+1).

EXAMPLE 54

Synthesis of 1-(3,5-dibromo-4-hydroxy-phenyl)-2-(2,3-dihydro-pyrido[4,3-b][1,4]oxazin-4-yl)-ethanone (compound 54)

a) Synthesis of 2-bromo-1-(3,5-dibromo-4-hydroxy-phenyl)-ethanone

In a 100 ml flask, 1-(3,5-dibromo-4-hydroxy-phenyl)-ethanone (1.2 g, 4.082 mmol) was dissolved in a solvent of anhydrous tetrahydrofuran: anhydrous diethyl ether (1:1, 12 ml). Acetic acid (0.4 ml) and bromine (2.1 ml, 4.082 mmol) were added thereto dropwise under nitrogen atmosphere and then stirred at room temperature for 2 hours. After completion of the reaction by adding water dropwise, the mixture was adjusted to pH 8 to 9 with saturated solution of sodium hydrogen carbonate and extracted with ethyl acetate, and the combined organic layer was dried over anhydrous sodium sulfate ($Na_2SO_4$), filtered and evaporated under reduced pressure. The residue was purified by column chromatography on silica eluting with a solvent of n-hexane:ethyl acetate=2:1. The fractions containing the product were collected and evaporated to obtain 2-bromo-1-(3,5-dibromo-4-hydroxy-phenyl)-ethanone as white solid (785 mg, 51.5%).

$^1$H-NMR($CDCl_3$, 300 MHz); δ=8.21 (s, 2H), 6.39 (br s, 1H), 4.36 (s, 2H).

MS(ESI); 370.8 ($M^+$+1).

b) Synthesis of 1-(3,5-dibromo-4-hydroxy-phenyl)-2-(2,3-dihydro-pyrido[4,3-b][1,4]oxazin-4-yl)-ethanone In a 10 ml flask, (3,4-dihydro-2H-pyrido[4,3-b][1,4]oxazine (60 mg, 0.44 mmol) was dissolved in anhydrous acetonitrile (5 ml). At room temperature, 2-bromo-1-(3,5-dibromo-4-hydroxy-phenyl)-ethanone (164 mg, 0.44 mmol) and potassium carbonate (121 mg, 0.88 mmol) were added thereto and then stirred at room temperature for 16 hours. The reaction mixture was filtered and the resulting white solid was recrystallized from methanol to obtain the target compound 54 as white solid (110 mg, 58.5%).

$^1$H-NMR($CDCl_3$, 300 MHz); δ=7.96-8.00 (m, 2H), 7.89 (s, 2H), 7.31 (d, J=6.3 Hz, 1H), 7.18 (br s, 1H), 5.87 (br s, 2H), 4.45-4.47 (m, 2H), 3.31-3.44 (m, 2H).

MS(ESI); 426.8 ($M^+$+1).

EXAMPLE 55

Synthesis of (3,5-dibromo-4-hydroxy-phenyl)-(2,3-dihydro-4-oxa-1,9-diaza-phenanthren-1-yl)-methanone (compound 55)

a) Synthesis of 3-amino-quinolin-4-ol

In a 100 ml flask, 3-nitro-quinolin-4-ol (500 mg, 2.629 mmol) was dissolved in methanol (50 ml) and 10% palladium on active carbon (1.2 g, 10 w/w %) was added thereto and then stirred for 3 hours at room temperature under hydrogen atmosphere. The reaction mixture was filtered on celite and then evaporated under reduced pressure to obtain brown liquid (445 mg, quantitative yield).

$^1$H-NMR(DMSO-$d_6$, 300 MHz); δ=11.50 (br s, 1H), 8.09 (d, J=8.4 Hz, 1H), 7.48 (s, 1H), 7.47 (m, 2H), 7.14-7.20 (m, 1H), 4.38 (br s, 2H).

b) Synthesis of 1H-4-oxa-1,9-diaza-phenanthren-2-one

In a 50 ml flask equipped with a reflux apparatus, 3-amino-quinolin-4-ol (421 mg, 2.628 mmol) was dissolved in N,N-dimethyl formamide (13 ml) under nitrogen atmosphere, and then chloroacetyl chloride (0.21 ml, 2.76 mmol) was added thereto dropwise at 0□, and then stirred at 0□ for 30 minutes. Potassium carbonate (24 g, 177 mmol) was added thereto and the mixture was heated to 100□ under reflux. After 16 hours, N,N-dimethyl formamide solvent was evaporated under reduced pressure and methanol was added to the residue, and then the mixture was filtered on celite. The filtrate was evaporated under reduced pressure to obtain the target compound, i.e., 1H-4-oxa-1,9-diaza-phenanthren-2-one, as brown solid (526 mg, quantitative yield).

$^1$H-NMR(DMSO-$d_6$, 300 MHz); δ=8.28 (s, 1H), 7.72-7.83 (m, 2H), 7.35 (m, 2H), 4.43 (s, 2H).

MS(ESI); 201.0 ($M^+$+1).

c) Synthesis of 2,3-dihydro-1H-4-oxa-1,9-diaza-phenanthrene 1H-4-oxa-1,9-diaza-phenanthren-2-one (526 mg, 2.63 mmol) was dissolved in tetrahydrofuran (13 ml) and then cooled to 0□. To the reaction mixture, 1.0M Lithium aluminum hydride dissolved in tetrahydrofuran (5.5 ml, 5.26 mmol) was added dropwise and stirred at room temperature for 2 hours. After completion of reaction, water (1 ml), 10% aqueous solution of sodium hydroxide (2 ml) and water (3 ml) were added thereto dropwise in this order and then stirred for 1 hour at room temperature. After filtering precipitates, the filtrate was extracted with ethyl acetate. The combined organic layer was dried over anhydrous sodium sulfate ($Na_2SO_4$), filtered and evaporated under reduced pressure. The residue was purified by column chromatography on amine silica eluting with a solvent of dichloromethane. The fractions containing the product were collected and evaporated to obtain colorless liquid (52 mg, 10.6%).

$^1$H-NMR($CDCl_3$, 300 MHz); δ=8.37 (s, 1H), 7.90-7.96 (m, 2H), 7.27-7.48 (m, 2H), 4.50 (m, 2H), 3.56 (m, 2H).

MS(ESI); 187.0 ($M^+$+1).

d) Synthesis of (3,5-dibromo-4-methoxy-phenyl)-(2,3-dihydro-4-oxa-1,9-diaza-phenanthren-1-yl)-methanone In a 10 ml flask, 2,3-dihydro-1H-4-oxa-1,9-diaza-phenanthrene (50 mg, 0.269 mmol) and 3,5-dibromo-4-methoxy-benzoyl chloride (88 mg, 0.269 mmol) were dissolved in dichloromethane. Triethylamine (0.51 ml, 3.7 mmol) was added thereto and then stirred at room temperature for 3 hours. After neutralizing with 1N hydrochloric acid solution, the mixture was extracted with dichloromethane, and the combined organic layer was dried over anhydrous sodium sulfate ($Na_2SO_4$), filtered and evaporated under reduced pressure. The residue was purified by column chromatography on amine silica eluting with a solvent of dichloromethane: methanol=20:1. The fractions containing the product were collected and evaporated to obtain the target compound as yellow solid (110 mg, 86%).

$^1$H-NMR($CDCl_3$, 300 MHz); δ=8.57 (br s, 1H), 7.96-8.14 (m, 2H), 7.73 (s, 2H), 7.54-7.73 (m, 2H), 4.65 (m, 2H), 4.11 (m, 2H), 3.94 (s, 3H).

MS(ESI); 475.9 ($M^+$+1).

e) Synthesis of (3,5-dibromo-4-hydroxy-phenyl)-(2,3-dihydro-4-oxa-1,9-diaza-phenanthren-1-yl)-methanone In a 10 ml flask, (3,5-dibromo-4-methoxy-phenyl)-(2,3-dihydro-4-oxa-1,9-diaza-phenanthren-1-yl)-methanone (30 mg, 0.063 mmol), lithium bromide (12 mg, 0.134 mmol) and piperazine (9 mg, 0.101 mmol) were dissolved in N,N-dimethyl formamide (3 ml), and then stirred at 100□ for 2 hours. After completion of the reaction by adding water dropwise, the mixture was adjusted to weak acidic condition (pH=6) by using 1N hydrochloric acid. The formed solid was filtered and washed with distilled water, and recrystallized from tetrahydrofuran and methanol to obtain the target compound 55, i.e., (3,5-dibromo-4-hydroxy-phenyl)-(2,3-dihydro-4-oxa-1,9-diaza-phenanthren-1-yl)-methanone, as yellow solid (10 mg, 34%).

¹H-NMR(DMSO-d₆, 300 MHz); δ=10.66 (br s, 1H), 8.71 (br s, 1H), 8.08 (d, J=8.4 Hz, 1H), 7.90 (d, J=6.9 Hz, 1H), 7.83 (s, 2H), 7.70-7.59 (m, 2H), 4.63 (m, 2H), 4.02 (m, 2H).
MS(ESI); 461.9 (M⁺+1).

EXAMPLE 56

Synthesis of 4-[2-(3,5-dibromo-4-hydroxy-phenyl)-2-oxo-ethyl)]-4H-pyrido[4,3-b][1,4]oxazin-3-one (compound 56)

In a 10 ml flask, 4H-pyrido[4,3-b][1,4]oxazin-3-one (50 mg, 0.33 mmol) was dissolved in N,N-dimethyl formamide (2.0 ml) and then cooled to 0□. Sodium hydride (15 mg, 0.37 mmol) was added thereto at 0□ and then stirred at room temperature for 30 minutes. The reaction mixture was cooled to 0□, 2-bromo-1-(3,5-dibromo-4-hydroxy-phenyl)-ethanone (124 mg, 0.33 mmol) was added thereto dropwise and stirred at 0□ for 30 minutes, and then the mixture was stirred at room temperature for 1 hour. The precipitates formed were filtered and washed with acetonitrile. The resulting solid was recrystallized from methanol to obtain the target compound 56, i.e., 4-[2-(3,5-dibromo-4-hydroxy-phenyl)-2-oxo-ethyl]-4H-pyrido[4,3-b][1,4]oxazin-3-one, as white solid (48 mg, 33%).
¹H-NMR(DMSO-d₆, 300 MHz); δ=11.66 (s, 1H), 8.36 (dd, J=6.9 Hz, 1.5 Hz, 1H), 8.15 (d, J=1.5 Hz, 1H), 7.88 (s, 2H), 7.60 (d, J=6.9 Hz, 1H), 5.99 (s, 2H), 5.02 (m, 2H).
MS(ESI); 440.9 (M⁺+1).

EXAMPLE 57

Synthesis of 4-(3,5-dibromo-4-methoxy-benzoyl)-4H-pyrido[4,3-b][1,4]oxazin-3-one (compound 57)

By the same method as in Example 56, 4H-pyrido[4,3-b][1,4]oxazin-3-one (200 mg, 1.33 mmol), sodium hydride (56 mg, 1.40 mmol) and 3,5-dibromo-4-methoxy-benzoyl chloride (437 mg, 1.33 mmol) were reacted, and then water was added thereto and the mixture was extracted with ethyl acetate. The combined organic layer was dried over anhydrous sodium sulfate (Na₂SO₄), filtered and evaporated under reduced pressure. The residue was purified by column chromatography on silica eluting with a solvent of ethyl acetate:methanol=9:1. The fractions containing the product were collected and evaporated to obtain the target compound 57, i.e., 4-(3,5-dibromo-4-methoxy-benzoyl)-4H-pyrido[4,3-b][1,4]oxazin-3-one, as white solid (125 mg, 21%).
¹H-NMR(DMSO-d₆, 300 MHz); δ=8.34 (s, 1H), 8.30 (s, 2H), 8.25 (d, J=5.4 Hz, 1H), 7.18 (d, J=5.4 Hz, 1H), 4.93 (s, 2H), 3.89 (s, 3H).
MS(ESI); 440.9 (M⁺+1).

EXAMPLE 58

Synthesis of (3,5-dibromo-4-methoxy-phenyl)-(6-methyl-2,3-dihydro-pyrido[2,3-b][1,4]oxazin-1-yl)-methanone (compound 58)

In a 10 ml flask, 6-methyl-2,3-dihydro-1H-pyrido[2,3-b][1,4]oxazine (110 mg, 0.73 mmol) and 3,5-dibromo-4-methoxy-benzoyl chloride (240 mg, 0.73 mmol) were dissolved in dichloromethane (5 ml). Triethylamine (0.26 ml, 1.8 mmol) was added thereto and then stirred at room temperature for 1 hour. After completion of the reaction by adding water dropwise, the mixture was extracted with dichloromethane, and the combined organic layer was dried over anhydrous sodium sulfate (Na₂SO₄), filtered and evaporated under reduced pressure. The residue was purified by column chromatography on amine silica (NH-silica gel) eluting with a solvent of dichloromethane:methanol=19:1. The fractions containing the product were collected and evaporated to obtain the target compound 58, i.e., (3,5-dibromo-4-methoxy-phenyl)-(6-methyl-2,3-dihydro-pyrido[2,3-b][1,4]oxazin-1-yl)-methanone, as white solid (230 mg, 71%).
¹H-NMR(DMSO-d₆, 300 MHz); δ=8.20-7.90 (br s, 1H), 7.87 (s, 2H), 6.79-6.82 (m, 1H), 4.37 (m, 2H), 3.84 (s, 3H), 3.82 (m, 2H), 2.31 (s, 3H).
MS(ESI); 440.9 (M⁺+1).

EXAMPLE 59

Synthesis of (2,3-dihydro-pyrido[4,3-b][1,4]oxazin-4-yl)-(2,4-dihydroxy-pyrimidin-5-yl)-methanone (compound 59)

2,4-dihydroxy-pyrimidin-5-carboxylic acid (125 mg, 0.80 mmol) was dissolved in N,N-dimethyl acetamide (3 ml) and then cooled to −15□. Thionyl chloride (0.066 ml, 0.90 mmol) was added thereto at −15□ and the reaction mixture was stirred at −5□ for 20 minutes. The reaction mixture was cooled to −15□, and potassium carbonate (138 mg, 1.0 mmol) and 3,4-dihydro-2H-pyrido[4,3-b][1,4]oxazine (109 mg, 0.80 mmol) were added thereto dropwise. The reaction mixture was stirred at −5□ for 30 minutes, and then stirred at room temperature for 3 hours. After the completion of the reaction, water was added thereto and the mixture was extracted with ethyl acetate, and the combined organic layer was dried over anhydrous sodium sulfate (Na₂SO₄), filtered and evaporated under reduced pressure. The residue was purified by column chromatography on silica eluting with a solvent of dichloromethane:methanol=9:1. The fractions containing the product were collected and evaporated to obtain the target compound 59 as white solid (47 mg, 21%).
¹H-NMR(DMSO-d₆, 300 MHz); δ=11.47 (s, 1H), 11.35 (s, 1H), 8.76 (br s, 1H), 8.08 (d, J=5.7 Hz, 1H), 7.85 (s, 1H), 6.92 (d, J=5.7 Hz, 1H), 4.34 (m, 2H), 3.84 (m, 2H).
MS(ESI); 275.0 (M⁺+1).

EXAMPLE 60

Synthesis of (2,3-dihydro-pyrido[4,3-b][1,4]oxazin-4-yl)-(2,6-dihydroxy-pyrimidin-4-yl)-methanone (compound 60)

By the same method as in Example 59, 2,6-dihydroxy-pyrimidin-4-carboxylic acid (125 mg, 0.80 mmol), thionyl chloride (0.066 ml, 0.90 mmol), potassium carbonate (138 mg, 1.0 mmol) and 3,4-dihydro-2H-pyrido[4,3-b][1,4]oxazine (109 mg, 0.80 mmol) were reacted and the reaction mixture was purified in the same manner to obtain the target compound 60, i.e., (2,3-dihydro-pyrido[4,3-b][1,4]oxazin-4-yl)-(2,6-dihydroxy-pyrimidin-4-yl)-methanone, as white solid (32 mg, 15%).
¹H-NMR(DMSO-d₆, 300 MHz); δ=11.35-11.29 (m, 2H), 9.06 (br s, 1H), 8.18 (d, J=5.4 Hz, 1H), 7.01 (d, J=5.4 Hz, 1H), 5.81 (s, 1H), 4.42 (m, 2H), 3.95 (m, 2H).
MS(ESI); 275.0 (M⁺+1).

EXAMPLE 61

Synthesis of (3,5-dibromo-4-hydroxy-phenyl)-(7-isoquinolin-4-yl-2,3-dihydro-pyrido[2,3-b][1,4]oxazin-1-yl)-methanone (compound 61)

a) Synthesis of 7-isoquinolin-4-yl-2,3-dihydro-1H-pyrido[2,3-b][1,4]oxazine

Under nitrogen atmosphere, in a 10 ml flask, 7-bromo-2,3-dihydro-1H-pyrido[2,3-b][1,4]oxazine (36.3 mg, 0.169 mmol), isoquinoline boronic acid (44 mg, 0.253 mmol), tetrakis triphenylphosphine palladium (19.5 mg, 0.017 mmol) and potassium carbonate (58.3 mg, 0.423 mmol) were dissolved in a solvent of tetrahydrofuran/water (6/1, 1.4 ml/0.3 ml). The reaction mixture was stirred for 30 minutes at 80° C. using microwave (40 W) device. After cooling to room temperature, the mixture was extracted with ethyl acetate, and the organic layer was washed with saturated saline solution. The combined organic layer was dried over anhydrous magnesium sulfate ($MgSO_4$), filtered and evaporated under reduced pressure. The residue was purified by column chromatography on amine silica eluting with a solvent of dichloromethane. The fractions containing the product were collected and evaporated to obtain brown oil (22.6 mg, 51%).

$^1$H-NMR($CDCl_3$, 300 MHz); δ=9.23 (s, 1H), 8.43 (s, 1H), 7.59-8.04 (m, 5H), 7.00 (d, J=2.1 Hz, 1H), 4.48-4.51 (m, 2H), 4.10 (s, 1H), 3.49-3.51 (m, 2H).

b) Synthesis of (3,5-dibromo-4-methoxy-phenyl)-(7-isoquinolin-4-yl-2,3-dihydro-pyrido[2,3-b][1,4]oxazin-1-yl)-methanone Under nitrogen atmosphere, in a 10 ml flask, 7-isoquinolin-4-yl-2,3-dihydro-1H-pyrido[2,3-b][1,4]oxazine (22.6 mg, 0.085 mmol) and 3,5-dibromo-4-methoxy-benzoyl chloride (42.2 mg, 0.129 mmol) were dissolved in dichloromethane (1.0 ml). After cooling to 0□, triethylamine (0.06 ml, 0.429 mmol) was added thereto at room temperature for 3 hours. After neutralizing with 1N hydrochloric acid solution, the mixture was extracted with dichloromethane, and the combined organic layer was dried over anhydrous magnesium sulfate ($MgSO_4$), filtered and evaporated under reduced pressure. The residue was purified by column chromatography on amine silica eluting with a solvent of ethyl acetate and n-hexane. The fractions containing the product were collected and evaporated to obtain white solid (11.0 mg, 23%).

$^1$H-NMR($CDCl_3$, 300 MHz); δ=9.25 (s, 1H), 8.34 (s, 1H), 8.19 (d, J=2.1 Hz, 1H), 8.02 (dd, J=6.6 Hz, 1.5 Hz, 1H), 7.58-7.76 (m, 6H), 4.59-4.63 (m, 2H), 4.06-4.09 (m, 2H), 3.92 (s, 3H).

c) Synthesis of (3,5-dibromo-4-hydroxy-phenyl)-(7-isoquinolin-4-yl-2,3-dihydro-pyrido[2,3-b][1,4]oxazin-1-yl)-methanone Under nitrogen atmosphere, in a 10 ml flask, (3,5-dibromo-4-methoxy-phenyl)-(7-isoquinolin-4-yl-2,3-dihydro-pyrido[2,3-b][1,4]oxazin-1-yl)-methanone (11.3 mg, 0.020 mmol) was dissolved in dichloromethane, and then cooled to 0□. 1.0M Boron tribromide dissolved in dichloromethane (0.2 ml, 0.203 mmol) was added thereto and then stirred at room temperature for 18 hours. After adjusting to pH 6 with 1N NaOH solution, the mixture was extracted with dichloromethane, and the combined organic layer was dried over anhydrous sodium sulfate ($Na_2SO_4$), filtered and evaporated under reduced pressure. Diethyl ether was added to the formed solid and stirred for 30 minutes and then filtered to obtain the target compound 61 as white solid (3.0 mg, 27%).

$^1$H-NMR ($CD_3OD$, 300 MHz); δ=9.47 (s, 1H), 8.32-8.42 (m, 2H), 8.12 (d, J=2.4 Hz, 1H), 8.00-7.66 (m, 6H), 4.66-4.63 (m, 2H), 4.09-4.07 (m, 2H).

MS(ESI); 539.8 ($M^+$+1).

EXAMPLE 62

Synthesis of (3,5-dibromo-4-hydroxy-phenyl)-(6,7-dihydro-pyrimido[4,5-b][1,4]oxazin-5-yl)-methasone (compound 62)

a) Synthesis of (6-chloro-5-nitro-pyrimidin-4-yloxy)-acetic acid methyl ester In a 50 ml flask at low temperature, methyl glycolate (0.22 ml, 2.8 mmol) and sodium hydride (114 mg, 2.8 mmol) were dissolved in N,N-dimethyl formamide (7 ml) and then stirred for 10 minutes. 4,6-dichloro-5-nitro-pyrimidine (500 mg, 2.6 mmol) dissolved in N,N-dimethyl formamide (6.5 ml) was added thereto dropwise and then stirred at the same temperature for additional 10 minutes, and then the temperature was raised to room temperature and stirred for additional 10 hours. After completion of the reaction by adding water, the mixture was extracted with dichloromethane, and the combined organic layer was washed with saturated saline solution, dried over anhydrous sodium sulfate ($Na_2SO_4$), filtered and evaporated under reduced pressure. The residue was purified by column chromatography eluting with a solvent of dichloromethane to obtain yellow liquid (280 mg, 44%).

$^1$H-NMR($CDCl_3$, 300 MHz); δ=8.62 (s, 1H), 5.08 (s, 2H), 3.80 (s, 3H).

MS(ESI); 248.0 ($M^+$+1).

b) Synthesis of 5H-pyrimido-[4,5-b][1,4]oxazin-6-one

In a 25 ml flask, (6-chloro-5-nitro-pyrimidin-4-yloxy)-acetic acid methyl ester (280 mg, 1.1 mmol) and tin tetrachloride (849 mg, 4.5 mmol) were dissolved in hydrochloric acid (7 ml) and heated for 1 hour at 80□. The reaction mixture was cooled to room temperature and neutralized by adding 10% sodium hydroxide solution dropwise, and the formed solid was removed by filtration. The filtrate was extracted with ethyl acetate, and the combined organic layer was washed with saturated saline solution, dried over anhydrous sodium sulfate ($Na_2SO_4$), filtered and evaporated under reduced pressure. The obtained yellow solid mixture (107 mg) was used in the next step without further purification.

$^1$H-NMR($CDCl_3$, 300 MHz); δ=8.58 (s, 1H), 8.19 (s, 1H), 4.95 (s, 2H), 4.33 (br s, 1H).

MS(ESI); 152.0 ($M^+$+1).

c) Synthesis of 6,7-dihydro-5H-pyrimido-[4,5-b][1,4]oxazine

In a 10 ml flask, the mixture of 5H-pyrimido-[4,5-b][1,4] oxazin-6-one (107 mg, 0.58 mmol) was dissolved in tetrahydrofuran (3 ml) and then cooled to 0° C. 1.0M Lithium aluminum hydride dissolved in tetrahydrofuran (1.15 ml, 1.2 mmol) was added thereto dropwise and the temperature was raised to room temperature and then stirred for additional 2 hours. After cooling to low temperature again, water, 10% sodium hydroxide solution and water were added in this order to quench the reaction. The mixture was filtered and the filtrate was extracted with ethyl acetate and the combined organic layer was washed with saturated saline solution, dried over anhydrous sodium sulfate (Na$_2$SO$_4$), filtered and evaporated under reduced pressure. The residue was purified by column chromatography on amine silica gel eluting with a solvent of dichloromethane to obtain white solid (20 mg, 25%).

$^1$H-NMR(CDCl$_3$, 300 MHz); δ=8.27 (s, 1H), 7.94 (s, 1H), 4.50-4.47 (m, 2H), 3.87 (br s, 1H), 3.49-3.45 (m, 2H).

MS(ESI); 137.9 (M$^+$+1).

d) Synthesis of (3,5-dibromo-4-methoxy-phenyl)-(6,7-dihydro-pyrimido[4,5-b][1,4]oxazin-5-yl)-methanone In a 10 ml flask, 6,7-dihydro-5H-pyrimido-[4,5-b][1,4]oxazine (20 mg, 0.15 mmol) and triethylamine (0.1 ml, 0.73 mmol) were dissolved in dichloromethane (1.5 ml). To the reaction mixture, 3,5-dibromo-4-methoxy-benzoyl chloride (50 mg, 0.15 mmol) was added and stirred at room temperature for 12 hours. The solvent was evaporated under reduced pressure and white non-crystalline compound (28 mg, 45%) was obtained by column chromatography on amine silica gel eluting with a solvent of dichloromethane:n-hexane=1:1.

$^1$H-NMR(CDCl$_3$, 300 MHz); δ=8.80 (s, 1H), 8.61 (s, 1H), 7.69 (s, 2H), 4.55-4.52 (m, 2H), 4.02-3.99 (m, 2H), 3.95 (s, 3H).

MS(ESI); 427.9 (M$^+$+1).

e) Synthesis of (3,5-dibromo-4-hydroxy-phenyl)-(6,7-dihydro-pyrimido[4,5-b][1,4]oxazin-5-yl)-methanone In a 10 ml flask, (3,5-dibromo-4-methoxy-phenyl)-(6,7-dihydro-pyrimido[4,5-b][1,4]oxazin-5-yl)-methanone (26 mg, 0.06 mmol), lithium bromide (16 mg, 0.18 mmol) and piperazine (8 mg, 0.09 mmol) were dissolved in N,N-dimethyl formamide (1.0 ml) and heated at 100□ for 6 hours. The reaction mixture was cooled to room temperature, evaporated under reduced pressure, and diluted by adding water. The diluted reaction mixture was neutralized with diluted hydrochloric acid, and the formed white solid was filtered to obtain the target compound 62 (25 mg, quantitative yield).

$^1$H-NMR(DMSO-d$_6$, 300 MHz); δ=10.6 (br s, 1H), 8.73 (br s, 1H), 8.49 (s, 1H), 7.79 (s, 2H), 4.52-4.49 (m, 2H), 3.93-3.91 (m, 2H).

MS(ESI); 413.9 (M$^+$+1).

EXAMPLE 63

Synthesis of (3,5-dibromo-4-hydroxy-phenyl)-[7-(3-trifluoromethyl-phenyl)-2,3-dihydro-pyrido[2,3-b][1,4]oxazin-1-yl]-methanone (compound 63)

a) Synthesis of 7-(3-trifluoromethyl-phenyl)-2,3-dihydro-1H-pyrido[2,3-b][1,4]oxazine By the same method as in the step b) of Example 45, 7-bromo-2,3-dihydro-1H-pyrido[2,3-b][1,4]oxazine (100 mg, 0.46 mmol), 3-dimethyl phenyl boronic acid (97.2 mg, 0.51 mmol), palladium triphenylphosphine (26.9 mg, 0.023 mol) and potassium carbonate (129 mg, 0.93 mmol) were dissolved in a solvent of tetrahydrofuran/water (3 ml/0.5 ml), and reacted at 800 for 6 hours to obtain 7-(3-trifluoromethyl-phenyl)-2,3-dihydro-1H-pyrido[2,3-b][1,4]oxazine as white solid (105 mg, 80.6%).

$^1$H-NMR(CDCl$_3$, 300 MHz); δ=7.80 (d, J=1.9 Hz, 1H), 7.75-7.65 (m, 2H), 7.62-7.50 (m, 2H), 7.07 (d, J=1.9 Hz, 1H), 4.50-4.41 (m, 2H), 3.98 (br s, 1H), 3.52-3.43 (m, 2H).

MS(ESI): 281.0 (M$^+$+1).

b) Synthesis of (3,5-dibromo-4-methoxy-phenyl)-[7-(3-trifluoromethyl-phenyl)-2,3-dihydro-pyrido[2,3-b][1,4]oxazin-1-yl]-methanone By the same method as in the step c) of Example 45, 7-(3-trifluoromethyl-phenyl)-2,3-dihydro-1H-pyrido[2,3-b][1,4]oxazine (99 mg, 0.35 mmol), 3,5-dibromo-4-methoxy-benzoyl chloride (139 mg, 0.42 mmol) and triethylamine (98.5 μl, 0.71 mmol) were dissolved in dichloromethane (3 ml) and reacted at room temperature for 3 hours to obtain (3,5-dibromo-4-methoxy-phenyl)-[7-(3-trifluoromethyl-phenyl)-2,3-dihydro-pyrido[2,3-b][1,4]oxazin-1-yl]-methanone as white solid (192 mg, 95%).

$^1$H-NMR(CDCl$_3$, 300 MHz); δ=8.28 (d, J=2.3 Hz, 1H), 8.14-7.95 (m, 1H), 7.78-7.72 (m, 2H), 7.66-7.50 (m, 4H), 4.58-4.48 (m, 2H), 4.07-3.98 (m, 2H), 3.94 (s, 3H).

MS(ESI): 570.9 (M$^+$+1).

c) Synthesis of (3,5-dibromo-4-hydroxy-phenyl)-[7-(3-trifluoromethyl-phenyl)-2,3-dihydro-pyrido[2,3-b][1,4]oxazin-1-yl]-methanone By the same method as in the step d) of Example 45, (3,5-dibromo-4-methoxy-phenyl)-[7-(3-trifluoromethyl-phenyl)-2,3-dihydro-pyrido[2,3-b][1,4]oxazin-1-yl]-methanone (165 mg, 0.29 mmol), lithium bromide (100 mg, 1.15 mmol) and piperazine (37.3 mg, 0.43 mmol) were dissolved in N,N-dimethyl formamide (2 ml) and reacted at 100□ to obtain the target compound 63, i.e., (3,5-dibromo-4-hydroxy-phenyl)-[7-(3-trifluoromethyl-phenyl)-2,3-dihydro-pyrido[2,3-b][1,4]oxazin-1-yl]-methanone, as white solid (90 mg, 56%).

$^1$H-NMR (CD$_3$OD, 300 MHz); 8.21 (d, J=2.3 Hz, 1H), 8.09-8.01 (m, 1H), 7.78 (s, 2H), 7.74-7.57 (m, 4H), 4.56-4.50 (m, 2H), 4.08-4.01 (m, 2H).

MS(ESI): 556.9 (M$^+$+1).

EXAMPLE 64

Synthesis of (3,5-dibromo-4-hydroxy-phenyl)-[7-(3-fluoromethyl-phenyl)-2,3-dihydro-pyrido[2,3-b][1,4]oxazin-1-yl]-methanone (compound 64)

a) Synthesis of 7-(3-fluoromethyl-phenyl)-2,3-dihydro-1H-pyrido[2,3-b][1,4]oxazine By the same method as in the step b) of Example 45, 7-bromo-2,3-dihydro-1H-pyrido[2,3-b][1,4]oxazine (100 mg, 0.46 mmol), 3-dimethyl phenyl boronic acid (71.6 mg, 0.51 mmol), palladium triphenylphosphine (26.9 mg, 0.023 mol) and potassium carbonate (129 mg, 0.93 mmol) were dissolved in a solvent of tetrahydrofuran/water (3 ml/0.5 ml) and reacted at 800 for 6 hours to obtain 7-(3-fluoromethyl-phenyl)-2,3-dihydro-1H-pyrido[2,3-b][1,4]oxazine as white solid (92 mg, 85.9%).

$^1$H-NMR(CDCl$_3$, 300 MHz); δ=7.83 (d, J=1.9 Hz, 1H), 7.43-7.32 (m, 1H), 7.30-7.28 (m, 1H), 7.22-7.16 (m, 1H), 7.07-6.98 (m, 2H), 4.49-4.41 (m, 2H), 3.96 (br s, 1H), 3.51-3.42 (m, 2H).

MS(ESI): 231.0 (M$^+$+1).

b) Synthesis of (3,5-dibromo-4-methoxy-phenyl)-[7-(3-fluoromethyl-phenyl)-2,3-dihydro-pyrido[2,3-b][1,4]oxazin-1-yl]-methanone By the same method as in the step c) of Example 45, 7-(3-fluoro-phenyl)-2,3-dihydro-1H-pyrido[2,3-b][1,4]oxazine (81 mg, 0.35 mmol), 3,5-dibromo-4-methoxy-benzoyl chloride (173 mg, 0.53 mmol) and triethylamine (98/i , 0.71 mmol) were dissolved in dichloromethane (3 ml) and reacted at room temperature for 3 hours to obtain (3,5-dibromo-4-methoxy-phenyl)-[7-(3-fluoromethyl-phenyl)-2,3-dihydro-pyrido[2,3-b][1,4]oxazin-1-yl]-methanone as white solid (180 mg, 98%).

$^1$H-NMR(CDCl$_3$, 300 MHz); δ=8.25 (d, J=2.3 Hz, 1H), 7.98-7.83 (m, 1H), 7.72 (s, 2H), 7.42-7.32 (m, 1H), 7.15 (d, J=7.6 Hz, 1H), 7.09-6.96 (m, 2H), 4.57-4.47 (m, 2H), 4.06-3.98 (m, 2H), 3.95 (s, 3H).

MS(ESI): 520.9 (M$^+$+1).

c) Synthesis of (3,5-dibromo-4-hydroxy-phenyl)-[7-(3-fluoromethyl-phenyl)-2,3-dihydro-pyrido[2,3-b][1,4]oxazin-1-yl]-methanone By the same method as in the step d) of Example 45, (3,5-dibromo-4-methoxy-phenyl)-[7-(3-fluoromethyl-phenyl)-2,3-dihydro-pyrido[2,3-b][1,4]oxazin-1-yl]-methanone (162 mg, 0.31 mmol), lithium bromide (108 mg, 1.24 mmol) and piperazine (40 mg, 0.47 mmol) were dissolved in N,N-dimethyl formamide (3 ml) and reacted at 100□ to obtain the target compound 64, i.e., (3,5-dibromo-4-hydroxy-phenyl)-[7-(3-fluoromethyl-phenyl)-2,3-dihydro-pyrido[2,3-b][1,4]oxazin-1-yl]-methanone, as white solid (69.4 mg, 44%).

$^1$H-NMR (CD$_3$OD, 300 MHz); δ=8.18 (d, J=2.3 Hz, 1H), 8.09-8.01 (m, 1H), 7.78 (s, 2H), 7.48-7.36 (m, 1H), 7.27-7.13 (m, 2H), 7.12-7.03 (m, 1H), 4.55-4.46 (m, 2H), 4.06-3.98 (m, 2H).

MS(ESI): 506.9 (M$^+$+1).

EXAMPLE 65

Synthesis of 4-[1-(3,5-dibromo-4-hydroxy-benzoyl)-2,3-dihydro-1H-pyrido[2,3-b][1,4]oxazin-7-yl]-benzonitrile (compound 65)

a) Synthesis of 4-(2,3-dihydro-1H-pyrido[2,3-b][1,4]oxazin-7-yl]-benzonitrile By the same method as in the step b) of Example 49, 7-bromo-2,3-dihydro-1H-pyrido[2,3-b][1,4]oxazine (120 mg, 0.56 mmol), 4-benzonitrile boronic acid (90.2 mg, 0.61 mmol), palladium triphenylphosphine (32.2 mg, 0.028 mol) and potassium carbonate (154 mg, 1.12 mmol) were dissolved in a solvent of tetrahydrofuran/water (3 ml/0.5 ml) and reacted at 800 for 6 hours to obtain 4-(2,3-dihydro-1H-pyrido[2,3-b][1,4]oxazin-7-yl]-benzonitrile as pale-green solid (81.7 mg, 62%).

$^1$H-NMR(CDCl$_3$, 300 MHz); δ=7.85 (d, J=1.9 Hz, 1H), 7.74-7.67 (m, 2H), 7.63-7.57 (m, 2H), 7.05 (d, J=2.3 Hz, 1H), 4.51-4.42 (m, 2H), 4.00 (br s, 1H), 3.51-3.44 (m, 2H).

MS(ESI): 238.0 (M$^+$+1).

b) Synthesis of 4-[1-(3,5-dibromo-4-methoxy-benzoyl)-2,3-dihydro-1H-pyrido[2,3-b][1,4]oxazin-7-yl]-benzonitrile By the same method as in the step c) of Example 45, 4-(2,3-dihydro-1H-pyrido[2,3-b][1,4]oxazin-7-yl]-benzonitrile (71.4 mg, 0.30 mmol), 3,5-dibromo-4-methoxy-benzoyl chloride (148 mg, 0.45 mmol) and triethylamine (84 μl, 0.60 mmol) were dissolved in dichloromethane (3 ml) and reacted at room temperature for 3 hours to obtain 4-[1-(3,5-dibromo-4-methoxy-benzoyl)-2,3-dihydro-1H-pyrido[2,3-b][1,4]oxazin-7-yl]-benzonitrile as white solid (120 mg, 75.6%).

$^1$H-NMR(CDCl$_3$, 300 MHz); δ=8.28 (d, J=2.3 Hz, 1H), 8.18-8.08 (m, 1H), 7.76-7.67 (m, 4H), 7.56-7.46 (m, 2H), 4.55-4.48 (m, 2H), 4.04-3.97 (m, 2H), 3.95 (s, 3H).

MS(ESI): 527.9 (M$^+$+1).

c) Synthesis of 4-[1-(3,5-dibromo-4-hydroxy-benzoyl)-2,3-dihydro-1H-pyrido[2,3-b][1,4]oxazin-7-yl]-benzonitrile By the same method as in the step d) of Example 45, 4-[1-(3,5-dibromo-4-methoxy-benzoyl)-2,3-dihydro-1H-pyrido[2,3-b][1,4]oxazin-7-yl]-benzonitrile (116 mg, 0.22 mmol), lithium bromide (76 mg, 0.88 mmol) and piperazine (29 mg, 0.33 mmol) were dissolved in N,N-dimethyl formamide (3 ml) and reacted at 1000 to obtain the target compound 65, i.e., 4-[1-(3,5-dibromo-4-hydroxy-benzoyl)-2,3-dihydro-1H-pyrido[2,3-b][1,4]oxazin-7-yl]-benzonitrile, as white solid (49 mg, 43%).

$^1$H-NMR(DMSO-d$_6$, 300 MHz); δ=8.36 (d, J=2.3 Hz, 1H), 8.29-8.19 (m, 1H), 7.90 (d, J=8.4 Hz, 2H), 7.80 (s, 2H), 7.71 (d, J=8.4 Hz, 2H), 4.51-4.42 (m, 2H), 3.97-3.87 (m, 2H).

MS(ESI): 513.9 (M$^+$+1).

EXAMPLE 66

Synthesis of (3,5-dibromo-4-hydroxy-phenyl)-[7-(4-trifluoromethoxy-phenyl)-2,3-dihydro-pyrido[2,3-b][1,4]oxazin-1-yl]-methasone (compound 66)

a) Synthesis of 7-(4-trifluoromethoxy-phenyl)-2,3-dihydro-1H-pyrido[2,3-b][1,4]oxazine By the same method as in the step b) of Example 49, 7-bromo-2,3-dihydro-1H-pyrido[2,3-b][1,4]oxazine (90 mg, 0.42 mmol), 3-dimethyl phenyl boronic acid (103 mg, 0.50 mmol), palladium triphenylphosphine (24.2 mg, 0.021 mol) and potassium carbonate (116 mg, 0.84 mmol) were dissolved in a solvent of tetrahydrofuran/water (3 ml/0.5 ml) and reacted at 800 for 6 hours to obtain 7-(4-trifluoromethoxy-phenyl)-2,3-dihydro-1H-pyrido[2,3-b][1,4]oxazine as white solid (86 mg, 69.4%).

$^1$H-NMR(CDCl$_3$, 300 MHz); δ=7.81 (d, J=2.3 Hz, 1H), 7.54-7.47 (m, 2H), 7.31-7.22 (m, 2H), 7.03 (d, J=2.3 Hz, 1H), 4.49-4.42 (m, 2H), 3.95 (br s, 1H), 3.51-3.43 (m, 2H).

MS(ESI): 297.0 (M$^+$+1).

b) Synthesis of (3,5-dibromo-4-methoxy-phenyl)-[7-(4-trifluoromethoxy-phenyl)-2,3-dihydro-pyrido[2,3-b][1,4]oxazin-1-yl]-methanone By the same method as in the step c) of Example 45, 7-(4-trifluoromethoxy-phenyl)-2,3-dihydro-1H-pyrido[2,3-b][1,4]oxazine (83 mg, 0.28 mmol), 3,5-dibromo-4-methoxy-benzoyl chloride (138 mg, 0.42 mmol) and triethylamine (78 μl, 0.56 mmol) were dissolved in dichloromethane (3 ml) and reacted at room temperature for 3 hours to obtain (3,5-dibromo-4-methoxy-phenyl)-[7-(4-trifluoromethoxy-phenyl)-2,3-dihydro-pyrido[2,3-b][1,4]oxazin-1-yl]-methanone as white solid (115 mg, 69.8%).

¹H-NMR(CDCl₃, 300 MHz); δ=8.24 (d, J=2.3 Hz, 1H), 8.02-7.93 (m, 1H), 7.72 (s, 2H), 7.43-7.39 (m, 2H), 7.30-7.22 (m, 2H), 4.55-4.48 (m, 2H), 4.04-3.98 (m, 2H), 3.94 (s, 3H).
MS(ESI): 586.9 (M⁺+1).

c) Synthesis of (3,5-dibromo-4-hydroxy-phenyl)-[7-(4-trifluoromethoxy-phenyl)-2,3-dihydro-pyrido[2,3-b]-[1,4]oxazin-1-yl]-methanone By the same method as in the step d) of Example 45, (3,5-dibromo-4-methoxy-phenyl)-[7-(4-trifluoromethoxy-phenyl)-2,3-dihydro-pyrido[2,3-b][1,4]oxazin-1-yl]-methanone (110 mg, 0.19 mmol), lithium bromide (65 mg, 0.75 mmol) and piperazine (25 mg, 0.29 mmol) were dissolved in N,N-dimethyl formamide (3 ml) and reacted at 100□ to obtain the target compound 66, i.e., (3,5-dibromo-4-hydroxy-phenyl)-[7-(4-trifluoromethoxy-phenyl)-2,3-dihydro-pyrido [2,3-b][1,4]oxazin-1-yl]-methanone, as white solid (54 mg, 48%).
¹H-NMR (CD₃OD, 300 MHz); δ=8.17 (d, J=2.3 Hz, 1H), 8.08 (s, 1H), 7.78 (s, 2H), 7.50 (m, 2H), 7.31 (m, 2H), 4.50 (t, J=4.6 Hz, 2H), 4.02 (t, J=4.6 Hz, 2H).
MS(ESI): 572.9 (M⁺+1).

EXAMPLE 67

Synthesis of 1-{4-[1-(3,5-dibromo-4-hydroxy?benzoyl)-2,3-dihydro-1H-pyrido[2,3-b][1,4]oxazin-7-yl]-phenyl}-ethanone (compound 67)

a) Synthesis of 1-[4-(2,3-dihydro-1H-pyrido[2,3-b][1,4]oxazin-7-yl)-phenyl]-ethanone To 3 ml of tetrahydrofuran/0.5 ml of distilled water, 7-bromo-2,3-dihydro-1H-pyrido[2,3-b][1,4]oxazine (80.0 mg, 0.37 mmol), 4-acetylphenyl boronic acid (71 mg, 0.55 mmol), potassium carbonate (103 mg, 0.74 mmol) and tetrakis triphenylphosphine palladium (21 mg, 0.02 mmol) were added and stirred at 80° C. for 2 hours. After completion of the reaction, the mixture was extracted ethyl acetate, and the combined organic layer was dried over anhydrous sodium sulfate (Na₂SO₄), filtered and evaporated under reduced pressure. The resulting solid was recrystallized from n-hexane and diethyl ether to obtain 1-[4-(2,3-dihydro-1H-pyrido[2,3-b][1,4]oxazin-7-yl)-phenyl]-ethanone as yellow solid (59 mg, 62%).
¹H-NMR(CDCl₃, 300 MHz); δ=8.01 (d, J=8.4 Hz, 2H), 7.89 (d, J=1.9 Hz, 1H), 7.60 (d, J=8.4 Hz, 2H), 7.09 (d, J=1.9 Hz, 1H), 4.47 (m, 2H), 3.96 (br s, 1H), 3.48 (m, 2H), 2.64 (s, 3H).
MS(ESI); 255.0 (M⁺+1).

b) Synthesis of 1-{4-[1-(3,5-dibromo-4-methoxy-benzoyl)-2,3-dihydro-1H-pyrido[2,3-b][1,4]oxazin-7-yl]-phenyl}-ethanone In a 10 ml flask, 1-[4-(2,3-dihydro-1H-pyrido[2,3-b][1,4] oxazin-7-yl)-phenyl]-ethanone (59 mg, 0.23 mmol) and 3,5-dibromo-4-methoxy-benzoyl chloride (287 mg, 0.87 mmol) were dissolved in dichloromethane. Triethylamine (0.32 ml, 2.3 mmol) was added thereto and then stirred at room temperature for 12 hours. After completion of the reaction by adding water dropwise, the mixture was extracted with dichloromethane, and the combined organic layer was dried over anhydrous sodium sulfate (Na₂SO₄), filtered and evaporated under reduced pressure. The residue was purified by column chromatography on amine silica eluting with a solvent of dichloromethane. The fractions containing the product were collected and evaporated to obtain 1-{4-[1-(3,5-dibromo-4-methoxy-benzoyl)-2,3-dihydro-1H-pyrido[2,3-b][1,4]oxazin-7-yl]-phenyl}-ethanone as white solid (119 mg, 94%).
¹H-NMR(CDCl₃, 300 MHz); δ=8.31 (d, J=1.9 Hz, 1H), 8.05 (br s, 1H), 8.00 (d, J=8.4 Hz, 2H), 7.73 (s, 2H), 7.48 (d, J=8.4 Hz, 2H), 4.53 (m, 2H), 4.01 (m, 2H), 3.96 (s, 3H), 2.63 (s, 3H).
MS(ESI); 544.9 (M⁺+1).

c) Synthesis of 1-{4-[1-(3,5-dibromo-4-hydroxy-benzoyl)-2,3-dihydro-1H-pyrido[2,3-b][1,4]oxazin-7-yl]-phenyl}-ethanone In a 10 ml flask, 1-{4-[1-(3,5-dibromo-4-methoxy-benzoyl)-2,3-dihydro-1H-pyrido[2,3-b][1,4]oxazin-7-yl]-phenyl}-ethanone (119 mg, 0.22 mmol), lithium bromide (189 mg, 2.2 mmol) and piperazine (28 mg, 0.33 mmol) were dissolved in 3 ml of N,N-dimethyl formamide, and then stirred at 100° C. for 2.5 hours. After completion of the reaction by adding water dropwise, the mixture was adjusted to weak acidic condition (pH=6) with 1N hydrochloric acid. The formed solid was filtered and washed with distilled water. The resulting solid was recrystallized from methanol to obtain the target compound 67, i.e., 1-{4-[1-(3,5-dibromo-4-hydroxy-benzoyl)-2,3-dihydro-1H-pyrido[2,3-b][1,4]oxazin-7-yl]-phenyl}-ethanone (65 mg, 56%).
¹H-NMR(CDCl₃+CD₃OD, 300 MHz); δ=8.27 (d, J=2.3 Hz, 1H), 8.01 (br s, 1H), 8.00 (d, J=8.0 Hz, 2H), 7.71 (s, 2H), 7.49 (d, J=8.4 Hz, 2H), 4.53 (m, 2H), 4.04 (m, 2H), 2.64 (s, 3H).
MS(ESI); 530.9 (M⁺+1).

EXAMPLE 68

Synthesis of (3,5-dibromo-4-hydroxy-phenyl)-[7-(5-methoxy-pyridin-3-yl)-2,3-dihydro-pyrido[2,3-b][1,4]oxazin-1-yl]-methasone (compound 68)

a) Synthesis of 7-(5-methoxy-pyridin-3-yl)-2,3-dihydro-1H-pyrido[2,3-b][1,4]oxazine To 3 ml of tetrahydrofuran/0.5 ml of distilled water, 7-bromo-2,3-dihydro-1H-pyrido[2,3-b][1,4]oxazine (80.0 mg, 0.37 mmol), 3-methoxy-5-(4,4,5,5-tetramethyl-[1,3,2] dioxaborolane-2-yl)-pyridine (105 mg, 0.45 mmol), potassium carbonate (103 mg, 0.74 mmol) and tetrakis triphenylphosphine palladium (129 mg, 0.11 mmol) were added and stirred at 80° C. for 4 hours. After completion of the reaction, the mixture was extracted with ethyl acetate, and the combined organic layer was dried over anhydrous sodium sulfate (Na₂SO₄), filtered and evaporated under reduced pressure. The residue was purified by column chromatography on amine silica eluting with a solvent of dichloromethane: methanol=40:1. The fractions containing the product were collected and evaporated to obtain 7-(5-methoxy-pyridin-3-yl)-2,3-dihydro-1H-pyrido[2,3-b][1,4]oxazine as white solid (72 mg, 80%).
¹H-NMR(CDCl₃, 300 MHz); δ=8.37 (d, J=1.7 Hz, 1H), 8.29 (d, J=2.7 Hz, 1H), 7.83 (d, J=2.3 Hz, 1H), 7.29 (m, 1H), 7.05 (d, J=2.3 Hz, 1H), 4.47 (m, 2H), 3.98 (br s, 1H), 3.92 (s, 3H), 3.48 (m, 2H).
MS(ESI); 244.0 (M⁺+1).

b) Synthesis of (3,5-dibromo-4-methoxy-phenyl)-[7-(5-methoxy-pyridin-3-yl)-2,3-dihydro-pyrido[2,3-b][1,4]oxazin-1-yl]-methanone In a 10 ml flask, 7-(5-methoxy-pyridin-3-yl)-2,3-dihydro-1H-pyrido[2,3-b][1,4]oxazine (72 mg, 0.30 mmol) and 3,5-dibromo-4-methoxy-benzoyl chloride (146 mg, 0.45 mmol) were dissolved in dichloromethane. Triethylamine (0.21 ml, 1.50 mmol) was added thereto and then stirred at room temperature for 3 hours. After completion of the reaction by adding water dropwise, the mixture was extracted with dichloromethane, and the combined organic layer was dried over anhydrous sodium sulfate ($Na_2SO_4$), filtered and evaporated under reduced pressure. The residue was purified by column chromatography on amine silica eluting with a solvent of dichloromethane. The fractions containing the product were collected and evaporated to obtain (3,5-dibromo-4-methoxy-phenyl)-[7-(5-methoxy-pyridin-3-yl)-2,3-dihydro-pyrido[2,3-b][1,4]oxazin-1-yl]-methanone as white solid (116 mg, 73%).

$^1$H-NMR($CDCl_3$, 300 MHz); δ=8.30 (d, J=2.7 Hz, 1H), 8.26 (d, J=2.3 Hz, 1H), 8.25 (br s, 1H), 7.90 (br s, 1H), 7.72 (s, 2H), 7.07 (br s, 1H), 4.54 (m, 2H), 4.03 (m, 2H), 3.95 (s, 3H), 3.88 (s, 3H).

MS(ESI); 533.9($M^+$+1).

c) Synthesis of (3,5-dibromo-4-hydroxy-phenyl)-[7-(5-methoxy-pyridin-3-yl)-2,3-dihydro-pyrido[2,3-b][1,4]oxazin-1-yl]-methanone In a 10 ml flask, (3,5-dibromo-4-methoxy-phenyl)-[7-(5-methoxy-pyridin-3-yl)-2,3-dihydro-pyrido[2,3-b][1,4]oxazin-1-yl]-methanone (110 mg, 0.21 mmol), lithium bromide (56 mg, 1.58 mmol) and piperazine (27 mg, 0.32 mmol) were dissolved in 3 ml of N,N-dimethyl formamide, and then stirred at 100° C. for 2 hours. After completion of the reaction by adding water dropwise, the mixture was adjusted to weak acidic condition (pH=6) with 1N hydrochloric acid. The formed solid was filtered and washed with distilled water. The resulting solid was recrystallized from methanol to obtain the target compound 68, i.e., (3,5-dibromo-4-hydroxy-phenyl)-[7-(5-methoxy-pyridin-3-yl)-2,3-dihydro-pyrido[2,3-h][1,4]oxazin-1-yl]-methanone (40 mg, 37%).

$^1$H-NMR($CDCl_3$+$CD_3OD$, 300 MHz); δ=8.22 (d, J=2.7 Hz, 1H), 8.19 (d, J=2.3 Hz, 1H), 8.10 (br s, 1H), 7.80 (br s, 1H), 7.70 (s, 2H), 7.16 (br s, 1H), 4.48 (m, 2H), 3.97 (m, 2H), 3.81 (s, 3H).

MS(ESI); 519.9($M^+$+1).

EXAMPLE 69

Synthesis of (4-hydroxy-3-trifluoromethyl-phenyl)-(7-methyl-2,3-dihydro-pyrido[2,3-b][1,4]oxazin-1-yl)-methanone (compound 69)

4-hydroxy-3-trifluoromethyl-benzoic acid (151 mg, 0.73 mmol) was dissolved in N,N-dimethyl acetamide (2.0 ml) and then cooled to −20° C. Thionyl chloride (0.073 ml, 100 mmol) was added thereto and stirred at −20° C. for 30 minutes. 5-methyl-2,3-dihydro-1H-pyrido[2,3-b][1,4]oxazine dissolved in N,N-dimethyl acetamide (1.0 ml) was added thereto dropwise and then stirred at −20° C. for 20 minutes, and then stirred at room temperature for 15 hours. Water was added thereto and the mixture was extracted with dichloromethane, and the combined organic layer was dried over anhydrous sodium sulfate ($Na_2SO_4$), filtered and evaporated under reduced pressure. The resulting solid residue was recrystallized from dichloromethane to obtain the target compound 69, i.e., (4-hydroxy-3-trifluoromethyl-phenyl)-(7-methyl-2,3-dihydro-pyrido[2,3-b][1,4]oxazin-1-yl)-methanone, as white solid (176 mg, 78%).

$^1$H-NMR(DMSO-$d_6$, 300 MHz); δ=11.27 (br s, 1H), 7.67-7.75 (m, 4H), 7.08 (d, J=8.4 Hz, 1H), 4.34 (m, 2H), 3.84 (m, 2H), 2.13 (s, 3H).

MS(ESI); 339.1($M^+$+1).

EXAMPLE 70

Synthesis of (3,5-dibromo-4-hydroxy-phenyl)-[7-(1H-indol-4-yl)-2,3-dihydro-pyrido[2,3-b][1,4]oxazin-1-yl]-methanone (compound 70)

a) Synthesis of 7-(1H-indol-4-yl)-2,3-dihydro-1H-pyrido[2,3-b][1,4]oxazine

To 3 ml of tetrahydrofuran (THF)/0.5 ml of distilled water, 7-bromo-2,3-dihydro-1H-pyrido[2,3-b][1,4]oxazine (80.0 mg, 0.37 mmol), 4-(4,4,5,5,-tetramethyl-[1,3,2]dioxaborolane-2-yl)-1H-indole (109 mg, 0.45 mmol), potassium carbonate (103 mg, 0.74 mmol) and tetrakis triphenylphosphine palladium (172 mg, 0.15 mmol) were added and stirred at 80° C. for 4 hours. After completion of the reaction, the mixture was extracted with ethyl acetate, and the combined organic layer was dried over anhydrous sodium sulfate ($Na_2SO_4$), filtered and evaporated under reduced pressure. The residue was purified by column chromatography on amine silica eluting with a solvent of dichloromethane:methanol=40:1. The fractions containing the product were collected and evaporated to obtain 7-(1H-indol-4-yl)-2,3-dihydro-1H-pyrido[2,3-b][1,4]oxazine as white solid (130 mg).

$^1$H-NMR($CDCl_3$, 300 MHz); δ=8.41 (br s, 1H), 7.96 (d, J=1.9 Hz, 1H), 7.39 (m, 1H), 7.27-7.25 (m, 2H), 7.19 (d, J=2.3 Hz, 1H), 7.11 (dd, J=7.3 Hz, 1.4 Hz, 1H), 6.69 (m, 1H), 4.47 (m, 2H), 3.91 (br s, 1H), 3.47 (m, 2H).

MS(ESI): 252.1 ($M^+$+1).

b) Synthesis of (3,5-dibromo-4-methoxy-phenyl)-[7-(1H-indol-4-yl)-2,3-dihydro-pyrido[2,3-b][1,4]oxazin-1-yl]-methanone In a 10 ml flask, 7-(1H-indol-4-yl)-2,3-dihydro-1H-pyrido[2,3-b][1,4]oxazine (130 mg, 0.52 mmol) and 3,5-dibromo-4-methoxy-benzoyl chloride (204 mg, 0.62 mmol) were dissolved in dichloromethane. Triethylamine (0.36 ml, 2.59 mmol) was added thereto and then stirred at room temperature for 3 hours. After completion of the reaction by adding water dropwise, the mixture was extracted with dichloromethane, and the combined organic layer was dried over anhydrous sodium sulfate ($Na_2SO_4$), filtered and evaporated under reduced pressure. The residue was purified by column chromatography on amine silica eluting with a solvent of dichloromethane. The fractions containing the product were collected and evaporated to obtain (3,5-dibromo-4-methoxy-phenyl)-[7-(1H-indol-4-yl)-2,3-dihydro-pyrido[2,3-b][1,4]oxazin-1-yl]-methanone as white solid (129 mg, 64% in two steps).

$^1$H-NMR ($CDCl_3$, 300 MHz); δ=8.37 (d, J=2.3 Hz, 1H), 8.30 (br s, 1H), 7.92 (br s, 1H), 7.74 (s, 2H), 7.39 (m, 1H), 7.24 (m, 1H), 7.20 (d, J=8.0 Hz, 1H), 6.98 (d, J=7.2 Hz, 1H), 6.32 (br s, 1H), 4.57 (m, 2H), 4.05 (m, 2H), 3.94 (s, 3H).

MS(ESI): 541.9 ($M^+$+1).

c) Synthesis of (3,5-dibromo-4-hydroxy-phenyl)-[7-(1H-indol-4-yl)-2,3-dihydro-pyrido[2,3-b][1,4]oxazin-1-yl]-methanone In a 10 ml flask, (3,5-dibromo-4-methoxy-phenyl)-[7-(1H-indol-4-yl)-2,3-dihydro-pyrido[2,3-b][1,4]oxazin-1-yl]-methanone (124 mg, 0.23 mmol), lithium bromide (246 mg, 2.83 mmol) and piperazine (29 mg, 0.34 mmol) were dissolved in 5 ml of N,N-dimethyl formamide (DMF), and then stirred at 100° C. for 2 hours. After completion of the reaction by adding water dropwise, the mixture was adjusted to weak acidic condition (pH=6) with 1N hydrochloric acid. The formed solid was filtered and washed with distilled water. The resulting solid was recrystallized from methanol to obtain the target compound 70, i.e., (3,5-dibromo-4-hydroxy-phenyl)-[7-(1H-indol-4-yl)-2,3-dihydro-pyrido[2,3-b][1,4]oxazin-1-yl]-methanone (77 mg, 64%).

$^1$H-NMR (DMSO-$d_6$, 300 MHz); δ=11.26 (br s, 1H), 10.62 (br s, 1H), 8.18 (d, J=1.9 Hz, 1H), 8.06 (br s, 1H), 7.82 (s, 2H), 7.39 (d, J=8.4 Hz, 1H), 7.32 (m, 1H), 7.11 (m, 1H), 6.98 (d, J=6.9 Hz, 1H), 6.17 (br s, 1H), 4.49 (m, 2H), 3.94 (m, 2H).

MS(ESI): 527.9 (M$^+$+1).

EXAMPLE 71

Synthesis of (3,5-dibromo-4-hydroxy-phenyl)-(2,3-dihydro-pyrido[4,3-b][1,4]oxazin-4-yl)-methanone sulfuric acid salt (compound 71)

In a 25 ml flask, (3,5-dibromo-4-hydroxy-phenyl)-(2,3-dihydro-pyrido[4,3-b][1,4]oxazin-4-yl)-methanone (100 mg, 0.24 mmol) was suspended in tetrahydrofuran (8 ml) and the mixture was dissolved under heating. After cooling to room temperature, 1M sulfuric acid solution was added thereto dropwise. The formed solid was filtered to obtain the target compound 71 as white solid (78 mg, 69%).

$^1$H-NMR(DMSO-$d_6$, 300 MHz); δ=9.01 (s, 1H), 8.44 (d, J=6.6 Hz, 1H), 7.82 (s, 2H), 7.53 (d, J=6.3 Hz, 1H), 4.60-4.50 (m, 2H), 4.05-3.96 (m, 2H).

MS(ESI); 412.9 (M$^+$+1).

EXAMPLE 72

Synthesis of (2,6-dibromo-4-(2,3-dihydro-pyrido[4,3-b][1,4]oxazin-4-carbonyl)-phenolate sodium salt (compound 72)

In a 100 ml flask, (3,5-dibromo-4-hydroxy-phenyl)-(2,3-dihydro-pyrido[4,3-b][1,4]oxazin-4-yl)-methanone (500 mg, 1.20 mmol) was suspended in tetrahydrofuran (40 ml) and the mixture was dissolved under heating. After cooling to room temperature, 10N sodium hydroxide solution was added thereto dropwise. The solvent was evaporated under reduced pressure, and the residue was dissolved in a solvent of acetonitrile and water (1:1 ratio, 80 ml) to obtain the target compound 72 as white non-crystalline form (240 mg, 48%).

$^1$H-NMR(DMSO-$d_6$, 300 MHz); δ=8.31 (s, 1H), 7.99 (d, J=5.7 Hz, 1H), 7.49 (s, 2H), 6.94 (d, J=5.7 Hz 1H), 4.38-4.21 (m, 2H), 3.97-3.85 (m, 2H).

MS(ESI); 412.8 (M$^+$+1).

EXAMPLE 73

Synthesis of (2,6-dibromo-4-(2,3-dihydro-pyrido[4,3-b][1,4]oxazin-4-carbonyl)-phenolate potassium salt (compound 73)

In a 100 ml flask, (3,5-dibromo-4-hydroxy-phenyl)-(2,3-dihydro-pyrido[4,3-b][1,4]oxazin-4-yl)-methanone (500 mg, 1.20 mmol) was suspended in tetrahydrofuran (40 ml) and the mixture was dissolved under heating. After cooling to room temperature, 10N potassium hydroxide solution was added thereto dropwise. The solvent was evaporated under reduced pressure, and the residue was dissolved in a solvent of acetonitrile and water (1:1 ratio, 80 ml), and freeze-dried to obtain the target compound 73 as white non-crystalline form (480 mg, 92%).

$^1$H-NMR(DMSO-$d_6$, 300 MHz); δ=8.30 (s, 1H), 7.98 (d, J=5.4 Hz, 1H), 7.47 (s, 2H), 6.89 (d, J=5.1 Hz 1H), 4.35-4.25 (m, 2H), 3.95-3.85 (m, 2H).

MS(ESI); 412.9 (M$^+$+1).

EXAMPLE 74

Synthesis of (3,5-dibromo-4-hydroxy-phenyl)-(2,3-dihydro-pyrido[4,3-b][1,4]oxazin-4-yl)-methanethione trifluoroacetic acid salt (compound 74)

In a 25 ml flask, (3,5-dibromo-4-methoxy-phenyl)-(2,3-dihydro-pyrido[4,3-b][1,4]oxazin-4-yl)-methanethione (100 mg, 0.22 mmol) was dissolved in N,N-dimethyl formamide, and piperazine (28.4 mg, 1.5 equivalents) and lithium bromide (76.4 mg, 4 equivalents) were added thereto, and then stirred at 100□ for 15 hours. Under reduced pressure, N,N-dimethyl formamide was removed and water was added, and then the suspension was adjusted to pH 6 to 7 with 1N hydrochloric acid and stirred for 30 minutes. The resulting solid was purified by medium pressure liquid chromatography (MPLC) eluting with a solvent of acetonitrile:water=90:1 containing 0.1% of trifluoroacetic acid. The fractions containing the product were collected and freeze-dried to obtain the target compound 74 as yellow solid (50 mg, 49%).

$^1$H-NMR(DMSO-$d_6$, 300 MHz); 8.22 (d, J=5.2 Hz, 1H), 8.10 (br s, 1H), 7.73 (s, 2H), 7.24 (d, J=5.2 Hz, 1H), 4.71 (m, 2H), 4.51 (m, 2H).

MS(ESI): 428.8(M$^+$+1).

EXAMPLE 75

Synthesis of 1-[1-(3,5-dibromo-4-hydroxy-benzoyl)-2,3-dihydro-1H-pyrido[2,3-b][1,4]oxazin-7-yl]-pyrrolidin-2-one (compound 75)

a) Synthesis of 1-(2,3-dihydro-1H-pyrido[2,3-b][1,4]oxazin-7-nyl)-pyrrolidin-2-one In a 5 ml flask, 7-bromo-2,3-dihydro-1H-pyrido[2,3-b][1,4]oxazine (120 mg, 0.558 mmol), pyrrolidin-2-one (142 mg, 1.668 mmol), tris(dibenzylidene acetone)dipalladium(0) (Pd$_2$dba$_3$) (51 mg, 0.056 mmol) and xantphos (96 mg, 0.166 mmol) were dissolved in N,N-dimethyl acetamide (1 ml). Cesium carbonate (Cs$_2$CO$_3$) (364 mg, 1.117 mmol) was added thereto and then stirred at room temperature for 10 minutes, and further reacted at 150□ for 20 minutes using microwave (50 W) apparatus. The reaction mixture was filtered on celite 545 and evaporated under reduced pressure. The resulting residue was purified by column chromatography on silica eluting with a solvent of dichloromethane:methanol=19:1. The fractions containing the product were collected and evaporated to obtain pale-yellow solid (120 mg, 98%).

MS(ESI); 220.2 (M$^+$+1).

b) Synthesis of 1-[1-(3,5-dibromo-4-methoxy-benzoyl)-2,3-dihydro-1H-pyrido[2,3-b][1,4]oxazin-7-nyl]-pyrrolidin-2-one In a 10 ml flask, 1-[1-(3,5-dibromo-4-methoxy-benzoyl)-2,3-dihydro-1H-pyrido[2,3-b][1,4]oxazin-7-nyl]-pyrrolidin- 2-one (120 mg, 0.547 mmol) was dissolved in dichloromethane (3 ml). Diisopropylamine (160 μl, 0.919 mmol) was added thereto and then stirred at 0□ for 10 minutes, and then 3,5-dibromo-4-methoxy-benzoyl chloride (180 mg, 0.264 mmol) was added and stirred at room temperature for 1 hour. To the reaction mixture, water (20 ml) was added and stirred at room temperature 10 minutes. The reaction mixture was extracted with ethyl acetate (30 ml) and evaporated under reduced pressure. The residue was purified by column chromatography on silica eluting with a solvent of dichloromethane:ethyl acetate=1:2. The fractions containing the product were collected and evaporated to obtain white solid (6 mg, 2.1%).

¹H-NMR(CD₃OD, 300 MHz); δ=8.23 (s, 1H), 8.17 (s, 1H), 7.68 (s, 2H), 4.46 (t, J=4.6 Hz, 2H), 3.99-3.92 (m, 2H), 3.93 (s, 3H), 3.77 (t, J=6.9 Hz, 2H), 2.55 (m, 2H), 2.22-2.12 (m, 2H).

c) Synthesis of 1-[1-(3,5-dibromo-4-hydroxy-benzoyl)-2,3-dihydro-1H-pyrido[2,3b][1,4]oxazin-7-nyl]-pyrrolidin-2-one In a 10 ml flask, 1-[1-(3,5-dibromo-4-methoxy-benzoyl)-2,3-dihydro-1H-pyrido[2,3-b][1,4]oxazin-7-nyl]-pyrrolidin-2-one (6 mg, 0.0117 mmol) was dissolved in dichloromethane (2 ml), and then cooled to 0□. 1.0M Boron tribromide dissolved in dichloromethane (0.2 ml, 0.2 mmol) was added thereto and then stirred at room temperature for 24 hours. Dichloromethane (3 ml) and methanol (0.1 ml) were added and then stirred for 10 minutes, filtered and evaporated under reduced pressure. The residue was purified by column chromatography on silica eluting with a solvent of dichloromethane:ethyl acetate:methanol=20:1:1. The fractions containing the product were collected and evaporated to obtain the target compound 75 as brown solid (4.6 mg, 79%).

¹H-NMR(CD₃OD, 300 MHz); δ=8.22 (s, 1H), 8.20 (s, 1H), 7.68 (s, 2H), 4.44 (t, J=4.6 Hz, 2H), 3.95 (t, J=4.6 Hz, 2H), 3.77 (t, J=7.6 Hz, 2H), 2.55 (m, 2H), 2.22-2.12 (m, 2H).

MS(ESI); 495.9(M⁺+1).

The structures of the compounds prepared in the above Examples are shown in the following table.

| Structure | Compound No. |
|---|---|
| (3,5-dibromo-4-hydroxyphenyl)(7-methyl-2,3-dihydro-[1,4]oxazino[3,2-b]pyridin-1(4H)-yl)methanone structure | 7 |
| (3,5-dibromo-4-hydroxyphenyl)(2,2-dimethyl-2,3-dihydro-[1,4]oxazino-pyridinyl)methanone structure | 8 |
| (3,5-dibromo-4-hydroxyphenyl)(7-cyclopropyl-2,3-dihydro-[1,4]oxazino[3,2-b]pyridin-1(4H)-yl)methanone structure | 9 |
| (3-chloro-4-hydroxyphenyl)(dihydro-oxazinopyridinium) methanone, bromide structure | 10 |
| (3-bromo-4-hydroxyphenyl)(dihydro-oxazinopyridinium) methanone, bromide structure | 11 |

| Structure | Compound No. |
|---|---|
| CF3-substituted dienone with oxazinopyridine structure | 12 |
| (3,5-dichloro-4-hydroxyphenyl)(dihydro-oxazinopyridinium) methanone, bromide structure | 13 |
| nitro/chloro dienone with oxazinopyridine structure | 14 |
| dichloro dienone with bis-pyridinium oxazine, bromide structure | 15 |
| 3-bromo-4-hydroxybenzaldehyde with oxazinopyridinium, bromide structure | 16 |

85
-continued
| Structure | Compound No. |
|---|---|
| 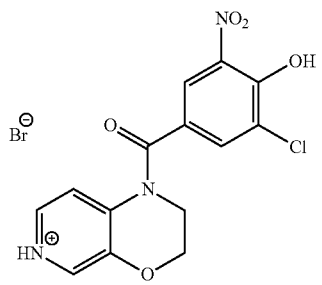 [SMILES: [Br-] ; O=C(c1cc(Cl)c(O)c([N+](=O)[O-])c1)N1CCOc2c[nH+]ccc21] | 17 |
| 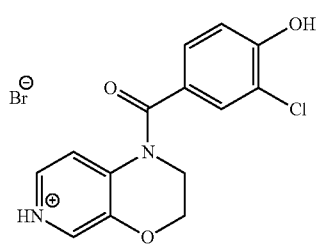 [SMILES: [Br-] ; O=C(c1ccc(O)c(Cl)c1)N1CCOc2c[nH+]ccc21] | 18 |
| 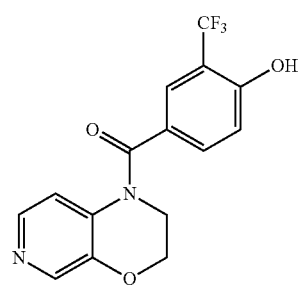 [SMILES: O=C(c1ccc(O)c(C(F)(F)F)c1)N1CCOc2cnccc21] | 19 |
| 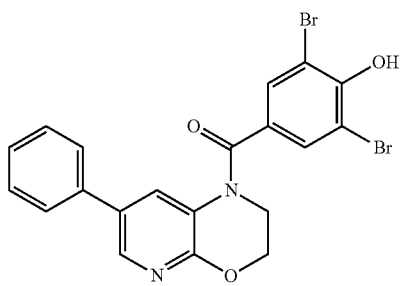 [SMILES: O=C(c1cc(Br)c(O)c(Br)c1)N1CCOc2ncc(-c3ccccc3)cc21] | 20 |
| 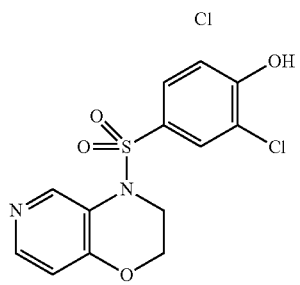 [SMILES: Cl ; O=S(=O)(c1ccc(O)c(Cl)c1)N1CCOc2ccncc21] | 21 |
86
-continued
| Structure | Compound No. |
|---|---|
| 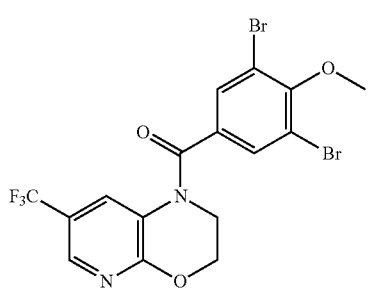 | 22-1 |
| 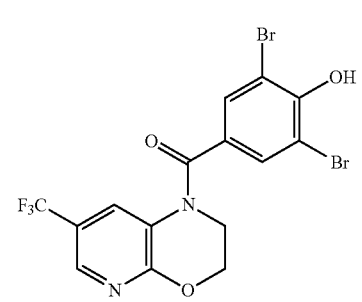 | 22-2 |
| 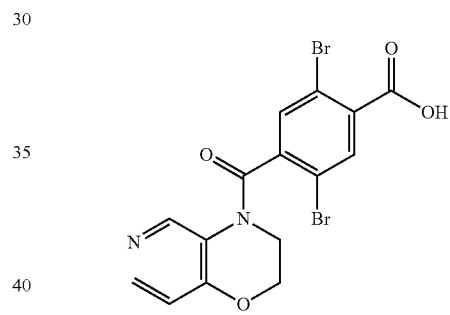 | 23 |
| 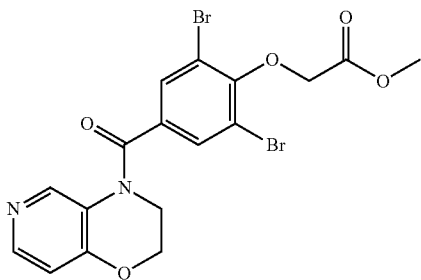 [SMILES: COC(=O)COc1c(Br)cc(C(=O)N2CCOc3ccncc32)cc1Br] | 24 |
| 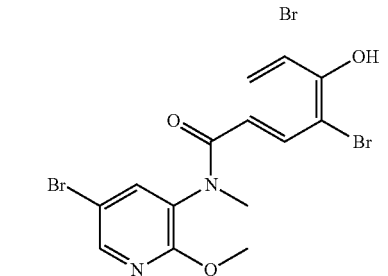 [SMILES: Br ; C=C/C(O)=C(Br)\C=C\C(=O)N(C)c1cc(Br)cnc1OC] | 25 |

| Structure | Compound No. |
|---|---|
| 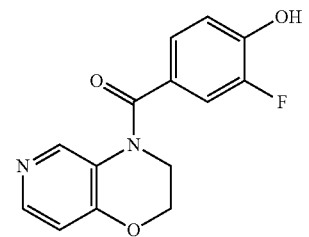 [SMILES: O=C(c1ccc(O)c(F)c1)N1CCOc2ccncc21] | 26 |
| 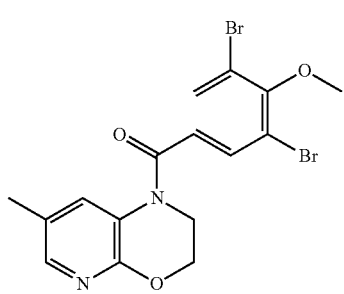 | 27-1 |
| 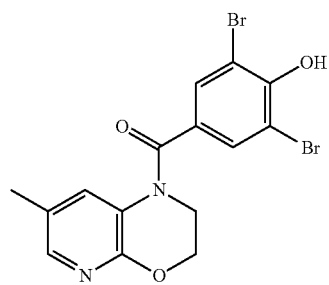 [SMILES: Cc1cnc2c(c1)N(C(=O)c1cc(Br)c(O)c(Br)c1)CCO2] | 27-2 |
| 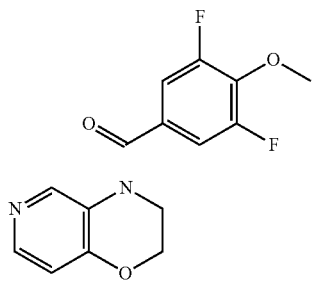 | 28 |
| 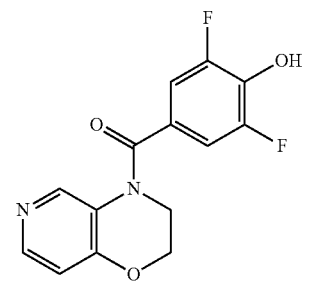 [SMILES: O=C(c1cc(F)c(O)c(F)c1)N1CCOc2ccncc21] | 29 |
| Structure | Compound No. |
|---|---|
| 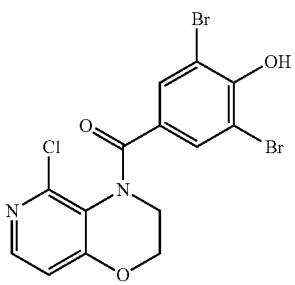 [SMILES: O=C(c1cc(Br)c(O)c(Br)c1)N1CCOc2ccnc(Cl)c21] | 30 |
| 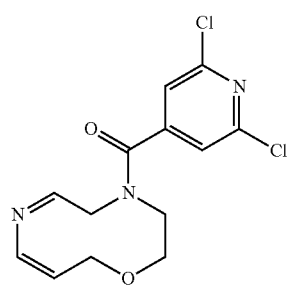 [SMILES: O=C(c1cc(Cl)nc(Cl)c1)N1C/C=N\C=C/COCC1] | 31 |
| 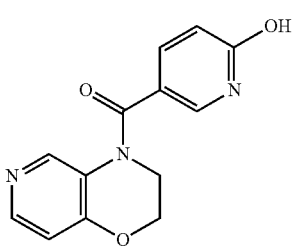 [SMILES: O=C(c1ccc(O)nc1)N1CCOc2ccncc21] | 32 |
| 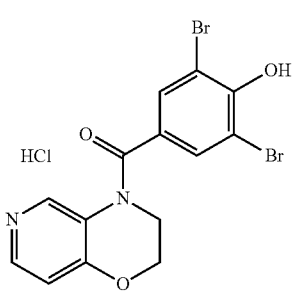 [SMILES: O=C(c1cc(Br)c(O)c(Br)c1)N1CCOc2ccncc21 ; Cl] | 33 |
| 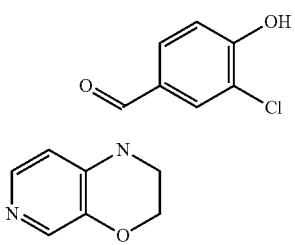 | 34 |

| Structure | Compound No. |
|---|---|
| 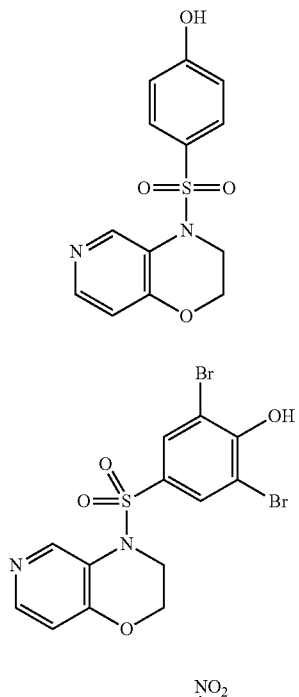 | 35-1 |
| | 35-2 |
| | 36 |
| | 37 |
| | 38 |
| Structure | Compound No. |
|---|---|
| 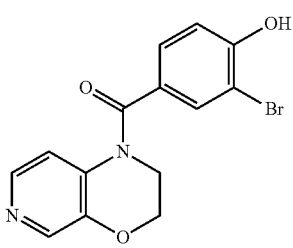 [SMILES: O=C(c1ccc(O)c(Br)c1)N1CCOc2cnccc21] | 39 |
| 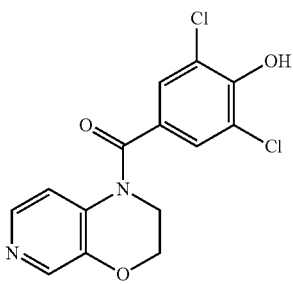 [SMILES: O=C(c1cc(Cl)c(O)c(Cl)c1)N1CCOc2cnccc21] | 40 |
| 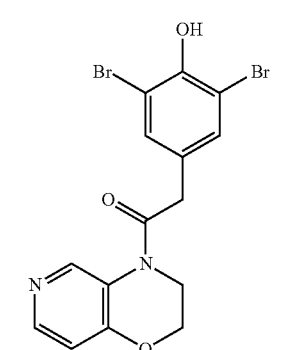 | 41 |
| | 42 |
| 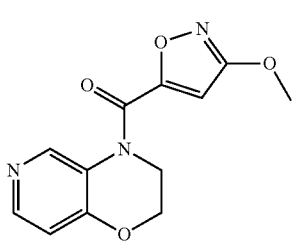 [SMILES: COc1cc(C(=O)N2CCOc3ccncc32)on1] | 43 |

| Structure | Compound No. |
|---|---|
| 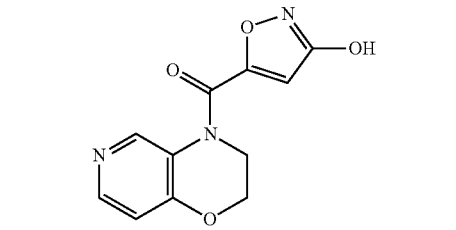 [SMILES: O=C(c1cc(O)no1)N1CCOc2ccncc21] | 44 |
| 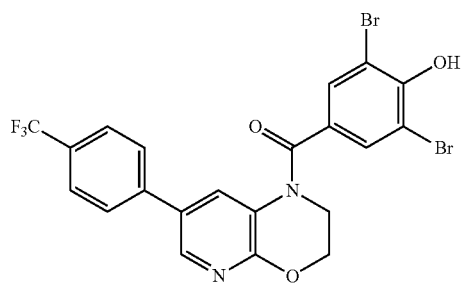 [SMILES: O=C(c1cc(Br)c(O)c(Br)c1)N1CCOc2ncc(-c3ccc(C(F)(F)F)cc3)cc21] | 45 |
| 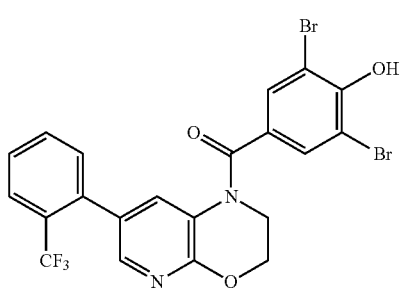 [SMILES: O=C(c1cc(Br)c(O)c(Br)c1)N1CCOc2ncc(-c3ccccc3C(F)(F)F)cc21] | 46 |
| 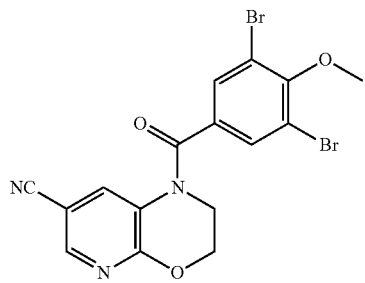 [SMILES: COc1c(Br)cc(C(=O)N2CCOc3ncc(C#N)cc32)cc1Br] | 47-1 |
| 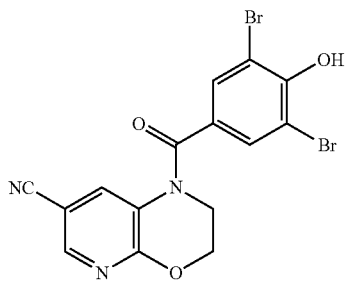 [SMILES: N#Cc1cnc2c(c1)N(C(=O)c1cc(Br)c(O)c(Br)c1)CCO2] | 47-2 |
| Structure | Compound No. |
|---|---|
| 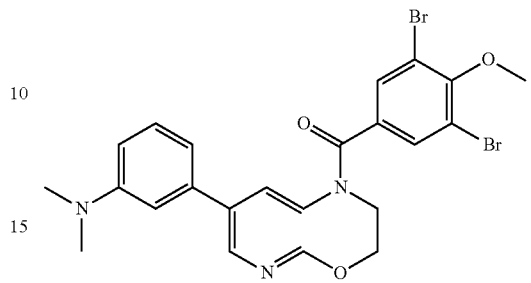 | 48 |
| 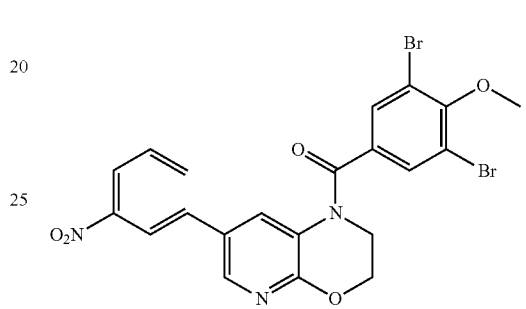 | 49 |
| 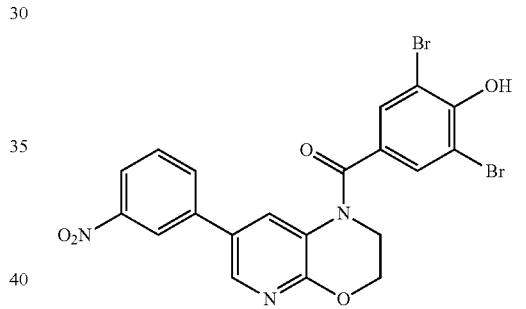 | 50 |
| 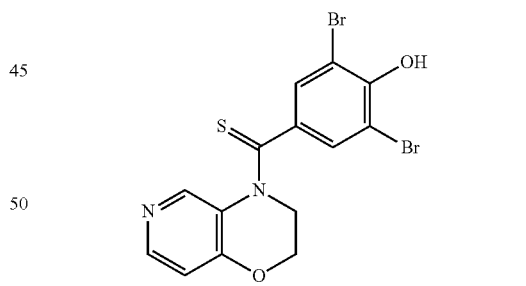 | 51 |
| 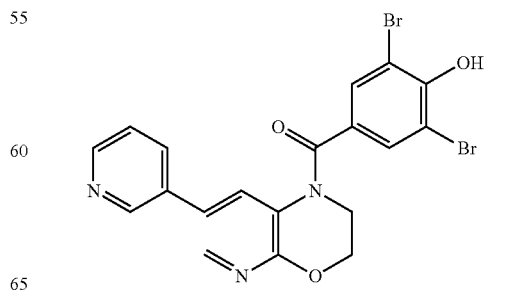 | 52 |

-continued

| Structure | Compound No. |
|---|---|
| (structure) | 53 |
| (structure) | 54 |
| (structure) | 55 |
| (structure) | 56 |
| (structure) | 57 |

-continued

| Structure | Compound No. |
|---|---|
| (structure) | 58 |
| (structure) | 59 |
| (structure) | 60 |
| (structure) | 61 |
| (structure) | 62 |

| Structure | Compound No. |
|---|---|
| (structure) | 63 |
| (structure) | 64 |
| (structure) | 65 |
| (structure) | 66 |
| (structure) | 67 |

| Structure | Compound No. |
|---|---|
| (structure) | 68 |
| (structure) | 69 |
| (structure) | 70 |
| (structure) | 71 |
| (structure) | 72 |

| Structure | Compound No. |
|---|---|
| 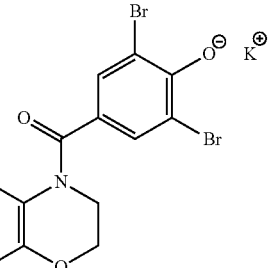 | 73 |
| 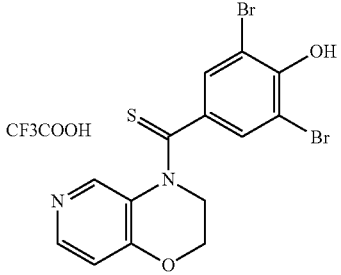 [SMILES: "CF3COOH" ; Oc1c(Br)cc(C(=S)N2CCOc3ccncc32)cc1Br] | 74 |
| 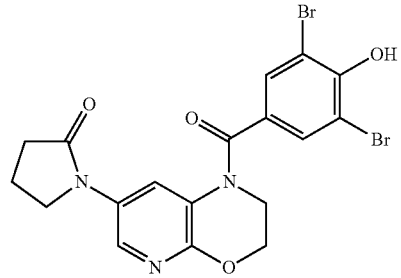 [SMILES: O=C1CCCN1c1cnc2c(c1)N(C(=O)c1cc(Br)c(O)c(Br)c1)CCO2] | 75 |

INTERMEDIATE SYNTHESIS EXAMPLE (1)

Synthesis of
5-methyl-2,3-dihydro-1H-pyrido[2,3-b][1,4]oxazine a) Synthesis of
5-methyl-1H-pyrido[2,3-b][1,4]oxazin-2-one 3-amino-5-methyl-pyridin-2-ol (1.32 g, 10.6 mmol) was dissolved in 50 ml of anhydrous N,N-dimethyl formamide under nitrogen atmosphere, and chloroacetyl chloride solution (1.02 ml, 12.72 mmol) was added thereto dropwise at room temperature. After stirring for 30 minutes, potassium carbonate (3.7 g, 26.5 mmol) was added thereto dropwise at room temperature, and the reaction mixture was heated to 100□ and then stirred for 18 hours. The reaction mixture was cooled to room temperature and the reaction was quenched by adding water. The organic layer was extracted with ethyl acetate, and the combined organic layer was washed with water and saturated saline solution, dried over anhydrous sodium sulfate ($Na_2SO_4$), filtered and evaporated under reduced pressure to obtain straw yellow solid (424 mg). The resulting solid was used in the next step without further purification.

$^1$H-NMR(DMSO-$d_6$, 300 MHz); δ=10.2 (br s, 1H), 8.00 (s, 1H), 7.30 (s, 1H), 4.74 (s, 2H), 2.00 (s, 3H).
MS(ESI); 165.0(M$^+$+1).

b) Synthesis of
5-methyl-2,3-dihydro-1H-pyrido[2,3-b][1,4]oxazine 5-methyl-1H-pyrido[2,3-b][1,4]oxazin-2-one (424 mg, 2.58 mmol) was dissolved in 20 ml of anhydrous tetrahydrofuran under nitrogen atmosphere, and then cooled to 0□. 1.0M Lithium aluminum hydride dissolved in tetrahydrofuran (5.16 ml, 5.16 mmol) was added thereto dropwise and then stirred for 30 minutes. The reaction temperature was raised to room temperature and then stirred for 1 hour. The reaction mixture was cooled to 0□ again and water (0.2 ml), 10% sodium hydroxide solution (0.4 ml) and water (0.6 ml) were added thereto dropwise in this order, and stirred vigorously at room temperature for 1 hour. The formed precipitate was filtered and washed with excess ethyl acetate. The filtrate was washed with water and saturated saline solution, dried over anhydrous sodium sulfate ($Na_2SO_4$), filtered and evaporated under reduced pressure to obtain 5-methyl-2,3-dihydro-1H-pyrido[2,3-b][1,4]oxazine as white solid (100 mg, 26% in two steps).

$^1$H-NMR(CDCl$_3$, 300 MHz); δ=7.42 (m, 1H), 6.68 (m, 1H), 4.37 (m, 2H), 3.74 (br s, 1H), 3.39 (m, 2H), 2.17 (s, 3H).
MS(ESI); 151.0(M$^+$+1).

INTERMEDIATE SYNTHESIS EXAMPLE (2)

Synthesis of
7-methyl-2,3-dihydro-1H-pyrido[2,3-b][1,4]oxazine a) Synthesis of 2-chloro-5-methyl-3-nitro-pyridine 5-methyl-3-nitro-pyridin-2-ol (5 g, 32.4 mmol) and benzyltrimethyl ammonium chloride (3.01 g, 16.2 mmol) were dissolved in acetonitrile, and phosphorus oxychloride (9.0 ml, 97.2 mmol) was added thereto and stirred at 800 for 6 hours. The reaction mixture was cooled and poured into ice water to quench the reaction, and extracted with dichloromethane. The combined organic layer was washed with saturated saline solution, dried over anhydrous sodium sulfate ($Na_2SO_4$), filtered and evaporated under reduced pressure. The residue was purified by column chromatography on silica eluting with a solvent of dichloromethane. The fractions containing the product were collected and evaporated to obtain 2-chloro-5-methyl-3-nitro-pyridine as yellow solid (5.39 g, 97%).

$^1$H-NMR(CDCl$_3$, 300 MHz); δ=8.45 (d, 1H, J=2.3 Hz), 8.04 (d, 1H, J=2.3 Hz), 2.46 (s, 3H).
MS(ESI); 173.0(M$^+$+1).

b) Synthesis of
(5-methyl-3-nitro-pyridin-2-yloxy)-acetic acid methyl ester

Hydroxy-acetic acid methyl ester (3.96 g, 47.0 mmol) was dissolved in 50 ml of anhydrous tetrahydrofuran under nitrogen atmosphere, and sodium hydride (2.01 g, 53.2 mmol) was added thereto at room temperature. After stirring for 30 minutes, 2-chloro-5-methyl-3-nitro-pyridine (5.39 g, 31.3 mmol) dissolved in 15 ml of anhydrous tetrahydrofuran was added dropwise at room temperature, and the reaction mixture was stirred at room temperature for 18 hours. After completion of the reaction by adding water, the mixture was extracted with ethyl acetate, and the combined organic layer was washed with water and saturated saline solution, dried over anhydrous sodium sulfate ($Na_2SO_4$), filtered and evaporated under reduced pressure. The resulting solid was recrystallized from dichloromethane and ether to obtain (5-methyl-3-nitro-pyridin-2-yloxy)-acetic acid methyl ester as yellow solid (5.47 g, 77%).

$^1$H-NMR(CDCl$_3$, 300 MHz); δ=8.16 (s, 2H), 5.05 (s, 2H), 3.76 (s, 3H), 2.36 (s, 3H).

MS(ESI); 227.0(M$^+$+1).

c) Synthesis of 7-methyl-1H-pyrido[2,3-b][1,4]oxazin-2-one

In a 250 ml round flask, (5-methyl-3-nitro-pyridin-2-yloxy)-acetic acid methyl ester (5.47 g, 23.9 mmol) and tin tetrachloride (18.1 g, 95.6 mmol) were dissolved in 24 ml of concentrated hydrochloric acid, and then stirred at 800 for 1 hour. The reaction mixture was cooled to room temperature, neutralized with 10% NaOH solution, and extracted with ethyl acetate. The combined organic layer was washed with water and saturated saline solution, dried over anhydrous sodium sulfate (Na$_2$SO$_4$), filtered and evaporated under reduced pressure. The residue was purified by column chromatography on silica eluting with a solvent of dichloromethane:methanol=19:1. The resulting solid was recrystallized from dichloromethane/methanol/tetrahydrofuran to obtain 7-methyl-1H-pyrido[2,3-b][1,4]oxazin-2-one as pale-brown solid (2.65 g, 67%).

$^1$H-NMR(CDCl$_3$, 300 MHz); δ=8.17 (br s, 1H), 7.75 (s, 1H), 6.94 (d, J=1.5 Hz, 1H), 4.81 (s, 2H), 2.29 (s, 3H).

MS(ESI); 165.0(M$^+$+1).

d) Synthesis of 5-methyl-2,3-dihydro-1H-pyrido[2,3-b][1,4]oxazine 5-methyl-1H-pyrido[2,3-b][1,4]oxazin-2-one (1.5 g, 9.1 mmol) was dissolved in 20 ml of anhydrous tetrahydrofuran under nitrogen atmosphere, and then cooled to 0° C. 1.0M Lithium aluminum hydride dissolved in tetrahydrofuran (11 ml, 10.9 mmol) was added thereto dropwise and then stirred for 30 minutes. The reaction temperature was raised to room temperature and stirred for 1 hour. The reaction mixture was cooled to 0° C. again and water (0.3 ml), 10% sodium hydroxide solution (0.6 ml) and water (0.9 ml) were added thereto dropwise in this order, and then stirred vigorously at room temperature for 1 hour. The formed solid was filtered and washed with excess ethyl acetate. The filtrate was washed with water and saturated saline solution, dried over anhydrous sodium sulfate (Na$_2$SO$_4$), filtered and evaporated under reduced pressure to obtain 5-methyl-2,3-dihydro-1H-pyrido [2,3-b][1,4]oxazine as white solid (680 mg, 50%).

$^1$H-NMR(CDCl$_3$, 300 MHz); δ=7.42 (m, 1H), 6.68 (m, 1H), 4.37 (m, 2H), 3.74 (br s, 1H), 3.39 (m, 2H), 2.17 (s, 3H).

MS(ESI); 151.0(M$^+$+1).

INTERMEDIATE SYNTHESIS EXAMPLE (3)

Synthesis of 7-bromo-1H-pyrido[2,3-b][1,4]oxazin-2-one a) Synthesis of (5-bromo-3-nitro-pyridin-2-yloxy)-acetic acid methyl ester

Hydroxy-acetic acid methyl ester (46 mg, 0.50 mmol) was dissolved in 2 ml of anhydrous tetrahydrofuran under nitrogen atmosphere, and sodium hydride (40 mg, 1.0 mmol) was added thereto at room temperature. After stirring for 30 minutes, 5-bromo-2-chloro-3-nitro-pyridine (100 mg, 0.42 mmol) dissolved in 1 ml of anhydrous tetrahydrofuran was added dropwise at room temperature, and the reaction mixture was stirred at room temperature for 18 hours. After completion of the reaction by adding water, the mixture was extracted with dichloromethane, and the organic layer was washed with water and saturated saline solution, dried over anhydrous sodium sulfate (Na$_2$SO$_4$), filtered and evaporated under reduced pressure. The residue was purified by column chromatography on silica eluting with a solvent of n-hexane: ethyl acetate=9:1. The fractions containing the product were collected and evaporated to obtain (5-bromo-3-nitro-pyridin-2-yloxy)-acetic acid methyl ester as yellow solid (144 mg, 99%).

$^1$H-NMR(CDCl$_3$, 300 MHz); δ=8.47 (d, J=2.3 Hz, 1H), 8.40 (d, J=2.3 Hz, 1H), 5.07 (s, 2H), 3.78 (s, 3H).

MS(ESI); 290.9(M$^+$+1).

b) Synthesis of 7-bromo-1H-pyrido[2,3-b][1,4]oxazin-2-one

In a 10 ml round flask, (5-bromo-3-nitro-pyridin-2-yloxy)-acetic acid methyl ester (144 mg, 0.49 mmol) and tin tetrachloride (375 mg, 1.96 mmol) were dissolved in 3 ml of concentrated hydrochloric acid, and then stirred at 80☐ for 1 hour. The reaction mixture was cooled to room temperature, neutralized with 10% sodium hydroxide solution, and extracted with dichloromethane. The combined organic layer was washed with water and saturated saline solution, dried over anhydrous sodium sulfate (Na$_2$SO$_4$), filtered and evaporated under reduced pressure. The resulting solid was recrystallized from tetrahydrofuran and methanol to obtain 7-bromo-1H-pyrido[2,3-b][1,4]oxazin-2-one as white solid (59 mg, 52%).

$^1$H-NMR(DMSO-d$_6$, 300 MHz); δ=11.0 (br s, 1H), 7.88 (d, J=2.3 Hz, 1H), 7.33 (d, J=2.3 Hz, 1H), 4.81 (s, 2H).

MS(ESI); 228.9(M$^+$+1).

INTERMEDIATE SYNTHESIS EXAMPLE (4)

Synthesis of 7-fluoro-1H-pyrido[2,3-b][1,4]oxazin-2-one a) Synthesis of 2-chloro-5-fluoro-3-nitro-pyridine 5-fluoro-3-nitro-pyridin-2-ol (2 g, 12.7 mmol) and benzyl-trimethyl ammonium chloride (1.17 g, 6.35 mmol) were dissolved in acetonitrile, and phosphorus oxychloride (3.5 ml, 38.1 mmol) was added thereto and stirred at 80° C. for 6 hours. The reaction mixture was cooled and poured into ice water to quench the reaction, and extracted with dichloromethane. The combined organic layer was washed with saturated saline solution, dried over anhydrous sodium sulfate (Na$_2$SO$_4$), filtered and evaporated under reduced pressure. The residue was purified by column chromatography on silica eluting with a solvent of dichloromethane:methanol=30:1. The fractions containing the product were collected and evaporated to obtain yellow liquid (1.57 g, 70%).

$^1$H-NMR(CDCl$_3$, 300 MHz); δ=8.56 (d, J=2.7 Hz, 1H), 8.40 (dd, J=6.5 Hz, 2.7 Hz, 1H).

MS(ESI); 176.9(M$^+$+1).

b) Synthesis of (5-fluoro-3-nitro-pyridin-2-yloxy)-acetic acid methyl ester Hydroxy-acetic acid methyl ester (0.96 g, 10.7 mmol) was dissolved in 2 ml of anhydrous tetrahydrofuran under nitrogen atmosphere, and sodium hydride (0.42 g, 10.7 mmol) was added thereto at room temperature. After stirring for 30 minutes, 2-chloro-5-fluoro-3-nitro-pyridine (1.57 g, 8.89 mmol) dissolved in 15 ml of anhydrous tetrahydrofuran was added dropwise at room temperature, and the reaction mixture was stirred at room temperature for 18 hours. After completion of the reaction by adding water, the mixture was extracted with dichloromethane, and the combined organic layer was washed with water and saturated saline solution, dried over anhydrous sodium sulfate ($Na_2SO_4$), filtered and evaporated under reduced pressure. The residue was purified by column chromatography on silica eluting with a solvent of n-hexane:ethyl acetate=9:1. The fractions containing the product were collected and evaporated to obtain (5-fluoro-3-nitro-pyridin-2-yloxy)-acetic acid methyl ester as yellow liquid (1.35 g, 66%).

$^1$H-NMR($CDCl_3$, 300 MHz); δ=8.25 (d, J=2.7 Hz, 1H), 8.40 (dd, J=6.9 Hz, 2.7H, 1 Hz), 5.06 (s, 2H), 3.78 (s, 3H).

MS(ESI); 231.1($M^+$+1).

c) Synthesis of 7-fluoro-1H-pyrido[2,3-b][1,4]oxazin-2-one

In a 250 ml round flask, (5-fluoro-3-nitro-pyridin-2-yloxy)-acetic acid methyl ester (1.35 g, 5.87 mmol) and tin tetrachloride (4.45 g, 23.48 mmol) were dissolved in 15 ml of concentrated hydrochloric acid, and then stirred at 80 t for 1 hour. The reaction mixture was cooled to room temperature, neutralized with 10% sodium hydroxide solution, and extracted with ethyl acetate. The combined organic layer was washed with water and saturated saline solution, dried over anhydrous sodium sulfate ($Na_2SO_4$), filtered and evaporated under reduced pressure. The resulting solid was recrystallized from tetrahydrofuran and methanol to obtain 7-fluoro-1H-pyrido[2,3-b][1,4]oxazin-2-one as beige solid (0.70 g, 71%).

$^1$H-NMR(DMSO-$d_6$, 300 MHz); δ=11.0 (br s, 1H), 7.77 (d, J=2.7 Hz, 1H), 7.10 (dd, J=8.4 Hz, 2.7 Hz, 1H), 4.78 (s, 2H).

MS(ESI); 168.9($M^+$+1).

INTERMEDIATE SYNTHESIS EXAMPLE (5)

Synthesis of 8-chloro-2,3-dihydro-1H-pyrido[2,3-b][1,4]oxazine a) Synthesis of 2,4-dichloro-3-nitro-pyridine 3-nitro-pyridin-2,4-diol (5.0 g, 0.032 mmol) was dissolved in phosphorus oxychloride (30 ml) and the reaction mixture was heated to 100□ and stirred for 18 hours. The reaction mixture was cooled to 0□ and the reaction was quenched by adding water slowly, and ammonia water ($NH_4OH$) was added thereto dropwise to neutralize the mixture. The organic layer was extracted with dichloromethane, and the combined organic layer was washed with water and saturated saline solution, dried over anhydrous sodium sulfate ($Na_2SO_4$), filtered and evaporated under reduced pressure. The residue was purified by column chromatography on silica eluting with a solvent of dichloromethane. The fractions containing the product were collected and evaporated under reduced pressure to obtain pale-brown solid (4.01 g, 65%).

$^1$H-NMR($CDCl_3$, 300 MHz); δ=8.44 (d, J=5.4 Hz, 1H), 7.46 (d, J=5.4 Hz, 1H).

b) Synthesis of 4-chloro-3-nitro-pyridin-2-ol 2,4-dichloro-3-nitro-pyridine (4.01 g, 20.8 mmol) and cesium acetate (8.0 g, 41.6 mmol) were dissolved in anhydrous N,N-dimethyl formamide (104 ml) under nitrogen atmosphere, and the reaction mixture was heated to 800 and stirred for 18 hours. The reaction mixture was cooled to room temperature the reaction was quenched by adding water. The organic layer was extracted with ethyl acetate, and the combined organic layer was washed with water and saturated saline solution, dried over anhydrous sodium sulfate ($Na_2SO_4$), filtered and evaporated under reduced pressure to obtain pale-yellow solid (1.69 g, 47%).

$^1$H-NMR(DMSO-$d_6$, 300 MHz); δ=8.24 (d, J=5.7 Hz, 1H), 7.09 (d, J=5.7 Hz, 1H).

c) Synthesis of 3-amino-4-chloro-pyridin-2-ol 4-chloro-3-nitro-pyridin-2-ol (1.69 g, 9.72 mmol) and tin tetrachloride dihydrate ($SnCl_2.2H_2O$) (10.97 g, 48.62 mmol) was dissolved in ethanol (32 ml), heated to 70□ and stirred for 2 hours. The reaction mixture was cooled to room temperature and the ethanol was evaporated under reduced pressure. The residue was neutralized with saturated aqueous solution of sodium hydrogen carbonate, and extracted with ethyl acetate. The combined organic layer was washed with water and saturated saline solution, dried over anhydrous sodium sulfate ($Na_2SO_4$), filtered and evaporated under reduced pressure to obtain pale-yellow solid (650 mg, 46%).

$^1$H-NMR(DMSO-$d_6$, 300 MHz); δ=10.8 (br s, 1H), 7.45 (d, J=5.4 Hz, 1H), 6.69 (d, J=5.1 Hz, 1H), 4.73 (br s, 2H).

d) Synthesis of 8-chloro-1H-pyrido[2,3-b][1,4]oxazin-2-one 3-amino-4-chloro-pyridin-2-ol (650 mg, 4.49 mmol) was dissolved in anhydrous N,N-dimethyl formamide (22 ml) under nitrogen atmosphere, and chloroacetyl chloride solution (0.394 ml, 4.94 mmol) was added thereto dropwise at room temperature and stirred for 30 minutes. Potassium carbonate (1.55 g, 11.24 mmol) was added thereto dropwise at room temperature, and the reaction mixture was heated to 1000 and stirred for 18 hours. The reaction mixture was cooled to room temperature and water was added to quench the reaction, and the organic layer was extracted with ethyl acetate. The combined organic layer was washed with water and saturated saline solution, dried over anhydrous sodium sulfate ($Na_2SO_4$), filtered and evaporated under reduced pressure. The residue was recrystallized from dichloromethane and diisopropyl ether to obtain white solid (608 mg, 73%).

$^1$H-NMR(DMSO-$d_6$, 300 MHz); δ=10.6 (s, 1H), 7.91 (d, J=5.7 Hz, 1H), 7.04 (d, J=5.4 Hz, 1H), 4.75 (s, 2H).

e) Synthesis of 8-chloro-2,3-dihydro-1H-pyrido[2,3-b][1,4]oxazine 8-chloro-1H-pyrido[2,3-b][1,4]oxazin-2-one (600 mg, 3.25 mmol) was dissolved in anhydrous tetrahydrofuran (16 ml) under nitrogen atmosphere, and then cooled to 0□. 1.0M Lithium aluminum hydride dissolved in tetrahydrofuran (6.5 ml, 6.50 mmol) was added thereto dropwise, and then stirred for 30 minutes. The reaction temperature was raised to room temperature and stirred for 1 hour. The reaction mixture was cooled to 0□ again, and water (0.26 ml), 10% sodium hydroxide solution (0.52 ml) and water (0.78 ml) were added thereto dropwise in this order, and then stirred vigorously at room temperature for 1 hour. The formed solid was filtered and washed with excess ethyl acetate.

The filtrate was washed with water and saturated saline solution, dried over anhydrous sodium sulfate ($Na_2SO_4$), filtered and evaporated under reduced pressure. The residue was purified by column chromatography on silica eluting with a solvent of dichloromethane:methanol=50:1. The fractions containing the product were collected and evaporated to obtain yellow solid (385 mg, 70%).

$^1$H-NMR(DMSO-d$_6$, 300 MHz); δ=7.47 (d, J=5.4 Hz, 1H), 6.72 (d, J=5.1 Hz, 1H), 5.81 (s, 1H), 4.19 (m, 2H), 6.72 (m, 2H).

EXPERIMENTAL EXAMPLE 1

Test for Inhibiting Urate Reuptake Activity Via hURAT1

[hURAT1 Overexpression by Transient Transfection in Human Kidney Cell Line]

A human kidney cell line, HEK293 was incubated by using OptiMEM medium in 100 mm dish at (3*10^6 cells) for 24 hours. In order for the expression of hURAT1, a transfection mixture solution (Fugene6 18 μl:hURAT1 DNA 6 μg=3:1, in 600 μl OptiMEM medium/dish) was prepared and kept for 15 minutes at room temperature. To each dish, 600 μl of the mixture solution was injected and then incubated in 37□ cell incubator for 24 hours. The hURAT1-overexpressed HEK293 cell line was trypsinized and cells were harvested. Cells were resuspended in medium and seeded at 6*10^5 cells/well and incubated for 24 hours in 24-well plate which was surface-coated with Poly-D-Lysine.

[Uric Acid Transport Assay in hURAT1-Overexpressed HEK293 Cell Line]

Each compound of the present invention prepared in the examples was dissolved in DMSO as 1000 fold concentrated stock sample solution with various concentration to examine. For each concentration, the stock sample solution was diluted in PBS (1 μl in 800 μl of PBS) as 1.25 fold concentrated working sample solution to obtain final concentrations of 0.01, 0.1, 1 and 10 μM. The hURAT1-overexpressed cell line was washed with 1 ml of PBS. After washing, PBS was discarded and the sample solution was diluted by 1.25 fold with PBS. Preincubation of cells with 200 μl/well of sample solution made above was conducted for 30 minutes in 37□ cell incubator. After the incubation, each well was treated with 50 μl of PBS containing 500 μM [$^{14}$C]-uric acid (final 100 μM of uric acid/well). Cells were incubated for 2 minutes. The cells were washed twice with 1 ml of PBS.

To measure the uric acid uptake, each well was treated with 150 μl of M-per buffer (PIERCE) and kept in 37° C. cell incubator for 30 minutes to make cell lysates. 150 μl of cell lysates was transferred into test tube and 4 ml of scintillation cocktail was added. CPM value of [$^{14}$C]-uric acid absorbed into cells was detected using liquid scintillation counter. IC$_{50}$ for the inhibition of uric acid uptake by each test sample was analyzed by computational numerical processing. The results are shown in Table 1.

TABLE 1

Level of uric acid reuptake inhibition

| Compound No. | IC$_{50}$ (μM) hURAT |
|---|---|
| 1 | 0.079 |
| 2 | 0.1365 |
| 3 | 0.0165 |
| 4 | 0.023 |
| 5 | 0.1745 |
| 6 | 0.0565 |
| 7 | 0.3 |

TABLE 1-continued

Level of uric acid reuptake inhibition

| Compound No. | IC$_{50}$ (μM) hURAT |
|---|---|
| 8 | 0.353 |
| 9 | 0.02 |
| 10 | 0.334 |
| 11 | 0.175 |
| 12 | 0.0408 |
| 13 | 0.337 |
| 14 | 0.1255 |
| 15 | 0.458 |
| 16 | 0.93 |
| 17 | 1 |
| 19 | 0.2687 |
| 20 | 0.034 |
| 21 | 0.954 |
| 22-1 | 0.0888 |
| 22-2 | 0.0043 |
| 24 | 0.3635 |
| 25 | 0.0073 |
| 27-1 | 0.036 |
| 27-2 | 0.012 |
| 29 | 0.2346 |
| 30 | 0.028 |
| 35-2 | 0.277 |
| 36 | 0.1745 |
| 37 | 0.2117 |
| 38 | 0.0964 |
| 39 | 0.0884 |
| 41 | 0.3755 |
| 42 | 0.2 |
| 45 | 0.0197 |
| 46 | 0.0047 |
| 47-1 | 0.5162 |
| 47-2 | 0.0179 |
| 48 | 0.0933 |
| 49 | 0.311 |
| 50 | 0.0044 |
| 51 | 0.0115 |
| 52 | 0.0103 |
| 53 | 0.0562 |
| 55 | 0.0488 |
| 58 | 0.7417 |
| 61 | 0.002 |
| 62 | 0.1284 |
| 63 | 0.0123 |
| 64 | 0.007 |
| 65 | 0.003 |
| 66 | 0.0358 |
| 67 | 0.0078 |
| 68 | 0.0232 |
| 69 | 0.0331 |
| 70 | 0.0048 |
| 74 | 0.006 |

EXPERIMENTAL EXAMPLE 2

CYP2C9 Enzyme Inhibition Assay

Each compound of the present invention prepared in the examples was dissolved in DMSO and adjust the concentration into 10 mM stock sample solution. Make serial dilution by 10 fold scale in DMSO starting from 10 mM to 0.01 mM (500 fold concentrated stock). After fully agitated for 10 seconds, sample solution was sonicated for 1 hour. The stock sample solution was diluted in distilled water by 125 fold (e.g. add 2 μl stock sample solution into 248 μl of distilled water, 4 fold concentrated working sample solution) and agitated for 15 minutes to obtain homogenous sample suspension. Plating the working sample solution into 96 well plate to make final concentrations of 0.02, 0.2, 2 and 20 μM. Each reagent used this assay was prepared following the manufacturer's instructions (Promega #V8792: V4790+V9790).

Preparation of the 4 Fold Concentrated CYP2C9 Reaction Mixture

According to the number of test samples, 1.25 µl of 1M potassium phosphate aqueous solution, 1 µl of Luciferin-H (5 mM) solution and 0.5 µl of CYP2C9 membrane were mixed and prepared in 9.75 µl of Luciferin-free, distilled water. For the calibration to the same amount of protein with CYP2C9 membrane, CYP2C9 membrane was substituted for 0.26 µl of control membrane and added to a mixture having the same composition above in 9.99 µl of Luciferin-free, distilled water.

Preparation of 2 Fold Concentrated CYP2C9 NADPH Regeneration System

According to the number of test samples, 2.5 µl of Solution A and 0.5 µl of Solution B provided by the kit were mixed and prepared in 22 µl of Luciferin-free, distilled water.

Preparation of Luciferin Detection Buffer

To a known luciferin indicator provided as powder, 50 ml of P450-Glo™ buffer solution was added and mixed, and then the resulting mixture was kept at −20□ under shading the light.

[Experiment]

Each of the test samples was allocated in a light-shaded, 96 well white plate with a volume of 12.5 µl, and as a blank, 12.5 µl of a solvent having the same condition as that of the test samples was added. The pre-formulated 4 fold concentrated CYP2C9 mixture solution was allocated to each test sample and the blank with a volume of 12.5 µl. As a control, 12.5 µl of distilled water was added to a well and 12.5 µl of control membrane was added thereto and mixed together. After keeping the resulting mixtures in 37° C. thermostatic device for 10 minutes, the pre-formulated 2 times concentrated NADPH mixture solution was allocated to each test sample and the control with a volume of 25 µl, mixed well, and kept in 37° C. thermostatic device for 30 minutes. After keeping the resulting mixtures, 50 µl of luciferin indicator was allocated to each test sample and control, mixed well, and kept in 37° C. thermostatic device for 20 minutes. The activity of the test sample to CYP2C9 enzyme was measured by phosphorescence detector. The level of enzyme inhibition ($IC_{50}$) was analyzed with using a formula provided by the kit.

The results are shown in Table 2. The reference $IC_{50}$ value of Benzbromaron was reported as 40 nM for inhibiting CYP2C9 enzyme [Dermot F. McGinnity et al., Drug Metabolism and Disposition, 33, p 1700-1707 (2005)]. In this experiment, $IC_{50}$ value of Benzbromarone was 51 nM and each result of test compounds were shown in Table 2.

TABLE 2

Level of enzyme inhibition

| Compound No. | $IC_{50}$ (µM) CYP2C9 |
|---|---|
| 1 | 12.08 |
| 2 | >12 |
| 3 | 24.5 |
| 4 | 24.3 |
| 6 | 3.05 |
| 7 | >20 |
| 8 | >20 |
| 9 | >20 |
| 10 | >60 |

TABLE 2-continued

Level of enzyme inhibition

| Compound No. | $IC_{50}$ (µM) CYP2C9 |
|---|---|
| 11 | >60 |
| 12 | >60 |
| 13 | >60 |
| 14 | 16.56 |
| 15 | 4.5 |
| 16 | 3.5 |
| 18 | 9.7 |
| 19 | 6.8 |
| 20 | 5.2 |
| 21 | 1.11 |
| 22-1 | 13.42 |
| 22-2 | 9.45 |
| 24 | >20 |
| 25 | >20 |
| 27-1 | >20 |
| 27-2 | >20 |
| 29 | >20 |
| 30 | >40 |
| 31 | >20 |
| 32 | >20 |
| 34 | 19.58 |
| 35-1 | >20 |
| 35-2 | >20 |
| 36 | 1.93 |
| 37 | >20 |
| 38 | >20 |
| 39 | >20 |
| 40 | 15.09 |
| 41 | >20 |
| 42 | 18.39 |
| 43 | >20 |
| 44 | >20 |
| 45 | 1.18 |
| 46 | 1.09 |
| 47-1 | >20 |
| 47-2 | >20 |
| 48 | 1.68 |
| 49 | >20 |
| 50 | 1.26 |
| 51 | 8.8 |
| 52 | >20 |
| 53 | 10.27 |
| 54 | >6 |
| 55 | 8.87 |
| 56 | >20 |
| 57 | >20 |
| 58 | >20 |
| 59 | >20 |
| 60 | >20 |
| 61 | 1.23 |
| 62 | >20 |
| 63 | 1.11 |
| 64 | 5.54 |
| 65 | 12.43 |
| 66 | 1.34 |
| 68 | 1.39 |
| 69 | >20 |
| 70 | 10.79 |
| 71 | >20 |
| 74 | 16.71 |
| 75 | 11.58 |

EXPERIMENTAL EXAMPLE 3

Test for Solubility According to pH

[First Solution]

2.0 g of sodium chloride was dissolved in 7.0 mL of hydrochloric acid and water to make the total volume of 1000 mL. This solution was colorless and clear. Its pH was about 1.2.

[Second Solution]

To 250 mL of 0.2 mol/L potassium dihydrogen phosphate solution, 118 mL of 0.2 mol/L sodium hydroxide solution and water were added to make the total volume of 1000 mL. This solution was colorless and clear. Its pH was about 6.8.

[Experiment]

For the compounds of present invention prepared in the examples, the test samples were prepared in each of the first and second solutions with 2 mg/mL concentration. This test sample solution was agitated for 10 seconds, sonicated for 1 minute and heated at 37° C. for 2 hours. The heated test sample solution was filtered to remove undissolved compounds therein. From filtered solution, 100 μl of the completely dissolved solution was sampled and 100 μl of acetonitrile was added thereto to make test sample solution. For each analysis of test sample solution, the solubility was measured by using liquid chromatography. The results of solubility test in the first and second solutions are shown in Table 3.

TABLE 3

| Compound No. | Solubility (μg/mL) | |
|---|---|---|
| | pH 1.2 | pH 6.8 |
| 1 | 56.1 | 276.8 |
| 3 | 1420.1 | 886.5 |
| 4 | 1927 | 970 |
| 7 | 105.8 | 109.1 |
| 8 | 986 | 344 |
| 12 | 1882 | 132 |
| 13 | 1395 | 847 |
| 14 | 1479 | 747.2 |
| 15 | 1511 | 453 |
| 17 | 1612 | 1890 |
| 22-2 | <0.1 | 153 |
| 24 | 1254.6 | 133.6 |
| 27-2 | 207.3 | 578.9 |
| 29 | 1085.7 | 381.9 |
| 30 | 7.2 | 332 |
| 31 | 1846.64 | 198.66 |
| 32 | 1960.9 | 1474 |
| 33 | 1576.5 | 809.5 |
| 35-2 | 1458.1 | 233.7 |
| 36 | 1561.7 | 743.1 |
| 37 | 1931.1 | 114.2 |
| 39 | 1339.3 | 480.5 |
| 40 | 1317.92 | 473.19 |
| 41 | 808.87 | 156.54 |
| 42 | 1310.4 | 142.6 |
| 43 | 1260.4 | 1007.6 |
| 44 | 1960 | 2095.4 |
| 47-2 | 6.4 | 329.6 |
| 59 | 2242.5 | 676.2 |
| 60 | 2125.3 | 599.6 |
| 62 | 34.8 | 624 |
| 71 | 2138.2 | 344.7 |
| 72 | 1873.1 | 375.4 |
| 73 | 1153.1 | 565.1 |

EXPERIMENTAL EXAMPLE 4

Test for Uricosuric Effect in Cebus Monkey

For the example 4 compound which showed superior activity as described above, its uricosuric activity was tested by measuring uric acid level in plasma and urine in Cebus monkey. Placebo control (0.5% MC solution) and Benzbromarone was administered as a negative and positive control, respectively.

The example 4 compound was administered orally according to the clinical administration pathway. The administered dose was 15 mg/kg for Benzbromarone, and 15 mg/kg (same dose), 7.5 mg/kg and 3.75 mg/kg (lower doses) for the example 4 compound. The example 4 compound was prepared by suspending in vehicle (0.5% MC solution). The prepared sample was stirred sufficiently to make homogenous suspension, filled in an injector and administered through oral catheter at once. The catheter was washed again with 0.5% MC solution to remove remaining suspension in catheter, thereby completely administered the total samples into Cebus monkey. The test samples prepared above were administered once a day.

After the administration, blood and urine were collected as indicated time points (0, 0.5, 1, 2, 4, 8, and 24 hours). The concentrations of uric acid, creatinine and lactic acid in plasma and urine were measured to analyze the lowered plasma uric acid as well as its enhanced urine excretion.

Fractional excretion rates of uric acid (FEua) by each test group (vehicle, Benzbromarone, example 4 compound) during 0~8 hours were measured. FEua of example 4 compound (3.75 mg/kg, 7.5 mg/kg and 15 mg/kg) were 24.1±13.3%, 31.6±13.3% and 33.2±19.8%, respectively, which showed superior effects compared with 8.5±1.5% of the placebo control group. The lowering effect of uric acid in plasma which is followed by enhanced urine excretion was measured at 4 hours after the administration of 3.75 mg/kg, 7.5 mg/kg and 15 mg/kg of example 4 compound. Plasma uric acid level was 3.88 mg/dL, 3.66 mg/dL and 3.40 mg/dL, respectively, suggesting its superior effects to 5.10 mg/dL of the placebo control group.

FEua of the Benzbromarone administered group during 0~8 hours of was 20.0±10.5%, and the uric acid level in plasma was 3.80 mg/dL at 4 hours after the administration.

From the above results, the uricosruic effect of example 4 compound showed a remarkably superior effect than Benzbromarone at 15 mg/kg showing 160% enhanced uricosuric effect during 0~8 hours in Cebus monkey. Furthermore, example 4 compound showed equal potency of uricosuric effect (24.1±13.3% of FEua) to 15 mg/kg of Benzbromarone (20.0±10.5% of FEua) at 3.75 mg/kg which was a quarter amount of Benzbromarone.

In summary, as a result of the test for the effect of enhancing uric acid excretion in Cebus monkey, the example 4 compound showed a superior uricosuric effect to the comparative drug, Benzbromarone.

Meanwhile, according to the results from comparison test of the example 3 compound with the compound disclosed in WO2006/057460, the example 3 compound showed 180% enhanced superior uricosuric activity compared to the compound disclosed in WO2006/057460.

All the study described above in Cebus monkey was performed by Japan Bioscience Center (JBS) which is one of the entrusted CRO in Japan.

The invention claimed is:

1. A heterocycle derivative compound having Formula I:

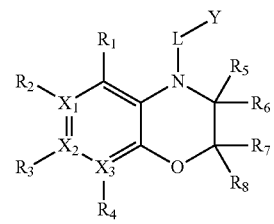

[Formula I]

wherein, in Formula I, each of $X_1$, $X_2$, and $X_3$ is independently carbon or nitrogen, provided that at least one of $X_1$, $X_2$, and $X_3$ is nitrogen, each of $R_1$, $R_2$, $R_3$ and $R_4$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; cyano; nitro; amino; carboxylic acid group; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; $C_2$-$C_7$ alkanoyl; $C_2$-$C_7$ alkoxycarbonyl; $C_2$-$C_7$ alkanoyloxy; $C_3$-$C_{12}$ mono or bicycloalkyl; $C_4$-$C_{12}$ cycloalkylalkyl; $C_6$-$C_{12}$ aryl unsubstituted or substituted with one or more substituents selected from the group consisting of $C_1$-$C_6$ haloalkoxy, $C_1$-$C_6$ haloalkyl, di-($C_1$-$C_6$)alkylamino, nitro, halogen, cyano and $C_2$-$C_7$ alkanoyl; saturated or unsaturated $C_3$-$C_{12}$ mono or polycarbocyclyl; and saturated or unsaturated 3- to 12-membered mono or polyheterocyclyl containing 1 to 3 heteroatoms which is unsubstituted or substituted with oxo or $C_1$-$C_6$ alkoxy, provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a saturated or unsaturated 5- to 11-membered carbocycle or heterocycle, each of $R_5$, $R_6$, $R_7$ and $R_8$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; $C_2$-$C_7$ alkanoyl; phosphoric acid group; N-oxide; amide; $C_1$-$C_6$ alkylamide; aldehyde; hydroxamic acid; $C_1$-$C_6$ alkylsulfide;-$C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; halogen; phenyl; cyano; nitro; amino; and carboxylic acid group, or $R_5$ and $R_6$ together with a carbon atom to which they are attached may form a carbonyl group (C=O) or thioxo group (C=S), or $R_7$ and $R_8$ together with a carbon atom to which they are attached may form a carbonyl group (C=O) or thioxo group (C=S), L is a carbonyl group (—C(=O)—), sulfonyl group (—S(=O)$_2$—), $C_1$-$C_6$ alkyl carbonyl, carbonyl $C_1$-$C_6$ alkyl or thioxo group (—C(=S)—), and Y is selected from the group consisting of saturated or unsaturated $C_3$-$C_{12}$ mono or polycarbocyclyl substituted with $R_9$, $R_{10}$, and $R_{11}$; and saturated or unsaturated 3- to 12-membered mono or polyheterocyclyl containing 1 to 3 heteroatoms and being substituted with $R_9$, $R_{10}$, and $R_{11}$, wherein each of $R_9$, $R_{10}$ and $R_{11}$ is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; $C_1$-$C_6$ alkylsulfide; $C_1$-$C_6$ alkylthioxo; hydroxamic acid; phenyl; cyano; nitro; amino; carboxylic acid group; amide; $C_1$-$C_6$ alkylamide; $C_2$-$C_7$ alkanoyl; aldehyde; $C_3$-$C_8$ ester; $C_3$-$C_8$ esteroxy; $C_1$-$C_6$ alkylsulfonyl; $C_1$-$C_6$ oximealkyl; $C_1$-$C_6$ aminoalkyl; $C_3$-$C_8$ alkylcarbonylalkyl; phosphoric acid group; and N-oxide, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen, or racemate, isomer or pharmaceutically acceptable salt thereof.

2. The compound according to claim 1, wherein L is a carbonyl group (—C(=O)—), sulfonyl group(—S(=O)$_2$—), or thioxo group (—C(=S)—), or racemate, isomer or pharmaceutically acceptable salt thereof.

3. The compound according to claim 1, wherein each of $R_5$, $R_6$, $R_7$ and $R_8$ may be same or different and is independently selected from the group consisting of hydrogen; hydroxy; $C_1$-$C_4$ alkyl; $C_1$-$C_4$ haloalkyl; $C_1$-$C_4$ alkoxy; $C_1$-$C_4$ haloalkoxy; $C_2$-$C_5$ alkanoyl; halogen; phenyl; cyano; nitro; amino; and carboxylic acid group; or $R_5$ and $R_6$ together with a carbon atom to which they are attached may form a carbonyl group (C=O) or thioxo group (C=S), or $R_7$ and $R_8$ together with a carbon atom to which they are attached may form a carbonyl group (C=O) or thioxo group (C=S), or racemate, isomer or pharmaceutically acceptable salt thereof.

4. The compound according to claim 1, wherein Y is selected from the group consisting of saturated or unsaturated $C_5$-$C_6$ carbocyclyl substituted with $R_9$, $R_{10}$ and $R_{11}$; and saturated or unsaturated 5- to 6-membered heterocyclyl containing 1 to 3 heteroatoms and being substituted with $R_9$, $R_{10}$ and $R_{11}$, wherein $R_9$, $R_{10}$ and $R_{11}$ are the same as defined in claim 1, or racemate, isomer or pharmaceutically acceptable salt thereof.

5. The compound according to claim 1, wherein each of $R_9$, $R_{10}$ and $R_{11}$ is independently selected from the group consisting of hydrogen; hydroxy; $C_1$-$C_4$ alkyl; $C_1$-$C_4$ haloalkyl; $C_1$-$C_4$ alkoxy; $C_1$-$C_4$ haloalkoxy; halogen; phenyl; cyano; nitro; amino; carboxylic acid group; amide; $C_1$-$C_6$ alkylamide; $C_{2-5}$ alkanoyl; aldehyde; $C_3$-$C_7$ ester; $C_3$-$C_7$ esteroxy; $C_1$-$C_4$ alkylsulfonyl; $C_1$-$C_4$ oximealkyl; $C_1$-$C_4$ aminoalkyl; $C_3$-$C_7$ alkylcarbonylalkyl; phosphoric acid group; and N-oxide, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen, or racemate, isomer or pharmaceutically acceptable salt thereof.

6. The compound according to claim 1, wherein each of $R_1$-$R_2$, $R_2$-$R_3$ and $R_3$-$R_4$ pairs is independently fused to form a saturated or unsaturated 5- to 6-membered carbocycle or heterocycle, wherein the heterocycle preferably contains 1 to 3 heteroatoms selected from N, O and S, or racemate, isomer or pharmaceutically acceptable salt thereof.

7. The compound according to claim 1, wherein each of $R_1$, $R_2$, $R_3$ and $R_4$ may be same or different and is independently selected from the group consisting of hydrogen; hydroxy; $C_1$-$C_4$ alkyl; $C_1$-$C_4$ haloalkyl; $C_1$-$C_4$ alkoxy; $C_1$-$C_4$ haloalkoxy; halogen; cyano; nitro; amino; carboxylic acid group; $C_2$-$C_5$ alkanoyl; $C_2$-$C_5$ alkoxycarbonyl; $C_2$-$C_5$ alkanoyloxy; $C_3$-$C_{10}$ mono or bicycloalkyl; $C_4$-$C_{11}$ cycloalkylalkyl; $C_6$-$C_{10}$ aryl unsubstituted or substituted with one or more substituents selected from the group consisting of $C_1$-$C_6$ haloalkoxy, $C_1$-$C_6$ haloalkyl, di-($C_1$-$C_6$)alkylamino, nitro, halogen, cyano and $C_2$-$C_7$ alkanoyl; saturated or unsaturated $C_3$-$C_{10}$ mono or polycarbocyclyl; and saturated or unsaturated 3- to 10-membered mono or polyheterocyclyl containing 1 to 3 heteroatoms unsubstituted or substituted with oxo or $C_1$-$C_6$ alkoxy, provided that when $X_1$ is nitrogen, $R_2$ does not exist; when $X_2$ is nitrogen, $R_3$ does not exist; and when $X_3$ is nitrogen, $R_4$ does not exist, or racemate, isomer or pharmaceutically acceptable salt thereof.

8. The compound according to claim 1, wherein the $C_3$-$C_{12}$ mono or bicycloalkyl is a monocycloalkyl selected from cyclopropyl, cyclobutyl, cyclopentyl, cyclohexyl, cycloheptyl, cyclooctyl and cyclononyl, or a bicycloalkyl obtained by the fusion of the same or different two of said monocycloalkyls, or racemate, isomer or pharmaceutically acceptable salt thereof.

9. The compound according to claim 1, wherein the $C_3$-$C_{12}$ mono or polycarbocyclyl is a monocycloalkyl selected from cyclopropyl, cyclobutyl, cyclopentyl, cyclohexyl, cycloheptyl, cyclooctyl and cyclononyl, or a polycycloalkyl obtained by the fusion of the same or different two or more of said monocycloalkyls, or carboaryl, or racemate, isomer or pharmaceutically acceptable salt thereof.

10. The compound according to claim 1, wherein the saturated or unsaturated 3- to 12-membered mono or polyheterocyclyl containing 1 to 3 heteroatoms is thienyl, thiazolyl, imidazolyl, benzimidazolyl, triazolyl, tetrahydropyranyl, pyridinyl, furanyl, pyranyl, pyrrolyl, pyrazolyl, pyrazinyl, pyrimidinyl, isothiazolyl, isoxazolyl, pyridazinyl, isobenzopyranyl, chromenyl, indolyl, indazolyl, quinolinyl, purinyl, pyrrolinyl, chromanyl, pyrazolidinyl, piperidinyl or piperazinyl, or racemate, isomer or pharmaceutically acceptable salt thereof.

11. The compound according to claim 1, wherein $X_2$ is carbon, and each of $X_1$ and $X_3$ is independently carbon or nitrogen, provided that at least one of $X_1$ and $X_3$ is nitrogen, or racemate, isomer or pharmaceutically acceptable salt thereof.

12. The compound according to claim 1, wherein each of $R_1$, $R_2$, $R_3$ and $R_4$ may be same or different and is independently selected from the group consisting of hydrogen; $C_1$-$C_4$ alkyl; $C_1$-$C_4$ haloalkyl; halogen; phenyl unsubstituted or substituted with one or more substituents selected from the group consisting of $C_1$-$C_6$ haloalkoxy, $C_1$-$C_6$ haloalkyl, di-($C_1$-$C_6$)alkylamino, nitro, halogen, cyano and $C_2$-$C_7$ alkanoyl; cyano; and saturated or unsaturated 3- to 10-membered mono or polyheterocyclyl containing 1 to 3 heteroatoms which is unsubstituted or substituted with oxo or $C_1$-$C_6$ alkoxy; or each of $R_1$-$R_2$, $R_2$-$R_3$ and $R_3$-$R_4$ pairs may be independently fused to form a saturated or unsaturated 5- to 6-membered carbocycle, provided that when $X_1$ is nitrogen, $R_2$ does not exist; when $X_2$ is nitrogen, $R_3$ does not exist; and when $X_3$ is nitrogen, $R_4$ does not exist, or racemate, isomer or pharmaceutically acceptable salt thereof.

13. The compound according to claim 1, wherein Y is an aromatic 5- to 6-membered carbocycle or heterocycle substituted with $R_9$, $R_{10}$ and $R_{11}$, wherein $R_9$, $R_{10}$ and $R_{11}$ are the same as defined in claim 1, or racemate, isomer or pharmaceutically acceptable salt thereof.

14. The compound according to claim 1, wherein each of $R_9$, $R_{10}$ and $R_{11}$ is independently selected from the group consisting of hydrogen; hydroxy; $C_1$-$C_4$ alkyl; $C_1$-$C_4$ haloalkyl; $C_1$-$C_4$ alkoxy; $C_1$-$C_4$ haloalkoxy; halogen; nitro; carboxylic acid group; and $C_3$-$C_7$ esteroxy, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen, or racemate, isomer or pharmaceutically acceptable salt thereof.

15. The compound according to claim 1 wherein each of $X_1$, $X_2$ and $X_3$ is independently carbon or nitrogen, provided that at least one of $X_1$, $X_2$ and $X_3$ is nitrogen, each of $R_1$, $R_2$, $R_3$ and $R_4$ may be same or different and is independently selected from the group consisting of hydrogen; hydroxy; $C_1$-$C_4$ alkyl; $C_1$-$C_4$ haloalkyl; $C_1$-$C_4$ alkoxy; $C_1$-$C_4$ haloalkoxy; halogen; cyano; nitro; amino; carboxylic acid group; $C_2$-$C_5$ alkanoyl; $C_2$-$C_5$ alkoxycarbonyl; $C_2$-$C_5$ alkanoyloxy; $C_6$-$C_{12}$ aryl unsubstituted or substituted with one or more substituents selected from the group consisting of $C_1$-$C_6$ haloalkoxy, $C_1$-$C_6$ haloalkyl, di-($C_1$-$C_6$)alkylamino, nitro, halogen, cyano and $C_2$-$C_7$ alkanoyl; and, saturated or unsaturated $C_3$-$C_{12}$ mono or polycarbocyclyl or heterocyclyl which is unsubstituted or substituted with oxo or $C_1$-$C_6$ alkoxy, provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a saturated or unsaturated 5- to 6-membered carbocycle or heterocycle, each of $R_5$, $R_6$, $R_7$ and $R_8$ may be same or different and is independently selected from the group consisting of hydrogen; hydroxy; $C_1$-$C_4$ alkyl; $C_1$-$C_4$ haloalkyl; $C_1$-$C_4$ alkoxy;-$C_1$-$C_4$ haloalkoxy; $C_2$-$C_5$ alkanoyl; halogen; cyano; nitro; amino; and carboxylic acid group, or $R_5$ and $R_6$ together with a carbon atom to which they are attached may form a carbonyl group (C=O), or $R_7$ and $R_8$ together with a carbon atom to which they are attached may form a carbonyl group (C=O), L is a carbonyl group (—C(=O)—), sulfonyl group (—S(=)$_2$—) or thioxo group (—C(=S)—), and Y is selected from the group consisting of saturated or unsaturated $C_3$-$C_{12}$ mono or polycarbocyclyl substituted with $R_9$, $R_{10}$ and $R_{11}$; and saturated or unsaturated 3- to 12-membered mono or polyheterocyclyl containing 1 to 3 heteroatoms and being substituted with $R_9$, $R_{10}$ and $R_{11}$, wherein the heterocycle preferably contains 1 to 3 heteroatoms selected from N, O and S, wherein each of $R_9$, $R_{10}$ and $R_{11}$ is independently selected from the group consisting of hydrogen; hydroxy; $C_1$-$C_4$ alkyl; $C_1$-$C_4$ haloalkyl; $C_1$-$C_4$ alkoxy; $C_1$-$C_4$ haloalkoxy; halogen; cyano; nitro; amino; carboxylic acid group; and $C_3$-$C_7$ esteroxy, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen, or racemate, isomer or pharmaceutically acceptable salt thereof.

16. The compound according to claim 1 wherein each of $X_1$, $X_2$ and $X_3$ is independently carbon or nitrogen, provided that at least one of $X_1$, $X_2$ and $X_3$ is nitrogen, each of $R_1$, $R_2$, $R_3$ and $R_4$ may be same or different and is independently selected from the group consisting of hydrogen; $C_1$-$C_4$ alkyl; $C_1$-$C_4$ haloalkyl; $C_1$-$C_4$ alkoxy; halogen; cyano; nitro; amino; and saturated or unsaturated $C_5$-$C_6$ carbocyclyl or heterocyclyl, provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a phenyl or a 6-membered heterocycle containing 1 to 2 atoms of nitrogen or oxygen, each of $R_5$, $R_6$, $R_7$ and $R_8$ may be same or different and is independently selected from the group consisting of hydrogen; $C_1$-$C_4$alkyl; $C_1$-$C_4$ alkoxy; halogen; cyano; nitro; and amino, L is a carbonyl group (—C(═O)—) or thioxo group (—C(═S)—), and Y is a phenyl which has a hydroxy group in para-position to the attachment position of L and is further substituted with 1 to 3 substituents independently selected from halogen and nitro, or racemate, isomer or pharmaceutically acceptable salt thereof.

17. The compound according to claim 1 which is selected from the group consisting of:

(3,5-dibromo-4-hydroxy-phenyl)-(2,3-dihydro-pyrido [2,3-b][1,4]oxazin-1-yl)-methanone (compound 1);

(3,5-dibromo-4-methoxy-phenyl)-(2,3-dihydro-pyrido[4,3-b][1,4]oxazin-4-yl)-methanone (compound 2);

(3,5-dibromo-4-hydroxy-phenyl)-(2,3-dihydro-pyrido[4,3-b][1,4]oxazin-4-yl)-methanone hydrobromic acid salt (compound 3);

(3,5-dibromo-4-hydroxy-phenyl)-(2,3-dihydro-pyrido[4,3-b][1,4]oxazin-4-yl)-methanone (compound 4);

(3,5-dibromo-4-methoxy-phenyl)-(2,3-dihydro-pyrido[3,4-b][1,4]oxazin-1-yl)-methanone (compound 5);

(3,5-dibromo-4-hydroxy-phenyl)-(2,3-dihydro-pyrido[3,4-b][1,4]oxazin-1-yl)-methanone (compound 6);

(3,5-dibromo-4-hydroxy-phenyl)-(6-methyl-2,3-dihydro-pyrido[2,3-b][1,4]oxazin-1-yl)-methanone (compound 7);

(3,5-dibromo-4-hydroxy-phenyl)-(2,2-dimethyl-2,3-dihydro-pyrido[4,3-b][1,4]oxazin-4-yl)-methanone (compound 8);

(3,5-dibromo-4-hydroxy-phenyl)-(7-cyclopropyl-2,3-dihydro-pyrido[2,3-b][1,4]oxazin-1-yl)-methanone (compound 9);

(3-chloro-4-hydroxy-phenyl)-(2,3-dihydro-pyrido[4,3-b][1,4]oxazin-4-yl)-methanone hydrobromic acid salt (compound 10);

(3-bromo-4-hydroxy-phenyl)-(2,3-dihydro-pyrido[4,3-b][1,4]oxazin-4-yl)-methanone hydrobromic acid salt (compound 11);

(2,3-dihydro-pyrido[4,3-b][1,4]oxazin-4-yl)-(4-hydroxy-3-trifluoromethyl-phenyl)-methanone (compound 12);

(3,5-dichloro-4-hydroxy-phenyl)-(2,3-dihydro-pyrido[4,3-b][1,4]oxazin-4-yl)-methanone hydrobromic acid salt (compound 13);

(3-chloro-4-hydroxy-5-nitro-phenyl)-(2,3-dihydro-pyrido[4,3-b][1,4]oxazin-4-yl)-methanone (compound 14);

(3,5-dichloro-4-hydroxy-phenyl)-(2,3-dihydro-pyrido[3,4-b][1,4]oxazin-1-yl)-methanone hydrobromic acid salt (compound 15);

(3-bromo-4-hydroxy-phenyl)-(2,3-dihydro-pyrido[3,4-b][1,4]oxazin-1-yl)-methanone hydrobromic acid salt (compound 16);

(3-chloro-4-hydroxy-5-nitro-phenyl)-(2,3-dihydro-pyrido[3,4-b][1,4]oxazin-1-yl)-methanone hydrobromic acid salt (compound 17);

(3-chloro-4-hydroxy-phenyl)-(2,3-dihydro-pyrido[3,4-b][1,4]oxazin-1-yl)-methanone hydrobromic acid salt (compound 18);

(2,3-dihydro-pyrido[3,4-b][1,4]oxazin-1-yl)-(4-hydroxy-3-trifluoromethyl-phenyl)-methanone (compound 19);

(3,5-dibromo-4-hydroxy-phenyl)-(7-phenyl-2,3-dihydro-pyrido[2,3-b][1,4]oxazin-1-yl)-methanone (compound 20);

2,6-dichloro-4-(2,3-dihydro-pyrido[4,3-b][1,4]oxazin-4-sulfonyl)-phenol (compound 21);

(3,5-dibromo-4-methoxy-phenyl)-(7-trifluoromethyl-2,3-dihydro-pyrido[2,3-b][1,4]oxazin-1-yl)-methanone (compound 22-1);

(3,5-dibromo-4-hydroxy-phenyl)-(7-trifluoromethyl-2,3-dihydro-pyrido [2,3-b][1,4]oxazin-1-yl)-methanone (compound 22-2);

2,5-dibromo-4-(2,3-dihydro-pyrido[4,3-b][1,4]oxazin-4-carbonyl)-benzoic acid (compound 23);

[2,6-dibromo-4-(2,3-dihydro-pyrido[4,3-b][1,4]oxazin-4-carbonyl)-phenoxy]-acetic acid methyl ester (compound 24);

(7-bromo-2,3-dihydro-pyrido[2,3-b][1,4]oxazin-1-yl)-(3,5-dibromo-4-hydroxy-phenyl)-methanone (compound 25);

(2,3-dihydro-pyrido[4,3-b][1,4]oxazin-4-yl)-(3-fluoro-4-hydroxy-phenyl)-methanone (compound 26);

(3,5-dibromo-4-methoxy-phenyl)-(7-methyl-2,3-dihydro-pyrido[2,3-b] [1,4]oxazin-1-yl)-methanone (compound 27-1);

(3,5-dibromo-4-hydroxy-phenyl)-(7-methyl-2,3-dihydro-pyrido[2,3-b] [1,4]oxazin-1-yl)-methanone (compound 27-2);

(3,5-difluoro-4-methoxy-phenyl)-(2,3-dihydro-pyrido[4,3-b][1,4]oxazin-4-yl)-methanone (compound 28);

(3,5-difluoro-4-hydroxy-phenyl)-(2,3-dihydro-pyrido[4,3-b][1,4]oxazin-4-yl)-methanone (compound 29);

(5-chloro-2,3-dihydro-pyrido[4,3-b][1,4]oxazin-4-yl)-(3,5-dibromo-4-hydroxy-phenyl)-methanone (compound 30);

(2,6-dichloro-pyridin-4-yl)-(2,3-dihydro-pyrido[4,3-b][1,4]oxazin-4-yl)-methanone (compound 31);

(2,3-dihydro-pyrido[4,3-b][1,4]oxazin-4-yl)-(6-hydroxy-pyridin-3-yl)-methanone (compound 32);

(3,5-dibromo-4-hydroxy-phenyl)-(2,3-dihydro-pyrido[4,3-b][1,4]oxazin-4-yl)-methanone hydrochloric acid salt (compound 33);

(3-chloro-4-hydroxy-phenyl)-(2,3-dihydro-pyrido[3,4-b][1,4]oxazin-1-yl)-methanone (compound 34);

4-(2,3-dihydro-ppido[4,3-b][1,4]oxazin-4-sulfonyl)-phenol (compound 35-1);

2,6-dibromo-4-(2,3-dihydro-pyrido[4,3-b][1,4]oxazin-4-sulfonyl)-phenol (compound 35-2);

(3-chloro-4-hydroxy-5-nitro-phenyl)-(2,3-dihydro-pyrido [3,4-b][1,4]oxazin-1-yl)-methanone (compound 36);

(3-chloro-4-hydroxy-phenyl)-(2,3-dihydro-pyrido[4,3-b][1,4]oxazin-4-yl)-methanone (compound 37);

(3-bromo-4-hydroxy-phenyl)-(2,3-dihydro-pyrido[4,3-b][1,4]oxazin-4-yl)-methanone (compound 38);

(3 ,5-dichloro-4-hydroxy-phenyl)-(2 ,3-dihydro-pyrido[4,3-b][1,4]oxazin-4-yl)-methanone (compound 39);

(3-bromo-4-hydroxy-phenyl)-(2,3-dihydro-pyrido[3,4-b][1,4]oxazin-1-yl)-methanone (compound 40);

(3,5-dichloro-4-hydroxy-phenyl)-(2,3-dihydro-pyrido[3,4-b][1,4]oxazin-1-yl)-methanone (compound 41);

2-(3,5-dibromo-4-hydroxy-phenyl)-1-(2,3-dihydro-pyrido[4,3-b][1,4]oxazin-4-yl)-ethanone (compound 42);

(2,3-dihydro-pyrido[4,3-b][1,4]oxazin-4-yl)-(3-methoxy-isoxazol-5-yl)-methanone (compound 43);

(2,3-dihydro-pyrido[4,3-b][1,4]oxazin-4-yl)-(3-hydroxy-isoxazol-5-yl)-methanone (compound 44);

(3,5-dibromo-4-hydroxy-phenyl)-[7-(4-trifluoromethyl-phenyl)-2,3-dihydro-pyrido[2,3-b][1,4]oxazin-1-yl]-methanone (compound 45);

(3,5-dibromo-4-hydroxy-phenyl)-[7-(2-trifluoromethyl-phenyl)-2,3-dihydro-pyrido[2,3-b][1,4]oxazin-1-yl]-methanone (compound 46);

1-(3,5-dibromo-4-methoxy-benzoyl)-2,3-dihydro-1H-pyrido[2,3-b][1,4]oxazin-7-carbonitrile (compound 47-1);

1-(3,5-dibromo-4-hydroxy-benzoyl)-2,3-dihydro-1H-pyrido[2,3-b][1,4]oxazin-7-carbonitrile (compound 47-2);

(3,5-dibromo-4-methoxy-phenyl)-[7-(3-nitro-phenyl)-2,3-dihydro-pyrido[2,3-b][1,4]oxazin-1-yl]-methanone (compound 48);

(3,5-dibromo-4-methoxy-phenyl)-[7-(3 -nitro-phenyl)-2,3-dihydro-pyrido [2,3-b][1,4]oxazin-1-yl]-methanone (compound 49);

(3,5-dibromo-4-hydroxy-phenyl)-[7-(3-dimethylamino-phenyl)-2,3-dihydro-pyrido[2,3-b][1,4]oxazin-1-yl]-methanone (compound 50);

(3,5-dibromo-4-hydroxy-phenyl)-(2,3-dihydro-pyrido[4,3-b][1,4]oxazin-4-yl)-methanethione (compound 51);

(3,5-dibromo-4-hydroxy-phenyl)-[7-pyridin-3-yl-2,3-dihydro-pyrido[2,3-b][1,4]oxazin-1-yl]-methanone (compound 52);

(3,5-dibromo-4-hydroxy-phenyl)-[7-furan-3-yl-2,3-dihydro-pyrido[2,3-b][1,4]oxazin-1-yl]-methanone (compound 53);

1-(3,5-dibromo-4-hydroxy-phenyl)-2-(2,3-dihydro-pyrido[4,3-b][1,4]oxazin-4-yl)-ethanone (compound 54);

(3,5-dibromo-4-hydroxy-phenyl)-(2,3-dihydro-4-oxa-1,9-diaza-phenanthren-1-yl)-methanone (compound 55);

4[2-(3,5-dibromo-4-hydroxy-phenyl)-2-oxo-ethyl)]-4H-pyrido[4,3-b][1,4]oxazin-3-one (compound 56);

4-(3,5-dibromo-4-methoxy-benzoyl)-4H-pyrido[4,3-b][1,4]oxazin-3-one (compound 57);

(3,5-dibromo-4-methoxy-phenyl)-(6-methyl-2,3-dihydro-pyrido[2,3-b][1,4]oxazin-1-yl)-methanone (compound 58);

(2,3-dihydro-pyrido[4,3-b][1,4]oxazin-4-yl)-(2,4-dihydroxy-pyrimidin-5-yl)-methanone (compound 59);

(2,3-dihydro-pyrido[4,3-b][1,4]oxazin-4-yl)-(2,6-dihydroxy-pyrimidin-4-yl)-methanone (compound 60);

(3,5-dibromo-4-hydroxy-phenyl)-(7-isoquinolin-4-yl-2,3-dihydro-pyrido[2,3-b][1,4]oxazin-1-yl)-methanone (compound 61);

(3,5-dibromo-4-hydroxy-phenyl)-(6,7-dihydro-pyrimido[4,5-b][1,4]oxazin-5-yl)-methanone (compound 62);

(3,5-dibromo-4-hydroxy-phenyl)-[7-(3-trifluoromethyl-phenyl)-2,3-dihydro-pyrido[2,3-b][1,4]oxazin-1-yl]-methanone (compound 63);

(3,5-dibromo-4-hydroxy-phenyl)-[7-(3-fluoromethyl-phenyl)-2,3-dihydro-pyrido[2,3-b][1,4]oxazin-1-yl]-methanone (compound 64);

4-[1-(3,5-dibromo-4-hydroxy-benzoyl)-2,3-dihydro-1H-pyrido [2,3-b][1,4]oxazin-7-yl]-benzonitrile (compound 65);

(3,5-dibromo-4-hydroxy-phenyl)-[7-(4-trifluoromethoxy-phenyl)-2,3-dihydro-pyrido[2,3-b][1,4]oxazin-1-yl]-methanone (compound 66);

1- {4- [1-(3,5-dibromo-4-hydroxy-benzoyl)-2,3-dihydro-1H-pyrido [2,3-b][1,4]oxazin-7-yl]-phenyl}-ethanone (compound 67);

(3,5-dibromo-4-hydroxy-phenyl)-[7-(5-methoxy-pyridin-3-yl)-2,3-dihydro-pyrido[2,3-b][1,4]oxazin-1-yl]-methanone (compound 68);

(4-hydroxy-3-trifluoromethyl-phenyl)-(7-methyl-2,3-dihydro-pyrido[2,3-b][1,4]oxazin-1-yl)-methanone (compound 69);

(3,5-dibromo-4-hydroxy-phenyl)-[7-(1H-indol-4-yl)-2,3-dihydro-pyrido[2,3-b][1,4]oxazin-1-yl]-methanone (compound 70);

(3,5-dibromo-4-hydroxy-phenyl)-(2,3-dihydro-pyrido[4,3-b][1,4]oxazin-4-yl)-methanone sulfuric acid salt (compound 71);

(2,6-dibromo-4-(2,3-dihydro-pyrido[4,3-b][1,4]oxazin-4-carbonyl)-phenolate sodium salt (compound 72);

(2,6-dibromo-4-(2,3-dihydro-pyrido[4,3-b][1,4]oxazin-4-carbonyl)-phenolate potassium salt (compound 73);

(3,5-dibromo-4-hydroxy-phenyl)-(2,3-dihydro-pyrido[4,3-b][1,4]oxazin-4-yl)-methanethione trifluoroacetic acid salt (compound 74); and 1-[1-(3,5-dibromo-4-hydroxy-benzoyl)-2,3-dihydro-1H-pyrido[2,3-b][1,4]oxazin-7-yl]-pyrrolidin-2-one (compound 75), or racemate, isomer or pharmaceutically acceptable salt thereof.

18. A method for preparing a compound of Formula II, or racemate, isomer or pharmaceutically acceptable salt thereof, comprising the steps of:

a) reducing Formula VII compound to obtain Formula VI compound, b) cyclizing the obtained Formula VI compound with Formula V compound to obtain Formula IV compound, and c) peptide-bonding the obtained Formula IV compound with Formula III compound to obtain Formula II compound:

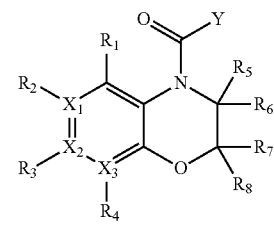

[Formula II]

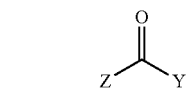

[Formula III]

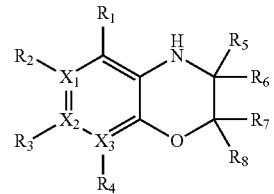

[Formula IV]

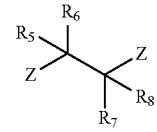

[Formula V]

-continued

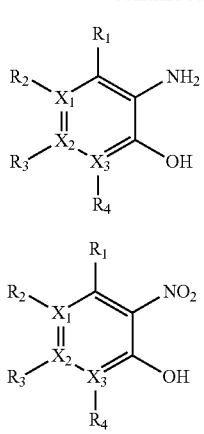

[Formula VI]

[Formula VII]

wherein, in Formulae II to VII,
each of $X_1$, $X_2$, and $X_3$ is independently carbon or nitrogen, provided that at least one of $X_1$, $X_2$, and $X_3$ is nitrogen,
each of $R_1$, $R_2$, $R_3$ and $R_4$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; cyano; nitro; amino; carboxylic acid group; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; $C_2$-$C_7$ alkanoyl; $C_2$-$C_7$ alkoxycarbonyl; $C_2$-$C_7$ alkanoyloxy; $C_3$-$C_{12}$ mono or bicycloalkyl; $C_4$-$C_{12}$ cycloalkylalkyl; $C_6$-$C_{12}$ aryl unsubstituted or substituted with one or more substituents selected from the group consisting of $C_1$-$C_6$ haloalkoxy, $C_1$-$C_6$ haloalkyl, di-($C_1$-$C_6$)alkylamino, nitro, halogen, cyano and $C_2$-$C_7$ alkanoyl; saturated or unsaturated $C_3$-$C_{12}$ mono or polycarbocyclyl; and saturated or unsaturated 3- to 12-membered mono or polyheterocyclyl containing 1 to 3 heteroatoms which is unsubstituted or substituted with oxo or $C_1$-$C_6$ alkoxy,
provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a saturated or unsaturated 5- to 11-membered carbocycle or heterocycle,
each of $R_5$, $R_6$, $R_7$ and $R_8$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; $C_2$-$C_7$ alkanoyl; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; halogen; phenyl; cyano; nitro; amino; and carboxylic acid group, or $R_5$ and $R_6$ together with a carbon atom to which they are attached may form a carbonyl group (C=O) or thioxo group (C=S), or $R_7$ and $R_8$ together with a carbon atom to which they are attached may form a carbonyl group (C=O) or thioxo group (C=S),
Y is selected from the group consisting of saturated or unsaturated $C_3$-$C_{12}$ mono or polycarbocyclyl substituted with $R_9$, $R_{10}$, and $R_{11}$; and saturated or unsaturated 3- to 12-membered mono or polyheterocyclyl containing 1 to 3 heteroatoms and being substituted with $R_9$, $R_{10}$, and $R_{11}$,
wherein each of $R_9$, $R_{10}$ and $_{11}$ is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; $C_1$-$C_6$ alkylsulfide; $C_1$-$C_6$ alkylthioxo; hydroxamic acid; phenyl; cyano; nitro; amino; carboxylic acid group; amide; $C_1$-$C_6$ alkylamide; $C_2$-$C_7$ alkanoyl; aldehyde; $C_3$-$C_8$ ester; $C_3$-$C_8$ esteroxy; $C_1$-$C_6$ alkylsulfonyl; $C_1$-$C_6$ oximealkyl; $C_1$-$C_6$ aminoalkyl; $C_3$-$C_8$ alkylcarbonylalkyl; phosphoric acid group; and N-oxide,
provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen, and Z represents a reactive leaving group.

19. A method for preparing a compound of Formula II, or racemate, isomer or pharmaceutically acceptable salt thereof, comprising the steps of:
a) halogenating Formula VII compound to obtain Formula X compound and then reacting the obtained Formula X compound with Formula IX compound to obtain Formula VIII compound, or conducting a Mitsunobu reaction of Formula VII compound and Formula IX compound to obtain Formula VIII compound,
b) cyclizing the obtained Formula VIII compound to obtain Formula IV compound, and
c) peptide-bonding the obtained Formula IV compound with Formula III compound to obtain Formula II compound:

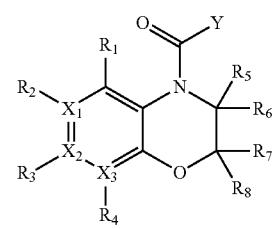

[Formula II]

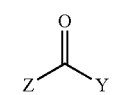

[Formula III]

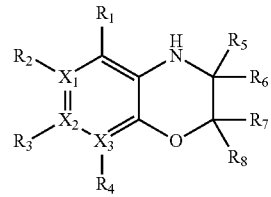

[Formula IV]

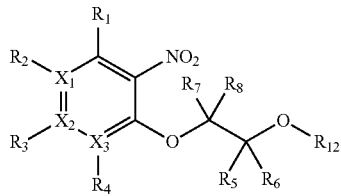

[Formula VIII]

-continued

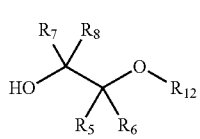
[Formula IX]

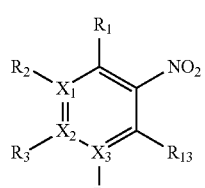
[Formula X]

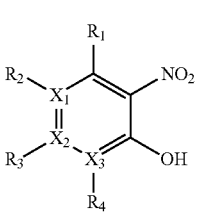
[Formula VII]

wherein, in Formulae II to X,
each of $X_1$, $X_2$, and $X_3$ is independently carbon or nitrogen, provided that at least one of $X_1$, $X_2$, and $X_3$ is nitrogen,
each of $R_1$, $R_2$, $R_3$ and $R_4$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; cyano; nitro; amino; carboxylic acid group; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; $C_2$-$C_7$ alkanoyl; $C_2$-$C_7$ alkoxycarbonyl; $C_2$-$C_7$ alkanoyloxy; $C_3$-$C_{12}$ mono or bicycloalkyl; $C_4$-$C_{12}$ cycloalkylalkyl; $C_6$-$C_{12}$ aryl unsubstituted or substituted with one or more substituents selected from the group consisting of $C_1$-$C_6$ haloalkoxy, $C_1$-$C_6$ haloalkyl, di-($C_1$-$C_6$)alkylamino, nitro, halogen, cyano and $C_2$-$C_7$ alkanoyl; saturated or unsaturated $C_3$-$C_{12}$ mono or polycarbocyclyl; and saturated or unsaturated 3- to 12-membered mono or polyheterocyclyl containing 1 to 3 heteroatoms which is unsubstituted or substituted with oxo or $C_1$-$C_6$ alkoxy,
provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a saturated or unsaturated 5- to 11-membered carbocycle or heterocycle,
each of $R_5$, $R_6$, $R_7$ and $R_8$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; $C_2$-$C_7$ alkanoyl; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; halogen; phenyl; cyano; nitro; amino; and carboxylic acid group, or $R_5$ and $R_6$ together with a carbon atom to which they are attached may form a carbonyl group (C=O) or thioxo group (C=S), or $R_7$ and $R_8$ together with a carbon atom to which they are attached may form a carbonyl group (C=O) or thioxo group (C=S), Y is selected from the group consisting of saturated or unsaturated $C_3$-$C_{12}$ mono or polycarbocyclyl substituted with $R_9$, $R_{10}$, and $R_{11}$; and saturated or unsaturated 3- to 12-membered mono or polyheterocyclyl containing 1 to 3 heteroatoms and being substituted with $R_9$, $R_{10}$, and $R_{11}$,
wherein each of $R_9$, $R_{10}$ and $R_{11}$ is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; $C_1$-$C_6$ alkylsulfide; $C_1$-$C_6$ alkylthioxo; hydroxamic acid; phenyl; cyano; nitro; amino; carboxylic acid group; amide; $C_1$-$C_6$ alkylamide; $C_2$-$C_7$ alkanoyl; aldehyde; $C_3$-$C_8$ ester; $C_3$-$C_8$ esteroxy; $C_1$-$C_6$ alkylsulfonyl; $C_1$-$C_6$ oximealkyl; $C_1$-$C_6$ aminoalkyl; $C_3$-$C_8$ alkylcarbonylalkyl; phosphoric acid group; and N-oxide,
provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen,
$R_{12}$ is a non-hydrogen substituent, and
$R_{13}$ represents a reactive leaving group.

20. A method for preparing a compound of Formula XI, or racemate, isomer or pharmaceutically acceptable salt thereof, comprising the step of reacting Formula II compound with Lawesson's reagent:

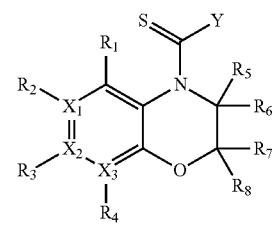
[Formula XI]

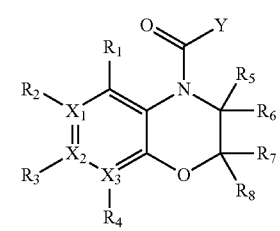
[Formula II]

wherein, in Formulae II and XI,
each of $X_1$, $X_2$, and $X_3$ is independently carbon or nitrogen, provided that at least one of $X_1$, $X_2$, and $X_3$ is nitrogen,
each of $R_1$, $R_2$, $R_3$ and $R_4$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; cyano; nitro; amino; carboxylic acid group; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; $C_2$-$C_7$ alkanoyl; $C_2$-$C_7$ alkoxycarbonyl; $C_2$-$C_7$ alkanoyloxy; $C_3$-$C_{12}$ mono or bicycloalkyl; $C_4$-$C_{12}$ cycloalkylalkyl; $C_6$-$C_{12}$ aryl unsubstituted or substituted with one or more substituents selected from the group consisting of $C_1$-$C_6$ haloalkoxy, $C_1$-$C_6$ haloalkyl, di-($C_1$-$C_6$)alkylamino, nitro, halogen, cyano and $C_2$-$C_7$ alkanoyl; saturated or unsaturated $C_3$-$C_{12}$ mono or polycarbocyclyl; and saturated or unsaturated 3- to 12-membered mono or polyheterocyclyl containing 1 to 3 heteroatoms which is unsubstituted or substituted with oxo or $C_1$-$C_6$ alkoxy, provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a saturated or unsaturated 5- to 11-membered carbocycle or heterocycle, each of $R_5$, $R_6$, $R_7$ and $R_8$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; $C_2$-$C_7$ alkanoyl; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; halogen; phenyl; cyano; nitro; amino; and carboxylic acid group, or $R_5$ and $R_6$ together with a carbon atom to which they are attached may form a carbonyl group (C=O) or thioxo group (C=S), or $R_7$ and $R_8$ together with a carbon atom to which they are attached may form a carbonyl group (C=O) or thioxo group (C=S), Y is selected from the group consisting of saturated or unsaturated $C_3$-$C_{12}$ mono or polycarbocyclyl substituted with $R_9$, $R_{10}$, and $R_{11}$; and saturated or unsaturated 3- to 12-membered mono or polyheterocyclyl containing 1 to 3 heteroatoms and being substituted with $R_9$, $R_{10}$, and $R_{11}$, wherein each of $R_9$, $R_{10}$ and $R_{11}$ is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; $C_1$-$C_6$ alkylsulfide; $C_1$-$C_6$ alkylthioxo; hydroxamic acid; phenyl; cyano; nitro; amino; carboxylic acid group; amide; $C_1$-$C_6$ alkylamide; $C_2$-$C_7$ alkanoyl; aldehyde; $C_3$-$C_8$ ester; $C_3$-$C_8$ esteroxy; $C_1$-$C_6$ alkylsulfonyl; $C_1$-$C_6$ oximealkyl; $C_1$-$C_6$ aminoalkyl; $C_3$-$C_8$ alkylcarbonylalkyl; phosphoric acid group; and N-oxide, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen.

21. A method for preparing a compound of Formula XII, or racemate, isomer or pharmaceutically acceptable salt thereof, comprising the step of amide-bonding Formula IV compound with Formula XIII compound in the presence of base:

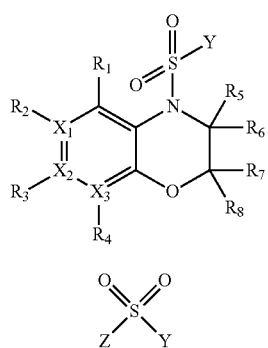

[Formula XII]

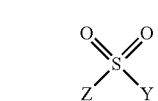

[Formula XIII]

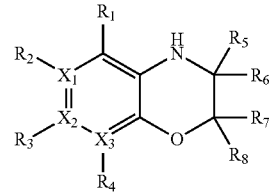

[Formula IV]

wherein, in Formulae IV, XII and XIII, each of $X_1$, $X_2$, and $X_3$ is independently carbon or nitrogen, provided that at least one of $X_1$, $X_2$, and $X_3$ is nitrogen, each of $R_1$, $R_2$, $R_3$ and $R_4$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; cyano; nitro; amino; carboxylic acid group; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; $C_2$-$C_7$ alkanoyl; $C_2$-$C_7$ alkoxycarbonyl; $C_2$-$C_7$ alkanoyloxy; $C_3$-$C_{12}$ mono or bicycloalkyl; $C_4$-$C_{12}$ cycloalkylalkyl; $C_6$-$C_{12}$ aryl unsubstituted or substituted with one or more substituents selected from the group consisting of $C_1$-$C_6$ haloalkoxy, $C_1$-$C_6$ haloalkyl, di-($C_1$-$C_6$)alkylamino, nitro, halogen, cyano and $C_2$-$C_7$ alkanoyl; saturated or unsaturated $C_3$-$C_{12}$ mono or polycarbocyclyl; and saturated or unsaturated 3- to 12-membered mono or polyheterocyclyl containing 1 to 3 heteroatoms which is unsubstituted or substituted with oxo or $C_1$-$C_6$ alkoxy, provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a saturated or unsaturated 5- to 11-membered carbocycle or heterocycle, each of $R_5$, $R_6$, $R_7$ and $R_8$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; $C_2$-$C_7$ alkanoyl; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; halogen; phenyl; cyano; nitro; amino; and carboxylic acid group, or $R_5$ and $R_6$ together with a carbon atom to which they are attached may form a carbonyl group (C=O) or thioxo group (C=S), or $R_7$ and $R_8$ together with a carbon atom to which they are attached may form a carbonyl group (C=O) or thioxo group (C=S), Y is selected from the group consisting of saturated or unsaturated $C_3$-$C_{12}$ mono or polycarbocyclyl substituted with $R_9$, $R_{10}$, and $R_{11}$; and saturated or unsaturated 3- to 12-membered mono or polyheterocyclyl containing 1 to 3 heteroatoms and being substituted with $R_9$, $R_{10}$, and $R_{11}$, wherein each of $R_9$, $R_{10}$ and $R_{11}$ is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; $C_1$-$C_6$ alkylsulfide; $C_1$-$C_6$ alkylthioxo; hydroxamic acid; phenyl; cyano; nitro; amino;

carboxylic acid group; amide; $C_1$-$C_6$ alkylamide; $C_2$-$C_7$ alkanoyl; aldehyde; $C_3$-$C_8$ ester; $C_3$-$C_8$ esteroxy; $C_1$-$C_6$ alkylsulfonyl; $C_1$-$C_6$ oximealkyl; $C_1$-$C_6$ aminoalkyl; $C_3$-$C_8$ alkylcarbonylalkyl; phosphoric acid group; and N-oxide, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen, Z represents a reactive leaving group.

22. A method for preparing a compound of Formula XIV, or racemate, isomer or pharmaceutically acceptable salt thereof, comprising the step of alkylating Formula IV compound with Formula XV compound in the presence of base:

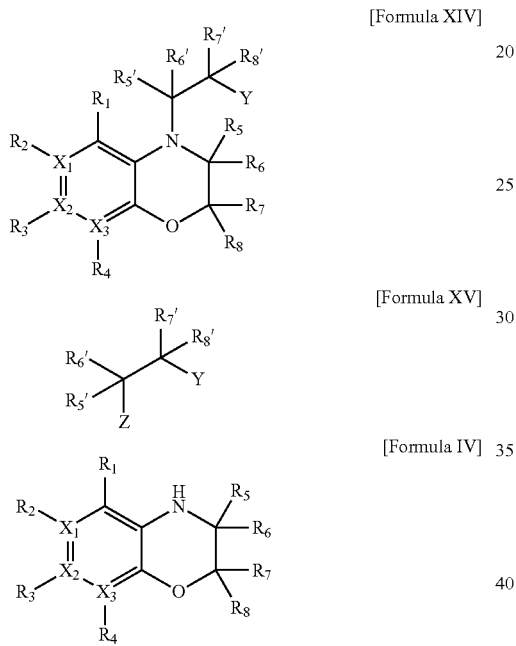

wherein, in Formulae IV to XV, each of $X_1$, $X_2$, and $X_3$ is independently carbon or nitrogen, provided that at least one of $X_1$, $X_2$, and $X_3$ is nitrogen, each of $R_1$, $R_2$, $R_3$ and $R_4$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; cyano; nitro; amino; carboxylic acid group; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; $C_2$-$C_7$ alkanoyl; $C_2$-$C_7$ alkoxycarbonyl; $C_2$-$C_7$ alkanoyloxy; $C_3$-$C_{12}$ mono or bicycloalkyl; $C_4$-$C_{12}$ cycloalkylalkyl; $C_6$-$C_{12}$ aryl unsubstituted or substituted with one or more substituents selected from the group consisting of $C_1$-$C_6$ haloalkoxy, $C_1$-$C_6$ haloalkyl, di-($C_1$-$C_6$)alkylamino, nitro, halogen, cyano and $C_2$-$C_7$ alkanoyl; saturated or unsaturated $C_3$-$C_{12}$ mono or polycarbocyclyl; and saturated or unsaturated 3- to 12-membered mono or polyheterocyclyl containing 1 to 3 heteroatoms which is unsubstituted or substituted with oxo or $C_1$-$C_6$ alkoxy, provided that when $X_1$ is nitrogen, $R_2$ does not exist; when $X_2$ is nitrogen, $R_3$ does not exist; and when $X_3$ is nitrogen, $R_4$ does not exist, or each of $R_1$-$R_2$, $R_2$-$R_3$ and $R_3$-$R_4$ pairs may be independently fused to form a saturated or unsaturated 5- to 11-membered carbocycle or heterocycle, each of $R_5$, $R_6$, $R_7$ and $R_8$ may be same or different and is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; $C_2$-$C_7$ alkanoyl; phosphoric acid group; N-oxide; amide; $C_1$-$C_6$ alkylamide; aldehyde; hydroxamic acid; $C_1$-$C_6$ alkylsulfide; $C_1$-$C_6$ alkylthioxo; $C_1$-$C_6$ alkylsulfonyl; $C_1$-$C_6$ oximealkyl; $C_1$-$C_6$ aminoalkyl; $C_3$-$C_8$ alkylcarbonylalkyl; halogen; phenyl; cyano; nitro; amino; and carboxylic acid group, or $R_5$ and $R_6$ together with a carbon atom to which they are attached may form a carbonyl group (C=O) or thioxo group (C=S), or $R_7$ and $R_8$ together with a carbon atom to which they are attached may form a carbonyl group (C=O) or thioxo group (C=S), Y is selected from the group consisting of saturated or unsaturated $C_3$-$C_{12}$ mono or polycarbocyclyl substituted with $R_9$, $R_{10}$, and $R_{11}$; and saturated or unsaturated 3- to 12-membered mono or polyheterocyclyl containing 1 to 3 heteroatoms and being substituted with $R_9$, $R_{10}$, and $R_{11}$, wherein each of $R_9$, $R_{10}$ and $R_{11}$ is independently selected from the group consisting of hydrogen; hydroxy; $C_1$-$C_6$ alkyl; $C_2$-$C_7$ alkenyl; $C_2$-$C_7$ alkynyl; $C_1$-$C_6$ hydroxyalkyl; $C_1$-$C_6$ haloalkyl; $C_1$-$C_6$ alkoxy; $C_1$-$C_6$ haloalkoxy; halogen; $C_1$-$C_6$ alkyl sulfide; $C_1$-$C_6$ alkylthioxo; hydroxamic acid; phenyl; cyano; nitro; amino; carboxylic acid group; amide; $C_1$-$C_6$ alkylamide; $C_2$-$C_7$ alkanoyl; aldehyde; $C_3$-$C_8$ ester; $C_3$-$C_8$ esteroxy; $C_1$-$C_6$ alkylsulfonyl; $C_1$-$C_6$ oximealkyl; $C_1$-$C_6$ aminoalkyl; $C_3$-$C_8$ alkylcarbonylalkyl; phosphoric acid group; and N-oxide, provided that when Y is phenyl, i) at least one of $R_9$, $R_{10}$ and $R_{11}$ is hydroxy or ii) all of $R_9$, $R_{10}$ and $R_{11}$ are other than hydrogen if none of $R_9$, $R_{10}$ and $R_{11}$ is hydroxy, and when Y is pyridinyl, at least one of $R_9$, $R_{10}$ and $R_{11}$ is not hydrogen;

Z represents a reactive leaving group, and each of $R_5'$, $R_6'$, $R_7'$ and $R_8'$ may be same or different and is independently selected from the group consisting of hydrogen; hydroxy; $C_1$-$C_6$ alkyl; $C_1$-$C_6$ haloalkyl; $C_1$-$C_6$ alkoxy; $C_1$-$C_6$ haloalkoxy; $C_2$-$C_7$ alkanoyl; halogen; phenyl; cyano; nitro; amino; and carboxylic acid group; or $R_5'$ and $R_6'$ together with a carbon atom to which they are attached may form a carbonyl group (C=O) or thioxo group (C=S), or $R_7'$ and $R_8'$ together with a carbon atom to which they are attached may form a carbonyl group (C=O) or thioxo group (C=S).

23. A pharmaceutical composition comprising an effective amount of the compound defined in claim 1 or racemate, isomer or pharmaceutically acceptable salt thereof as active ingredient, and pharmaceutically acceptable carrier.

24. A method for treatment or prophylaxis of hyperuricemia, gout disease, nephritis, chronic renal failure, nephrolithiasis, uremia, urolithiasis, or disease associated with uric acid comprising administering the pharmaceutical composition as defined in claim 23 to a subject in need thereof.

25. The method according to claim 24, wherein the gout disease is acute gouty arthritis, chronic gouty arthritis, tophus or gout nephrosis.

26. The method according to claim 24, wherein the disease associated with uric acid is hyperlipidemia, ischemic heart disease, myocardial infarction, cerebral infarction, cerebrovascular disease, diabetes or hypertension.

27. The pharmaceutical composition according to claim 23 which is formulated for oral administration.

28. The method according to claim 24, wherein said method is for the treatment of hyperuricemia, gout disease, nephritis, chronic renal failure, nephrolithiasis, uremia, urolithiasis, disease associated with uric acid, acute gouty arthritis, chronic gouty arthritis, tophus, gout nephrosis, hyperlipidemia, ischemic heart disease, myocardial infarction, cerebral infarction, cerebrovascular disease, diabetes, or hypertension.

* * * * *